(12) United States Patent
Sword

(10) Patent No.: US 11,807,586 B2
(45) Date of Patent: Nov. 7, 2023

(54) FUNGAL ENDOPHYTES FOR IMPROVED CROP YIELDS AND PROTECTION FROM PESTS

(71) Applicant: The Texas A&M University System, College Station, TX (US)

(72) Inventor: Gregory A. Sword, College Station, TX (US)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 57 days.

(21) Appl. No.: 15/853,057

(22) Filed: Dec. 22, 2017

(65) Prior Publication Data

US 2018/0177196 A1   Jun. 28, 2018

Related U.S. Application Data

(60) Provisional application No. 62/567,113, filed on Oct. 2, 2017, provisional application No. 62/546,959, filed on Aug. 17, 2017, provisional application No. 62/438,966, filed on Dec. 23, 2016.

(51) Int. Cl.
| | |
|---|---|
| C05F 11/08 | (2006.01) |
| A01N 63/30 | (2020.01) |
| A01C 1/06 | (2006.01) |
| A01H 17/00 | (2006.01) |
| A01N 25/04 | (2006.01) |

(52) U.S. Cl.
CPC ............... *C05F 11/08* (2013.01); *A01C 1/06* (2013.01); *A01H 17/00* (2013.01); *A01N 25/04* (2013.01); *A01N 63/30* (2020.01)

(58) Field of Classification Search
CPC ........ A01N 63/30; A01N 63/10; A01N 25/04; A01C 1/06; A01H 5/10; A01H 17/00; C05F 11/08
See application file for complete search history.

(56) References Cited

U.S. PATENT DOCUMENTS

| | | | |
|---|---|---|---|
| 2,200,532 A | 5/1940 | Sherman | |
| 4,642,131 A * | 2/1987 | Hoitink | C12R 1/885 71/6 |
| 4,940,834 A | 7/1990 | Hurley et al. | |
| 5,041,290 A | 8/1991 | Gindrat et al. | |
| 5,113,619 A | 5/1992 | Leps et al. | |
| 5,229,291 A | 7/1993 | Nielsen et al. | |
| 5,292,507 A | 3/1994 | Charley | |
| 5,300,127 A | 4/1994 | Williams | |
| 5,415,672 A | 5/1995 | Fahey et al. | |
| 5,730,973 A | 3/1998 | Morales et al. | |
| 5,919,447 A | 7/1999 | Marrone et al. | |
| 5,989,543 A | 11/1999 | Davide et al. | |
| 5,994,117 A | 11/1999 | Bacon et al. | |
| 6,072,107 A | 6/2000 | Latch et al. | |
| 6,077,505 A | 6/2000 | Parke et al. | |
| 6,337,431 B1 | 1/2002 | Tricoli et al. | |
| 6,495,133 B1 | 12/2002 | Xue | |
| 6,602,500 B1 | 8/2003 | Kharbanda et al. | |
| 6,681,186 B1 | 1/2004 | Denisov et al. | |
| 6,689,880 B2 | 2/2004 | Chen et al. | |
| 6,823,623 B2 | 11/2004 | Minato et al. | |
| 7,037,879 B2 | 5/2006 | Imada et al. | |
| 7,080,034 B1 | 7/2006 | Reams | |
| 7,084,331 B2 | 8/2006 | Isawa et al. | |
| 7,335,816 B2 | 2/2008 | Kraus et al. | |
| 7,341,868 B2 | 3/2008 | Chopade et al. | |
| 7,435,411 B2 | 10/2008 | Park et al. | |
| 7,485,451 B2 | 2/2009 | VanderGheynst et al. | |
| 7,555,990 B2 | 7/2009 | Beaujot | |
| 7,632,985 B2 | 12/2009 | Malven et al. | |
| 7,763,420 B2 | 7/2010 | Stritzker et al. | |
| 7,906,313 B2 | 3/2011 | Henson et al. | |
| 7,977,550 B2 | 7/2011 | West et al. | |
| 8,019,694 B2 | 9/2011 | Fell et al. | |
| 8,143,045 B2 | 3/2012 | Miansnikov et al. | |
| 8,455,198 B2 | 6/2013 | Gao et al. | |
| 8,455,395 B2 | 6/2013 | Miller et al. | |
| 8,465,963 B2 | 6/2013 | Rolston et al. | |
| 8,728,459 B2 | 5/2014 | Isawa et al. | |
| 8,975,489 B2 | 3/2015 | Craven | |
| 9,049,814 B2 | 6/2015 | Marx et al. | |
| 9,113,636 B2 | 8/2015 | von Maltzahn et al. | |

(Continued)

FOREIGN PATENT DOCUMENTS

| | | |
|---|---|---|
| AU | 2015201322 A1 | 4/2015 |
| CA | 1041788 | 11/1978 |

(Continued)

OTHER PUBLICATIONS

Lopez et al 2014 The Entomopathogenic Fungal Endophytes, Department of Entomology, Texas A&M (Year: 2014).*
Zhang et al 2012 Diversity and Antimicrobial Activity of Culturable Fungi, Microbial Ecology (Year: 2012).*
BB-CBI, (*Beauveria bassiana* (white muscardine fungus), Invasive Species Compendium, CABI, Webpage, 2021) (Year: 2021).*
PL-NCBI, Purpureocillium lilacinum, NCBI Taxonomy Browser, Webpage, 2021 (Year: 2021).*
Zhou et al., A fungal endophyte defensive symbiosis affects plant-nematode interactions in cotton, Plant Soil (2018) 422:251-266 (Year: 2018).*
Sequence-Search-1-95, Sequence search results, 2022 (Year: 2022).*
Sequence-Search-2-95, Sequence search results, 2022 (Year: 2022).*
Sequence-search-3-94 (Year: 2022).*

(Continued)

*Primary Examiner* — Louise W Humphrey
*Assistant Examiner* — John Paul Selwanes
(74) *Attorney, Agent, or Firm* — Fenwick & West LLP

(57) ABSTRACT

Synthetic compositions comprising a plant element and at least one fungal endophyte are described. The fungal endophyte is capable of improving plant tolerance to biotic stress as compared to a reference plant element not further comprising the endophyte. Examples of biotic stress include the biotic stress caused by a nematode, an aphid, a fleahopper, a *lygus* bug, a stink bug, a soy looper, a cabbage looper, or a fungus.

8 Claims, 48 Drawing Sheets

Specification includes a Sequence Listing.

(56) References Cited

U.S. PATENT DOCUMENTS

| | | |
|---|---|---|
| 9,277,751 B2 | 3/2016 | Sword |
| 9,288,995 B2 | 3/2016 | von Maltzahn et al. |
| 9,295,263 B2 | 3/2016 | von Maltzahn et al. |
| 9,364,005 B2 | 6/2016 | Mitter et al. |
| 9,408,394 B2 | 8/2016 | von Maltzahn et al. |
| 9,532,572 B2 | 1/2017 | von Maltzahn et al. |
| 9,532,573 B2 | 1/2017 | von Maltzahn et al. |
| 9,545,111 B2 | 1/2017 | Sword |
| 9,622,485 B2 | 4/2017 | von Maltzahn et al. |
| 9,652,840 B1 | 5/2017 | Shriver et al. |
| 9,687,001 B2 | 6/2017 | Vujanovic et al. |
| 9,756,865 B2 | 9/2017 | Sword |
| 10,058,101 B2 | 8/2018 | von Maltzahn et al. |
| 10,076,120 B2 | 9/2018 | von Maltzahn et al. |
| 10,104,862 B2 | 10/2018 | Vujanovic et al. |
| 10,136,646 B2 | 11/2018 | Von Maltzahn et al. |
| 10,212,912 B2 | 2/2019 | Vujanovic et al. |
| 10,306,890 B2 | 6/2019 | Mitter et al. |
| 10,362,787 B2 | 7/2019 | Mitter et al. |
| 10,499,652 B2 | 12/2019 | von Maltzahn et al. |
| 10,499,653 B2 | 12/2019 | von Maltzahn et al. |
| 10,499,654 B2 | 12/2019 | von Maltzahn et al. |
| 10,640,783 B2 | 5/2020 | Riley |
| 10,645,938 B2 | 5/2020 | Riley |
| 10,667,523 B2 | 6/2020 | Ambrose et al. |
| 10,750,711 B2 | 8/2020 | Djonovic et al. |
| 10,932,469 B2 | 3/2021 | Mitter et al. |
| 11,119,086 B2 | 9/2021 | Mitter et al. |
| 11,151,379 B2 | 10/2021 | Freitag et al. |
| 2001/0032162 A1 | 10/2001 | Alsberg et al. |
| 2002/0059091 A1 | 5/2002 | Hay et al. |
| 2002/0120555 A1 | 8/2002 | Lerner |
| 2002/0142917 A1 | 10/2002 | Triplett et al. |
| 2002/0147670 A1 | 10/2002 | Lange |
| 2003/0050901 A1 | 3/2003 | Jester et al. |
| 2003/0195822 A1 | 10/2003 | Tatge et al. |
| 2003/0236738 A1 | 12/2003 | Lange et al. |
| 2005/0008619 A1 | 1/2005 | Park et al. |
| 2005/0070435 A1 | 3/2005 | Chopade et al. |
| 2005/0072047 A1 | 4/2005 | Conkling et al. |
| 2006/0046246 A1 | 3/2006 | Zeng et al. |
| 2006/0178269 A1 | 8/2006 | Medina-Vega |
| 2006/0185207 A1 | 8/2006 | Mitcheltree |
| 2007/0028318 A1 | 2/2007 | Livore et al. |
| 2007/0055456 A1 | 3/2007 | Raftery et al. |
| 2007/0142226 A1 | 6/2007 | Franco |
| 2007/0292953 A1 | 12/2007 | Mankin et al. |
| 2008/0229441 A1 | 9/2008 | Young et al. |
| 2008/0289060 A1 | 11/2008 | De Beuckeleer et al. |
| 2009/0155214 A1 | 6/2009 | Isawa et al. |
| 2009/0300781 A1 | 12/2009 | Bancroft et al. |
| 2010/0064392 A1 | 3/2010 | Yang et al. |
| 2010/0095396 A1 | 4/2010 | Voeste et al. |
| 2010/0114753 A1 | 5/2010 | Osmanski et al. |
| 2010/0130365 A1 | 5/2010 | Notten et al. |
| 2010/0205690 A1 | 8/2010 | Biasing et al. |
| 2010/0227357 A1 | 9/2010 | Redman et al. |
| 2011/0033436 A1 | 2/2011 | Chen et al. |
| 2011/0182862 A1 | 7/2011 | Green et al. |
| 2011/0195406 A1 | 8/2011 | Sorenson et al. |
| 2011/0208636 A1 | 8/2011 | Bachu et al. |
| 2012/0108431 A1 | 5/2012 | Williams et al. |
| 2012/0116943 A1 | 5/2012 | Abramson |
| 2012/0131696 A1 | 5/2012 | Aayal et al. |
| 2012/0144533 A1* | 6/2012 | Craven .................. A01N 63/30 800/300 |
| 2012/0149571 A1 | 6/2012 | Kloepper et al. |
| 2012/0178624 A1 | 7/2012 | Kaminskyj et al. |
| 2012/0324599 A1 | 12/2012 | Kerns et al. |
| 2013/0031673 A1 | 1/2013 | Grandlic et al. |
| 2013/0071425 A1 | 3/2013 | Vidal et al. |
| 2013/0079225 A1 | 3/2013 | Smith et al. |
| 2013/0150240 A1 | 6/2013 | Newman et al. |
| 2013/0233501 A1 | 9/2013 | Van Zyl et al. |
| 2014/0020136 A1 | 1/2014 | Van Der Wolf et al. |
| 2014/0109249 A1 | 4/2014 | Turner et al. |
| 2014/0115731 A1 | 4/2014 | Turner et al. |
| 2014/0134629 A1 | 5/2014 | Turner et al. |
| 2014/0147425 A1 | 5/2014 | Henn et al. |
| 2014/0342905 A1 | 11/2014 | Bullis et al. |
| 2015/0020239 A1 | 1/2015 | von Maltzahn et al. |
| 2015/0033420 A1 | 1/2015 | Rodriguez et al. |
| 2015/0126365 A1* | 5/2015 | Sword ..................... A01H 5/10 504/100 |
| 2015/0218568 A1 | 8/2015 | Jones et al. |
| 2015/0230478 A1 | 8/2015 | Vujanovic et al. |
| 2015/0242970 A1 | 8/2015 | Avey et al. |
| 2015/0282490 A1 | 10/2015 | Wachendorff-Neumann et al. |
| 2015/0289518 A1 | 10/2015 | Andersch et al. |
| 2015/0296802 A1 | 10/2015 | Wachendorff-Neumann et al. |
| 2015/0296803 A1 | 10/2015 | Andersch et al. |
| 2015/0296804 A1 | 10/2015 | Andersch et al. |
| 2015/0305348 A1 | 10/2015 | Andersch et al. |
| 2015/0320050 A1 | 11/2015 | von Maltzahn et al. |
| 2015/0320051 A1 | 11/2015 | Wachendorff-Neumann et al. |
| 2015/0335029 A1 | 11/2015 | Mitter et al. |
| 2015/0342199 A1 | 12/2015 | Carrion Villanovo et al. |
| 2015/0366217 A1 | 12/2015 | Vujanovic et al. |
| 2015/0368607 A1 | 12/2015 | Arnold et al. |
| 2015/0370935 A1 | 12/2015 | Starr |
| 2015/0373993 A1 | 12/2015 | von Maltzahn et al. |
| 2016/0000091 A1 | 1/2016 | Andersch et al. |
| 2016/0021891 A1 | 1/2016 | von Maltzahn et al. |
| 2016/0150796 A1 | 6/2016 | von Maltzahn et al. |
| 2016/0174570 A1 | 6/2016 | Vujanovic et al. |
| 2016/0192662 A1 | 7/2016 | Sword |
| 2016/0205947 A1 | 7/2016 | Sword |
| 2016/0235074 A1 | 8/2016 | von Maltzahn et al. |
| 2016/0255844 A1 | 9/2016 | Mitter et al. |
| 2016/0260021 A1 | 9/2016 | Marek |
| 2016/0286821 A1 | 10/2016 | Sword |
| 2016/0290918 A1 | 10/2016 | Xu et al. |
| 2016/0316760 A1 | 11/2016 | Ambrose et al. |
| 2016/0316763 A1 | 11/2016 | Sword |
| 2016/0330976 A1 | 11/2016 | Mitter et al. |
| 2016/0338360 A1 | 11/2016 | Mitter et al. |
| 2016/0350855 A1 | 12/2016 | Lerner |
| 2016/0366892 A1 | 12/2016 | Ambrose et al. |
| 2017/0020138 A1 | 1/2017 | von Maltzahn et al. |
| 2017/0161560 A1 | 6/2017 | Itzhaky et al. |
| 2017/0164619 A1 | 6/2017 | von Maltzahn et al. |
| 2017/0164620 A1 | 6/2017 | von Maltzahn et al. |
| 2017/0215358 A1 | 8/2017 | Franco et al. |
| 2017/0223967 A1 | 8/2017 | Mitter et al. |
| 2018/0020677 A1 | 1/2018 | Ambrose et al. |
| 2018/0060771 A1 | 3/2018 | Mangin |
| 2018/0092365 A1 | 4/2018 | Sword |
| 2018/0153174 A1* | 6/2018 | Riley ..................... A01N 63/30 |
| 2018/0189564 A1 | 7/2018 | Freitag et al. |
| 2018/0213800 A1 | 8/2018 | Djonovic et al. |
| 2018/0249716 A1 | 9/2018 | Riley |
| 2018/0251776 A1* | 9/2018 | Riley ................. C12N 15/8262 |
| 2018/0322426 A1 | 11/2018 | Schmaltz et al. |
| 2019/0130999 A1 | 5/2019 | Oppenheim et al. |
| 2021/0372997 A1 | 12/2021 | Von Maltzahn et al. |

FOREIGN PATENT DOCUMENTS

| | | |
|---|---|---|
| CA | 1229497 | 11/1987 |
| CA | 2562175 | 1/2013 |
| CA | 2916678 | 12/2014 |
| CA | 2960032 | 3/2015 |
| CA | 2935218 | 7/2015 |
| CA | 2953466 | 12/2015 |
| CA | 2953697 | 12/2015 |
| CN | 1604732 | 4/2005 |
| CN | 1948459 | 4/2007 |
| CN | 101311262 A | 11/2008 |
| CN | 101423810 A | 5/2009 |
| CN | 101570738 | 11/2009 |
| CN | 101693881 A | 4/2010 |
| CN | 102123596 | 7/2011 |
| CN | 102168022 A | 8/2011 |
| CN | 102352327 A | 2/2012 |

(56) References Cited

FOREIGN PATENT DOCUMENTS

| | | | |
|---|---|---|---|
| CN | 102010835 B | 4/2012 | |
| CN | 102533601 B | 10/2013 | |
| CN | 103642725 A | 3/2014 | |
| CN | 103865837 | 6/2014 | |
| CN | 104250616 | 12/2014 | |
| CN | 104560742 A | 1/2015 | |
| CN | 104388356 A | 3/2015 | |
| CN | 105274008 A | * | 1/2016 |
| CN | 105886428 | 8/2016 | |
| CN | 106434493 | 2/2017 | |
| EP | 0192342 | 8/1986 | |
| EP | 0223662 | 5/1987 | |
| EP | 0378000 | 7/1990 | |
| EP | 0494802 | 7/1992 | |
| EP | 0818135 | 1/1998 | |
| EP | 1389767 | 2/2004 | |
| EP | 1621632 | 2/2006 | |
| EP | 1935245 | 6/2008 | |
| EP | 1967057 A1 | 9/2008 | |
| EP | 2114118 B1 | 9/2012 | |
| EP | 2676536 | 12/2013 | |
| EP | 2959779 A1 | 12/2015 | |
| EP | 3041338 | 7/2016 | |
| EP | 3659414 | 6/2020 | |
| JP | 2003-300804 | 10/2003 | |
| JP | 2009/072168 | 4/2009 | |
| KR | 10-2005-0039979 A | 5/2005 | |
| KR | 20100114806 A | 10/2010 | |
| KR | 10-1066283 | 9/2011 | |
| KR | 101091151 | 12/2011 | |
| KR | 10-2012-0004958 A | 1/2012 | |
| KR | 20130023491 | 3/2013 | |
| RU | 2043028 C1 | 9/1995 | |
| WO | WO 1988/009114 | 1/1988 | |
| WO | WO 1994/016076 | 7/1994 | |
| WO | WO 98/35017 | 8/1998 | |
| WO | WO 99/59412 | 11/1999 | |
| WO | WO 2000/029607 | 5/2000 | |
| WO | WO 2001/046774 | 6/2001 | |
| WO | WO 2001/083697 | 11/2001 | |
| WO | WO 2001/083818 | 11/2001 | |
| WO | WO 2002/065836 | 8/2002 | |
| WO | WO 2003/038066 A1 | 5/2003 | |
| WO | WO 2004/046357 | 6/2004 | |
| WO | WO 2005/003328 | 1/2005 | |
| WO | WO 2007/021200 | 2/2007 | |
| WO | WO 2007/107000 | 9/2007 | |
| WO | WO 2008/103422 | 8/2008 | |
| WO | WO 2008/107097 A1 | 9/2008 | |
| WO | WO 2009/012480 A2 | 1/2009 | |
| WO | WO 2009/078710 A1 | 6/2009 | |
| WO | WO 2009/126473 A1 | 10/2009 | |
| WO | WO 2010/109436 | 9/2010 | |
| WO | WO 2010/115156 | 10/2010 | |
| WO | WO 2011/001127 | 1/2011 | |
| WO | WO 2011/011627 | 1/2011 | |
| WO | WO 2011/082455 | 7/2011 | |
| WO | WO 2011/112781 | 9/2011 | |
| WO | WO 2011/117351 | 9/2011 | |
| WO | WO 2012/016140 | 2/2012 | |
| WO | WO 2012/034996 | 3/2012 | |
| WO | WO 2013/016361 | 1/2013 | |
| WO | WO 2013/029112 | 3/2013 | |
| WO | WO 2013/054272 A2 | 4/2013 | |
| WO | WO 2013/090628 | 6/2013 | |
| WO | WO 2013/122473 | 8/2013 | |
| WO | WO 2013/148290 | 10/2013 | |
| WO | WO 2013/177615 | 12/2013 | |
| WO | WO 2013/190082 | 12/2013 | |
| WO | WO 2014/046553 | 3/2014 | |
| WO | WO 2014/079728 A1 | 5/2014 | |
| WO | WO 2014/082950 | 6/2014 | |
| WO | WO 2014/086747 A2 | 6/2014 | |
| WO | WO 2014/086749 A2 | 6/2014 | |
| WO | WO 2014/086750 A2 | 6/2014 | |
| WO | WO 2014/086752 A1 | 6/2014 | |
| WO | WO 2014/086753 A2 | 6/2014 | |
| WO | WO 2014/086756 A1 | 6/2014 | |
| WO | WO 2014/086758 A2 | 6/2014 | |
| WO | WO 2014/086759 A2 | 6/2014 | |
| WO | WO 2014/086764 A2 | 6/2014 | |
| WO | WO 2014/086776 A2 | 6/2014 | |
| WO | WO 2014/121366 | 8/2014 | |
| WO | WO 2014/206953 | 12/2014 | |
| WO | WO 2014/210372 | 12/2014 | |
| WO | WO 2015/035099 | 3/2015 | |
| WO | WO 2015/069708 A1 | 5/2015 | |
| WO | WO 2015/069938 | 5/2015 | |
| WO | WO 2015/100431 | 7/2015 | |
| WO | WO 2015/100432 | 7/2015 | |
| WO | WO 2015/114552 | 8/2015 | |
| WO | WO 2015/116838 A1 | 8/2015 | |
| WO | WO 2015/192172 | 12/2015 | |
| WO | WO 2015/200852 | 12/2015 | |
| WO | WO 2015/200902 | 12/2015 | |
| WO | WO 2016/020371 | 2/2016 | |
| WO | WO 2016/050726 A1 | 4/2016 | |
| WO | WO 2016/057991 | 4/2016 | |
| WO | WO 2016/090212 | 6/2016 | |
| WO | WO 2016/109758 | 7/2016 | |
| WO | WO 2016/179046 | 11/2016 | |
| WO | WO 2016/179047 | 11/2016 | |
| WO | WO 2016/200987 | 12/2016 | |
| WO | WO 2018/094027 | 5/2018 | |
| WO | WO 2018/102733 | 6/2018 | |
| WO | WO 2018/119419 | 6/2018 | |
| WO | WO 2018/160244 | 9/2018 | |
| WO | WO 2018/160245 | 9/2018 | |
| WO | WO 2019/046909 | 3/2019 | |
| WO | WO 2019/084380 | 5/2019 | |
| WO | WO 2019/113468 | 6/2019 | |

OTHER PUBLICATIONS

CN105274008-Espacenet-Machine-Translation (Year: 2022).*
Raafat, I. et al., "Nezara viridula (Hemiptera: Pentatomidae) Cuticle as a Barrier for *Beauveria bassiana* and *Paecilomyces* sp. Infection," African Entomology, vol. 23, Iss. 1, Mar. 2015, pp. 75-87.
Spurgeon, D.W., "Efficacy of Beauveria bassiana Against Lygus hesperus (Hemiptera: Miridae) at Low Temperatures," Journal of Entomological Science, vol. 45, Iss. 3, Jul. 2010, pp. 211-219.
Sword, G. A. et al., "Endophytic fungi alter sucking bug responses to cotton reproductive structures," Insect Science, vol. 24, Mar. 22, 2017, pp. 1003-1014.
Castillo Lopez, D. et al., "The Entomopathogenic Fungal Endophytes Purpureocillium lilacinum (Formerly Paecilomyces lilacinus) and Beauveria bassiana Negatively Affect Cotton Aphid Reproduction under Both Greenhouse and Field Conditions," PLoS One, vol. 9. Iss. 8, e103891, Aug. 2014, pp. 1-8.
Ehteshamul-Haque, S. et al., "Biological control of root rot diseases of okra, sunflower, soybean and mungbean," Pakistan Journal of Botany, vol. 22, No. 2, Jun. 1990, pp. 121-124.
Kepenekci, I. et al., "Pathogenicity of the Entomopathogenic Fungus, Purpureocillium Lilacinum TR1 Against the Black Cherry Aphid, Myzus Cerasi Fabricus (Hemiptera: Aphididae)," Mun. Ent. Zool., vol. 10, No. 1, Jan. 2015, pp. 53-60.
O'Callaghan, M., "Microbial inoculation of seed for improved crop performance: issues and opportunities," Applied Microbiology and Biotechnology, vol. 100, May 2016, pp. 5729-5746.
Pandey, R. K. et al., "Effect of different bioformulations of Paecilomyces lilacinus against root-knot nematode (*Meloidogyne incognita*) infecting tomato (*Solanum esculentum*)," Indian Journal of Agricultural Sciences, vol. 81, No. 3, Mar. 2011, pp. 261-267.
Rajinikanth, R. et al., "Management of nematode induced disease complex in seedlings of cauliflower (*Brsassica oleraceae* var. *botrytis*) using bio-pesticides," Pest Management in Horticultural Ecosystems, vol. 19, No. 2, Dec. 2013, pp. 203-210.
Singh, S. et al., "Bio-control activity of Purpureocillium lilacinum strains in managing root-knot disease of tomato caused by Meloidogyne incognita," Biocontrol Science and Technology, vol. 23, No. 12, Sep. 2013, pp. 1469-1489.

(56) References Cited

OTHER PUBLICATIONS

Abello, J., et al., "Agrobacterium-mediated transformation of the endophytic fungus Acremonium implicatum associated with Brachiaria grasses", Mycological Research, pp. 407-413, vol. 112, Pt 3.
Allard, G. et al., "SPINGO: a rapid species-classifier for microbial amplicon sequences," BMC Bioinformatics, 2015, vol. 16, No. 324, 8 pages.
Anders, S. et al., "Differential expression analysis for sequence count data," Genome Biology, 2010, vol. 11, No. 11, pp. R106.
Antony-Badu, S., et al., "Multiple Streptomyces species with distinct secondary metabolomes have identical 16S rRNA gene sequences." Scientific Reports 7.1, Sep. 2017, No. 7, 11089, pp. 1-8.
Ardakani, M.R. et al., "Absorption of N, P, K through triple inoculation of wheat (*Triticum aestivum* L.) by Azospirillum brasilense, *Streptomyces* sp., Glomus intraradices and manure application," Physiol Mol Biol Plants, 2011, vol. 17, No. 2, pp. 181-192.
Artursson, V., et al., "Interactions between arbuscular mycorrhizal fungi and bacteria and their potential for stimulating plant growth", Environmental Microbiology, vol. 8, No. 1, Jan. 1, 2006, pp. 1-10.
Azcon, R., et al., "Selective interactions between different species of mycorrhizal fungi and Rhizobium meliloti strains, and their effects on growth, N2-fixation (15N) and nutrition of Medicago sativa L.," New PhytoL., 1991, vol. 117, pp. 399-404.
Bandara, W.M.M.S., et al., "Interactions among endophytic bacteria and fungi: effects and potentials", Journal of Biosciences, Dec. 2006, vol. 31, No. 5, pp. 645-650.
Bevivino, A. et al., "Characterization of a free-living maize-rhizosphere population of Burkholderia cepacia: effect of seed treatment on disease suppression and growth promotion of maize," FEMS Microbiology Ecology, 1998, vol. 27, pp. 225-237.
Bragantia, et al.: "Identificaqao E Avaliaqao De Rizobacterias Isoladas De Raizes De Milho," Jan. 1, 2010, pp. 905-911, Retrieved from the Internet: URL:http://www.scielo.br/pdf/brag/v69n4/v69n4a17.pdf (With English Abstract).
Chen, F. et al., "Assessing Performance of Orthology Detection Strategies Applied to Eukaryotic Genomes," PLoS ONE, Apr. 2007, No. 4, pp. e383.
Ciccillo. F. et al., "Effects of two different application methods of *Burkholderia ambifaria* MCI 7 on plant growth and rhizospheric bacterial diversity," Environmental Microbiology, 2002, vol. 4, No. 4, pp. 238-245.
Cole, J.R. et al., "Ribosomal Database Project: data and tools for high throughput rRNA analysis," Nucleic Acids Research, 2014, vol. 42, pp. D633-D642.
Compant, S., et al., "Endophytes of Grapevines Flowers, Berries, and Seeds: Identification of Cultivable Bacteria, Comparison with Other Plant Parts, and Visualization of Niches of Colonization," Microbial Ecology, 2011, pp. 188-197, vol. 62.
De Santi, M. et al., "A combined morphologic and molecular approach for characterizing fungal microflora from a traditional Italian cheese (Fossa cheese)." Inter. Dairy J., 2010, vol. 10, No. 7, pp. 465-471.
De Medeiros, L., et al., "Evaluation of Herbicidal Potential of Depsides from Cladosporium uredinicola an Endophytic Fungus found in Guava Fruit," J. Braz. Chem. Soc., 2012, vol. 23, No. 8, p. 1551-1557.
Deshpande, V. et al., "Fungal identification using a Bayesian classifier and the Warcup training set of internal transcribed spacer sequences," Mycologia, 2016, vol. 108, No. 1, pp. 1-5.
Eberhardt, C. et al., "Proteomic Analysis of Kveim Reagent Identifies Targets of Cellular Immunity in Sarcoidosis," PLOS One, Jan. 23, 2017, vol. 12, No. 1, pp. 1-16.
Edgar, R.C., "UNOISE2: Improved Error-Correction for Illumina 16Sand ITS Amplicon Sequncing," BioRxiv, 2016, No. 081257, 21 pages.
Enright, A.J. et al., "An efficient algorithm for large-scale detection of protein families," Nucleic Acids Research, 2002, vol. 30, No. 7, pp. 1575-1584.

Enright, A.J. et al., "Protein families and TRIBES in genome sequence space," Nucleic Acids Research, 2003, vol. 31, No. 15, pp. 4632-4638.
Estrada, P. et al., "A N2-fixing endophytic *Burkholderia* sp. Associated with maize plants cultivated in Mexico," Canadian Journal of Microbiology, 2002, vol. 48, No. 4, pp. 285-294.
Fierer, N., et al., "Cross-Biome Metagenomic Analyses of Soil Microbial Communities and Their Functional Attributes," Proc Natl Acad Sci USA, 2012, pp. 21390-21395, vol. 109, No. 52.
Fox, G., et al., "How close is close: 16S rRNA sequence identity may not be sufficient to guarantee species identity." International Journal of Systematic and Evolutionary Microbiology 42.1, 1992, pp. 166-170.
Friedman, J. et al., "Regularization Path for Generalized Linear Models via Coordinate Descent," Journal of Statistical Software, 2010, vol. 33, No. 1, pp. 1-22.
NCBI GenBank: Accession No. JX880250.1, "Enterobacteriaceae bacterium Clerol 16S ribosomal RNA gene, partial sequence," NIH, Jun. 24, 2015, 2 Pages, can be retreived at <URL:https://www.ncbi.nlm.nih.gov/nucleotide/JX880250.1?report=genbank&logS=nuclalign&blast_rank=80 &RID=KWUPBV08015>.
NCBI, GenBank Accession No. XP_002568042, Aug. 14, 2009, 4 Pages, Berg, V.D., et al., "Genome sequencing and analysis of the filamentous fungus," Nat. Biotechnol. 26 (10), 1161-1168 (2008).
Goudjal, Y., et al., "Biocontrol of Rhizoctonia solanidamping-off and promotion of tomato plant growth by endophytic actinomycetes isolated from native plants of Algerian Sahara", Microbiological Research, 2014, vol. 169, No. 1, pp. 59-65.
Guo, X., et al., "Red Soils Harbor Diverse Culturable Actinomycetes That Are Promising Sources of Novel Secondary Metabolites", Applied and Environmental Microbiology, Feb. 27, 2015, vol. 81, No. 9, pp. 3086-3103.
Hain, T., et al., "Chitinolytic transgenes from *Streptomyces albidoflavus* as phytochemicals defences against herbivorous insects, use in transgenic plants and effect in plant development", International Journal of Systematic Bacteriology, Jan. 1997, vol. 47, No. 1, pp. 202-206.
Hanshew, A., et al., "Characterization of Actinobacteria Associated with Three Ant-Plant Mutualisms", Microbial Ecology, August, 6, 2017, vol. 69, No. 1, pp. 192-203.
Hardoim, P. R., et al., "Assessment of Rice Root Endophytes and Their Potential for Plant Growth Promotion," In: Hardoim, P.R., Bacterial Endophytes of Rice—Their Diversity, Characteristics and Perspectives, Groningen, 2011, pp. 77-100.
Hjort, K., et al., "Chitinase genes revealed and compared in bacterial isolates, DNA extracts and a metagenomic library from a phytopathogen-suppressive soil", FEMS Microbiology Ecology, Feb. 2010, vol. 71, No. 2, pp. 197-207.
Hubbard, M., et al., 2011. "Agricultural Potential of Fungal Endophytes of Grasses, Cereals and Wheat," In: Wheat: Genetics, Crops and Food Production. Nova Science Publishers Hauppauge, NY, USA. pp. 333-345.
Kanbar, A., et al., "Relationship between Root and Yield Morphological Characters in Rainfed Low Land Rice (*Oryza sativa* L.)," Cereal Research Communications, 2009, vol. 37, No. 2, pp. 261-268.
Kang, B. H., et al., "Members of the Arabidopsis Dynamin-Like Gene Family, ADL1, are Essential for Plant Cytokinesis and Polarized Cell Growth," Plant Cell, 2003, pp. 899-913, vol. 15.
Koljalg. U. et al., "Towards a unified paradigm for sequence-based identification of fungi," Molecular Ecology, 2013, vol. 22, pp. 5271-5277.
Kozich, J.J. et al., "Development of a Dual-Index Sequencing Strategy and Curation Pipeline for Analyzing Amplicon Sequence Data on the MiSeq Illumina Sequencing Platform," Applied and Environmental Microbiology, Sep. 2013, vol. 79, No. 17, pp. 5112-5120.
Langille, M.G.I. et al., "Predictive functional profiling of microbial communities using 16S rRNA marker gene sequences," Nature Biotechnology, 2013, vol. 31, No. 9, pp. 814-821.
Li, M., et al., "ATP Modulates the Growth of Specific Microbial Strains", Current Microbiology, May 30, 2010, vol. 62, No. 1, pp. 84-89.

(56) References Cited

OTHER PUBLICATIONS

Li, W et al., "Ultrafast clustering algorithms for metagenomic sequence analysis," Briefings in Bioinformatics, Nov. 1, 2012, vol. 13, No. 6., pp. 656-668.
McMurdie, P.J. et al., "Waste Not, Want Not: Why Rarefying Microbiome Data Is Inadmissible," PLOS Computational Biology, 2014, vol. 10, No. 4, pp. e1003531.
Needleman, S.B. et al., "A General Method Applicable to the Search for Similarities in the Amino Acid Sequence of Two Proteins," Journal of Molecular Biology, 1970, vol. 28, No. 3, pp. 443-453.
Ogbo, F., et al., "Some Characteristics of a Plant Growth Promoting iEnterobacter/isp. Isolated from the Roots of Maize", Advances in Microbiology, Jan. 1, 2012, vol. 02, No. 03, pp. 368-374.
Partida-Martinez, L.P., et al., "Endosymbiont-Dependent Host Reproduction Maintains Bacterial-Fungal Mutualism", Current Biology, May 1, 2007, vol. 17, No. 9, pp. 773-777.
Quast, C. et al., "The SILVA ribosomal RNA gene database project: improved data processing and web-based tools," Nucleic Acids Research, 2013, vol. 41, pp. D590-D596.
Rideout, J.R. et al., "Subsampled open-reference clustering creates consistent, comprehensive OTU definitions and scales to billions of sequences," PeerJ, 2014, 2:e545.
Roth, A.C. J. et al., "Algorithm of OMA for large-scale orthology inference," BMC Bioinformatics, 2008, vol. 9, p. 518.
Sarkar, S., et al., "New report of additional enterobacterial species causing wilt in West Bengal, India," Canadian Journal of Microbiology, 2015, vol. 61, No. 7, pp. 477-486.
NCBI, GenBank Accession No. KX641980.1, Jul. 29, 2017, Scott, M., et al., "*Dothideomycetes* sp. isolate FT14-6 internal transcribed spacer 1, partial sequence; 5.8S ribosomal RNA gene and internal transcribed spacer 2, complete sequence; and large subunit ribosomal RNA gene, partial sequence," 2 Pages.
"Sequence Alignment of JQ047949 with Instant SEQ ID No. 2," Search conducted on Jan. 2, 2019. 2 pages.
Sharma et al., "Detection and identification of bacteria intimately associated with fungi of the order Sebacinales", Cellular Microbiology, Aug. 5, 2008, pp. 2235-2246, vol. 10, No. 11.
Sharma, V.K. et al., "Enhancement of verticillium wilt resistance in tomato transplants by in vitro co-culture of seedlings with a plant growth promoting rhizobacterium (*Pseudomonas* sp. Strain PsJN)," Canadian Journal of Microbiology, Jun. 1998, vol. 44, No. 6, pp. 528-536.
Shenoy, B.D. et al., "Impact of DNA sequence-data on the taxonomy of anamorphic fungi," Fungal Diversity, 2007, vol. 26, No. 10, pp. 1-54.
Shibuya, H. et al., "Transformation of Cinchona Alkaloids into 1-N-Oxide Derivatives by *Endophytic Xylaria* sp. Isolated from Chinchona pubescens," Chern Pharm Bull, 2003, vol. 41, No. 1, pp. 71-74.
Smith, T.F. et al., "Identification of Common Molecular Subsequences," Journal of Molecular Biology, 1981, vol. 147, pp. 195-197.
Xu, M., et al., "Bacterial Community Compositions of Tomato (*Lycopersicum esculentum* Mill.) Seeds and Plant Growth Promoting Activity of ACC Deaminase Producing Bacillus subtilis (HYT-12-1) on Tomato Seedlings," World J Microbiol Biotechnol., 2014, pp. 835-845, vol. 30.
Yashiro et al., "Effect of Streptomycin Treatment on Bacterial Community Structure in the Apple Phyllosphere," PLOS One, May 21, 2012, vol. 7, No. 5, 10 pages.
Zhang, Y., et al., "BcGs1, a glycoprotein from Botrytis cinerea, elicits defence response and improves disease resistance in host plants," Biochemical and Biophysical Research Communications, 2015, vol. 457, No. 4, pp. 627-634.
PCT Invitation to Pay Additional Fees, PCT Application No. PCT/CA2013/000091, Mar. 27, 2013, 2 Pages.
PCT International Search Report and Written Opinion for PCT/CA2013/000091, dated Sep. 20, 2013, 17 Pages.
PCT International Search Report and Written Opinion for PCT/EP2013/062976, dated Dec. 22, 2014, 9 Pages.
PCT International Search Report, Application No. PCT/US2014/044427, dated Dec. 3, 2014, 9 Pages.
PCT International Search Report and Written Opinion, Application No. PCT/US2014/054160, dated Dec. 9, 2014, 21 Pages.
PCT Invitation to Pay Additional Fees, PCT Application No. PCT/US2014/064411, Feb. 5, 2015, 2 Pages.
PCT International Search Report and Written Opinion, International Application No. PCT/US2014/064411, dated Mar. 27, 2015, 15 Pages.
PCT Invitation to Pay Additional Fees, PCT Application No. PCT/US2014/072399, Apr. 14, 2015, 2 Pages.
PCT International Search Report and Written Opinion, International Application No. PCT/US2014/072399, dated Jun. 26, 2015, 22 Pages.
PCT Invitation to Pay Additional Fees, PCT Application No. PCT/US2014/072400, Apr. 16, 2015, 6 Pages.
PCT International Search Report and Written Opinion, Application No. PCT/US2014/072400, dated Jul. 8, 2015, 38 Pages.
PCT International Search Report and Written Opinion, Application No. PCT/AU2014/000360, dated Aug. 5, 2015, 12 Pages.
PCT Invitation to Pay Additional Fees, PCT Application No. PCT/US2015/038110, Sep. 22, 2015, 8 Pages.
PCT Invitation to Pay Additional Fees, PCT Application No. PCT/US2015/038187, Oct. 14, 2015, 5 Pages.
PCT International Search Report and Written Opinion, PCT Application No. PCT/US2015/038110, dated Dec. 11, 2015, 36 Pages.
PCT International Search Report and Written Opinion, PCT Application No. PCT/US2015/038187, dated Jan. 22, 2016, 36 Pages.
PCT Invitation to Pay Additional Fees, PCT Application No. PCT/US2015/068206, Apr. 12, 2016, 5 Pages.
PCT International Search Report and Written Opinion, PCT Application No. PCT/US2015/068206, dated Jun. 27, 2016, 20 Pages.
PCT International Search Report and Written Opinion, PCT Application No. PCT/US2016/030292, dated Aug. 12, 2016, 20 Pages.
PCT International Preliminary Report on Patentability, PCT Application No. PCT/US2016/030292, dated Aug. 2, 2017, 23 Pages.
PCT International Search Report and Written Opinion, PCT Application No. PCT/US2016/030293, dated Aug. 11, 2016, 23 Pages.
PCT International Search Report and Written Opinion, PCT Application No. PCT/US2016/036504, dated Nov. 4, 2016, 18 Pages.
PCT International Search Report and Written Opinion, PCT Application No. PCT/US2016/039191, dated Nov. 29, 2016, 20 Pages.
PCT International Search Report and Written Opinion, PCT Application No. PCT/US2016/068144, dated May 18, 2017, 30 Pages.
PCT Invitation to Pay Additional Fees, PCT Application No. PCT/US2017/064351, Feb. 9, 2018, 18 Pages.
PCT International Search Report and Written Opinion, PCT Application No. PCT/US2017/064351, dated Apr. 9, 2018, 25 Pages.
PCT Invitation to Pay Additional Fees, PCT Application No. PCT/US2017/064361, Mar. 7, 2018, 18 Pages.
PCT Invitation to Pay Additional Fees, PCT Application No. PCT/US2017/064292, Mar. 5, 2018, 15 Pages.
PCT International Search Report and Written Opinion, PCT Application No. PCT/USS2017/068255, dated Mar. 19, 2018, 14 Pages.
Canadian Patent Office, Office Action, Canadian Patent Application No. CA 2,953,466, dated Dec. 11, 2017, 7 Pages.
Canadian Patent Office, Office Action, Canadian Patent Application No. 2,916,678, dated Feb. 8, 2017, 8 Pages.
Canadian Patent Office, Office Action, Canadian Patent Application No. 2,935,218, dated Jun. 13, 2017, 5 Pages.
Canadian Patent Office, Office Action, Canadian Patent Application No. 2,935,218, dated May 8, 2018, 5 Pages.
Canadian Patent Office, Office Action, Canadian Patent Application No. CA 2,953,697, dated Oct. 12, 2017, 6 Pages.
Canadian Patent Office, Office Action, Canadian Patent Application No. CA 2,952,057, dated Oct. 12, 2017, 4 Pages.
Canadian Patent Office, Office Action, Canadian Patent Application No. CA 2,929,487, dated Dec. 7, 2017, 4 Pages.
Chinese Patent Office, Office Action, Chinese Patent Application No. 201480072142.7, dated Apr. 25, 2017, 14 Pages (with English translation).

(56) References Cited

OTHER PUBLICATIONS

Chinese Patent Office, 2nd Office Action for Chinese Patent Application No. CN 201480072142.7, dated Oct. 30, 2017, 13 Pages, (with English translation).
European Patent Office, Supplementary Partial European Search Report, European Patent Application No. 13874703.5, dated Jun. 21, 2016, 3 Pages.
European Patent Office, Supplementary European Search Report, European Patent Application No. 13874703.5, dated Oct. 21, 2016, 16 Pages.
European Patent Office, Communication Pursuant to Article 94(3) EPC for European Patent Application No. 13874703.5, dated Jan. 5, 2018, 4 Pages.
European Patent Office, Supplementary European Search Report, European Patent Application No. 14860187.5, dated May 24, 2017, 9 Pages.
European Patent Office, Supplementary European Search Report, European Patent Application No. 14874589.6, dated Jul. 11, 2017, 9 Pages.
European Patent Office, Communication Pursuant to Article 94(3) EPC for European Patent Application No. EP 14748326.7, dated Feb. 15, 2018, 7 Pages.
European Patent Office, Examination Report, European Patent Application No. 14748326.7, dated Jul. 19, 2017, 4 Pages.
European Patent Office, Examination Report for European Patent Application No. EP 14777213.1, dated Oct. 20, 2017, 12 Pages.
European Patent Office, Supplementary European Search Report, European Patent Application No. EP 15809264.3, dated Dec. 4, 2017, 16 Pages.
European Patent Office, Communication Pursuant to Article 94(3) EPC for European Patent Application No. 15810847.2, dated Nov. 17, 2017, 17 Pages.
European Patent Office, Supplementary European Search Report for European Patent Application No. 15810847.2, dated Feb. 28, 2018, 19 Pages.
European Patent Office, Supplementary European Search Report, European Patent Application No. EP 15812324.0, dated Nov. 2, 2017, 19 Pages.
European Patent Office, Extended European Search Report, European Patent Application No. EP 15812324.0, dated Feb. 21, 2018, 23 Pages.
European Patent Office, Extended European Search Report, European Patent Application No. EP 15809264.3, dated Mar. 12, 2018, 14 Pages.
Intellectual Property Australia, Examination Report for Australian Patent Application No. 2016202480, dated Apr. 28, 2016, 2 Pages.
Intellectual Property Australia, Examination Report for Australian Patent Application No. 2014346664, dated Nov. 24, 2016, 3 Pages.
Intellectual Property Australia, Examination Report for Australian Patent Application No. 2014315191, dated Jul. 15, 2017, 6 Pages.
Intellectual Property Australia, Examination Report for Australian Patent Application No. 2015279600, dated Jul. 21, 2017, 7 Pages.
Intellectual Property Australia, Examination Report for Australian Patent Application No. 2015278238, dated Jul. 24, 2017, 3 Pages.
Intellectual Property Australia, Examination Report No. 1 for Australian Patent Application No. AU 2017254880, dated Nov. 15, 2017, 2 Pages.
Intellectual Property Australia, Examination Report No. 1 for Australian Patent Application No. AU 2017201009, dated Apr. 4, 2018, 3 Pages.
Intellectual Property Australia, Examination Report No. 1 for Australian Patent Application No. AU 2017210482, dated May 15, 2018, 4 Pages.
New Zealand Intellectual Property Office, First Examination Report, New Zealand Patent Application No. 715728, dated May 10, 2016, 4 Pages.
New Zealand Intellectual Property Office, First Examination Report, New Zealand Patent Application No. 715728, dated Dec. 5, 2016, 3 Pages.
New Zealand Intellectual Property Office, First Examination Report, New Zealand Patent Application No. 727449, dated Jun. 8, 2017, 7 Pages.
New Zealand Intellectual Property Office, First Examination Report, New Zealand Patent Application No. 726116, dated Jun. 29, 2017, 2 Pages.
New Zealand Intellectual Property Office, First Examination Report, New Zealand Patent Application No. 726116, dated Sep. 26, 2017, 5 Pages.
New Zealand Intellectual Property Office, Further Examination Report, New Zealand Patent Application No. 726116, dated Feb. 27, 2018, 6 Pages.
New Zealand Intellectual Property Office, First Examination Report, New Zealand Patent Application No. 728495, dated Jul. 12, 2017, 5 Pages.
New Zealand Intellectual Property Office, First Examination Report for New Zealand Patent Application No. NZ 728483, dated Dec. 8, 2017, 2 Pages.
Russian Patent Office, Office Action for Russian Patent Application No. RU 2017127214, dated Nov. 22, 2017, 4 Pages, (with English translation).
Russian Patent Office, Office Action for Russian Patent Application No. RU 2015137613, dated Jun. 7, 2017, 14 Pages (with English translation).
Ukraine Patent Office, Office Action for Ukrainian Patent Application No. a201508515, dated May 19, 2017, 14 Pages (with English translation).
Ukraine Patent Office, Office Action for Ukrainian Patent Application No. a201508515, dated Feb. 20, 2018, 9 Pages (with English translation).
Office Action for Israel Patent Application No. IL 255682, dated Mar. 15, 2018, 2 Pages (Translation).
Office Action for Israel Patent Application No. IL 255684, dated Mar. 19, 2018, 2 Pages (Translation).
Office Action for Israel Patent Application No. IL 255685, dated Mar. 20, 2018, 2 Pages (Translation).
Office Action for Israel Patent Application No. IL 255688, dated Mar. 22, 2018, 2 Pages (Translation).
Office Action for Israel Patent Application No. IL 245385, dated Mar. 23, 2018, 3 Pages (With Concise Explanation of Relevance).
Abarenkov, K., et al., "PlutoF—A Web Based Workbench for Ecological and Taxonomic Research, with an Online Implementation for Fungal ITS Sequences," Evol Bioinform Online, 2010, pp. 189-196, vol. 6.
Abarenkov, K., et al., "The UNITE Database for Molecular Identification of Fungi—Recent Updates and Future Perspectives," New Phytol., 2010, pp. 281-285, vol. 186.
Abdellatif, L., et al., "Endophytic hyphal compartmentalization is required for successful symbiotic Ascomycota association with root cells," Mycological Research, 2009, pp. 782-791, vol. 113.
Abdellatif, L., et al., "Characterization of virulence and PCR-DGGE profiles of Fusarium avenaceum from western Canadian Prairie Ecozone of Saskatchewan,"Canadian Journal of Plant Pathology, 2010, pp. 468-480.
Abdou, R., et al., "Botryorhodines A-D, antifungal and cytotoxic depsidones from Botryosphaeria rhodina, an endophyte of the medicinal plant Bidens pilosa," Phytochemistry, 2010, vol. 71, pp. 110-116.
Abou-Shanab, R. A., et al.: "Characterization of Ni-resistant bacteria in the rhizosphere of the hyperaccumulator Alyssum murale by 16S rRNA gene sequence analysis", World Journal of Microbiology and Biotechnology, vol. 26, No. 1, Aug. 15, 2009, pp. 101-108.
Adhikari, M., et al., "A New Record of Pseudeurotium bakeri from Crop Field Soil in Korea," The Korean Journal of Mycology, 2016, pp. 145-149, vol. 44.
Ahmad, F., et al., "Screening of Free-Living Rhizospheric Bacteria for Their Multiple Plant Growth Promoting Activities," Microbiol Res., 2008, pp. 173-181, vol. 163.
Alvarez-Perez, S., et al., "Zooming-in on floral nectar: a first exploration of nectar-associated bacteria in wild plant communities," FEMS Microbiol. Ecol., 2012, vol. 80, No. 3, pp. 591-602.

(56) References Cited

OTHER PUBLICATIONS

Amann, R., et al., "The Identification of Microorganisms by Fluorescence in Situ Hybridisation," Curr Opin Biotechnol., 2001, pp. 231-236, vol. 12.

Amatuzzi, R.F., et al., "UNIVERS1DADE Federal Do Parana," Jan. 1, 2014, 52 Pages. (With English Abstract).

Amatuzzi, R.F., et al., "Potential of endophytic fungi as biocontrol agents of Duponchelia fovealis (Zeller) (Lepidoptera:Crambidae)," Brazilian Journal of Biology, Nov. 9, 2017, 7 Pages.

Apel, K., et al., "Reactive Oxygen Species: Metabolism, Oxidative Stress, and Signal Transduction," Annu Rev Plant Biol., 2004, pp. 373-399, vol. 55.

Arendt, K. R., et al., "Isolation of endohyphal bacteria from foliar Ascomycota and in vitro establishment of their symbiotic associations," Appl. Environ. Microbiol., 2016, pp. 2943-2949, vol. 82, No. 10.

Ashrafuzzaman, M., et al., "Efficiency of plant growth-promoting rhizobacteria (PGPR) for the enhancement of rice growth," African Journal of Biotechnology, 2009, pp. 1247-1252, vol. 8, No. 7.

Aveskamp, M., et al., "DNA phylogeny reveals polyphyly of Phoma section Peyronellaea and multiple taxonomic novelties," Mycologia, 2009, vol. 101, No. 3, pp. 363-382.

Bacon, C. W., et al., "Isolation, In Planta Detection, and Uses of Endophytic Bacteria for Plant Protection," Manual of Environmental Microbiology, 2007, pp. 638-647.

Baker, K. F., et al., "Dynamics of Seed Transmission of Plant Pathogens," Annu Rev Phytopathol., 1966, pp. 311-334,vol. 4.

Baltruschat, H., et al., "Salt tolerance of barley induced by the root endophyte Piriformospora indica is associated with a strong increase in antioxidants," New Phytologist., 2008, pp. 501-510, vol. 180.

Bensch, K., et al., "Species and ecological diversity within the Cladosporium cladosporioides complex (Davidiellaceae, Capnodiales)," Studies in Mycology, 2010, pp. 1-94, vol. 67.

Bethlenfalvay, G., et al., "Mycorrhizal fungi effects on nutrient composition and yield of soybean seeds", Journal of Plant Nutrition, vol. 20, No. 4-5, Apr. 1, 1997, pp. 581-591.

Block, C. C., et al., "Seed Transmission of Pantoea stewartii in Field and Sweet Corn," Plant Disease, 1998, pp. 775-780, vol. 82.

Brinkmeyer, R., et al., "Uncultured Bacterium Clone ARKMP-100 16S Ribosomal RNA Gene, Partial Sequence," NCBI GenBank Accession No. AF468334, Submitted Jan. 14, 2002.

Brodie, E.L., et al., "Uncultured Bacterium Clone BANW722 16S Ribosomal RNA Gene, Partial Sequence," NCBI GenBank Accession No. DQ264636, Submitted Oct. 25, 2005.

Bulgarelli, D., et al., "Structure and Functions of the Bacterial Microbiota of Plants," Annu Rev Plant Biol., 2013, pp. 807-838, vol. 64.

Buttner, D., et al., "Regulation and secretion of Xanthomonas virulence factors," FEMS Microbiology Reviews, 2010, pp. 107-133, vol. 34, No. 2.

Caporaso, J.G., et al., "Ultra-High-Throughput Microbial Community Analysis on the Illumina HiSeq and MiSeq Platforms," ISME J., 2012, pp. 1621-1624, vol. 6.

Castillo, D., et al., "Fungal Entomopathogenic Endophytes: Negative Effects on Cotton Aphid Reproduction in Greenhouse and Field Conditions," Power Point Presentation dated Mar. 23, 2013.

Castillo, D., et al., "Fungal Endophytes: Plant Protective Agents Against Herbivores," Power Point Presentation dated Aug. 4, 2013.

Cavalier-Smith, T., "A Revised Six-Kingdom System of Life," Biol Rev Camb Philos Soc., 1998, pp. 203-266, vol. 73.

Cha, C., et al., "Production of Acyl-Homoserine Lactone Quorum-Sensing Signals by Gram-Negative Plant Associated Bacteria," Mol Plant Microbe Interact., 1998, pp. 1119-1129, vol. 11, No. 11.

Chagas, F., et al., "A Mixed Culture of Endophytic Fungi Increases Production of Antifungal Polyketides," J. Chem Ecol., Oct. 2013, pp. 1335-1342, vol. 39.

Chernin, L. S., et al., "Chitinolytic Activity in Chromobacterium violaceum: Substrate Analysis and Regulation by Quorum Sensing," J Bacteriol., 1998, pp. 4435-4441, vol. 180, No. 17.

Clark, E. M., et al., "Improved Histochemical Techniques forthe Detection of Acremonium coenophilum in Tall Fescue and Methods of in vitro Culture of the Fungus," J. Microbiol Methods, 1983, pp. 149-155, vol. 1.

Clarridge, J., "Impact of 16S rRNA Gene Sequence Analysis for Identification of Bacteria on Clinical Microbiology and Infectious Diseases," Clinical Microbiology Reviews, Oct. 2004, pp. 840-862, vol. 17, No. 4.

Clay, K., "Effects of fungal endophytes on the seed and seedling biology of Lolium perenne and Festuca arundinacea " Oecologia, 1987, pp. 358-362, vol. 73.

Clough, S. J., et al., "Floral Dip: A Simplified Method for Agrobacterium-mediated Transformation of *Arabidopsis thaliana*," Plant J., 1998, pp. 735-743, vol. 16, No. 6.

Coombs, J. T., et al., "Isolation and Identification of Actinobacteria from Surface-Sterilized Wheat Roots," Applied and Environmental Microbiology, 2003, pp. 5603-5608, vol. 69, No. 9.

Conn, V. M., "Effect of Microbial Inoculants on the Indigenous Actinobacterial Endophyte Population in the Roots of Wheats as Determined by Terminal Restriction Fragment Length Polymorphism," Applied and Environmental Microbiology, 2004, pp. 6407-6413, vol. 70, No. 11.

Cottyn, B., et al., "Phenotypic and genetic diversity of rice seed-associated bacteria and their Yole in pathogenicity and biological control," Journal of Applied Microbiology, 2009, pp. 885-897, vol. 107.

Cox, C. D., "Deferration of Laboratory Media and Assays for Ferric and Ferrous Ions," Methods Enzymol., 1994, pp. 315-329, vol. 235.

Craine, J. M., et al., "Global Diversity of Drought Tolerance and Grassland Climate-Change Resilience," Nature Climate Change, 2013, pp. 63-67, vol. 3.

Dalal, J.M., et al., "Utilization of Endophytic Microbes for Induction of Systemic Resistance (ISR) in Soybean (*Glycine max* (L) Merril) Against Challenge Inoculation with R. solani," Journal of Applied Science and Research, 2014, pp. 70-84, vol. 2, No. 5.

Danhorn, T., et al., "Biofilm Formation by Plant-Associated Bacteria," Annu Rev Microbiol., 2007, pp. 401-422, vol. 61.

Daniels, R., et al., "Quorum Signal Molecules as Biosurfactants Affecting Swarming in Rhizobium etli," PNAS, 2006, pp. 14965-14970, vol. 103, No. 40.

Darsonval, A., et al., "Adhesion and Fitness in the Bean Phyllosphere and Transmission to Seed of *Xanthomonas fuscans* subsp. *fuscans*," Molecular Plant-Microbe Interactions, 2009, pp. 747-757, vol. 22, No. 6.

Darsonval, A., et al., "The Type III Secretion System of *Xanthomonas fuscans* subsp. *fuscans* is involved in the Phyllosphere Colonization Process and in Transmission to Seeds of Susceptible Beans," Applied and Envioronmental Mirobiology, 2008, pp. 2669-2678, vol. 74, No. 9.

DBGET, "Orthology: K14454," 2005, 2 pages, can be retrieved at <URL:http://www.genome.jp/dbget-bin/www_bget?ko:K14454>.

De Freitas, J. R., et al., "Phosphate-Solubilizing Rhizobacteria Enhance the Growth and Yield but not Phosphorus Uptake of Canola (*Brassica napus* L.)," Biol Fertil Soils, 1997, pp. 358-364, vol. 24.

De Lima Favaro, L. C., et al., "Epicoccum nigrum P16, a Sugarcane Endophyte, Produces Antifungal Compounds and Induces Root Growth," PLoS One, 2012, pp. 1-10, vol. 7, No. 6.

De Melo Pereira, G. V., et al. "A Multiphasic Approach forthe Identification of Endophytic Bacterial in Strawberry Fruit and their Potential for Plant Growth Promotion," Microbial Ecology, 2012, pp. 405-417, vol. 63, No. 2.

De Souza, J. J., et al., "Terpenoids from Endophytic Fungi," Molecules, 2011, pp. 10604-10618, vol. 16, No. 12.

Dennis, C., et al., "Antagonistic Properties of Species Groups of Trichoderma," Trans Brit Mycol Soc, 1971, pp. 25-39, vol. 57, No. 1.

Desiro, A., et al., "Detection of a novel intracellular microbiome hosted in arbuscular mycorrhizal fungi," ISME Journal, 2014, pp. 257-270, vol. 8.

Djordjevic, D., et al., "Microtiter Plate Assay for Assessment of Listeria monocytogenes Biofilm Formation," Anni Environ Microbiol., 2002, pp. 2950-2958, vol. 68, No. 6.

(56) References Cited

OTHER PUBLICATIONS

Don, R. H., et al., "Properties of Six Pesticide Degradation Plasmids Isolated From Alcaligenes Paradoxus and Alcaligenes eutrophus," J Bacteriol., 1981, pp. 681-686, vol. 145, No. 2.

Dunbar, J, et al., "Uncultured Bacterium Clone NT42a2_20488 16S Ribosomal RNA Gene, Partial Sequence," NCBI GenBank Accession No. JQ378705. Submitted Novembers, 2012, 1 Page.

Eberhard, A., et al., "Structural Identification of Autoinducer of Photobacterium fischeri Luciferase," Biochem., 1981, pp. 2444-2449, vol. 20.

Edgar, R. C., "Search and Clustering Orders of Magnitude Faster than BLAST," Bioinformatics, 2010, pp. 2460-2461, vol. 26, No. 19.

Edgar, R. C., "Uparse: Highly Accurate OTU Sequences From Microbial Amplicon Reads," Nat Methods, 2013, pp. 996-998, vol. 10, No. 10.

Ek-Ramos, M. J., "Ecology, Distribution and Benefits of Fungal Endophytes Isolated from Cultivated Cotton (*Gossypium hirsutum*) in Texas," Power Point Presentation dated Nov. 7, 2012, 27 Pages.

Ek-Ramos, M. J., et al., "Spatial and Temporal Variation in Fungal Endophyte Communities Isolated from Cultivated Cotton (*Gossypium hirsutum*)," PLoS ONE, 2013, vol. 8, No. 6, 13 Pages, e66049.

Ek-Ramos, M. J., et al., "Spatial and Temporal Variation in Fungal Endophyte Communities Isolated from Cultivated Cotton (*Gossypium hirsutum*)," Power Point Presentation dated Jan. 7, 2013, 18 Pages.

El-Shanshoury, A. R., "Growth Promotion of Wheat Seedlings by *Streptomyces atroolivaceus*," Journal of Agronomy and Crop Science, 1989, pp. 109-114, vol. 163.

Emerson, D., et al., Identifying and Characterizing Bacteria in an Era of Genomics and Proteomics, BioScience, 2008, pp. 925-936, vol. 58, No. 10.

Endre, G., et al., "A Receptor Kinase Gene Regulating Symbiotic Nodule Development," Nature, 2002, pp. 962-966, vol. 417.

Faria, D. C., et al., "Endophytic Bacteria Isolated from Orchid and Their Potential to Promote Plant Growth," World J Microbiol Biotechnol., 2013, pp. 217-221, vol. 29.

Ferrando, L., et al., "Molecular and Culture-Dependent Analyses Revealed Similarities in the Endophytic Bacterial Community Composition of Leaves from Three Rice (*Oryza sativa*) Varieties," FEMS Microbiol Ecol., 2012, pp. 696-708, vol. 80.

Fiehn, O., et al., "Metabolite Profiling for Plant Functional Genomics," Nature Biotechnol., 2000, pp. 1157-1161, vol. 8.

Fincher, G. B., "Molecular and Cellular Biology Associated with Endosperm Mobilization in Germinating Cereal Grains," Annu Rev Plant Physiol Plant Mol Biol., 1989, pp. 305-346, vol. 40.

Fisher, P. J., et al., "Fungal saprobes and pathogens as endophytes office (*Oryza sativa* L.)," New Phytol., 1992, pp. 137-143, vol. 120.

Fisher, P. R., et al., "Isolation and Characterization of the Pesticide-Degrading Plasmid pJP1 from Alcaligenes paradoxus," J Bacteriol., 1978, pp. 798-804, vol. 135, No. 3.

Franco, C., et al., "Actinobacterial Endophytes for Improved Crop Performance," Australasian Plant Pathology, 2007, pp. 524-531, vol. 36.

Fulthorpe, R. R., et al., "Distantly Sampled Soils Carry Few Species in Common," Isme J., 2008, pp. 901-910, vol. 2.

Gantner, S., et al., "Novel Primers for 16S rRNA-based Archaeal Community Analyses in Environmental Samples," J Microbiol Methods, 2011, pp. 12-18, vol. 84.

Gao, Z., et al., "Quantitation of Major Human Cutaneous Bacterial and Fungal Populations," J Clin Microbiol., 2010, pp. 3575-3581, vol. 48, No. 10.

Garazzino, S., et al., "Osteomyelitis Caused by Enterobacter cancerogenus Infection following a Traumatic Injury: Case Report and Review of the Literature," J Clin Microbiol., Mar. 2005, vol. 43, No. 3, pp. 1459-1461.

Gasser, I., et al., "Ecology and Characterization of Polyhydroxyalkanoate-Producing Microorganisms on and in Plants," FEMS Microbiol Ecol., 2010, pp. 142-150, vol. 70.

Gavrish, E., et al., "*Lentzea* sp. MS6 16S Ribosomal RNA Gene, Partial Sequence," NCBI GenBank Accession No. EF599958. Submitted May 9, 2007, 1 Page.

Gebhardt, J., et al., "Characterization of a single soybean cDNA encoding cytosolic and glyoxysomal isozymes of aspartate aminostransferase," Plant Molecular Biology, 1998, pp. 99-108, vol. 37.

GenBank: AF034210.1 "Glycine max aspartate aminotransferase glyoxysomal isozyme AAT1 precursor and aspartate aminotransferase cytosolic isozyme AAT2 (AAT) mRNA, complete cds," NCBI, May 26, 1998, 2 Pages, can be retrieved at <URL:https://www.ncbi.nlm.nih.gov/nuccore/AF034210>.

GenBank: JN210900.1, "*Enterobacter* sp. WS05 16S ribosomal RNA gene, partial sequence," NCBI, Sep. 24, 2012, 1 Page, can be retrieved at <URL:https://www.ncbi.nlm.nih.gov/nuccore/jn210900>.

GenBank: NP_001237541.1, "aspartate aminotransferase glyoxysomal isozyme AAT1 precursor [Glycine max]," NCBI, Oct. 29, 2016, 2 Pages, can be retrieved at <URL:https://www.ncbi.nlm.nih.gov/protein/NP_001 237541.1>.

NCBI GenBank: CP000653.1 "*Enterobacter* sp. 638, complete genome" Jan. 28, 2014, 5 Pages, Can be retrieved at <URL:https://www.ncbi.nlm.nih.gov/nuccore/CP000653.1>.

NCBI GenBank: CP000653.1 "*Enterobacter* sp. 638, complete genome" ASM1632v1, Apr. 18, 2007, 2 Pages, Can be retrieved at <URL:https://www.ncbi.nlm.nih.gov/assembly/GCA_000016325.1 >.

NCBI GenBank: EU340965.1 "*Enterobacter* sp. 638 16S ribosomal RNA gene, partial sequence" Jan. 30, 2009, 1 Page, Can be retrieved at <URL:https://www.ncbi.nlm.nih.gov/nuccore/EU340965.1>.

NCBI GenBank: EBI accession No. EM STD:JQ759988, "*Dothideomycetes* sp. genotype 226 isolate FL0175 internal transcribed spacer 1, partial sequence; 5.8S ribosomal RNA gene and internal transcribed spacer 2, complete sequence; and 28S ribosomal RNA gene, partial sequence," May 17, 2012, 2 Pages.

NCBI GenBank: EBI accession No. EM STD:GU055658, "Uncultured Periconia clone NG R 806 18S ribosomal RNA gene, partial sequence; internal transcribed spacer 1,5.8S ribosomal RNA gene, and internal transcribed spacer 2, complete sequence; and 28S ribosomal RNA gene, partial sequence," Oct. 27, 2009, 2 Pages.

GenEmbl Database, GenEmbl Record No. KF673660, Sandberg, et al., "Fungal endophytes of aquatic macrophytes: diverse host-generalists characterized by tissue preferences and geographic structure," 2013, 35 Pages.

GenEmbl Database, GenEmbl Record No. KP991588, Huang, et al., "Pervasive effects of wildfire on foliar endophyte communities in montane forest trees," Mar. 2015, 35 Pages.

GenEmbl Database, GenEmbl Record No. JN872548, 38 Pages, Alvarez-Perez, S., et al., "Zooming-in on floral nectar: a first exploration of nectar-associated bacteria in wild plant communities," FEMS Microbiol. Ecol., 2012, vol. 80, No. 3, pp. 591-602.

GenEmbl database, GenEmbl Record No. EU 977189, Jan. 21, 2009, 4 pages, Smith, S.A., et al., "Bioactive endophytes warrant intensified exploration and conservation," PLoS One 3(8):E3052, 2008.

GenEmbl database, GenEmbl Record No. KF011597, Paenlbacillus strain No. HA 13, Aug. 26, 2013, 5 Pages, Park, H.J., et al., "Isolation and characterization of humic substances-degrading bacteria from the subarctic Alaska grasslands," J Basic Microbiol, 2013.

Database Geneseq Database accession No. BAP97938 "Pantoea dispersa strain KACC91642P 16S rDNA sequence, Seq ID 1." Aug. 15, 2013, 1 Page.

Gilmour, S. J., et al., "Overexpression of the Arabidopsis CBF3 Transcriptional Activator Mimics Multiple Biochemical Changes Associated with Cold Acclimation," Plant Physiol., 2000, pp. 1854-1865, vol. 124.

Giraldo, A., et al., "Phylogeny of Sarocladium (Hypocreales)," Persoonia, 2015, pp. 10-24, vol. 34.

Gitaitis, R., et al., "The Epidemiology and Management of Seedborne Bacterial Diseases," Annu Rev Phytopathol., 2007, pp. 371-397, vol. 45.

(56) References Cited

OTHER PUBLICATIONS

Grondona, I., et al., "TUSAL®, a commercial biocontrol formulation based on Trichoderma," Bulletin OILB/SROP, 2004, pp. 285-288, vol. 27, No. 8.
Gu, O., et al., "*Glycomyces sambucus* sp. nov., an endophytic actinomycete islolated from the stem of Sambucus adnata Wall," International Journal of Systematic and Evolutionary Microbiology, 2007, pp. 1995-1998, vol. 57.
Haake, V., et al., "Transcription Factor CBF4 is a Regulator of Drought Adaptation in *Arabidopsis,*" Plant Physiol., 2002, pp. 639-648, vol. 130.
Haas, D., et al., "R Factor Variants with Enhanced Sex Factor Activity in Pseudomonas aeruginosa," Mol Gen Genet., 1976, pp. 243-251, vol. 144.
Hahm, M-S., et al., "Biological Control and Plant Growth Promoting Capacity of Rhizobacteria and Pepper Under Greenhouse and Field Conditions," The Journal of Microbiology, The Microbiological Society of Korea, Heidelberg, Jun. 30, 2012, pp. 380-385, vol. 50, No. 3.
Hallman, J., et al., "Bacterial Endophytes in Agricultural Crops," Canadian J Microbiol., 1997, pp. 895-914, vol. 43.
Hamayun, M., et al., "Cladosporium sphaerospermum as a new plant growth-promoting endophyte from the roots of Glycine max (L.) Merr," World Journal of Microbiology and Biotechnology, Kluwer Academic Publishers, Feb. 15, 2009, pp. 627-632, vol. 25, No. 4.
Hanson, L.E., "Reduction of Verticillium Wilt Symptoms in Cotton Following Seed Treatment with Trichoderma virens," The Journal of Cotton Science, 2000, pp. 224-231, vol. 4, No. 4.
Hanson, L.E., "Reduction of Verticillium Wilt Symptoms in Cotton Following Seed Treatment with Trichoderma virens," Proceedings Beltwide Cotton Conferences, 2000, vol. 1. (Abstract), 1 Page.
Hardegree, S. P. et al., "Effect of Polyethylene Glycol Exclusion on the Water Potential of Solution-Saturated Filter Paper," Plant Physiol., 1990, pp. 462-466, vol. 92.
Hardoim, P. R., et al., "Dynamics of Seed-Borne Rice Endophytes on Early Plant Growth Stages," PLoS One, 2012, vol. 7, No. 2, 13 Pages.
Harman, G.E., et al., "Symposium: biocontrol and biotechnological methods for controlling cotton pests," Proceedings of the Beltwide Cotton Production Research Conf., 1989, Memphis, Tennessee, USA, pp. 15-20. (Abstract).
Hepler, P. K., et al., "Polarized Cell Growth in Higher Plants," Annu Rev Cell Dev Biol., 2001, pp. 159-187, vol. 17.
Hiatt, E. E., et al., "Tall Fescue Endophyte Detection: Commerical Immunoblot Test Kit Compared with Microscopic Analysis," Crop Science, 1999, pp. 796-799, vol. 39.
Hibbett, D. S., et al., "A Higher-Level Phylogenetic Classification of the Fungi," Mycol Res., 2007, pp. 509-547, vol. 111.
Hill, N. S., et al., "Endophyte Survival during Seed Storage: Endophyte-Host Interactions and Heritability," Crop Sci., 2009, pp. 1425-1430, vol. 49.
Hill N. S., et al., "Endophyte Survival during Seed Storage: Endophyte-Host Interactions and Heritability," PowerPoint, Dept. Crop Soil Sciences, University of Georgia, Nov. 16, 2012, 3 Pages.
Hinton, D. M., et al., "Enterobacter cloacae is an endophytic symbiont of corn," Mycopathologia, 1995, pp. 117-125, vol. 129.
Hoffman, M., et al., "Diverse Bacteria Inhabit Living Hyphae of Phylogenetically Diverse Fungal Endophytes," Applied and Environmental Microbiology, Jun. 2010, pp. 4063-4075, vol. 76, No. 12.
Hoffman, M., et al., "Endohyphal Bacterium Enhances Production of Indole-3-Acetic Acid by a Foliar Fungal Endophyte," PLOS One, Sep. 24, 2013, pp. 1-8, vol. 8, Issue 9, e73132.
Howell, C.R., et al., "Induction of Terpenoid Synthesis in Cotton Roots and Control of Rhizoctonia solani by Seed Treatment with Trichoderma virens," Phytopathology, 2000, pp. 248-252, vol. 90, No. 3.
Hubbard, M., et al., "Fungal Endophytes Improve Wheat Seed Germination Under Heat and Drought Stress," Botany, 2012, pp. 137-149, vol. 90.

Humann, J., et al., "Complete genome of the onion pathogen Enterobacter cloacae EcWSU1," Standard in Genomic Sciences, Dec. 31, 2011, vol. 5, No. 3, pp. 279-286.
Hung, P. Q., et al., "Isolation and Characterization of Endophytic Bacteria in Soybean (*Glycine* Sp.)," Omonrice, 2004, pp. 92-101, vol. 12.
Idris, A., et al., "Efficacy of Rhizobacteria for Growth Promotion in Sorghum Under Greenhouse Conditions and Selected Modes of Action Studies," J Agr Sci., 2009, pp. 17-30, vol. 147.
Ikeda, S., et al., "The Genotype of The Calcium/Calmodulin-Dependent Protein Kinase Gene (CCaMK) Determines Bacterial Community Diversity in Rice Roots Under Paddy and Upland Field Conditions," Applied and Environmental Microbiology, 2011, pp. 4399-4405, vol. 77, No. 13.
Imoto, K., et al., "Comprehensive Approach to Genes Involved in Cell Wall Modifications in *Arabidopsis thaliana,*" Plant Mol Biol., 2005, pp. 177-192, vol. 58.
Jalgaonwala, R., et al., "A Review on Microbial Endophytes from Plants: A Treasure Search for Biologically Active Metabolites," Global Journal of Research on Medicinal Plants & Indigenous Medicine, 2014, pp. 263-277, vol. 3, No. 6.
Janda, J. M., et al., "16S rRNA Gene Sequencing for Bacterial Identification in the Diagnostic Laboratory: Pluses, Perils, and Pitfalls," Journal of Clinical Microbiology, 2007, pp. 2761-2764, vol. 45, No. 9.
Johnston-Monje, D., et al., "Conservation and Diversity of Seed Associated Endophytes in Zea Across Boundaries of Evolution, Ethnography and Ecology," PLOS One, vol. 6, No. 6, Jun. 3, 2011, p. 20396, 22 Pages.
Johnston-Monje, D., et al., "Plant and Endophyte Relationships: Nutrient Management," Comprehensive Biotechnol., 2011, pp. 713-727, vol. 4.
Johnston-Monje, D., "Microbial Ecology of Endophytic Bacteria in Zea Species as Influenced by Plant Genotype, Seed Origin, and Soil Environment," Thesis, University of Guelph, 2011, 230 Pages.
Jones, K.L., "Fresh Isolates of Actinomycetes in which the Presence of Sporogenous Aerial Mycelia is a Fluctuating Characteristic," J Bacteriol., 1949, pp. 141-145, vol. 57, No. 2.
Jung, C., et al., "The Effects of Endohyphal Bacteria on Anti-Cancer and Anti-Malaria Metabolites of Endophytic Fungi," Honors Thesis, University of Arizona, May 2012, 15 Pages.
Kaga, H., et al., "Rice Seeds as Sources of Endophytic Bacteria," Microbes Environ., 2009, pp. 154-162, vol. 24, No. 2.
Kalns, L., et al., "The Effects of Cotton Fungal Endophytes in the Field on Arthropod Community Structure," Power Point Presentation dated Jan. 7, 2013.
Kasana, R. C., et al., "A Rapid and Easy Method forthe Detection of Microbial Cellulases on Agar Plates Using Gram's Iodine," Curr Microbiol., 2008, pp. 503-507, vol. 57.
Khan, A.L., et al., "Salinity Stress Resistance Offered by Endophytic Fungal Interaction Between Penicillium minioluteum LHL09 and Glycine max. L," J. Microbiol. Biotechnol., 2011, pp. 893-902, vol. 21, No. 9.
Kim, M., et al., "Towards a taxonomic coherence between average nucleotide identity and 16S Yrna gene sequence similarity for species demarcation of prokaryotes", Int J Systematic Evolutionary Microbial., 2014, vol. 64, pp. 346-351.
Klaubauf, S., et al., "Molecular diversity of fungal conmunities in agricultural soils from Lower Austria," Fungal Diversity, Aug. 13, 2010, pp. 65-75, vol. 44, No. 1.
Knapp, D., et al., "Inter- and intraspecific functional diversity of fungal root endophytes of semiarid sandy grasslands," Acta Microbiologica et Immunologica Hungarica, Nov. 2017, pp. 1-101, vol. 64, Issue Supplement 1.
Kruger, M., et al., "DNA-Based Species Level Detection of Glomeromycota: One PCR Primer Set for All Arbuscular Mycorrhizal Fungi," New Phvtol., 2009, pp. 212-223, vol. 183.
Kuklinsky-Sobral, J., et al., "Isolation and Characterization of Endophytic Bacteria from Soybean (*Glycine max*) Grown in Soil Treated with Glyphosate Herbicide," Plant and Soil, 2005, pp. 91-99, vol. 273.

(56) References Cited

OTHER PUBLICATIONS

Kuklinsky-Sobral, J., et al., "Isolation and characterization of soybean-associated bacteria and their potential for plant growth promotion," Environmental Microbiology, 2004, pp. 1244-1251, vol. 6, No. 12.
Kumar, S., et al., "MEGA7: Molecular Evolutionary Genetics Analysis version 7.0 for bigger datasets," Molecular Biology and Evolution, Mar. 22, 2016, vol. 33, pp. 1870-1874.
Kumar, A., et al., "Bio-control potential of *Cladosporium* sp. (MCPL-461), against a noxious weed *Parthenium hysterophorus* L.," J. Environ Biol., Mar. 2009, pp. 307-312, vol. 30, Issue 2.
Kusari, S., et al. "Chemical ecology of endophytic fungi: origins of secondary metabolites," Cell Press, Chem & Biol., 2012, pp. 792-798, vol. 19.
Labeda, D.P., et al., "Phylogenetic study of the species within the family Streptomycetaceae," Antonie van Leeuwenhoek, 2012, vol. 101, pp. 73-104, Springer.
Lanver, D., et al., "Sho1 and Msb2-Related Proteins Regulate Appressorium Development in the Smut Fungus Ustilago aydis," Plant Cell, 2010, pp. 2085-2101, vol. 22.
Laus, M. C., et al., "Role of Cellulose Fibrils and Exopolysaccharides of Rhizobium Teguminosarum in Attachment to and Infection of Vicia sativa Root Hairs," Mol Plant Microbe Interact., 2005, pp. 533-538, vol. 18, No. 6.
Le, X.H., et al., "Effects of endophytic *Streptomyces* on the lucerne (*Medicago sativa* L.) symbiosis at different levels of nitrogen," 17th Australian Nitrogen Fixation Conference 2014 Proceedings, Sep. 29, 2014, ed. Gupta, V.V.S.R., Unkovich, M. and Kaiser, B. N., ASNF, University of Adelaide, pp. 66-67.
Le, X.H., et al., "Isolation and characterisation of endophytic actinobacteria and their effect on the early growth and nodulation of lucerne (*Medicago sativa* L.)," 17th Australian Nitrogen Fixation Conference 2014 Proceedings, Sep. 29, 2014, ed. Gupta, V.V.S.R., Unkovich, M. and Kaiser, B. N., ASNF, University of Adelaide, pp. 134-136.
Lehman, S.G., "Treat Cotton Seed," Review of Applied Mycology, 1945, 24, 369, 16 Pages.
Lehman, S.G., "Treat Cotton Seed," Research and Farming III, Progr. Rept., 1945, 3, 5, 16 Pages.
Leonard, C. A., et al., "Random Mutagenesis of the Aspergillus oryzae Genome Results in Fungal Antibacterial Activity," Int J Microbiol., 2013, vol. 2013, Article ID 901697, 6 Pages.
Li, H. M., et al., "Expression of a Novel Chitinase by the Fungal Endophyte in Poa ampla," Mycologia, 2004, pp. 526-536, vol. 96, No. 3.
Li, H., et al., "Endophytes and their role in phytoremediation," Fungal Diversity, 2012, pp. 11-18, vol. 54.
Li, Q., "Agrobacterium tumefaciens Strain TA-AT-10 16S Ribosomal RNA Gene, Partial Sequence: GenBank: KF673157.1," Submitted Sep. 17, 2013.
Liu, M., et al., "A Novel Screening Method for Isolating Exopolysaccharide-Deficient Mutants," Appl Environ Microbiol., 1998, pp. 4600-4602, vol. 64, No. 11.
Liu, Y., et al., "Investigation on Diversity and Population Succession Dynamics of Endophytic Bacteria from Seeds of Maize (*Zea mays* L., Nongda108) at Different Growth Stages," Ann Microbiol., 2013, pp. 71-79, vol. 63.
Liu, D., et al., "Osmotin Overexpression in Potato Delays Development of Disease Symptoms," Proc Natl Acad Sci USA, 1994, pp. 1888-1892, vol. 91.
Liu, Y., et al., "Phylogenetic relationships among ascomycetes: evidence from an RNA polymerase II subunit," Mol. Biol. Evol. 1999. vol. 16, No. 12, pp. 1799-1808.
Liu, Y., et al., "Study on Diversity of Endophytic Bacterial Communities in Seeds of Hybrid Maize and their Parental Lines," Arch Microbiol., 2012, pp. 1001-1012, vol. 194.
Long, H. H., et al., "The Structure of the Culturable Root Bacterial Endophyte Community of Nicotiana attenuata is Organized by Soil Composition and Host Plant Ethylene Production and Perception," New Phytol., 2010, pp. 554-567, vol. 185.
Lopez-Lopez, A., et al., "Phaseolus vulgaris Seed-Borne Endophytic Community with Novel Bacterial Species such as *Rhizobium endophyticum* sp. nov.," Systematic Appl Microbiol., 2010, pp. 322-327, vol. 33.
Lorck, H., "Production of Hydrocyanic Acid by Bacteria," Physiol Plant, 1948, pp. 142-146, vol. 1.
Lugtenberg, B., et al., "Plant-Growth-Promoting Rhizobacteria," Ann. Rev. Microbiol., 2009, pp. 541-556, vol. 63.
Lundberg, D. S., et al., "Defining the Core *Arabidopsis thaliana* Root Microbiome," Nature, 2012, pp. 86-90, vol. 488, No. 7409.
Lundberg, D. S., et al., "Practical Innovations for High-Throughput Amplicon Sequencing," Nat Methods, 2013, pp. 999-1002, vol. 10, No. 10.
Ma, Y., et al., "Plant Growth Promoting Rhizobacteria and Endophytes Accelerate Phytoremediation of Metalliferous Soils," Biotechnology Advances, 2011, pp. 248-258, vol. 29.
Madi, L. et al., "Aggregation in Azospirillum brasilense Cd: Conditions and Factors Involved in Cell-to-Cell Adhesion," Plant Soil, 1989, pp. 89-98, vol. 115.
Mandyam, K., et al., "Mutualism-parasitism paradigm synthesized from results of root-endophyte models", Frontiers in Microbiology, Jan. 12, 2015, pp. 1-14, vol. 5.
Mannisto, M.K., et al., "Characterization of Psychrotolerant Heterotrophic Bacteria From Finnish Lapland," Svst Appl Microbiol., 2006, pp. 229-243, vol. 29.
Mano, H., et al., "Culturable Surface and Endophytic Bacterial Flora of the Maturing Seeds of Rice Plants (*Oryza sativa*) Cultivated in a Paddy Field," Microbes Environ., 2006, vol. 21, No. 2.
Manter, D. K., et al., "Use of the ITS Primers, ITS1F and ITS4, to Characterize Fungal Abundance and Diversity in Mixed-Template Samples by qPCR and Length Heterogeneity Analysis," J Microbiol Methods, 2007, pp. 7-14, vol. 71.
Mao, W., et al., "Seed Treatment with a Fungal or a Bacterial Antagonist for Reducing Corn Damping-off Caused by Species of Pythium and Fusarium," Plant Disease, 1997, pp. 450-454, vol. 81, No. 5.
Marasco, R., et al., "A Drought Resistance-Promoting Microbiome is Selected by Root System Under Desert Farming," PLoS ONE, 2012, vol. 7, No. 10, 14 Pages.
Marquez, L. M., et al., "A Virus In a Fungus in a Plant: Three-Way Symbiosis Required for Thermal Tolerance," Science, 2007, pp. 513-515, vol. 315.
Mastretta, C., et al., "Endophytic Bacteria from Seeds of Nicotiana Tabacum Can Reduce Cadmium Phytotoxicity," Intl J Phytoremediation, 2009, pp. 251-267, vol. 11.
Mateos, P. F., et al., "Cell-Associated Pectinolytic and Cellulolytic Enzymes in Rhizobium Teguminosarum biovartrifolii," Appl Environ Microbiol., 1992, pp. 816-1822, vol. 58, No. 6.
McDonald, D., et al., "An Improved Greengenes Taxonomy with Explicit Ranks for Ecological and Evolutionary Analyses of Bacteria and Archaea," ISME J., 2012, pp. 610-618, vol. 6.
McGuire, K.L., et al., "Digging the New York City Skyline: Soil Fungal Communities in Green Roofs and City Parks," PloS One, 2013, vol. 8, No. 3, 13 Pages.
Medina, P., et al., "Rapid Identification of Gelatin and Casein Hydrolysis Using TCA," J Microbiol Methods, 2007, pp. 391-393, vol. 69.
Mehnaz, S., et al., "Growth Promoting Effects of Corn (*Zea mays*) Bacterial Isolates Under Greenhouse and Field Conditions," Soil Biology and Biochemistry, 2010, pp. 1848-1856, vol. 42.
Mehnaz, S., et al., "Isolation and 16S rRNA sequence analysis of the beneficial bacteria from the rhizosphere of rice," Canada Journal of Microbiology, 2001, pp. 110-117, vol. 47, No. 2.
Mei, C., et al., "The Use of Beneficial Microbial Endophytes for Plant Biomass and Stress Tolerance Improvement," Recent Patents on Biotechnology, 2010, pp. 81-95, vol. 4.
Michel, B. E., et al., "The Osmotic Potential of Polyethylene Glycol 6000," Plant Physiol., 1973, pp. 914-916, vol. 51.
Misk, A., et al., "Biocontrol ofchickpea root rot using endophytic actinobacteria", Biocontrol, vol. 56, No. 5,Mar. 12, 2011, pp. 811-822, XP036215297.

(56) References Cited

OTHER PUBLICATIONS

Miyoshi-Akiyama, T., et al., "Multilocus Sequence Typing (MLST) for Characterization of Enterobacter cloacae," PLoS ONE, 2013, vol. 8, No. 6, 10 Pages, e66358.

Moe, L. A., "Amino Acids in the Rhizosphere: From Plants to Microbes," American Journal of Botany, 2013, pp. 1692-1705, vol. 100, No. 9.

Mohiddin, F. A., et al., "Tolerance of Fungal and Bacterial Biocontrol Agents to Six Pesticides Commonly Used in the Control of Soil Borne Plant Pathogens," African Journal of Agricultural Research, 2013, pp. 5331-5334, vol. 8, No. 43.

Mousa, W. K., et al., "The Diversity of Anti-Microbial Secondary Metabolites Produced by Fungal Endophytes: An Interdisciplinary Perspective," Front Microbiol., 2013, vol. 4, No. 65, 18 Pages.

Mundt, J.O., et al., "Bacteria Within Ovules and Seeds," Appl Environ Microbiol., 1976, pp. 694-698, vol. 32, No. 5.

Naik, B. S., et al., "Study on the diversity of endophytic communities from rice (Oryza sativa L.) and their antagonistic activities in vitro," Microbiological Research, 2009, pp. 290-296, vol. 164.

Naveed, M., "Maize Endophytes—Diversity, Functionality and Application Potential," University of Natural Resources and Life Sciences, 2013, pp. 1-266 and 81-87; Tables 1-3; Figure 2.

Nejad, P. et al., "Endophytic Bacteria Induce Growth Promotion and Wilt Disease Suppression in Oilseed Rape and Tomato," Biological Control, 2000, pp. 208-215, vol. 18.

Neslon, E.B., "Microbial Dynamics and Interactions in the Spermosphere," Ann. Rev. Phytopathol., 2004, pp. 271-309, vol. 42.

Nikolcheva, L.G., et al., "Taxon-Specific Fungal Primers Reveal Unexpectedly High Diversity During Leaf Decomposition in a Stream," Mycological Progress, 2004, pp. 41-49, vol. 3, No. 1.

Nimnoi, P., et al., "Co-Inoculation of Soybean (Glycin Max) with Actinomycetes and Bradyrhizobium Japonicum Enhances Plant Growth, Nitrogenase Activity and Plant Nutrition," Journal of Plant Nutrition, 2014, pp. 432-446, vol. 37.

Nishijima, K.A., et al., "Demonstrating Pathogenicity of Enterobacter cloacae on Macadamia and Identifying Associated Volatiles of Gray Kernel of Macadamia in Hawaii," Plant Disease, Oct. 2007, vol. 91, No. 10, pp. 1221-1228.

Normander, B., et al., "Bacterial Origin and Community Composition in the Barley Phytosphere as a Function of Habitat and Presowing Conditions," Appl Environ Microbiol., Oct. 2000, pp. 4372-4377, vol. 66, No. 10.

Okunishi, S., et al., "Bacterial Flora of Endophytes in the Maturing Seeds of Cultivated Rice (Oryza sativa)," Microbes and Environment, 2005, pp. 168-177, vol. 20, No. 3.

Op De Beeck, M., et al., "Comparison and Validation of Some ITS Primer Pairs Useful for Fungal Metabarcoding Studies," PLOS One, Jun. 2014, vol. 9, Issue 6, e97629, pp. 1-11.

Orole, O. O., et al., "Bacterial and fungal endophytes associated with grains and roots of maize," Journal of Ecology and the Natural Enviornment, 2011, pp. 298-303, vol. 3, No. 9.

Partida-Martinez, L.P., et al., "The Microbe-Free Plant: Fact or Artifact?" Front Plant Sci., 2011, vol. 2, No. 100, 16 Pages.

Pearson, W.R., et al., "Rapid and Sensitive Sequence Comparison With FASTP and FASTA," Methods Enzymol., 2011, pp. 63-98, vol. 183.

Pedraza, R. O., et al., "Azospirillum inoculation and nitrogen fertilization effect on grain yield and on the diversity of endophytic bacteria in the phyllosphere of rice rainfed crop," European Journal of Soil Biology, 2009, pp. 36-43, vol. 45.

Perez-Fernandez, M. A., et al., "Simulation of Germination of Pioneer Species Along an Experimental Drought Gradient," J Environ Biol., 2006, pp. 669-685, vol. 27, No. 4.

Perez-Miranda, S., et al., "O-CAS, A Fast and Universal Method for Siderophore Detection," J Microbiol Methods, 2007, pp. 127-131, vol. 70.

Petti, C. A., "Detection and Identification of Microorganisms by Gene Amplification and Sequencing," Clinical Infectious Diseases, 2007, pp. 1108-1114, vol. 44.

Phalip, V., et al., "A Method for Screening Diacetyl and Acetoin-Producing Bacteria on Agar Plates," J Basic Microbiol., 1994, pp. 277-280, vol. 34.

Philippot, L., et al., "Going Back to the Roots: The Microbial Ecology of the Rhizosphere," Nat Rev Microbiol., Nov. 2013, pp. 789-799, vol. 11.

Philrice Batac, Philippine Rice R&D Highlights, 2012, Area-Based R&D Projects, 52 Pages, [online][Retrieved Aug. 11, 2016] Retrieved from the Internet <URL:http://www.philrice.gov.ph/2012-rd-highlights/>.

Pillay, V. K., et al., "Inoculum Density, Temperature, and Genotype Effects on in vitro Growth Promotion and Epiphytic and Endophytic Colonization of Tomato (Lycopersicon esculentum L.) Seedlings Inoculated with a Pseudomonad Bacterium," Can J Microbiol., 1997, pp. 354-361, vol. 43.

Powell, W. A., et al., "Evidence of Endophytic Beauveria Bassiana in Seed-Treated Tomato Plants Acting as a Systemic Entomopathogen to Larval Helicoverpa zea (Lepidoptera Noctuidae)," J. Entomol. Sci., 2009, pp. 391-396, vol. 44, No. 4.

Quadt-Hallmann, A., et al., "Bacterial Endophytes in Cotton: Mechanisms of Entering the Plant," Can J Microbiol., 1997, pp. 577-582, vol. 43.

R Core Team, "R: A Language and Environment for Statistical Computing," R Foundation for Statistical Computing, Vienna, Austria, May 2013, ISBN: 3-900051-07-0. Available online at http://www.R- 25 project.org/, 3604 Pages.

Rae, R., et al., "A subset of naturally isolated Bacillus strains show extreme virulence to the free-living nematodes Caenorhabditis elegans and Pristionchus pacificus", Environmental Microbiology, 2010, pp. 3007-3021, vol. 12, No. 11.

Rasmussen, S., et al., "Grass-endophyte interactions: a note on the role of monosaccharide transport in the Neotyphodium Iolii-Lolium perenne symbiosis," New Phytologist, 2012, pp. 7-12, vol. 196.

Ravel, C., et al., "Beneficial effects of Neotyphodium lolii on the growth and the water status in perennial ryegrass cultivated under nitrogen deficiency or drought stress," Agronomie, 1997, pp. 173-181, vol. 17.

Redman, R. S., et al., "Thermotolerance Generated by Plant/Fungal Symbiosis," Science, Nov. 2002, vol. 298, 1 Page (with 4 pages of supplemental material).

Reiter, B., et al., "Response of Endophytic Bacterial Communities in Potato Plants to Infection with Erwinia carotovora subsp. atroseptica," Appl Environ Microbiol., 2001, pp. 2261-2268, vol. 68, No. 5.

Ren, Y., et al., "Complete Genome Sequence of Enterobacter cloacae subsp. cloacae Type Strain ATCC 13047," J. Bacteriol. May 2010, vol. 192, No. 9, pp. 2463-2464.

Riess, K., et al., "High genetic diversity at the regional scale and possible speciation in Sebacina epigaea and S. incrustans," BMC Evolutionary Biology, 2013, vol. 13, No. 102, 17 Pages.

Riken, GI No. GMFL01-01-D03, 2 Pages, [online] [Retrieved on Dec. 18, 2017] Retrieved from the internet <URL:http://spectra.psc.riken.jp/menta.cgi/rsoy/datail?id=GMFL01-01-D03>.

Rodriguez, H., et al., "Expression of a Mineral Phosphate Solubilizing Gene From Erwinia herbicola in Two Rhizobacterial Strains," J Biotechnol., 2001, pp. 155-161, vol. 84.

Rodriguez, R.J., et al., "Stress Tolerance in Plants via Habitat-Adapted Symbiosis," ISME J., 2008, pp. 404-416, vol. 2.

Rodriguez-Navarro, D., et al., "Soybean Interactions with Soil Microbes, Agronomical and Molecular Aspects," Agronomy for Sustainable Development, 2011, pp. 173-190, vol. 31, No. 1.

Roessner, U., et al., "Metabolic Profiling Allows Comprehensive Phenotyping of Genetically or Environmentally Modified Plant Systems," Plant Cell, 2001,pp. 11-29, vol. 13.

Rosado, A. S., et al., "Phenotypic and Genetic Diversity of Paenibacillus azotofixans Strains Isolated from the Rhizoplane or Rhizosphere Soil of Different Grasses," J App Microbiol., 1998, pp. 216-226, vol. 84.

Rosenblueth, A., et al., "Seed Bacterial Endophytes: Common Genera, Seed-to-Seed Variability and Their Possible Role in Plants," Acta Hort., 2012, pp. 39-48, vol. 938.

Rosenblueth, M., et al., "Bacterial Endophytes and Their Interactions With Host," Molecular Plant-Microbe Interactions, 2006, pp. 827-837, vol. 19, No. 8.

(56) References Cited

OTHER PUBLICATIONS

Ross, P.L., et al., "Multiplexed Protein Quantitation in *Saccharomyces cerevisiae* Using Amine-Reactive Isobaric Tagging Reagents," Mol Cell Proteomics, 2004, pp. 1154-1169, vol. 3, No. 12.

Saleem, M., et al., "Perspective of Plant Growth Promoting Rhizobacteria (PGPR) Containing ACC Deaminase in Stress Agriculture," J Ind Microbiol Biotechnol., Oct. 2007, pp. 635-648, vol. 34.

Samac, D.A., et al., "Recent Advances in Legume-Microbe Interactions: Recognition, Defense Response, and Symbiosis from a Genomic Perspective," Plant Physiol., 2007, pp. 582-587, vol. 144.

Samways, M.J., et al., "Assessment of the Fungus Cladosporium Oxyspoum (BERK. and CURT.) as a Potential BioControl Agent Against Certain Homoptera," Elsevier Science Publioshers B.V., Jan. 1, 1986, pp. 231-239.

Sardi, P., et al., "Isolation of Endophytic Streptomyces Strains from Surface Sterilized Roots," Applied and Environmental Microbiology, 1992, pp. 2691-2693, vol. 58, No. 8.

Sarwar, M., et al., "Tryptophan Dependent Biosynthesis of Auxins in Soil," Plant Soil, 1992, pp. 207-215, vol. 147.

Saunders, M., et al., "Host-Synthesized Secondary Compounds Influence the In Vitro Interactions between Fungal Endophytes of Maize", Applied and Environmental Microbiology, Nov. 9, 2007, pp. 136-142, vol. 74 , No. 1.

Schmieder, R., et al., "Quality Control and Preprocessing of Metagenomic Datasets," Bioinformatics, 2011, pp. 863-864, vol. 27, No. 6.

Schneider, C., et al., "Endophytes for plant protection: the state of the art Proceedings," DPG Spectrum Phytomedizin, Proceedings of the 5th International Symposium on Plant Protection and Plant Health in Europe, May 26-29, 2013, 347 Pages.

Schoch, C. L, et al., "Nuclear Ribosomal Internal Transcribed Spacer (ITS) Region as a Universal DNA Barcode Marker for Fungi," Proc Natl Acad Sci USA, 2012, pp. 6241-6246, vol. 109, No. 16.

Schwyn, B. et al., "Universal Chemical Assay forthe Detection and Determination of Siderophores," Analytical Biochemistry, 1987, pp. 47-56, vol. 160.

Senthilkumar, M., et al., "Biocontrol Potential of Soybean Bacterial Endophytes Against Charcoal Rot Fungus, Rhizoctonia bataliola," Current Microbiology, 2009, vol. 58, pp. 288-293.

Sessitsch, A., et al., "*Burkholderia phytofirmans* sp. Nov., a novel plant-associated bacterium with plant-beneficial properties," International Journal of Systematic and Evoluntary Microbiology, 2005, pp. 1187-1192, vol. 55.

Shapiro-Ilan, D.I., et al., "The Potential for Enhanced Fungicide Resistance in Beauveria Bassiana Through Strain Discovery and Artificial Selection," Journal of Invertebrate Pathology, 2002, pp. 86-93, vol. 81.

Shankar, M., et al.."Root colonization of a rice growth promoting strain of Enterobacter cloacae," Journal of Basic Microbiology, 2011, pp. 523-530, vol. 51.

Shiraishi, A., et al., "Nodulation in black locust by the ammaproteobacteria *Pseudomonas* sp. and the Betaproteobacteria *Burkholderia* sp", Systematic and Applied Microbiology, Aug. 2010, pp. 269-274, vol. 33, No. 5.

Simola, L., et al., "The Effect of Some Protein and Non-Protein Amino Acids on the Growth of Cladosporium herbarum and Trichotheeium roseum," Effect of Amino Acids on Fungi, Physiologia Plantarum, 1979, pp. 381-387, vol. 46.

Singh, A. K., et al., "Uncultured *Actinomyces* sp. Clone EMLACT 80 IV (New) 16S Ribosomal RNA Gene, Partial Sequence," NCBI GenBank Accession No. JQ285908. Submitted Dec. 13, 2011.

Soares, M. M. C. N., et al., "Screening of Bacterial Strains for Pectinolytic Activity Characterization of the Polygalacturonase Produced by Bacillus SP," Revista de Microbiolgia, 1999, pp. 299-303, vol. 30.

Soe, K.M., et al., "Effects of endophytic actinomycetes and Bradyrhizobium japonicum strains on growth, nodulation, nitrogen fixation and seed weight of different soybean varieties," Soil Science and Plant Nutrition, 2012, pp. 319-325, vol. 58, No. 3.

Soe, K.M., et al., "Low-Density Co-Inoculation of Myanmar Bradyrhizobium yuanmingense MAS34 and Streptomyces griseoflavus P4 to Enhance Symbiosis and Seed Yield in Soybean Varieties," American Journal of Plant Sciences, 2013, pp. 1879-1892, vol. 4.

Sogonov, M.V., et al., "The hyphomycete *Teberdinia hygrophila* gen. nov., sp. nov. and related anamorphs of *Pseudeurotium* species," Mycologia, May 2005, pp. 695-709, vol. 97, No. 3.

Song, M., et al., "Effects of Neotyphodium Endophyte on Germination of Hordeum brevisubulatum under Temperature and Water Stress Conditions," Acta Agrestia Sinica, 2010, pp. 834-837, vol. 18, No. 6. (English Abstract).

Souleimanov, A., et al., "The Major Nod Factor of Bradyrhizobium japonicum Promotes Early Growth of Soybean and Corn," J. Exp. Bot., 2002, pp. 1929-1934, vol. 53, No. 376.

Spiekermann, P., et al., "A Sensitive, Viable-Colony Staining Method Using Nile Red for Direct Screening of Bacteria that Accumulate Polyhydroxyalkanoic Acids and Other Lipid Storage Compounds," Arch Microbiol., 1999, pp. 73-80, vol. 171.

Staudt, A. K., et al., "Variations in Exopolysaccharide Production by Rhizobium tropici," Arch Microbiol., 2012, pp. 197-206, vol. 194.

Stielow, J.B., et al., "One fungus, which genes? Development and assessment of universal primers for potential secondary fungal DNA barcodes," Persoonia: Molecular Phylogeny and Evolution of Fungi, 2015, vol. 35, pp. 242-263.

Strobel, G. A., "Endophytes as Sources of Bioactive Products," Microbes and Infection, 2003, pp. 535-544, vol. 5.

Sturz, A. V., et al., "Weeds as a Source of Plant Growth Promoting Rhizobacteria in Agricultural Soils," Can J Microbiol., 2001, pp. 1013-1024, vol. 47, No. 11.

Surette, M. A., et al. "Bacterial Endophytes in Processing Carrots (*Daucus carota* L. var. *sativus*): Their Localization, Population Density, Biodiversity and Their Effects on Plant Growth," Plant and Soil, 2003, pp. 381-390, vol. 253, No. 2.

Suto, M., et al., "Endophytes as Producers of Xylanase," J Biosci Bioeng., 2002, pp. 88-90, vol. 93, No. 1.

Sword, G., "Manipulating Fungal Endophytes to Protect Plants from Insects and Nematodes," Power Point Presentation dated Aug. 7, 2013.

Sword, G., et al., "Manipulating Fungal Endophytes forthe Protection of Cotton in the Field," Power Point Presentation dated Jan. 7, 2013.

Sword, G., et al., "Field Trials of Potentially Beneficial Fungal Endophytes in Cotton," Power Point Presentation dated Jan. 7, 2013.

Sword, G., "Fungal Endophytes to Protect Cotton from Insects and Nematodes," Power Point Presentation dated Dec. 7, 2012, 20 Pages.

Sword, G., "Natural Enemies—The Forgotten Basis of IPM?," Power Point Presentation dated Sep. 6, 2013.

Taghavi, S., et al., "Genome Survey and Characterization of Endophytic Bacteria Exhibiting a Beneficial Effect on Growth and Development of Poplar Trees," Applied and Environmental Microbiology, 2009, pp. 748-757, vol. 75, No. 3.

Taghavi, S., et al., "Genome Sequence of the Plant Growth promoting Endophytic Bacterium *Enterobacter* sp. 638", PLoS Genet., May 2010, pp. 1-15, vol. 6, Issue 5, e1000943.

Tamura, K., et al., "Estimation of the number of nucleotide substitutions in the control region of mitochondrial DNA in humans and chimpanzees," Molecular Biology and Evolution, 1993, vol. 10, No. 3, pp. 512-526.

Taylor, A. G., et al., "Concepts and Technologies of Selected Seed Treatments," Annu. Rev. Phytopathol., 1990, pp. 321-339, vol. 28.

Teather, R. M., et al., "Use of Congo Red-Polysaccharide Interactions in Enumeration and Characterization of Cellulolytic Bacteria from the Bovine Rumen," Appl Environ Microbiol., 1982, pp. 777-780, vol. 43, No. 4.

Thakur, A., et al., "Detrimental effects of endophytic fungus *Nigrospora* sp. on survival and development of Spodoptera litura," Biocontrol Science and Technology, Feb. 1, 2012, pp. 151-161, vol. 22, No. 2.

(56) References Cited

OTHER PUBLICATIONS

Thakur, A., et al., "Enhanced Resistance to Spodoptera litura in Endophyte Infected Cauliflower Plants," Environmental Entomology, Apr. 1, 2013, pp. 240-246, vol. 42, No. 2.
Thakur, A., et al., "Suppression of Cellular Immune Response in Spodoptera litura (Lepidoptera Noctuidae) Larvae by Endophytic Fungi Nigrospora oryzae and Cladosporium uredinicola,", Annals of the Entomological Society of America, May 1, 2014, pp. 674-679, vol. 107, No. 3.
Theis, K. R., et al., "Uncultured Bacterium Clone GM2GI8201A64RC 16S Ribosomal RNA Gene, Partial Sequence," NCBI GenBank Accession No. JX051943, Submitted May 14, 2012.
Thomas, L., et al., "Development of Resistance to Chlorhexidine Diacetate in Pseudomonas aeruginosa and the Effect of a "Residual" Concentration," J Hosp Infect., 2000, pp. 297-303, vol. 46.
Thomashow, M. F., "So What's New in the Field of Plant Cold Acclimation? Lots!," Plant Physiol., 2001, pp. 89-93, vol. 125.
Tokala, R. T., et al., "Novel Plant-Microbe Rhizosphere Interaction Involving *Streptomyces Lydicus* WYEC108 and the Pea Plant (*Pisum Sativum*)," Applied and Environmental Microbiology, May 2002, pp. 2161-2171, vol. 68, No. 5.
Trichoderma definition, 2016, 6 Pages, [online] [Retrieved on Sep. 16, 2016,] Retrieved from the Internet <URL:https://en.wikipedia.org/wiki/Trichoderma>.
Trotel-Aziz, P., et al., "Characterization of New Bacterial Biocontrol Agents Acinetobacter, Bacillus, Pantoea and *Pseudomonas* spp. Mediating Grapevine Resistance Against Botrytis cinerea," Environmental and Experimental Botany, 2008, pp. 21-32, vol. 64.
Truyens, S., et al., "Changes in the Population of Seed Bacteria of Transgenerationally Cd-Exposed *Arabidopsis thaliana*," Plant Biol., 2013, pp. 971-981, vol. 15.
U'ren, J.M., et al., "Host and geographic structure of endophytic and endolichenic fungi at the continental scale," American Journal of Botany, May 1, 2012, pp. 898-914, vol. 99, No. 5.
Usadel, B., et al., "The Plant Transcriptome-From Integrating Observations to Models," Front Plant Sci., 2013, pp. 1-3, vol. 4., Article 48, 3 Pages.
Vacheron, J., et al., "Plant Growth-Promoting Rhizobacteria and Root System Functioning," Frontiers Plant Sci., 2013, vol. 4, Article 356, 19 Pages.
Valencia, C. U., et al., "Endophytic Establishment as an Unintended Consequence of Biocontrol with Fungal Entomopathogens," Power Point Presentation dated Jan. 7, 2013, 10 Pages.
Valencia, E., et al., "Mini-review: Brazilian fungi diversity for biomass degradation," Fungal Genetics and Biology, 2013, pp. 9-18, vol. 60.
Van Der Lelie, D., et al., "Poplar and its Bacterial Endophytes: Coexistence and Harmony," Critical Rev Plant Sci., 2009, pp. 346-358, vol. 28.
Verkley, G., et al., "Paraconiothyrium, a new genus to accommodate the mycoparasite Coniothyrium minitans, anamorphs of Paraphaeosphaeria, and four new species," Studies in Mycology, 2004, pp. 323-335, vol. 50.
Vining, K., et al., "Methylome Reorganization During in vitro Dedifferentiation and Regeneration of Populus trichocarpa," BMC Plant Biol., 2013, vol. 13, No. 92, 15 Pages.
Viruel, E., et al., "Pseudomonas thiveralensis Strain IEHa 16S Ribosomal RNA Fene, Partial Sequence," NCBI GenBank Accession No. GQ169380.1, Submitted May 15, 2009.
Msagie, C.M., et al., "Identification and nomenclature of the genus Penicillium," Studies in Mycology, Jun. 2014, pp. 343-371, vol. 78.
Vujanovic, V., et al., "Viability Testing of Orchid Seed and the Promotion of Colouration and Germination," Annals of Botany, Mar. 17, 2000, pp. 79-86, vol. 86.
Vujanovic, V., et al., "Endophytic hyphal compartmentalization is required for successful mycobiont-wheat interaction as revealed by confocal laser microscopy," The proceedings of the Soils and Crops conference in Saskatoon (2008) published 2009, 7 Pages.
Vujanovic, V., et al., "A comparative study of endophytic mycobiota in leaves of Acer saccharum in eastern North America," Mycological Progress, May 2002, pp. 147-154, vol. 1, Issue 2.
Vujanovic, V., et al., "Orchid seed viability testing by fungal bioassays and molecular phylogeny," Floriculture, ornamental and plant biotechnology, 2006, vol. 63, pp. 563-569.
Vujanovic, V., et al., "Mycovitality—a new concept of plant biotechnology," Canadian Journal Plant Pathol, 2007, vol. 29, p. 451.
Vujanovic, V., et al., "19th International Conference on *Arabidopsis*. Research Proceedings—ICAR13,"Jul. 23-27, 2008, 264 Pages, Montreal, QC, Canada.
Vujanovic, V., et al., "Mycovitality and mycoheterotrophy: where lies dormancy in terrestrial orchid and plants with minute seeds?" Symbiosis, 2007, vol. 44, pp. 93-99.
Vujanovic, V., et al., "Seed endosymbiosis: a vital relationship in providing prenatal care to plants," Can. J. Plant Sci., NRC Research Press, Feb. 6, 2017, pp. 972-981, vol. 97.
Waller, F., et al., "The Endophytic Fungus Piriformospora indica Reprograms Barley to Salt-Stress Tolerance, Disease Resistance, and Higher Yield," PNAS, 2005, pp. 13386-13391, vol. 102, No. 38.
Wang, B., et al., "Fungal endophytes of native *Gossypium* species in Australia," Mycological Research, 2007, pp. 347-354, vol. 111, No. 3.
Wang, K., et al., "Monitoring in Planta Bacterial Infection at Both Cellular and Whole-Plant Levels Using the Green Fluorescent Protein Variant GFPuv," New Phytol., 2007, pp. 212-223, vol. 174.
Wang, Q., et al., "Naive Bayesian Classifier for Rapid Assignment of rRNA Sequences into the New Bacterial Taxonomy," Appl. Environ. Microbiol., 2007, pp. 5261-5267, vol. 73, No. 16.
Waqas, M., et al., "Endophytic Fungi Produce Gibberellins and Indoleacetic Acid and Promotes Host-Plant Growth during Stress," Molecules, 2012, pp. 10754-10773, vol. 17.
Weaver, P.F., et al., "Characterization of Rhodopseudomonas capsulata,"Arch Microbiol., 1975, pp. 207-216, vol. 105.
Weindling, R., "Relation of dosage to control of cotton seedling diseases by seed treatment," Plant Disease Reporter, 1943, 27, pp. 68-70.
Welty, R.E., et al., "Influence of Moisture Content, Temperature, and Length of Storage on Seed Germination and Survival of Endophytic Fungi in Seeds of Tall Fescue and Perennial Ryegrass," Phytopathyol., 1987, pp. 893-900, vol. 77, No. 6.
White, J. F., et al., "A Proposed Mechanism for Nitrogen Acquisition by Grass Seedlings Through Oxidation of Symbiotic Bacteria," Symbiosis, 2012, pp. 161-171, vol. 57.
Wiegand, I., et al., "Agar and Broth Dilution Methods to Determine the Minimal Inhibitory Concentration (MIC) of Antimicrobial Substances," Nature Protocols, 2008, pp. 163-175, vol. 3, No. 2.
Xu, Y., et al., "Biosynthesis of the Cyclooligomer Despipeptide bassianolide, an Insecticidal Virulence Factor of Beauveria bassiana," Fungal Genetics and Biology, 2009, pp. 353-364, vol. 46.
Xue, Q.Y., et al., "Evaluation of the Strains of Acinetobacter and Enterobacter as potential Biocontrol Agents Against Ralstonia Wilt of Tomato," Biological Control, 2009, vol. 48, pp. 252-258.
Yandigeri, M. S., et al., "Drought-tolerant endophytic actinobacteria promote growth of wheat (*Triticum aestivum*) under water stress conditions," Plant Growth Regulation, 2012, pp. 411-420, vol. 68.
Yennamalli, R., et al., "Endoglucanases: insights into thermostability for biofuel applications", Biotech Biofuels, 2013, vol. 6, Issue 136, pp. 1-9.
Yezerski, A., et al., "The Effects of the Presence of Stored Product Pests on the Microfauna of a Flour Community," Journal of Applied Microbiology, 2005, pp. 507-515, vol. 98.
You, Y., et al., "Analysis of Genomic Diversity of Endophytic Fungal Strains Isolated from the Roots of Suaeda japonica and S. maritima for the Restoration of Ecosystems in Buan Salt Marsh," Korean Journal of Microbiology and Biotechnology, 2012, pp. 287-295, vol. 40, No. 4, (with English Abstract).
Youssef, Y.A., et al., "Production of Plant Growth Substances by Rhizosphere Myoflora of Broad Bean and Cotton," Biologia Plantarum, 1975, pp. 175-181, vol. 17, No. 3.
Zhang, J., et al.: "Isolation and Characterization of Plant Growth-Promoting Rhizobacteria from Wheat Roots by Wheat Germ Agglu-

(56) References Cited

OTHER PUBLICATIONS tinin Labeled with Fluorescein Isothiocyanate", The Journal of Microbiology, Apr. 27, 2012, vol. 50, No. 2, pp. 191-198, GenBank Accession No. JN210900.
Zhao, J.H., et al., "Bioactive secondary metabolites from *Nigrospora* sp. LLGLM003, an endophytic fungus of the medicinal plant *Moringa oleifera* Lam." World Journal of Microbiology and Biotechnology, Kluwer Academic Publishers, Feb. 12, 2012, pp. 2107-2112, vol. 28, No. 5.
Zhou, W., et al., "Effects of the Fungal *Endophyte Paecilomyces* sp. in Cotton on the Roo-Knot Nematode Meloidogyne incognita," poster dated Jan. 7, 2013.
Zhu et al., Helminthosporium velutinum and *H. aquaticum* sp. nov. from aquatic habitats in Yunnan Province, China. Phytotaxa, 2016, vol. 253, No. 3, pp. 179-190.
Zimmerman, N.B., et al., "Fungal Endophyte Communities Reflect Environmental Structuring Across a Hawaiian Landscape," Proc Natl Acad Sci USA, 2012, pp. 13022-13027, vol. 109, No. 32.
Zuccaro, A., et al., "Endophytic Life Strategies Decoded by Genome and Transcriptome Analyses of the Mutualistic Root Symbiont Piriformospora indica," PLOS Pathogens, 2011, vol. 7, No. 10, e1002290.
Zuniga, A., et al., "Quorum Sensing and Indole-3-Acetic Acid Degradation Play a Role in Colonization and Plant Growth Promotion of *Arabidopsis thaliana* by Burkholderia phytofirmans PsJN," Mol Plant Microbe Interact., 2013, pp. 546-553, vol. 26, No. 5.
PCT International Search Report and Written Opinion for PCT/US2017/064292, dated May 11, 2018, 20 Pages.
PCT International Search Report and Written Opinion for PCT/US2017/064361, dated May 11, 2018, 22 Pages.
Database EMBL [Online] Oct. 1, 2001, "Setosphaeria monoceras 28S ribosomal RNA gene, partial sequence," XP002777918, retrieved from EBI accession No. EM_STD:AY016368 Database accession No. AY016368 sequence.
Amr H Nassar et al., "Promotion of plant growth by an auxin-producing isolate of the yeast *Williopsis saturnus* endophytic in maize (*Zea mays* L.) roots", Biology and Fertility of Soils; Cooperating Journal of International Society of Soil Science, Springer, Berlin, DE, vol. 42, No. 2, Nov. 1, 2005, pp. 97-108.
Bing Lori Anderson et al., "Suppression of Ostrinia nubilalis (Huebner) (Lepidoptera Pyralidae) by Endophytic Beauveria bassiana (Balsamo) Vui 11 emi n", Environmental Entomol, Entomological Society of America, College Park, MD, US, vol. 20, Jan. 1, 1991, pp. 1207-1211.
O'Hanlon Karen A et al., "Exploring the potential of symbiotic fungal endophytes in cereal disease suppression", Biological Control, vol. 63, No. 2, Sep. 5, 2012, pp. 69-78.
A.E. Impullitti et al.,"Fungal endophyte diversity in soybean", Journal of Applied Microbiolog, vol. 114, No. 5, May 1, 2013, pp. 1500-1506.
Vladimir Vujanovic et al.: "Fungal communities associated with durum wheat production system: A characterization by growth stage, plant organ and preceding crop", Crop Protection, Elsevier Science, GB, vol. 37, Feb. 19, 2012, pp. 26-34.
Wenming Zhang et al., Host range of Exserohilum monoceras, a potential bioherbicide for the control of Echinochloa species, Canadian Journal of Botany/Journal Canadien De Botan, National Research Council, Ottawa, CA, vol. 75, Jan. 1, 1997, pp. 685-692.
NCBI GenBank: EU852929.1, Jee, H-J. et al., "Bacillus subtilis strain R2-1 16S ribosomal RNA gene, partial sequence," Jul. 1, 2009, two pages, Can be retrieved at <URL: https://www.ncbi.nlm.nih.gov/nuccore/EU852929.1>.
NCBI GenBank: FJ435676.1, Choi, N-S. et al., "Bacillus licheniformis strain DJ-2 16S ribosomal RNA gene, partial sequence," Apr. 6, 2011, two pages, Can be retrieved at <URL: https://www.ncbi.nlm.nih.gov/nuccore/FJ435676>.
NCBI GenBank: FJ793201.1, Jiang, L., "Bacillus subtilis strain jllsy 16S ribosomal RNA gene, partial sequence," Apr. 1, 2009, two pages, Can be retrieved at <URL: https://www.ncbi.nlm.nih.gov/nuccore/FJ793201>.
NCBI GenBank: HQ536000.0, Peng, S. et al., "Bacillus subtilis strain CCM9 16S ribosomal RNA gene, partial sequence," Dec. 18, 2010, two pages, Can be retrieved at <URL: https://www.ncbi.nlm.nih.gov/nuccore/HQ536000>.
NCBI GenBank: JF496331.1, Liu, H.J. et al., "Bacillus subtilis strain A2-9 16S ribosomal RNA gene, partial sequence," Aug. 19, 2011, two pages, Can be retrieved at <URL: https://www.ncbi.nlm.nih.gov/nuccore/JF496331/>.
NCBI GenBank: JN256114.1, Li, C., "Bacillus subtilis strain B2-1 16S ribosomal RNA gene, partial sequence," Sep. 6, 2011, two pages, Can be retrieved at <URL: https://www.ncbi.nlm.nih.gov/nuccore/JN256114>.
NCBI GenBank: JQ734536.1, Zhao, Y. et al., "Bacillus amyloliquefaciens strain BGP14 16S ribosomal RNA gene, partial sequence," May 2, 2012, two pages, Can be retrieved at <URL: https://www.ncbi.nlm.nih.gov/nuccore/JQ734536>.
Arnold, A. Elizabeth et al.; "*Coniochaeta elegans* sp. nov., *Coniochaeta montana* sp. nov. and *Coniochaeta nivea* sp. nov., three new species of endophytes with distinctive morphology and functional traits", Int J Syst Evolu Microb vol. 71 No. 11, p5003. Published 2021.
Database accession No. JQ759107, European Nucleotide Archive [Online] EMBL's European Bioinformatics Institute; Mar. 7, 2012, U'ren J M et al.: "*Sordariomycetes* sp.genotype 60 isolate AK0688 internal transcribed spacer.".
Database accession No. MG917011, European Nucleotide Archive [Online] EMBL's European Bioinformatics Institute; Feb. 21, 2019, Lagarde A. et al.: "Coniochaeta sp.isolate Gir_07 internal transcribed spacer 1, partial sequence.".
Database accession Nos. MZ267873, MZ267979, MZ267926, MZ267820; European Nucleotide Archive [Online] EMBL's European Bioinformatics Institute; Sep. 11, 2021, Arnold A E: "*Coniochaeta nivea* isolate LG0013 various submissions.".
Database accession Nos. MZ267874, MZ267980, MZ267927, MZ267821; European Nucleotide Archive [Online] EMBL's European Bioinformatics Institute; Sep. 11, 2021, Arnold A E: "*Coniochaeta nivea* isolate LG0023.".
Kokaew, J. et al.; "*Coniochaeta ligniaria* an endophytic fungus from Baeckea frutescens and its antagonistic effects against plant pathogenic fungi", Thai Journal of Agricultural Science, vol. 44, Jun. 1, 2011, pp. 123-131.
Lagarde A. et al.: "Antiproliferative and antibiofilm potentials of endolichenic fungi associated with the lichen Nephroma laevigatum", Journal of Applied Microbiology, vol. 126, No. 4, Jan. 30, 2019, pp. 1044-1058.
Nilsson et al.; "Correspondence: Intraspecific ITS Variability in the Kingdom Fungi as Expressed in the International Sequence Databases and Its Implications for Molecular Species Identification", Evolutionary Bioinformatics, Jan. 1, 2008, pp193-201.
Shah Sujit et al.: "Colonization with non-mycorrhizal culturable endophytic fungi enhances orchid growth and indole acetic acid production", BMC Microbiology, vol. 22, No. 1, Jan. 1, 2022, pp. 1-13.
Trifonova R. et al.; "Interactions of plant-beneficial bacteria with the ascomycete *Coniochaeta ligniaria*", Journal of Applied Microbiology, vol. 106, No. 6, Jun. 1, 2009, pp. 1859-1866.
U'ren, Jana M., et al.; "Community Analysis Reveals Close Affinities Between Endophytic and Endolichenic Fungi in Mosses and Lichens", Microbial Ecology, vol. 60, No. 2, Jul. 13, 2010, pp. 340-353.
Abaid-Ullah, M., et al., "Plant Growth Promoting Rhizobacteria: An Alternate Way to Improve Yield and Quality of Wheat (Triticum aestivum)", International Journal of Agriculture and Biology, vol. 17, No. 1, Jan. 1, 2015, pp. 51-60.
Aerts A et al.: "NCBI Reference Sequence: XP_024757499.1: glycoside hydrolase family 18 protein [Trichoderma asperellum CBS 433.97]", Apr. 26, 2018 (Apr. 26, 2018), pp. 1-2, XP055973177.
Al-Askar AA, "Microbiological studies on the in vitro inhibitory effect of Streptomyces collinus albescens against some phytopathogenic fungi", African Journal of Microbiology Research, 2012, 6: 3277-3283 & GenBank Accession No. AB184101, May 20, 2008.
Amann, R., et al., "Single-cell identification in microbial communities by improved fluorescence in situ hybridization techniques", Nature Reviews Microbiology, 6: 339-348 (2008).

(56) References Cited

OTHER PUBLICATIONS

Andreolli, M., et al., "Endophytic Burkholderia fungorum DBT1 can improve phytoremediation efficiency of polycyclic aromatic hyrocarbons", Chemosphere, Pergamon Press, Oxford, GB, vol. 92, No. 6, May 21, 2013, pp. 688-694.

Anesi, A., et al., "Towards a scientific interpretation of the terrior concept: platicisity of the grape berry metabolome", BMP plant biology 15:191, 17 pages (Year: 2015).

Ansari, M.A.; Brownbridge, M.; Shah, F.A.; Butt, T.M. Efficacy of entomopathogenic fungi against soil-dwelling life stages of western flower thrips, Frankliniella occidentalis, in plant-growing media. Entomol. Exp. Appl. 2008, 127, 80-87.

Arend, J., et al., "Hydroquinone: O-glucosytransferase from cultivated Rauvolfia cells: enrichment and partial amino acid sequences", Phytochemistry (2000) 53:187-193.

Asaff, A.; Cerda-García-Rojas, C.; De la Torre, M. Isolation of dipicolinic acid as an insecticidal toxin from Paecilomyces fumosoroseus. Appl. Microbiol. Biotechnol. 2005, 68, 542-547.

Bais, H., et al., "The Role of Root Exudates in Rhizosphere Interactions with Plants and Other Organisms", Annual Review. Plant Biol. (2006) 57:233-266.

Bal, H.B et al., "Isolation of ACC deaminase producting PGPR from rice rhizosphere and evaluating their plant growth promoting activity under salt stress". Plant Soil (2013) 366: 93-105 doi: 10/1007/s11104-012-1402-5.

Barnett, S., et al., "Selection of microbes for control of Rhizoctonia root rot on wheat using a high throughput pathosystem", Biological Control, Jul. 6, 2017, 113: 45-57.

Bashan, Yoav E., et al., "Alginate Beads as Synthetic Inoculant Carriers for Slow Release of Bacteria that Affect Plant Growth," Applied and Environmental Microbiology, pp. 1089-1098, May 1986.

Bashan, Yoav Ed, et al., "Inoculants of plant growth-promoting bacteria for use in agriculture," Biotechnology Advances, Elsevier Publishing, Barking, GB, vol. 16, No. 4, Jul. 1, 1998, pp. 729-770, XP004123985.

Bentley, S.D., et al., Complete genome sequence of the model actinomycete Streptomyces coelicolor A3(2), Nature. May 9, 2002;417(6885):141-7. (Year: 2002).

Beris, E.I.; Papachristos, D.P.; Fytrou, A.; Antonatos, S.A.; Kontodimas, D.C. Pathogenicity of three entomopathogenic fungi on pupae and adults of the Mediterranean fruit fly, Ceratitis capitata (Diptera: Tephritidae). J. Pest Sci. 2013, 86, 275-284.

Bicego, M., et al., "Investigating Topic Models' Capabilities in Expression Microarray Data Classification", IEEE/transactions on computational biology and bioinformatics, 9:8 1831-1836 (Year: 2012).

Bulgari, D., et al., "Endophytic Bacterial Diversity in Grapevine (*Vitis vinifera* L.) Leaves Described by 16S rRna Gene Sequence Analysis and Length Beterogeneity-PCR", The Journal of Microbiology, Aug. 2009, p. 393-401, vol. 47, No. 4.

Chakraborty et al., "Evaluation of Ochrobactrum anthropi TRS-2 and its talcbased formulation for enhancement of growth of tea plants and management of brown root rot disease." Journal of Applied Microbiology, 2009, 107(2):625-634 DOI:10.1111/j.1365-2672.2009.04242.x <https://doi.org/10.1111/j.1365-2672.2009.04242.x.

Chaves, J., et al., "Identification and Phylogeny of Streptomyces Based on Gene Sequences", Research Journal of Microbiology, vol. 13, No. 1, Dec. 15, 2017, pp. 13-20, XP055675917.

Chelius, M.K., et al., "The Diversity of Archaea and Bacteria in Association with the Roots of *Zea mays* L.", Microb Ecol (2001) 41:252-263.

Chenhua Li , et al., "Change in deep soil microbial communities due to long-term fertilization," Soil Biology and Biochemistry, vol. 75, Mar. 5, 2014, pp. 264-272, XP055530941.

Cheow, W.S., et al., "Biofilm-like Lactobacillus rhamnosus Probiotices Encapsulated in Algiinate and Carrageenan Microcapsules Exhibiting Enhanced Thermotolerance and Freeze-drying Resistance," Biomacromolecules 2013, vol. 14(9):3214-3222.

Chung, E., et al.: *Chitinophaga oryziterrae* sp. nov., isolated from the rhizosphere soil of rice (*Oryza sativa* L.) II, International Journal of Systematic and Evolutionary Microbiology, vol. 62, No. Pt_12, Dec. 1, 2012 (Dec. 1, 2012), pp. 3030-3035.

Colla, G., et al., "Coating seeds with endophytic fungi enhances growth, nutrient uptake, yield and grain quality of winter wheat", International Journal of Plant Production, vol. 9, No. 2, Apr. 1, 2015, pp. 171-190.

Combined printouts of term definitions from world wide web, performed by mkz Oct. 19, 2022 (Year: 2022).

Database Genbank [Online] NIH; Jan. 1, 2008 (Jan. 1, 2008), Hanada RE et al.: "Trichoderma hamatum strain DIS 65G 18S ribosomal RNA gene, partial sequence; internal transcribed spacer 1", XP055973221, Database accession No. EU264000 abstract.

Database GenBank [Online] NIH; Oct. 1, 2010 (Oct. 1, 2010), Aslam Z. et al.: "*Chitinophaga* sp.Z2-YC6856 16S ribosomal RNA gene", XP055948442, accession No. GQ369124 Database accession No. GQ369124.1 abstract.

Database GenBank [Online] NIH; Jun. 10, 2014 (Jun. 10, 2014), Zhang B. G.: "Chitinophaga oryziterrae strain ZBGKL4 16S ribosomal RNA gene", XP055948443, accession No. KJ734873 Database accession No. KJ734873.1 abstract.

Database GenBank [Online] NIH; Mar. 10, 2017 (Mar. 10, 2017), Shaffer JP et al.: "Uncultured bacterium clone EHB-PS0362 16S ribosomal RNA gene", XP055948435, accession No. KU978322 Database accession No. KU978322.1 abstract.

Database Genbank [Online] NIH; Apr. 11, 2019 (Apr. 11, 2019), Chaverri P et al.: "Trichoderma hamatum strain GJS 04-207 calmodulin (CAL) gene, partial eds" , XP055973272, Database accession No. FJ442285 abstract.

Database GenBank [Online] NIH; Jan. 15, 2019 (Jan. 15, 2019), Hu C. J. et al.: "*Chitinophaga* sp. strain N15203 16S ribosomal RNA gene", XP055948438, accession No. MK389338 Database accession No. MK389338.1 abstract.

Database GenBank [Online] NIH; Sep. 2, 2017 (Sep. 2, 2017), Jiayu T. J.: "*Chitinophaga* sp. strain PRd7 16S ribosomal RNA gene", XP055948441, accession No. KY203972 Database accession No. KY203972.1 abstract.

Database Genbank [Online] NIH; May 23, 2005 (May 23, 2005), Steyaert J M et al.: "Trichoderma hamatum alkaline proteinase (prbl) gene, complete eds", XP055973243, Database accession No. AY258899 abstract.

Database Genbank [Online] NIH; Jul. 25, 2016 (Jul. 25, 2016), Steyaert J M et al.: "Trichoderma hamatum endochitinase (chit42) gene, partial eds", XP055973252, Database accession No. AY258898 abstract.

Database Genbank [Online] NIH; Sep. 25, 1998 (Sep. 25, 1998), Giczey G et al.: "endochitinase [Trichoderma hamatum] ", XP055973364, Database accession No. AAC60385 abstract.

Database Genbank [Online] NIH; Sep. 25, 1998 (Sep. 25, 1998), Giczey G et al.: "Trichoderma hamatum endochitinase gene, complete eds", XP055973251, Database accession No. U88560 abstract.

Database GenBank [Online] NIH; Nov. 26, 2014 (Nov. 26, 2014), Han J. H. et al.: "*Chitinophaga* sp. NR 1-07 16S ribosomal RNA gene", XP055948440, accession No. KM253104 Database accession No. KM253104.1 abstract.

Database GenBank [Online] NIH; Jan. 29, 2016 (Jan. 29, 2016), Wu JR: "Chitinophaga pinensis strain CSB3-50 16S ribosomal RNA gene", XP055948434, accession No. KU305719 Database accession No. KU305719.1 abstract.

Database Genbank [Online] NIH; Sep. 6, 2013 (Sep. 6, 2013), Samuels G J et al.: "Trichoderma hamatum strain Dis 240j actin (act) gene, partial eds", XP055973271, Database accession No. EU856256 abstract.

Database Geneseq [Online] Sep. 30, 2010 (Sep. 30, 2010), "Cellulomonas fermentans 16s rRNA gene Seq ID:39.", retrieved from EBI accession No. GSN:AWL84299 Database accession No. AWL84299; & JP 2009 072168 A (Univ of Occupational & ENVIRON) Apr. 9, 2009 (Apr. 9, 2009).

Djian, C. et al., Acetic acid: A selective nematicidal metabolite from culture filtrates of Paecilomyces lilacinus (Thom) Samson and Trichoderma longibrachiatum Rifai. Nematologica 1991, 37, 101-112.

(56) References Cited

OTHER PUBLICATIONS

Doster, M.A. et al., ""Biocontrol of Aflatoxins in Figs,"" Proceedings of the Third International Symposium on Fig, 798, 2008, pp. 223-226.
Douglas, G., et al., "PICRUSt2 for prediction of metagenome functions", Nature Biotechnology, vol. 38, No. 6, Jun. 1, 2020, pp. 685-688.
Dunn,R., et al., "Home Life: Factors Structuring the Bacterial Diversity Found within and between Homes", PLOS One, vol. 8, Issue 5, May 2013.
Edwards, U., et al., "Isolation and direct complete nucleotide determination of entire genes. Characterization of a gene coding for 16S ribosomal RNA", Nucleic Acids Research 17: 7843-7853 (1989).
Elad, Y., et al.: "Control of Rhizoctonia solani in cotton by seed-coating with *Trichoderma* spp. spores", Plant and Soil, vol. 66, No. 2, Jun. 1, 1982 (Jun. 1, 1982), pp. 279-281.
Enchev, R., et al., "Protein neddylation: beyond cullin-RING ligases", (Nature Reviews: Molecular Cell Biology (2015) 16:30-44.
Engelhard, M., et al., "Preferential occurrence of diazotrophic endophytes, *Azoarcus* spp., in wild rice species and land races of Oryza sativa in comparison with moder races", Environmental Microbiology (2000) 2(2), 131-141.
Faria, M.; Wraight, S.P. Biological control of Bemisia tabaci with fungi. Crop Prot. 2001, 20, 767-778.
Fatima, Z., "Antifungal activity of plant growth-promoting rhizobacteria isolates against Rhizoctonia solani in wheat", African Journal of Biotechnology, vol. 8(2), pp. 219-225, Jan. 19, 2009, pp. 219-225.
Fiedler, Ż.; Sosnowska, D. Nematophagous fungus Paecilomyces lilacinus (Thom) Samson is also a biological agent for control of greenhouse insects and mite pests. BioControl 2007, 52, 547-558.
Freitas, R., et al.: "Cloning and characterization of a protein elicitor Sml gene from Trichoderma harzianum", Biotechnology Letters, vol. 36, No. 4, Dec. 10, 2013 (Dec. 10, 2013), pp. 783-788.
Frichot, E., et al., "Testing for Associations between loci and environmental gradients using latent factor mixed models", Mol. Biol. Evol. 30:7 1687-1699 (Year: 2013).
Gabor, J., et al., "Mycorrhizal fungi effects on nutrient composition and yield of soybean seeds," Journal of Plant Nutrition, 20:4-5, 581-591, 1997.
GenBank Accession AF394537, dated Jul. 2, 2002. (Year: 2002).
GenBank Accession No. AY148074 published Nov. 30, 2002.
GenBank Accession No. FM998026 published Feb. 10, 2011.
GenBank Accession No. KJ494315 published May 3, 2014.
GenBank Accession NR_041978, dated Aug. 8, 2011. (Year: 2011).
GenBank Accession No. KF951483, Jan. 5, 2014.
GenBank Accession No. KJ152029, May 6, 2015.
GenBank Accession No. KJ162248, Apr. 8, 2014.
GenBank Accession No. KY643705, Feb. 27, 2017.
GenEmbl Database, GenEmbl Record No. JN872548.1, 2 Pages.
Gerber, G., et al., "Inferring Dynamic Signatures of Microbes in Complex Host Ecosystems", PLOS Computational Biology 8:8 e1002624, 14 pages (Year: 2012).
Gibbs, A., et al., "Chemical Diversity: Definition and Quantification", IN Exploiting chemical diversity for drug discovery, Bartlett et al.EDS. eIBSN 978-1-84755-255-6 p. 137-160.
Giczey, G., et al.: "Homologous transformation of Trichoderma hamatum with an endochitinase encoding gene, resulting in increased levels of chitinase activity", FEMS Microbiology Letters, Jan. 1, 1998 (Jan. 1, 1998), pp. 247-252.
Girard, G., et al., "A novel taxonomic marker that discriminates between morphologically complex actinomycetes", Open Biology, vol. 3, No. 10, Oct. 2013, p. 130073,XP055675916.
Goepfert, S., et al., "Molecular Identification and Characterization of the Arabidopsis D3,5, D2,4-Dienoyl-Coenzyme A Isomerase, a Peroxisomal Enzyme Participating in the b-Oxidation Cycle of Unsaturated Fatty Acids1", Plant Physiology (2005) 138:1947-1956.

Gopalakrishnan, S. et al., "Plant growth-promoting activities of *Streptomyces* spp. In sorghum and rice", SpringerPlus, 2/1/574, pp. 1-8, http://www.springerplus.com/content/2/1/574, 2013.
Govindarajan, M. et al., "Effects of the Inoculation of Burkholderia vietnamensis and Related Endophytic Diaztrophic Bacteria on Grain Yield of Rice", Microbiol Ecology, Apr. 4, 2007, 17 Pages.
Grady, E., et al., "Current knowledge and perspectives of Paenibacillus: a review" Microb Cell Fact (2016) 15:203.
Groppe, K., et al., "Interaction between the endophytic fungus Epichloë bromicola and the grass Bromus erectus: effects of endophyte infection, fungal concentration and environment on grass growth and flowering," Mol Ecol., 8:1827-1835, 1999.
Guo, Y., et al. "A multi locus phylogeny of the Streptomyces griseus 16S rRNA gene clade: use of multilocus sequence analysis for streptomycete systematics", International Journal of Systematic and Evolutionary Microbiology, vol. 58, No. 1, 2008, pp. 149-159, XP055675936.
Halligan, B., et al., "Cloning of the murine cDNA encoding VDJP, a protein homologous to the large subunit of replication factor C and bacterial DNA ligases", GENE (1995) 217-222.
Hamayun, M., et al., "Gibberellin production and plant growth promotion from pure cultures of *Cladosporium* sp. MH-6 isolated from cucumber (*Cucumis sativus* L.)". Mycologia, 102 (5), 2010, pp. 989-995.
Harman, G.E., et al.: "Factors affecting Trichoderma hamatum applied to seeds as a biocontrol agent" , Phytopathology, Jun. 1, 1981 (Jun. 1, 1981), pp. 569-572.
Harman, G.E., et al.: "Trichoderma hamatum effects on seed and seedling disease induced in radish and pea by *Pythium* spp. or Rhizoctonia solani", Phytopathology, Dec. 1, 1980 (Dec. 1, 1980), pp. 1167-1172.
Heydari, A., "A Review on Biological Control of Fungal Plant Pathogens Using Microbial Antagonists", Journal of Biological Sciences, vol. 10 (4) 273-290 (Year: 2010).
Hill, S.T., The pursuit of hoppiness: propelling hop into the genomic era. Thesis, Oregon State University, 80 pages (Year: 2016).
Holmes, I., et al., "Dirichlet Multinomial Mixtures: Generative Models for Microbial Metagenomics", PLoSONE 7:2, e30126, 15 pages (Year: 2012).
Hoy, M.A .; Singh, R.; Rogers, M.E. Evaluations of a novel isolate of Isaria fumosorosea for control of the Asian citrus psyllid, Diaphorina citri (Hemiptera: Psyllidae). Fla. Entomol. 2010, 93, 24-32.
Hubbard, M., "Fungal Endophytes that Confer Heat and Drought Tolerance to Wheat," Doctoral dissertation, University of Saskatchewan, 2012.
Hurek, T., et al., "*Azoarcus* sp. strain BH72 as a model for nitrogen-fixing grass endophytes", Journal of Biotechnology 106 (2003) 169-178.
Ikeda, H., et al., "Complete genome sequence and comparative analysis of the industrial microorganism Streptomyces avermitilis," Nat Biotechnol. May 2003;21 (5) :526-31. Epub Apr. 14, 2003. (Year: 2003).
Iverson, C., et al., "The taxonomy of Enterobacter sakazakii: proposal of a new genus *Cronobacter* gen. nov. and descriptions of *Cronobacter sakazakii* comb. nov. *Cronobacter sakazakii* subsp. *sakazakii*, comb. nov., *Cronobacter sakazakii* subsp. *malonaticus* subsp. nov., *Cronobacter turicensis* sp. nov., *Cronobacter muytjensii* sp. nov., *Cronobacter dublinensis* sp. nov. and *Cronobacter* genomospecies I", BMC Evolutionary Biology 2007, Apr. 17, 2017, 11 pages.
Joe, M.M. et al., "Development of alginate-based aggregate inoculants of *Methylobacterium* sp. And Azospirillum brasilense tested under in vitro conditions to promote plant growth," Journal of Applied Microbiology 2013, 116(2):408-423, XP055225426, Nov. 22, 2013.
Kazemian, M., et al., "Improved accuracy of supervised CRM discovery with interpolated Markov models and cross- specieis comparison", Nucleic Acids Research, 2011, vol. 39, No. 22, 9463-9472.
Kemp, N., et al., "Sarocladium zeae is a systemic endophyte of wheat and an effective biocontrol agent against Fusarium head blight", Biological Control, vol. 149, Publication No. 104329, 10 pages (2020).

(56) References Cited

OTHER PUBLICATIONS

Kim, S., et al., "Physiological and proteomic analyses of Korean F1 maize (*Zea mays* L.) hybrids under water-deficit stress during flowering", Appl. Biol. Chem. (2019) 62:32.

Kim, Y., et al., "Deciphering the human microbiome using next-generation sequencing data and bioinformatics approaches", Methods 79-80, p52-59 (Year: 2015).

Langner Dos Santos Miriam et al.: "Benefits Associated with the Interaction of Endophytic Bacteria and Plants", Brazilian Archives of Biology and Technology, vol. 61, No. 0, Jan. 1, 2018 (Jan. 1, 2018), p. 18160431-2018.

Larran, S., et al., "Endophytes from wheat as biocontrol agents against tan spot disease", Biological Control, vol. 92, Sep. 11, 2015, pp. 17-23.

Lee, J., et al., "*Streptomyces koyangensis* sp. nov., a novel actinomycete that produces 4-phenyl-3-butenoic acid," Int J Syst Evol Microbiol. Jan. 2005; 55(Pt 1):257-62. (Year: 2005).

Li, J., et al., "Antitumour and antimicrobial activities of endophytic stretomycetes from pharmaceutical plants in rainforest", Lett Appl Microbiol. Dec. 2008; 47(6): 574-80. (Year: 2008).

Li, M., et al., "Persistent homology and the branching topologies of plants", American Journal of Botany, 104:3, 349-353 (Year: 2017).

Lind, A., et al., "Drivers of genetic diversity in secondary metabolic gene clusters within a fungal species", PLOS Biology, Nov. 17, 2017, 26 pages.

Manoharan, M. J. et al., "Survival of flocculated cells in alginate and its inoculatin effect on growth and yield of maize under water deficit conditions," EP J of Soil Biology, Gauthier-Villars, Montrouge, FR, vol. 50, Mar. 7, 2012, pp. 198-206, XP028421147.

Massol-Deya, A., et al., "Bacterial community fingerprinting of amplified 16S and 16-23S ribosomal DNA gene sequences and restriction endonuclease analysis (ARDRA)", Molecular Microbial Ecology Manual 3.3.2: 1-8, 1995.

Mehta, S., et al., "An Efficient Method for Qualitative Screening of Phosphate-Solubilizing Bacteria", Current Microbiology vol. 43 (2001), pp. 51-56.

Mezeal, I.A.; Mizil, S.N.; Hussin, M.S. Researching biocontrol of Trichoderma viride, Paecilomyces lilacinus in contradiction of effectiveness of fungi insulated as of selected therapeutic herbals. Plant Arch. 2018, 18, 1631-1637.

Minamisawa K., et al., "Anaerobic Nitrogen-Fixing Consortia Consisting of Clostridia Isolated from Gramineous Plants", Applied and Environmental Microbiology, May 2004, p. 3096-3102, vol. 70, No. 5.

Muhammad, N., et al., "Endophytes in biotechnology and agriculture", E-Cost FA1103 Working Group Meeting in Trento/S. Michele, Italy Nov. 2012. (poster).

Murali, Gopal, et al., "Microbiome Selection Could Spur Next-Generation Plant Breeding Strategies," Frontiers in Microbiology, vol. 7, Dec. 7, 2016, XP055531064.

Naveed, M., et al., "The endophyte *Enterobacter* sp. FD17: a maize growth enhancer selected based on rigorous testing of plant beneficial traits and colonization characteristics", Biol Fertil Soils (2014) 50:249-262.

NCBI GenBank: Accession No. XP55670271, "*Enterobacter* sp. MLB05 16S ribosomal RNA gene, partial sequence—Nucleotide", Jun. 9, 2012, 1 Page, can be retreived at URL:https://www.ncbi.nlm.nih.gov/nuccore/JQ765415.1/.

NCBI GenBank: Accession No. XP55670274, "*Enterobacter* sp. CR 6-3 16S ribosomal RNA gene, partial sequence—Nucleotide", Mar. 27, 2013, 1 Page, can be retreived at URL:https://www.ncbi.nlm.nih.gov/nuccore/KC355340.

NCBI GenBank: Accession No. XP55670279, "Uncultured bacterium clone bb2s4 16S ribosomal RNA gene, partial seque - Nucleotide", May 6, 2005, 1 Page, can be retreived at URL:https://www.ncbi.nlm.nih.gov/nuccore/DQ068880.

Ngom, A et al., "A novel symbiotic nitrogen-fixing member of the Ochrobactrum clade isolated from root nodues of Acacia mangium". J. Gen. Appl. Microbiol. (2004) 50: 17-27.

Orakç Ge et al., "Selection of antagonistic actinomycete isolates as biocontrol agents against root-rot fungi", Fresenius Environmental Bulletin, 2010, 19: 417-424 & GenBank Accession No. GQ475299, Oct. 5, 2009.

Pacovsky, R., "Carbohydrate, protein and amino acid status of Glycine-Glomus-Bradyrhizobium symbioses," Physiologia Pantarium; 75:346-354, 1989).

Pan, J., et al., "Effects of host plant environment and Ustilago maydis infection on the fungal endophyte community of maize (*Zea mays*)", New Phytologist, vol. 178, pp. 147-156 (2008).

Panyasiri, C.; Attathom, T.; Poehling, H.M. Pathogenicity of entomopathogenic fungi-potential candidates to control insect pests on tomato under protected cultivation in Thailand. J. Plant Dis. Prot. 2007, 114, 278- 287.

Paul, N.C.; Deng, J.X.; Lee, J.H.; Yu, S.H. New records of endophytic Paecilomyces inflatus and Bionectria ochroleuca from chili pepper plants in Korea. Mycobiology 2013, 41, 18-24.

Peiffer, J., et al., "The Genetic Architecture of Maize Height", Genetics, vol. 196, p. 1337-1356 (Year: 2015).

Perveen, Z.; Shahzad, S.A. Comparative study of the efficacy of Paecilomyces species against root-knot nematode Meloidogyne incognita. Pak. J. Nematol. 2013, 31, 125-131.

Pitkowski, J.; Krzyzewska, U.; Nawrot, U. Antifungal activity of enthomopathogenic species of the genus Paecilomyces. Mikol. Lek. 2003, 10, 93-99 (with copy of abstract).

Prischl, M., et al., "Genetically modified Bt maize lines containing cry3Bb1, cry1A105 or cry1Ab2 do not affect the structure and functioning of root-associated endophyte communities", Applied Soil Ecology 54 (2012) 39-48.

Proença Diogo Neves et al.: "*Chitinophaga costaii* sp. nov., an endophyte of Pinus pinaster, and emended description of Chitinophaga niabensis", International Journal of Systematic and Evolutionary Microbiology, vol. 64, No. Pt_4, Apr. 1, 2014 (Apr. 1, 2014), pp. 1237-1243.

Rashid, M., et al., "Inorganic polyphosphate is needed for swimming, swarming, and twitching motilities of Pseudomonas aeruginosa", PNAS vol. 97, No. 9, Apr. 25, 2000, pp. 4885-4890.

Ratnalikar, K.K. et al., "Biological management of root-rot of cotton caused by Rhizoctonia bataticola," Indian Phytopathol. 44-45, Suppl., XV, 1993, pp. 1-2.

Result 11 from a search in the GenEmbl database, GenEmbl Record No. EU 977189, Smith et al., "Bioactive endophytes warrant intensified exploration and conservation," PLoS ONE 3(8):E3052, 2008.

Result 3 from a search in the GenEmbl database, GenEmbl Record No. KF011597, Paenibacillus strain No. HA13, Park et al., "Isolation and characterization of humic substances-degrading bacteria from the subarctic Alaska grasslands," J Basic Microbiol, 2013.

Sarangi, S., et al., "Agricultural Activity Recognition with Smartshirt and Crop Protocol", IEEE global humanitarian technology conference, p. 298-305 (Year: 2015).

Sato, I., et al., "Suppressive Potential of Paenibacillus Strains Isolated from the Tomato Phyllosphere against Fusarium Crown and Root Rot of Tomato", Microbes Environ, vol. 29, No. 2, 168-177, 2014.

Schuerger, A., "Microbial Ecology of a Crewed Rover Traverse in the Arctic: Low Microbial Dispersal and Implications for Planetary Protection on Human Mars Missions", Astrobiology, vol. 15, No. 6, 2015, pp. 478-491.

Seghers, D., et al., "Impact of Agricultural Practices on the *Zea mays* L. Endophytic Community", Applied and Environmental Microbiology, Mar. 2004, p. 1475-1482, vol. 70, No. 3.

Sessitsch, A., et al., "Cultivation-independent poplulation analysis of bacterial endophytes in three potato varieties based on eubacterial and Actinomycetes-specific PCR of 16S rRNA genes", FEMS Microbiology Ecology 39 (2002) 23-32.

Sessitsch, A., et al., "Endophytic bacterial communities of field-grown potato plants and their plant-growth-promoting and antagonistic abilities", Can. J. Microbiol. 50: 239-249 (2004).

Sessitsch, A., et al., "Functional Characteristics of an Endophyte Community Colonizing Rice Roots as Revealed by Metagenomic Analysis", MPMP vol. 25, No. 1, 2012, pp. 28-36.

(56) References Cited

OTHER PUBLICATIONS

Sha, T. et al., "Genetic diversity of the endemic gourmet mushroom Thelephora ganbajun from southwestern China", Microbiology (2008), 154, 3460-3468.
Shupeng, T., et al. "Advances in Study of Interactions between Mycorrhizal Fungi and Bacteria", Journal of Qingdao Agricultural University (Natural Science Edition), vol. 30, Issue 4, pp. 240-246, Dec. 31, 2013.
Sivakumar, T.; Eswaran, A.; Balabaskar, P. Bioefficacy of antagonists against for the management of *Fusarium oxysporum* f. sp. lycopersici and Meloidogyne incognita disease complex of tomato under field condition. Plant Arch. 2008, 8, 373-377 (with copy of abstract).
Soe, K.M, et al., "Evaluation of effective Myanmar Bradyrhizobium strains isolated from Myanmar soybean and effects of coinoculation with Streptomyces griseoglavus P4 for nitrogen fixation", Soil science and plant nutrition 59.3 (2013): 361-370 (Year: 2013).
Sugita, T. et al., "Intraspecies Diversity of Cryptococcus laurentii as Revealed by Sequences of Internal Transcribed Spacer Regions and 28S rRNA Gene and Taxonomic Position of C. laurentii Clinical Isolates", Journal of Clinical Microbiology, Apr. 2000, p. 1468-1471.
Sulistiyani, et al., "Population and Diversity of Endophytic Bacteria Associated with Medicinal Plan Curumma zedoaria ", Microbiology Indonesia 8.2 (2014):4.
Thomas, P., et al.: "Endophytic Bacteria Associated with Growing Shoot Tips of Banana (*Musa* sp.) cv. Grand Naine and the Affinity of Endophytes to the Host", Microbial Ecology, Springer-Verlag, NE, vol. 58, No. 4, Jul. 25, 2009 (Jul. 25, 2009), pp. 952-964, XP019757395, ISSN: 1432-184X, DOI: 10.1007 /S00248-009-9559-Z.
Timmusk, S., "Paenibacillus polymyxa antagonizes oomycete plant pathogens Phytophthora palmivora and Pythium aphanidermatum", Journal of Applied Microbiology, GB, vol. 105, No. 5, Jan. 5, 2009, pp. 1473-1481.
Trujillo, M.E et al., "Nodulation of Lupinus albus by strins of *Ochrobactrum lupini* sp. nov." Appl. Environ Microbiol Mar. 2005; 71(3): 1318-1327.
Wang, L. et al. Application of Bioorganic Fertilizer Significantly Increased Apple Yields and Shaped Bacterial Community Structure in Orchard Soil.
Whelehan, et al., "Microencapsulation using vibrating technology," Journal of Microencapsulation 2011, vol. 28(8), pp. 669-688.
Wicklow, D., et al., "A protective endophyte of maize: Acremonium zeae antibiotics inhibitory to Aspergillus flavus and Fasarium verticillioides", Mycol. Res. 109 (5):610-618 (May 2005).
Wicklow, D., et al., "Occurrence of pyrrocidine and dihydroresorcylide production among Acremonium zeae populations from maize grown in different regions", Canadian Journal of Plant Pathology, vol. 30, pp. 425-433 (2008).
Wiebold, M., et al., "Agriculture Experiment Station, College of Agriculture, Food & Natural Resources, University of Missouri, Special Report 589, pp. 1-124)."
Yeh, J.H., "Protein Remote Homology Detection Based on Latent Topic Vector Model", International conference on Networking and information technology, p. 456-460, (Year: 2010).
Yeo, H.; Pell, J.K.; Alderson, P.G.; Clark, S.J.; Pye, B.J. Laboratory evaluation of temperature effects on the germination and growth of entomopathogenic fungi and on their pathogenicity to two aphid species. Pest Manag. Sci. 2003, 59, 156-165.
Yuan, J., et al., "Roots from distinct plant developmental stages are capable of rapidly selecting their own microbiome without the influence of environmental and soil edaphic factors", Soil Biology and Biochemistry 89 (2015): 206-209.
Zhao, Jun, et al., "Effects of organic-inorganic compound fertilizer with reduced chemical fertilizer application on crop yields, soil biological activity and bacterial community structure in a rice-wheat cropping system," Applied Soil Ecology, vol. 99, Nov. 28, 2015, pp. 1-12, XP055530937.

\* cited by examiner

FUNGAL ENDOPHYTES FOR IMPROVED CROP YIELDS AND PROTECTION FROM PESTS

CROSS REFERENCE TO RELATED APPLICATIONS

This application claims priority to Provisional Application No. 62/438,966, filed Dec. 23, 2016; Provisional Application No. 62/546,959, filed Aug. 17, 2017; and Provisional Application No. 62/567,113, filed Oct. 2, 2017, the disclosures of which are incorporated by reference in their entirety.

SEQUENCE LISTING

The instant application contains a Sequence Listing with 115 sequences which has been submitted via EFS-Web and is hereby incorporated by reference in its entirety. Said ASCII copy, created on Dec. 20, 2017, is named 39063_61001_Sequence_Listing.txt, and is 97,593 bytes in size.

FIELD OF THE INVENTION

The present invention relates to fungal endophytes of agricultural crops for improving yield and/or for protection from pests.

BACKGROUND OF THE INVENTION

Fungal endophytes are fungi that internally colonize plant tissues without causing evident damage or disease. Particular fungal endophytes, such as mycorrhiza, survive within various host plant tissues, often colonizing the intercellular spaces of host leaves, stems, flowers or roots. The symbiotic endophyte-host relationships can provide several fitness benefits to the host plant, such as enhancement of nutrition, and/or increased drought tolerance. Root-colonizing mycorrhizae survive on photosynthetic carbohydrates from the plant, and in return, aid in the solubilization and uptake of water and minerals to the host, which can lead to the promotion of seed germination and plant growth. Additionally, the association of a fungal endophyte with a host plant can provide tolerance to a variety of biotic and abiotic stresses. Host growth, fitness promotion and protection are thought to be achieved through multiple beneficial properties of the endophyte-host association. For instance, the endophytic organisms may produce growth-regulating substances to induce biomass production and alkaloids or other metabolites. Additionally, fungal endophytes may directly suppress or compete with disease-causing microbes, protecting the plant from potential pathogens.

SUMMARY OF THE INVENTION

In some embodiments, the invention described herein provides a synthetic composition, comprising a plant element and at least one fungal endophyte selected from Table 3, wherein the fungal endophyte is capable of improving plant tolerance to biotic stress as compared to a reference plant element not further comprising the endophyte.

In some embodiments, the invention described herein provides a synthetic composition, comprising: a) a fungal endophyte comprising at least one endophyte from Table 3; and b) at least one carrier, wherein the fungal endophyte is in contact with the carrier; and wherein the fungal endophyte, when heterologously disposed to a plant element, is capable of improving plant tolerance to biotic stress as compared to a reference plant element not further comprising the endophyte. In some embodiments, the carrier comprises alginic acid, carrageenan, dextrin, dextran, pelgel™, polyethelene glycol, polyvinyl pyrrolidone, methyl cellulose, polyvinyl alcohol, gelatin, or combinations thereof. In some embodiments, the synthetic composition further comprises water, a detergent, an insecticide, a fungicide, or combinations thereof. In some embodiments, the weight ratio between fungal endophyte and carrier is 1:1-10, 1:10-50, 1:50-100, 1:100-500, 1:500-1000, or 1:1000-5000. In some embodiments, the synthetic composition is a fluid or a powder. In some embodiments of any of the compositions described herein, the composition comprises at least 1, 2, 3, 4, 5, 6, 7, 8, 9, 10, 11, 12, 13, 14, 15, 16, 17, 18, 19, or 20 endophytes. In some embodiments of any of the compositions described herein, the fungal endophyte comprises fungal spores. In some embodiments, the fungal spores are present in about $10^2$, $10^3$, $10^4$, $10^5$, $10^6$, $10^7$, $10^8$, or $10^9$ colony forming units per gram or spores per gram. In some embodiments of any of the compositions provided herein, the composition further comprises a plant element. In some embodiments, the plant element is a dicot. In some embodiments, the dicot is soybean. In some embodiments, the dicot is cotton. In some embodiments, the plant element is a seed. In some embodiments of any of the synthetic compositions provided herein, the fungal endophyte is heterologously disposed to a seed in a seed coating. In some embodiments, the plant element comprises leaf tissue. In some embodiments of any of the synthetic compositions provided herein, the fungal endophyte is heterologously disposed to a leaf in a foliar spray or powder. In some embodiments, the plant element comprises root tissue. In some embodiments of any of the synthetic compositions provided herein, the fungal endophyte is heterologously disposed to a root in a root drench or soil treatment.

In some embodiments of any of the synthetic compositions provided herein, the at least one fungal endophyte is selected from the group consisting of: *Cladosporium, Alternaria, Bipolaris, Chaetomium, Verticillium, Preussia, Pleospora, Epicoccum*, or combinations thereof. In some embodiments, the fungal endophyte comprises a nucleic acid sequence that is at least 97% identical to a nucleic acid sequence selected from the group consisting of SEQ ID NOs: SEQ ID NOs: 26-115.

In some embodiments, the invention described herein provides a synthetic composition comprising a fungal endophyte capable of improving plant tolerance to biotic stress, wherein the biotic stress is caused by a nematode, an aphid, a fleahopper, a *lygus* bug, a stink bug, a soy looper, a cabbage looper, a fungus, or combinations thereof. In some embodiments, the biotic stress is caused by root knot nematode. In some embodiments, biotic stress is caused by reniform nematode. In some embodiments, biotic stress is caused by a Lepidoptera larvae. In some embodiments, the biotic stress is caused by a Lepidoptera larvae of the family Noctuidae. In some embodiments, the biotic stress is caused by *Chrysodeixis includens*. In some embodiments, the biotic stress is caused by *Trichoplusia ni*. In some embodiments, the biotic stress is caused by a Hemiptera insect. In some embodiments, the biotic stress is caused by *Nezara viridula*. In some embodiments, the biotic stress is caused by *Lygus hesperus*. In some embodiments, the biotic stress is caused by *Aphis gossypii*. In some embodiments, the biotic stress is caused by a fungi of the genus *Rhizoctonia*. In some embodiments, the biotic stress is caused by *Rhizoctonia solani*. In some embodiments, the biotic stress is caused by a fungi of the genus *Fusarium*. In some embodiments, the biotic stress is *Fusarium virguliforme*. In some embodiments, the biotic stress is caused by *Fusarium oxysporum*. In some embodiments, the biotic stress is caused by a plant pest or pathogen and improved plant tolerance is demonstrated by at least increased emergence, increased stand, increased survival, increased plant height, increased shoot biomass, increased root biomass, decreased disease score, increased leaf area, decreased pest abundance, decreased pest biomass, increased yield, improved vigor, or improved resistance to pathogenic bacteria, fungi or viruses. In some embodiments, the pest is of an order selected from the group consisting of: Lepidoptera, Hemiptera, or Tylenchida. In some embodiments, the pathogen is of a genus selected from the group consisting of: *Fusarium* or *Rhizoctonia*.

In some embodiments, the invention described herein provides a method of improving a plant phenotype, comprising inoculating plant elements with a formulation comprising a fungal endophyte heterologously disposed to the plant elements, wherein: a) the fungal endophyte is selected from Table 3; b) a phenotype is improved as compared to plant elements of reference plants not inoculated with the formulation; and c) the plant phenotype is selected from the group consisting of: increased disease resistance, increased pest resistance, increased herbivore resistance, increased resistance to a fungal pathogen, increased resistance to a bacterial pathogen, increased resistance to a viral pathogen, increased resistance to a nematode, increased insect resistance, increased leaf area in the presence of a biotic stressor, increased yield in the presence of a biotic stressor, or combinations thereof. In some embodiments, the plant phenotype is increased yield in the presence of a biotic stressor and the increase of yield is at least about 1%, 2%, 3%, 4%, 5%, 10%, 15%, 20%, or 25%. In some embodiments, the plant phenotype is leaf area is at least about 5%, 15%, 20%, or 25%.

In some embodiments, the invention described herein provides a method for reducing damage due to biotic stress, comprising inoculating plant elements with a formulation comprising a fungal endophyte heterologously disposed to the plant elements, wherein the fungal endophyte comprises a nucleic acid sequence having at least 97% identity to a nucleic acid sequence selected in Table 3, wherein damage due to biotic stress is reduced as compared to plant elements of reference plants not inoculated with the formulation. In some embodiments, the crop is cotton and the reduction of damage comprises reduced boll damage. In some embodiments, the reduction of boll damage comprises a decrease in the loss of bolls of about 1%, 2%, 3%, 4%, 5%, 10%, 15%, 20%, 30%, 40%, or 45%. In some embodiments, the reduction of damage comprises increased leaf area of about 5%, 10%, 15%, 20%, 30%, 40%, or 45%. In some embodiments, the reduction of damage improves yield as compared to reference plants not inoculated with the formulation.

In some embodiments, the invention described herein provides a method for treating biotic stress, comprising inoculating plant elements with a formulation comprising a fungal endophyte heterologously disposed to the plant elements, wherein the fungal endophyte comprises a nucleic acid sequence having at least 97% identity to a nucleic acid sequence selected in Table 3, wherein the fungal endophyte is capable of improving tolerance to biotic stress in the plants comprising or derived from the inoculated plant elements compared to plants comprising or derived from reference plant elements not inoculated with the formulation.

In some embodiments, the invention described herein provides a method for preventing pest infestation, comprising inoculating plant elements with a formulation comprising a fungal endophyte heterologously disposed to the plant elements, wherein the fungal endophyte is selected from Table 3, wherein pests are less abundant on the plants comprising or derived from the inoculated plant elements compared to plants comprising or derived from reference plant elements not inoculated with the formulation.

In some embodiments, the invention described herein provides a method for preventing pest infestation, comprising inoculating plant elements with a formulation comprising a fungal endophyte heterologously disposed to the plant elements, wherein the fungal endophyte is selected from Table 3, wherein pests are smaller on the plants comprising or derived from the inoculated plant elements compared to plants comprising or derived from reference plant elements not inoculated with the formulation.

In some embodiments of any of the methods described herein, the fungal endophyte is selected from the group consisting of: *Cladosporium, Alternaria, Bipolaris, Chaetomium, Verticillium, Preussia, Pleospora, Epicoccum*, or combinations thereof.

In some embodiments of any of the methods described herein, the fungal endophyte comprises a nucleic acid sequence that is at least 97% identical to a nucleic acid sequence selected from the group consisting of SEQ ID NOs: 26-115. In some embodiments of any of the methods described herein, the formulation comprises at least 1, 2, 3, 4, 5, 6, 7, 8, 9, 10, 11, 12, 13, 14, 15, 16, 17, 18, 19, or 20 endophytes. In some embodiments of any of the methods described herein, the plant element is a seed. In some embodiments of any of the methods described herein, the plant element is a dicot. In some embodiments of any of the methods described herein, the dicot is soybean. In some embodiments of any of the methods described herein, the dicot is cotton. In some embodiments of any of the methods described herein, the method further comprises sterilizing the seeds to remove microorganisms prior to combining the seeds with the endophyte composition.

In some embodiments of any of the methods described herein for treating or preventing biotic stress, reducing plant damage due to biotic stress, or improving a plant phenotype of a plant experiencing biotic stress, the biotic stress is caused by a nematode, an aphid, a fleahopper, a *lygus* bug, a stink bug, a soy looper, a cabbage looper, a fungus, or combinations thereof. In some embodiments the biotic stress is caused by root knot nematode. In some embodiments the biotic stress is caused by reniform nematode. In some embodiments the biotic stress is caused by a Lepidoptera larvae. In some embodiments the biotic stress is caused by a Lepidoptera larvae of the family Noctuidae. In some embodiments the biotic stress is caused by *Chrysodeixis includens*. In some embodiments the biotic stress is caused by *Trichoplusia ni*. In some embodiments the biotic stress is caused by a Hemiptera insect. In some embodiments the biotic stress is caused by *Nezara viridula*. In some embodiments the biotic stress is caused by *Lygus Hesperus*. In some embodiments the biotic stress is caused by *Aphis gossypii*. In some embodiments the biotic stress is caused by a fungi of the genus *Rhizoctonia*. In some embodiments the biotic stress is caused by *Rhizoctonia solani*. In some embodiments the biotic stress is caused by a fungi of the genus *Fusarium*. In some embodiments the biotic stress is caused by *Fusarium virguliforme*. In some embodiments the biotic stress is caused by *Fusarium oxysporum*.

Figure 68:
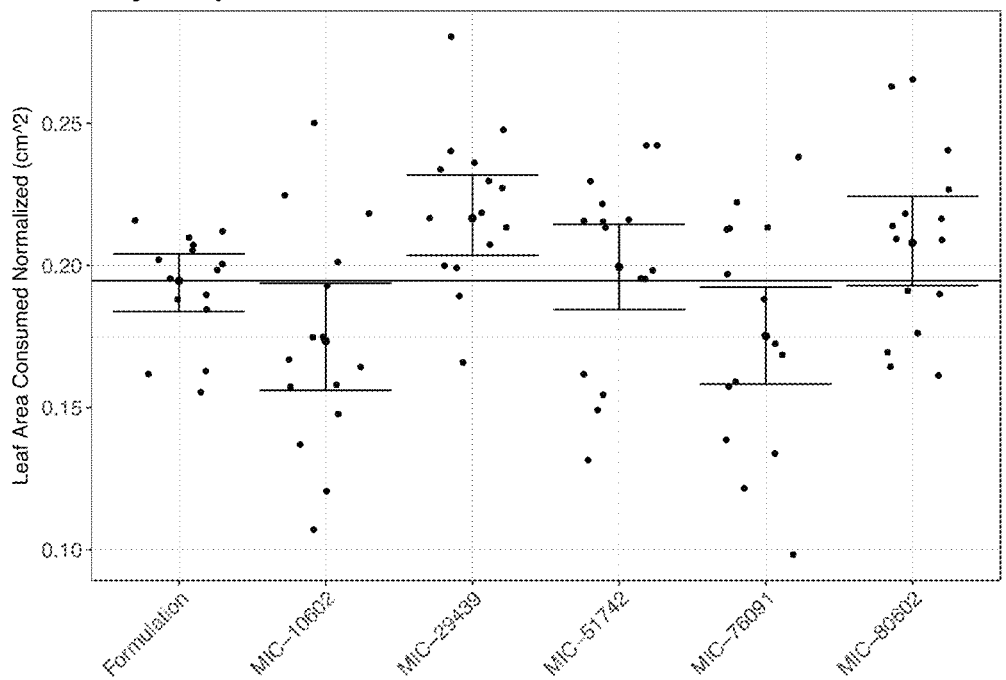

FIG. 68. Leaf area consumed (cm^2) as assessed normalized by average larval weight (mg) after 7 days of herbivory by soy looper larvae on a soy leaflet grown from seeds treated with fungal endophytes MIC-76091 (TAM00194), MIC-29439 (TAM00201), MIC-10602 (TAM00248), MIC-80602 (TAM00249), or MIC-51742 (TAM00251). GH3—This round received 3 larvae per leaflet and larvae were transferred to a fresh leaflet from the same plant after 5 days. n=15 plants per treatment.

Figure 69:
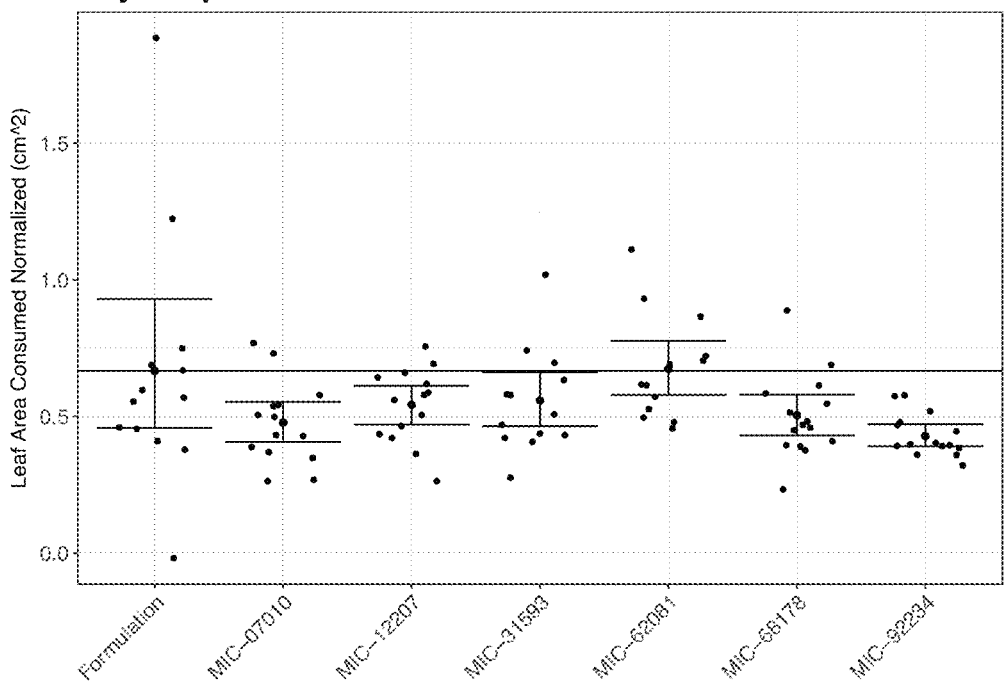

FIG. 69. Leaf area consumed (cm^2) as assessed normalized by average larval weight (mg) after 7 days of herbivory by soy looper larvae on a soy leaflet grown from seeds treated with fungal endophytes MIC-92234 (TAM00013), MIC-68178 (TAM00032), MIC-62081 (TAM00103), MIC-07010 (TAM00105), MIC-31593 (TAM00189), or MIC-12207 (TAM00296). GH6—This round received 3 larvae per leaflet and larvae were transferred to a fresh leaflet from the same plant after 5 days. n=15 plants per treatment.

Figure 70:
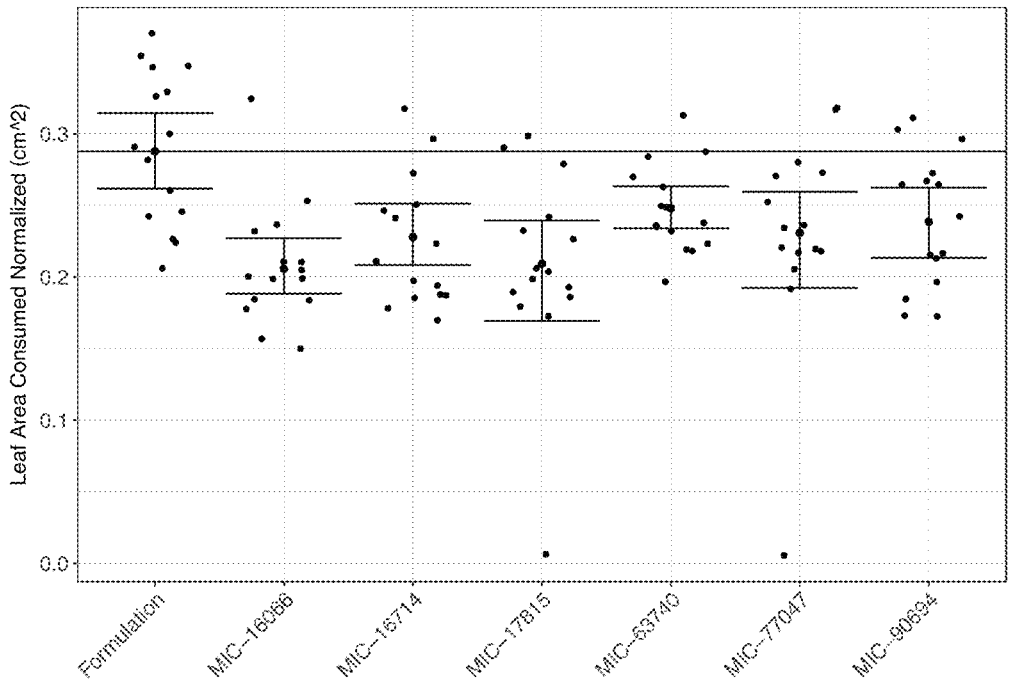

FIG. 70. Leaf area consumed (cm^2) as assessed normalized by average larval weight (mg) after 7 days of herbivory by soy looper larvae on a soy leaflet grown from seeds treated with fungal endophytes MIC-90694 (TAM00046), MIC-77047 (TAM00100), MIC-63740 (TAM00504), MIC-17815 (TAM00518), MIC-16714 (TAM00531), or MIC-16066 (TAM00536). GH8—This round received 3 larvae per leaflet and larvae were transferred to a fresh leaflet from the same plant after 5 days. n=15 plants per treatment.

Figure 71:
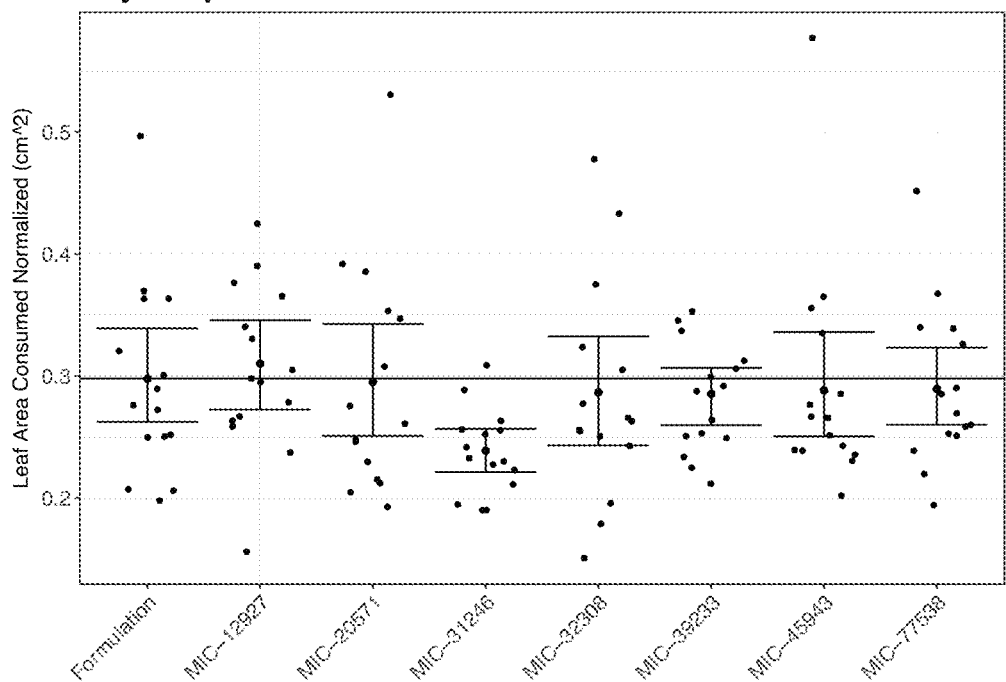

FIG. 71. Leaf area consumed (cm^2) as assessed normalized by average larval weight (mg) after 7 days of herbivory by soy looper larvae on a soy leaflet grown from seeds treated with fungal endophytes MIC-20571 (TAM00160), MIC-12927 (TAM00193), MIC-39233 (TAM00323), MIC-45943 (TAM00362), MIC-77538 (TAM00439), MIC-32308 (TAM00473), or MIC-31246 (TAM00501). GH9—This round received 3 larvae per leaflet and larvae were transferred to a fresh leaflet from the same plant after 5 days. n=15 plants per treatment.

Figure 72:
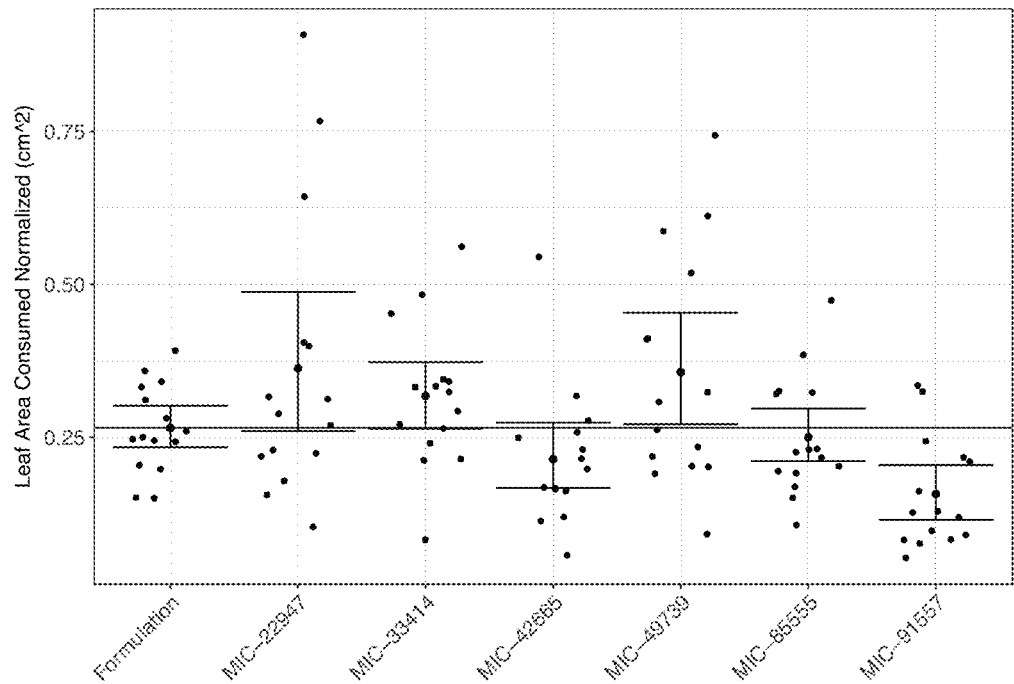

FIG. 72. Leaf area consumed (cm^2) as assessed normalized by average larval weight (mg) after 7 days of herbivory by soy looper larvae on a soy leaflet grown from seeds treated with fungal endophytes MIC-85555 (TAM00074), MIC-91557 (TAM00463), MIC-42665 (TAM00524), MIC-49739 (TAM00533), MIC-33414 (TAM00554), or MIC-22947 (TAM00559). GH10—This round received 3 larvae per leaflet and larvae were transferred to a fresh leaflet from the same plant after 5 days. n=15 plants per treatment.

Figure 73:
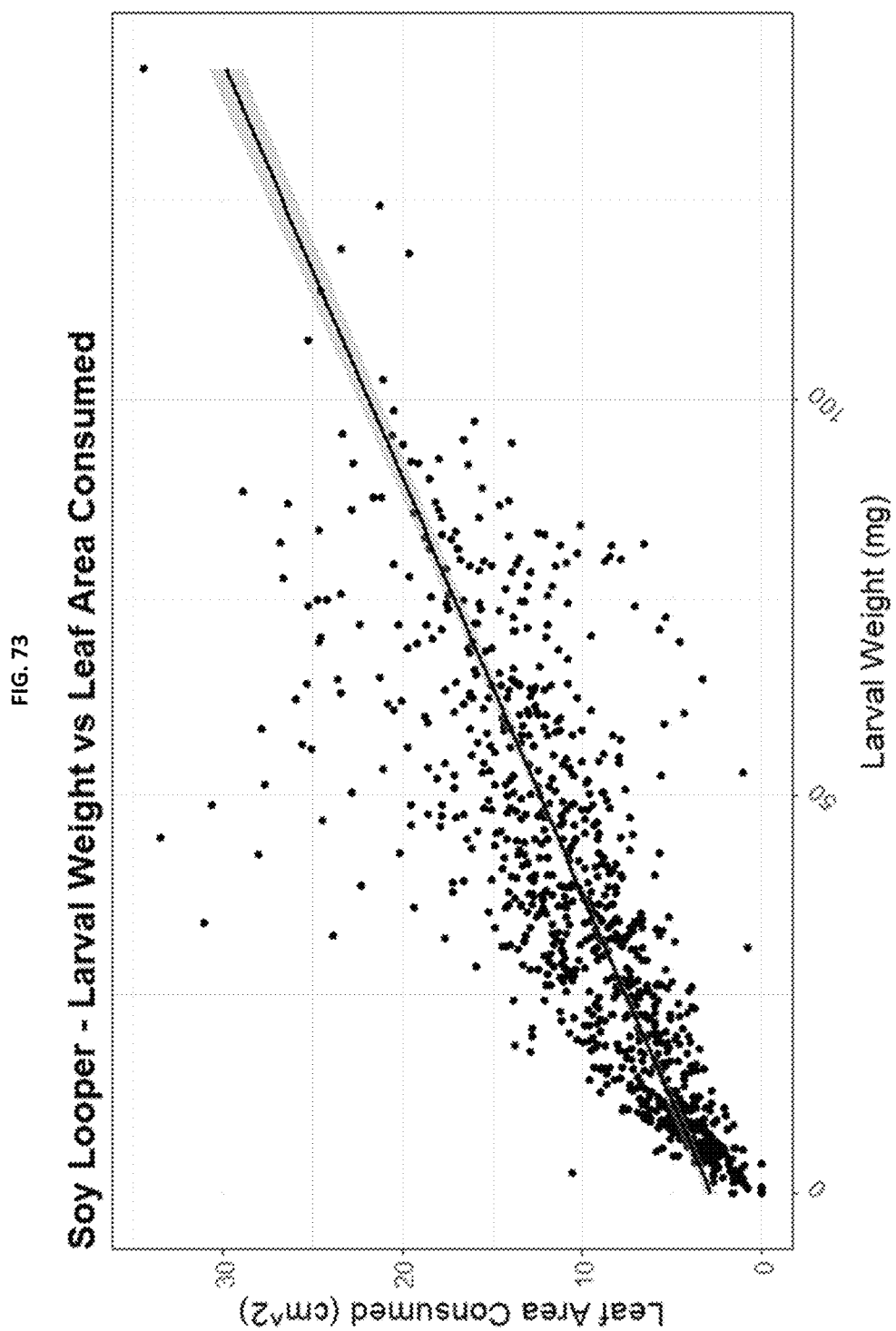

FIG. 73. Relationship between soy looper larval weight and leaf area consumed, data from all rounds of the assay are shown.

Figure 74A:
Figure 74B:
Figure 74C:
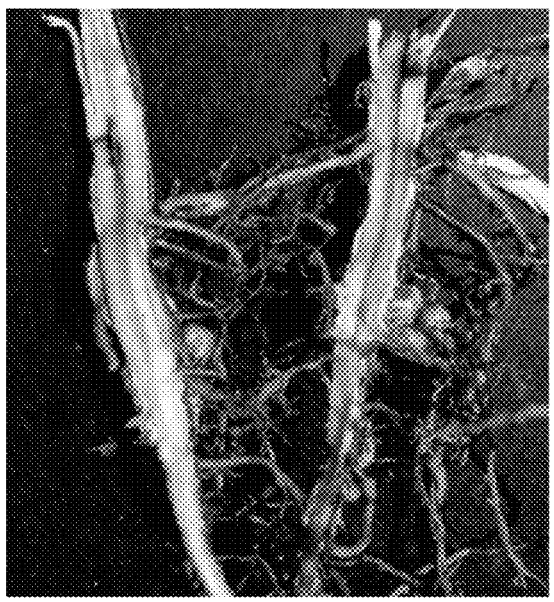
Figure 74D:

FIG. 74A, FIG. 74B, FIG. 74C, AND FIG. 74D. Exemplary photographs showing disease rating at a 0-3 scale (3 denotes strong disease symptoms) using the split-root scoring system at 45 days post planting are shown. FIG. 74A shows an exemplary photo of a healthy root showing no disease symptoms which would receive a "0" rating. FIG. 74B shows an exemplary photo of a root showing mild disease symptoms which would receive a "1" rating. FIG. 74C shows an exemplary photo of a root showing mild disease symptoms which would receive a "2" rating. FIG. 74D shows an exemplary photo of a root showing strong disease symptoms which would receive a "3" rating.

Figure 75:
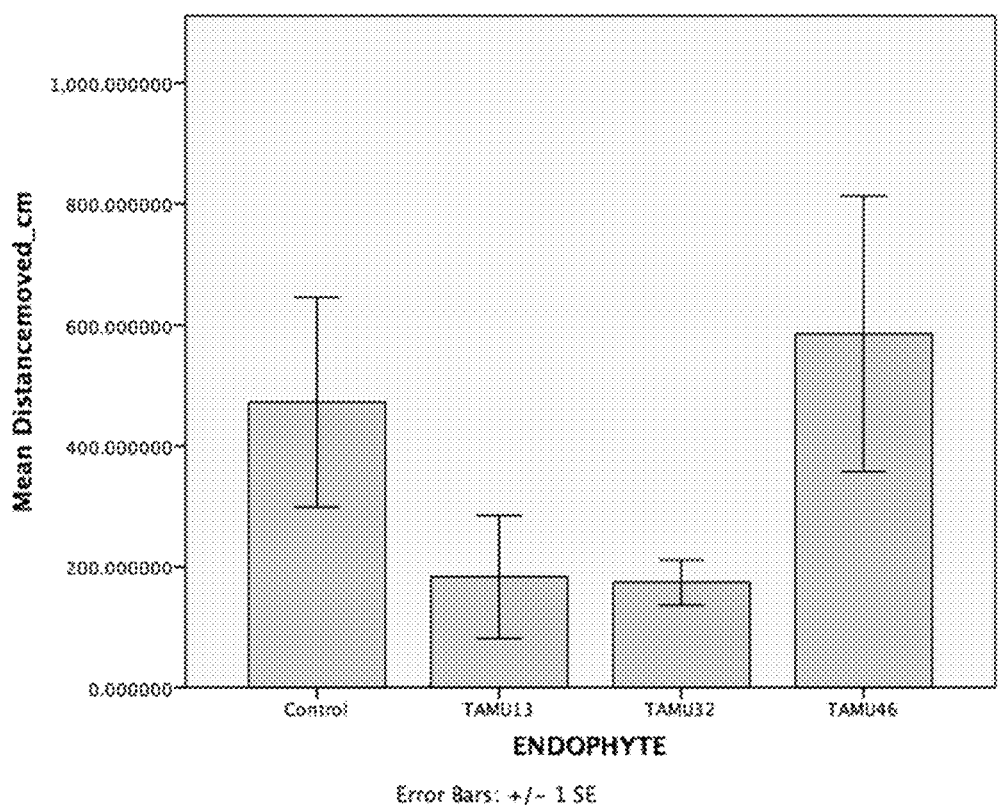

FIG. 75. This figure shows the mean distance moved by Southern Green Stink Bugs (*Nezara viridula*) when in closed containers with cotton bolls collected from endophyte treated and reference ("control") plants, as captured during the 6 hour observation period in video behavior assays described in Example 11. Stink bugs in the presence of cotton bolls from plants treated with MIC-92234 (TAM00013) and MIC-68178 (TAM00032), on average, moved shorter distances during the observation period than did stink bugs in the presence of untreated reference plants.

Figure 76:
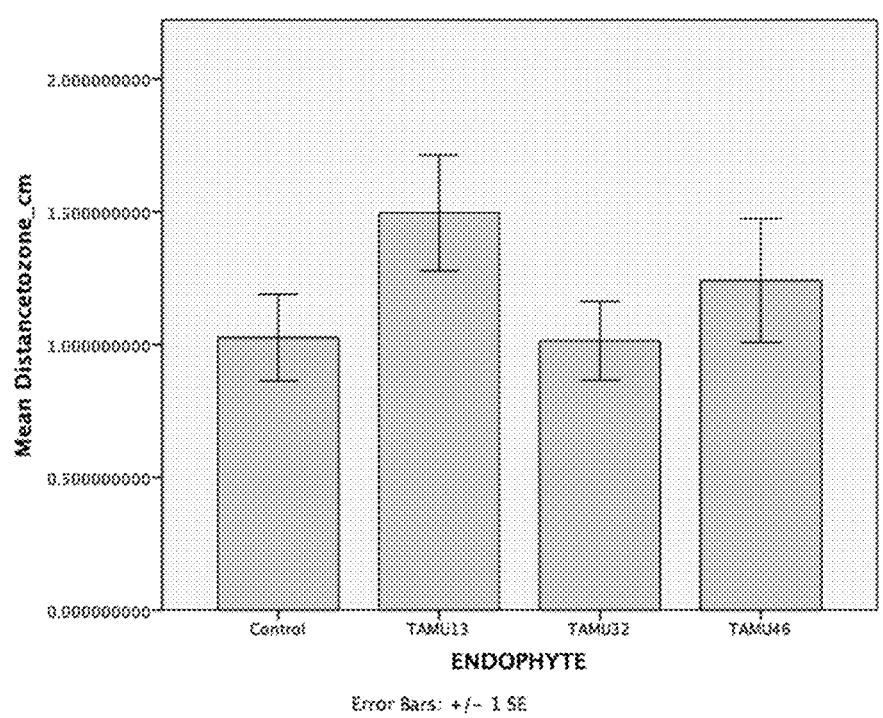

FIG. 76. This figure shows the mean distance of Southern Green Stink Bugs (*Nezara viridula*) from the boll when in closed containers with cotton bolls collected from endophyte treated and reference ("control") plants, as captured during the 6 hour observation period in video behavior assays described in Example 11. Stink bugs in the presence of cotton bolls from plants treated with MIC-92234 (TAM00013) and MIC-90694 (TAM00046), on average, stayed farther away from the boll than stink bugs in the presence of untreated reference plants.

Figure 77:
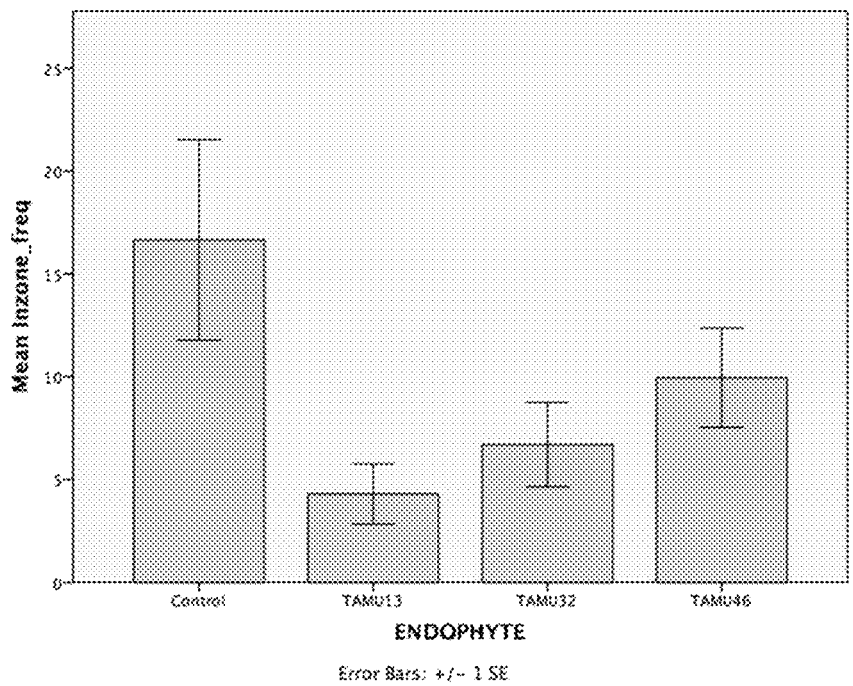

FIG. 77. This figure shows the mean frequency of Southern Green Stink Bugs (*Nezara viridula*) coming in contact with or in direct proximity (within 0.5 cm) to the boll when in closed containers with cotton bolls collected from endophyte treated and reference ("control") plants, as captured during the 6 hour observation period in video behavior assays described in Example 11. Stink bugs in the presence of cotton bolls from plants treated with MIC-92234 (TAM00013), MIC-68178 (TAM00032) and MIC-90694 (TAM00046), on average, had less frequent contact with the boll zone than stink bugs in the presence of untreated reference plants.

Figure 78:
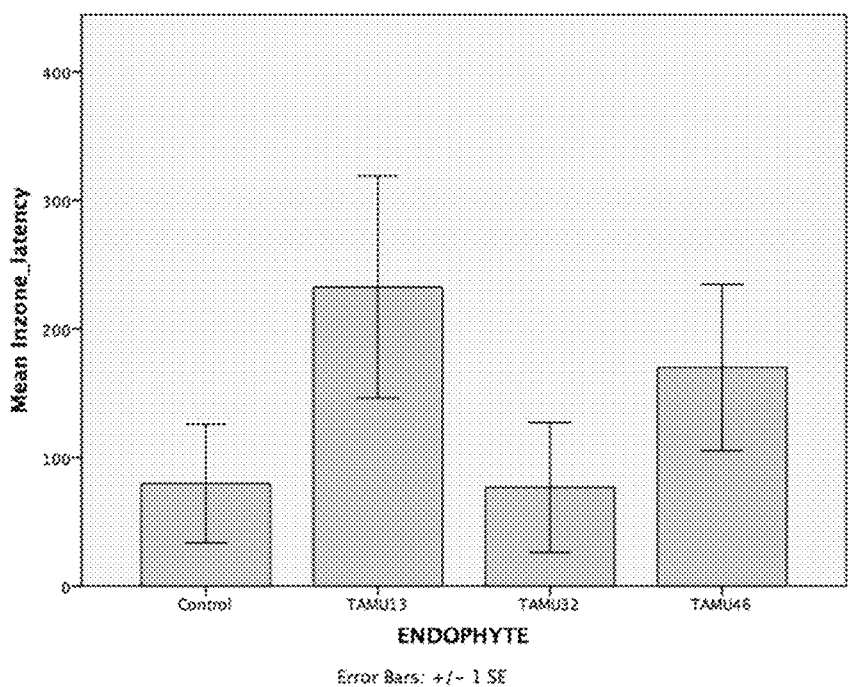

FIG. 78. This figure shows the mean time until first contact with the boll by Southern Green Stink Bugs (*Nezara viridula*) when in closed containers with cotton bolls collected from endophyte treated and reference ("control") plants, as captured during the 6 hour observation period in video behavior assays described in Example 11. Stink bugs in the presence of cotton bolls from plants treated with MIC-92234 (TAM00013) and MIC-90694 (TAM00046), on average, took more time to make first contact with the boll than stink bugs in the presence of untreated reference plants. Each 1 increment on the y-axis represents 20 seconds.

Figure 79:
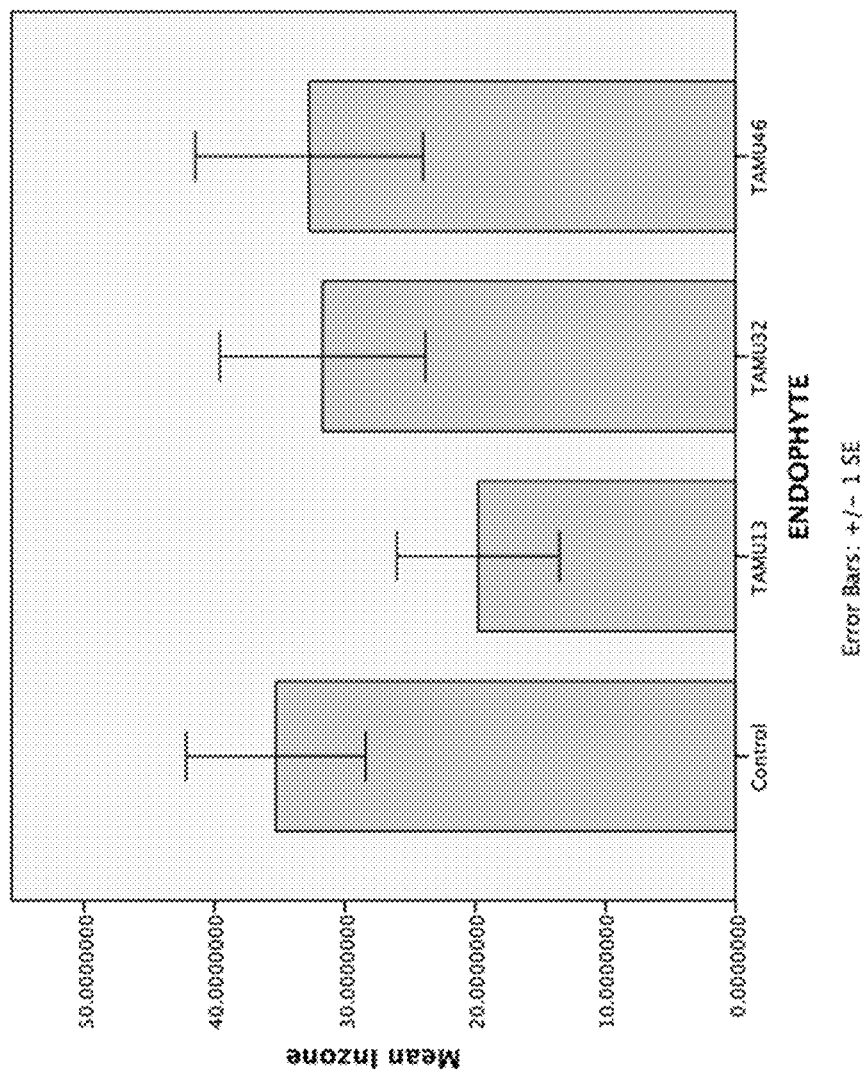

FIG. 79. This figure shows the mean percent of the 6 hour observation period that Southern Green Stink Bugs (*Nezara viridula*) spent in contact with or in direct proximity of the boll when in closed containers with cotton bolls collected from endophyte treated and reference ("control") plants, as captured during the video behavior assays described in Example 11. Stink bugs in the presence of cotton bolls from plants treated with MIC-92234 (TAM00013), on average, spent less than 20% of the observation period on or in the direct proximity of the boll. In contrast, stink bugs in the presence of untreated reference plants spent, on average, more than 35% of the observation period on or in the direct proximity of the boll. Insects in direct proximity of the boll are within the region directly surrounding the boll referred to as the "boll zone"; the boll zone is depicted in FIG. 80 B.

Figure 80:
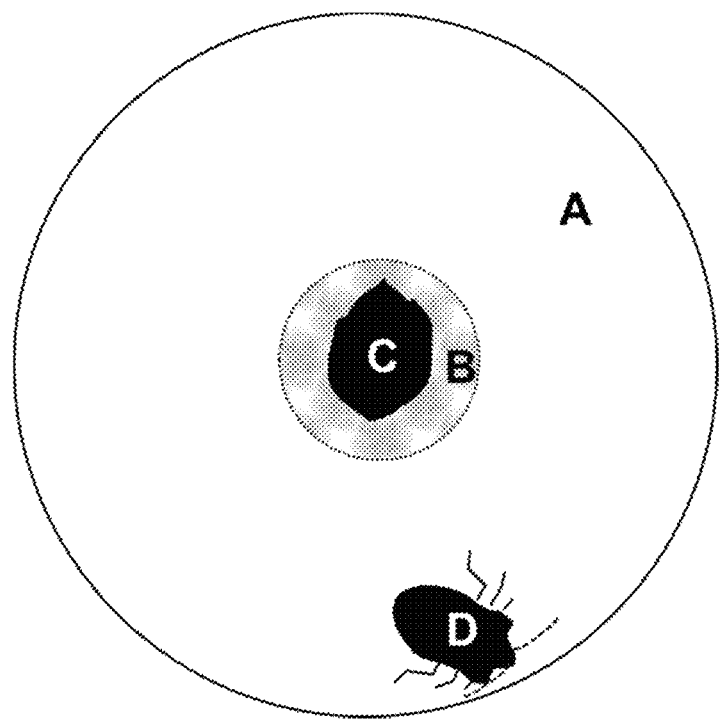

FIG. 80. This figure shows a schematic petri dish "arena" as used in the video behavior assays described in Example 11. A cotton boll (labeled C) is visible at the center of the plate. The region surrounding the boll is represented by the shaded region labeled B; this region is referred to as the boll zone. The boll zone is the region in direct proximity to the cotton boll. The outer area with the label A shows the region of the plate which is not in direct proximity to the cotton boll. A Southern Green Stink Bug (*Nezara viridula*) is depicted at the lower right edge of the arena and is labeled D.

Figure 81:
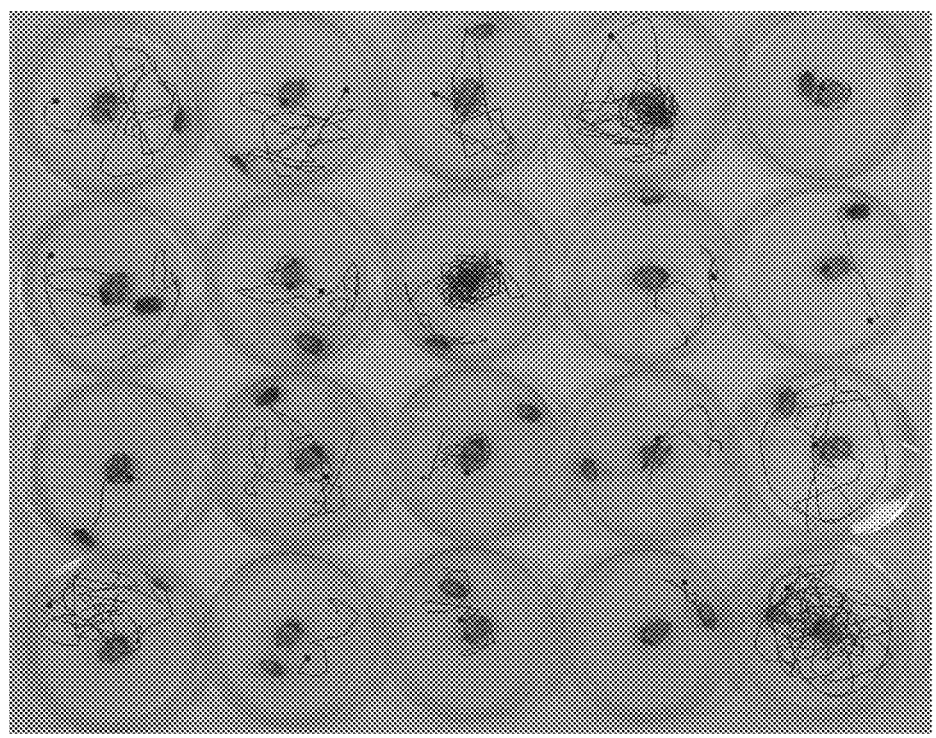

FIG. 81. This figure shows an exemplary photo of 20 petri plate arenas as used in the video behavior assays described in Example 11. A cotton boll is visible at the enter of each arena. The other dark mass in each arena is a Southern Green Stink Bug (*Nezara viridula*). The lines within each arena represent the output of the video tracking software and are a visualization of the path over which the insect in that arena has traveled over the observation period.

Figure 82:
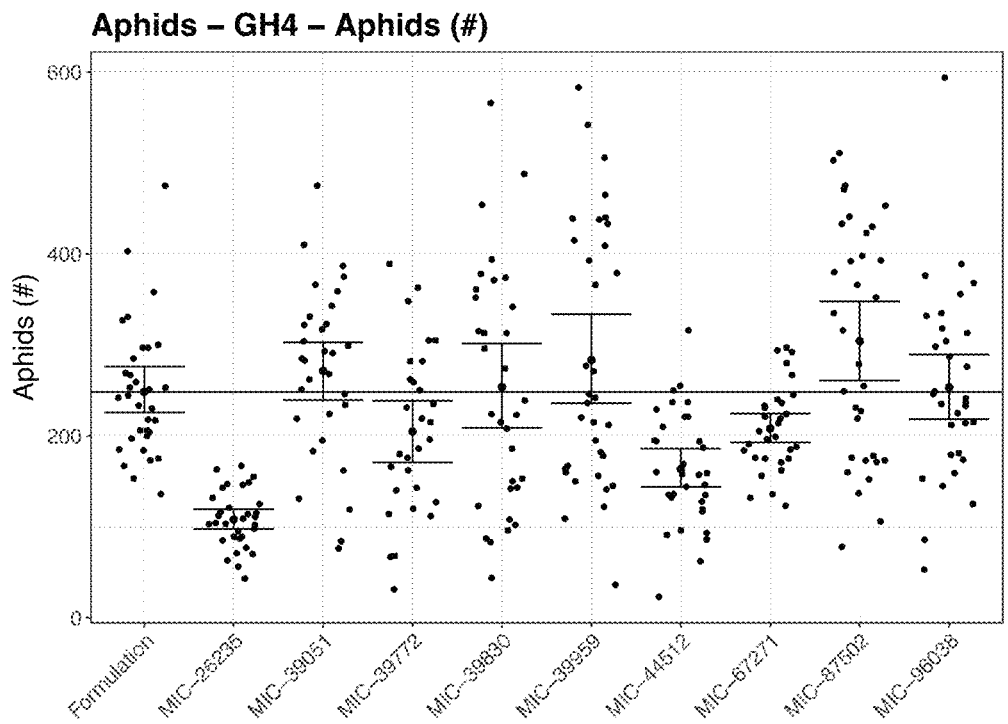

FIG. 82 exemplifies the total number of aphids on each plant 7 days after infestation, for cottons grown from seeds treated with fungal endophytes TAM00452 (MIC-26235), TAM00514 (MIC-39051), TAM00317 (MIC-39772), TAM00129 (MIC-39830), MIC-39959 (TAM00333), TAM00560 (MIC-44512), TAM00089 (MIC-67271), TAM00340 (MIC-87502), MIC-96038 (TAM00505) or treatment controls; plants were treated and grown as described in Example 10.

Figure 83:
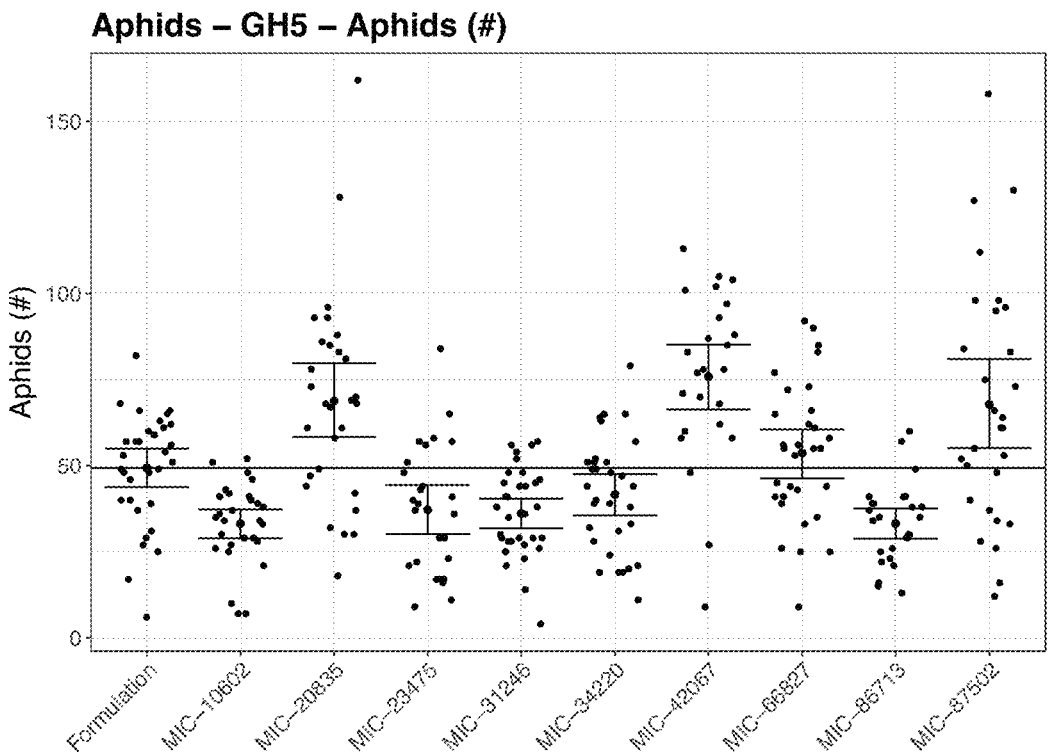

FIG. 83 exemplifies the total number of aphids on each plant 7 days after infestation, for cottons grown from seeds treated with fungal endophytes TAM00248 (MIC-10602), TAM00565 (MIC-20835), (MIC-23475), TAM00501 (MIC-31246), TAM00474 (MIC-34220), SYM02486 (MIC-42067), TAM00110 (MIC-66827), TAM00179 (MIC-86713), TAM00340 (MIC-87502), or treatment controls; plants were treated and grown as described in Example 10.

Figure 84:
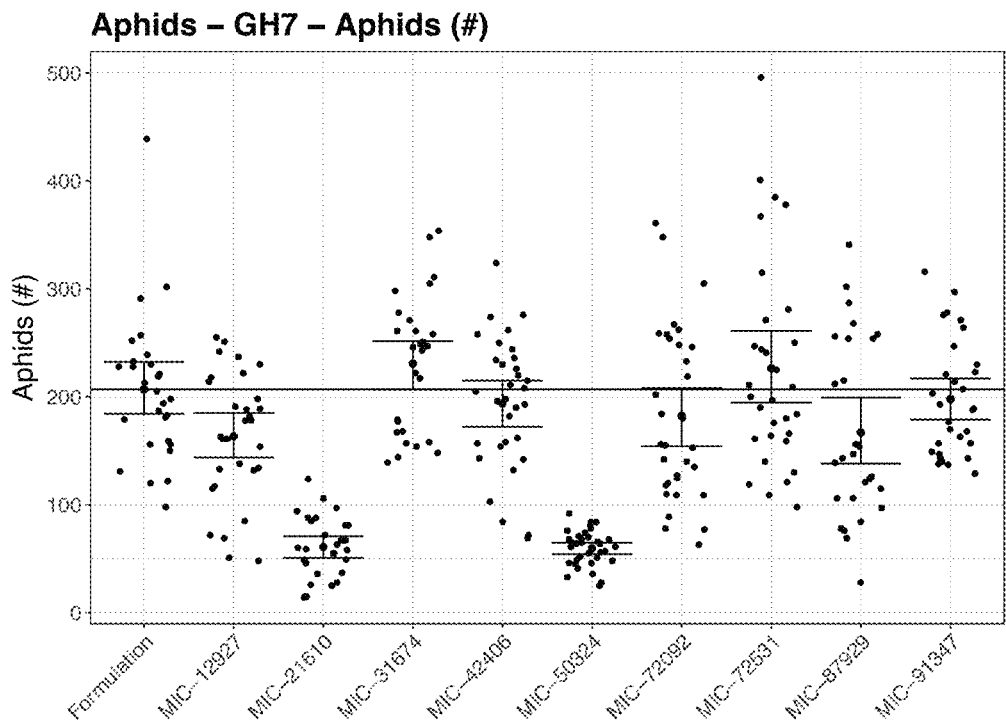

FIG. 84 exemplifies the total number of aphids on each plant 7 days after infestation, for cottons grown from seeds treated with fungal endophytes TAM00193 (MIC-12927), TAM00424 (MIC-21610), TAM00416 (MIC-31674), TAM00190 (MIC-42406), TAM00413 (MIC-50324), TAM00508 (MIC-72092), TAM00517 (MIC-72531), TAM00415 (MIC-87929), TAM00169 (MIC-91347) or treatment controls; plants were treated and grown as described in Example 10.

Figure 85:
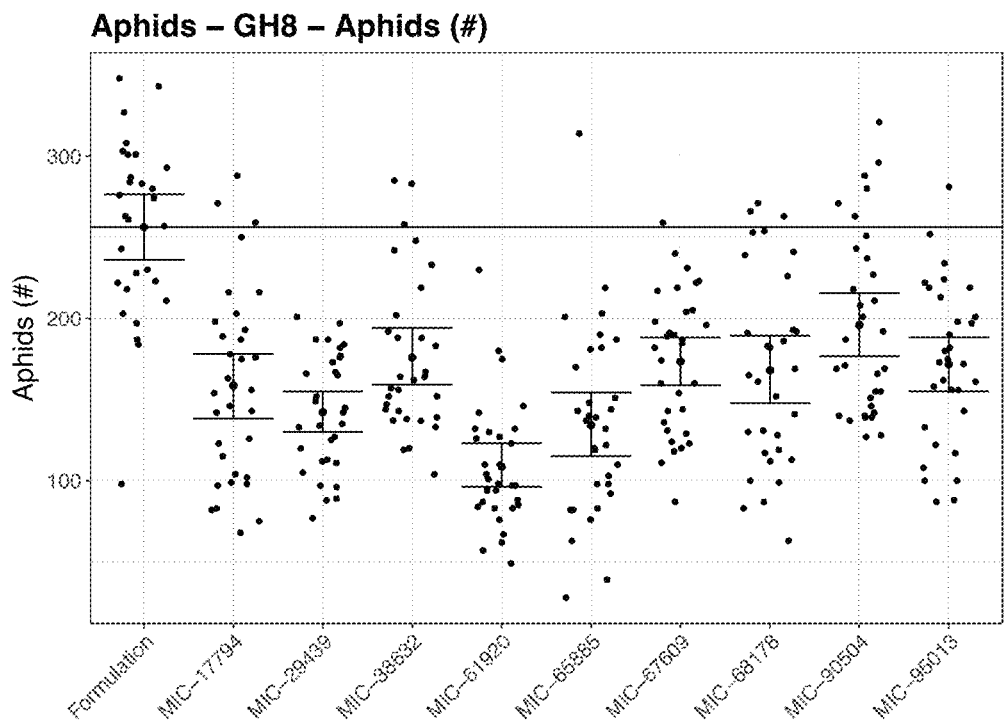

FIG. 85 exemplifies the total number of aphids on each plant 7 days after infestation, for cottons grown from seeds treated with fungal endophytes TAM00304 (MIC-17794), TAM00201 (MIC-29439), TAM00489 (MIC-38632), TAM00529 (MIC-61920), TAM00057 (MIC-65885), TAM00512 (MIC-67609), TAM00032 (MIC-68178), TAM00497 (MIC-90504), TAM00526 (MIC-95013) or treatment controls; plants were treated and grown as described in Example 10.

Figure 86:
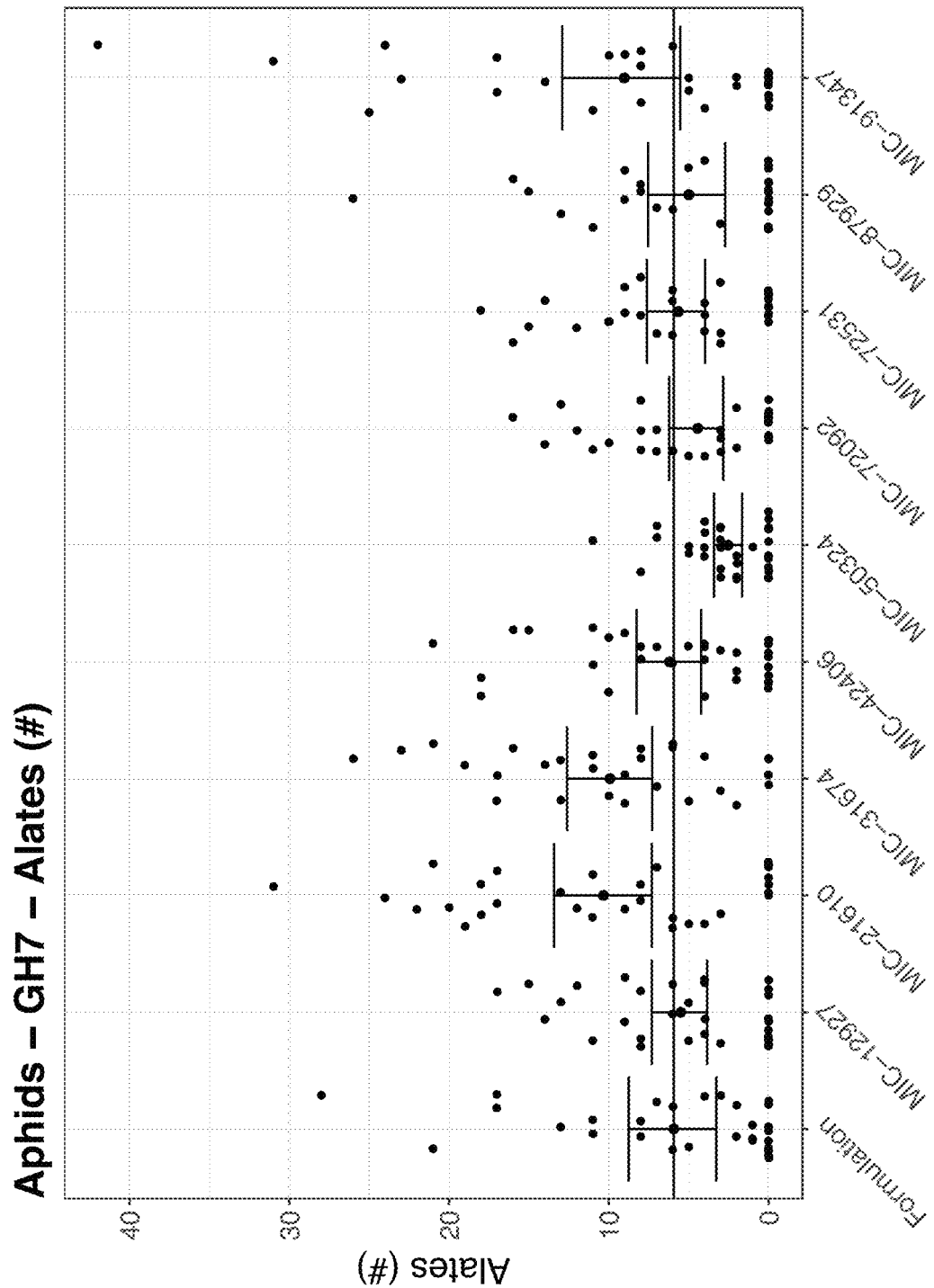

FIG. 86 exemplifies the total number of alates on each plant 7 days after infestation, for cottons grown from seeds treated with fungal endophytes TAM00193 (MIC-12927), TAM00424 (MIC-21610), TAM00416 (MIC-31674), TAM00190 (MIC-42406), TAM00413 (MIC-50324), TAM00508 (MIC-72092), TAM00517 (MIC-72531), TAM00415 (MIC-87929), TAM00169 (MIC-91347) or treatment controls; plants were treated and grown as described in Example 10.

DETAILED DESCRIPTION

Definitions

In the description and tables herein, a number of terms are used. In order to provide a clear and consistent understanding of the specification and claims, the following definitions are provided. Unless otherwise noted, terms are to be understood according to conventional usage by those of ordinary skill in the relevant art.

When a term is provided in the singular, the inventors also contemplate aspects of the invention described by the plural of that term. The singular form "a," "an," and "the" include plural references unless the context clearly dictates otherwise. For example, the term "a cell" includes one or more cells, including mixtures thereof.

The term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and agriculturally acceptable carriers. "Consisting of" shall mean excluding more than trace elements of other ingredients and substantial method steps for applying the compositions of this invention. Embodiments defined by each of these transition terms are within the scope of this invention.

Biological control: the term "biological control" and its abbreviated form "biocontrol," as used herein, is defined as control of a pest, pathogen, or insect or any other undesirable organism by the use of at least one endophyte.

As used herein, an "agricultural seed" is a seed used to grow plants in agriculture (an "agricultural plant"). The seed may be of a monocot or dicot plant, and is planted for the production of an agricultural product, for example grain, food, fiber, etc. As used herein, an agricultural seed is a seed that is prepared for planting, for example, in farms for growing. Agricultural seeds are distinguished from commodity seeds in that the former is not used to generate products, for example commodity plant products.

A "plant element" is intended to generically reference either a whole plant or a plant component, including but not limited to plant tissues, parts, and cell types. A plant element is preferably one of the following: whole plant, seedling, meristematic tissue, ground tissue, vascular tissue, dermal tissue, seed, leaf, root, shoot, stem, flower, fruit, stolon, bulb, tuber, corm, keikis, shoot, bud.

As used herein, a "commodity plant product" refers to any composition or product that is comprised of material derived from a plant, seed, plant cell, or plant part of the present invention. Commodity plant products may be sold to consumers and can be viable or nonviable. Nonviable commodity products include but are not limited to nonviable seeds and grains; processed seeds, seed parts, and plant parts; dehydrated plant tissue, frozen plant tissue, and processed plant tissue; seeds and plant parts processed for animal feed for terrestrial and/or aquatic animal consumption, oil, meal, flour, flakes, bran, fiber, and any other food for human or animal consumption; and biomasses and fuel products. Any such commodity plant product that is derived from the plants of the present invention may contain at least a detectable amount of the specific and unique DNA corresponding to the endophytes described herein. Any standard method of detection for polynucleotide molecules may be used, including methods of detection disclosed herein.

As used herein, the phrase "agronomically elite plants" refers to a genotype or cultivar with a phenotype adapted for commercial cultivation. Traits comprised by an agronomically elite plant may include biomass, carbohydrate, and/or seed yield; biotic or abiotic stress resistance, including drought resistance, insect resistance, fungus resistance, virus resistance, bacteria resistance, cold tolerance, and salt tolerance; improved standability, enhanced nutrient use efficiency, and reduced lignin content.

In certain embodiments, cotton agronomically elite plants include, for example, known cotton varieties AM 1550 B2RF, NG 1511 B2RF, NG 1511 B2RF, FM 1845LLB2, FM 1944GLB2, FM 1740B2F, PHY 499 WRF, PHY 375 WRF, PHY 367 WRF, PHY 339 WRF, PHY 575 WRF, DP 1252 B2RF, DP 1050 B2RF, DP 1137 B2RF, DP 1048 B2RF, and/or DP 1137 B2RF.

As used herein, the phrase "culture filtrate" refers to broth or media obtained from cultures inoculated with a strain of fungi and allowed to grow. The media is typically filtered to remove any suspended cells, leaving the nutrients, hormones, or other chemicals.

As used herein, the term "endophyte" refers to an organism capable of living within a plant or plant tissue. An endophyte may comprise a fungal organism that may confer an increase in yield, biomass, resistance, or fitness in its host plant. Fungal endophytes may occupy the intracellular or extracellular spaces of plant tissue, including the leaves, stems, flowers, or roots.

The phrase "pest resistance" refers to inhibiting or reducing attack from pests. Pest resistance provides at least some increase in pest resistance over that which is already possessed by the plant. In some embodiments, a pest is of an order selected from the group consisting of: Lepidoptera, Hemiptera, or Tylenchida.

As used herein, the term "genotypes" refers to the genetic constitution of a cell or organism.

As used herein, the term "phenotype" refers to the detectable characteristics of a cell or organism, which characteristics are either the direct or indirect manifestation of gene expression.

As used herein, the phrase "host plant" refers to any plant that an endophytic fungi colonizes. In certain embodiments, the host plant comprises progeny of colonized plant.

As used herein, the phrase "increased yield" refers to an increase in biomass or seed weight, seed or fruit size, seed number per plant, seed number per unit area, bushels per acre, tons per acre, kilo per hectare, carbohydrate yield, or cotton yield. Such increased yield is relative to a plant or crop that has not been inoculated with the endophyte. In certain embodiments, the increase yield is relative to other commonly used pest treatments or other methods of addressing the biotic or abiotic stress.

As used herein, the phrase "biomass" means the total mass or weight (fresh or dry), at a given time, of a plant tissue, plant tissues, an entire plant, or population of plants, usually given as weight per unit area. The term may also refer to all the plants or species in the community (community biomass).

As used herein, an "agriculturally acceptable" excipient or carrier is one that is suitable for use in agriculture without undue adverse side effects to the plants, the environment, or to humans or animals who consume the resulting agricultural products derived therefrom commensurate with a reasonable benefit/risk ratio.

In some embodiments, a treatment is applied to a plant or plant element by heterologously disposing the treatment to the plant or plant element. A treatment is "heterologously disposed" when mechanically or manually applied, artificially inoculated or disposed onto or into a plant element, seedling, plant or onto or into a plant growth medium or onto or into a treatment formulation so that the treatment exists on or in the plant element, seedling, plant, plant growth medium, or formulation in a manner not found in nature prior to the application of the treatment, e.g., said combination which is not found in nature in that plant variety, at that time in development, in that tissue, in that abundance, or in that growth condition (for example drought).

In some embodiments, a treatment is applied mechanically or manually or artificially inoculated to a plant element in a seed treatment, root wash, seedling soak, foliar application, soil inocula, in-furrow application, sidedress application, soil pre-treatment, wound inoculation, drip tape irrigation, vector-mediation via a pollinator, injection, osmopriming, hydroponics, aquaponics, aeroponics, and combinations thereof. Application to the plant may be achieved, for example, as a powder for surface deposition onto plant leaves, as a spray to the whole plant or selected plant element, as part of a drip to the soil or the roots, or as a coating onto the plant element prior to or after planting. Such examples are meant to be illustrative and not limiting to the scope of the invention.

A "synthetic composition" comprises one or more endophytes combined by human endeavor with a heterologously disposed plant element or a treatment formulation, said combination which is not found in nature. In some embodiments, the term "synthetic composition" means one or more plant elements or formulation components combined by human endeavor with an isolated, purified endophyte composition. In some embodiments, said purified endophyte composition is mechanically or manually applied, artificially inoculated or disposed on a plant element in a manner that is not found on or in the plant element before application of the purified endophyte composition, e.g., said combination or association which is not found in nature. In some embodiments, "synthetic composition" is used to refer to a treatment formulation comprising an isolated, purified population of endophytes heterologously disposed to a plant element. In some embodiments, "synthetic composition" refers to a purified population of endophytes in a treatment formulation comprising additional compositions with which said endophytes are not found in nature.

A "treatment formulation" refers to a mixture of chemicals that facilitate the stability, storage, and/or application of the endophyte composition(s). Treatment formulations may comprise any one or more agents such as: surfactant, a buffer, a tackifier, a microbial stabilizer, a fungicide, an anticomplex agent, an herbicide, a nematicide, an insecticide, a plant growth regulator, a rodenticide, a desiccant, a nutrient, an excipient, a wetting agent, a salt.

In some embodiments, an "agriculturally compatible carrier" or "carrier" can be used to formulate an agricultural formulation or other composition that includes a purified endophyte preparation. As used herein an "agriculturally compatible carrier" refers to any material, that can be added to a plant element without causing or having an adverse effect on the plant element (e.g., reducing seed germination) or the plant that grows from the plant element, or the like. In some embodiments, the weight ratio between fungal endophyte and a carrier is 1:1-10, 1:10-50, 1:50-100, 1:100-500, 1:500-1000, or 1:1000-5000. As used herein, a carrier may be a "sticker". A sticker is a compound to enhance binding of spores to the seed surface, non-limiting examples of such compounds are alginic acid, carrageenan, dextrin, dextran, pelgel™, polyethelene glycol, polyvinyl pyrrolidone, methyl cellulose, polyvinyl alcohol, or gelatin. In some embodiments, a composition comprising a carrier further comprises water, a detergent, an insecticide, a fungicide, or combinations thereof.

The present invention contemplates the use of "isolated" microbe. As used herein, an isolated microbe is a microbe that is isolated from its native environment, and carries with it an inference that the isolation was carried out by the hand of man. An isolated microbe is one that has been separated from at least some of the components with which it was previously associated (whether in nature or in an experimental setting) or occurs at a higher concentration, viability, or other functional aspect than occurring in its native environment. Therefore, an "isolated" microbe is partially or completely separated from any other substance(s) as it is found in nature or as it is cultured, propagated, stored or subsisted in naturally or non-naturally occurring environments. Specific examples of isolated microbes include partially pure microbes, substantially pure microbes and microbes cultured in a medium that is non-naturally occurring.

As used herein, a microbe is considered to be "native" to a plant or a portion of the plant, and is said to be "natively" present in the plant or a portion of plant, if that plant or portion of the plant contains the microbe, for example, in the absence of any contacting with the microbe preparation, or contains the microbe at much lower concentrations than the contacting with the microbe preparation would provide.

Some of the methods described herein allow the colonization of plant seeds by microbes. As used herein, a microbe is said to "colonize" a plant or seed when it can exist in a symbiotic or non-detrimental relationship with the plant in the plant environment, for example on, in close proximity to or inside a plant, including the seed. The terms "percent colonization", "percentage of colonization", and derivations thereof are used interchangeably and as used herein refer to the percent of individual plants sampled within each experimental treatment that exhibited evidence of positive colonization. Similarly, the term "colonization frequency" and derivations thereof, as used herein, refer to the number of individual plants sampled within each experimental treatment that exhibited evidence of positive colonization. Methods of determining positive colonization are well known in the art and include, for example: sequencing, microscopy and culture based methods.

A "population" of plants, as used herein, refers to a plurality of plants that were either grown from the seeds treated with the endophytes as described herein, or are progeny of a plant or group of plants that were subjected to the inoculation methods. The plants within a population are typically of the same species, and/or typically share a common genetic derivation.

A "reference plant", "reference plant element", "reference agricultural plant" or "reference seed" a similarly situated plant or seed of the same species, strain, or cultivar to which a treatment, formulation, composition or endophyte preparation as described herein is not administered/contacted. A reference plant, therefore, is identical to the treated plant except for the presence of the active ingredient to be tested and can serve as a control for detecting the effects of the treatment conferred to the plant. A plurality of reference plants may be referred to as a "reference population".

Endophytes

Endophytic fungi are ubiquitous in nature, infecting virtually all plants in both natural and agronomic ecosystems. Plants commonly harbor a diversity of fungi living within their tissues as asymptomatic endophytes that can provide protection from a range of biotic and abiotic stressors. The present disclosure describes certain fungal endophytes that can be pathogens, parasites or antagonists to plant pathogens, insects, and nematode pests, thereby providing health and performance benefits to crop plants. The symbiotic endophyte-host relationships can provide several general health and fitness benefits to the host plant, such as enhancement of nutrition, increased drought tolerance and/or chemical defense from potential herbivores and often enhanced biomass production. Root-colonizing mycorrhizae survive on photosynthetic carbohydrates from the plant, and in return, aid in the solubilization and uptake of water and minerals to the host, which can lead to the promotion of seed germination and plant growth. Additionally, the association of a fungal endophyte with a host plant often provides protection from pathogens or tolerance to a variety of biotic and abiotic stresses, such as insect infestation, grazing, water or nutrient deficiency, heat stress, salt or aluminum toxicity, and freezing temperatures. Host growth and fitness promotion and protection are thought to be achieved through multiple beneficial properties of the endophyte-host association.

These fungal endophytes provided in Table 3 were originally collected as fungal endophytes of cotton. These endophytic fungi can be inoculated to live within cotton using either seed, soil or foliar applications and exhibited surprisingly beneficial effects by providing protection from pest infestation. Pests can be nematode and/or insect pests.

Described is the application of beneficial fungi to establish endophytically within crop plants to improve plant performance and yield while conferring protection against insect and nematode pests. In this regard, the present invention overcomes the limitations of the prior art such as the susceptibility of the fungi to degradation by UV light, desiccation or heat after exposure to the environment following application as an inundative soil or foliar biopesticide. Inoculation and endophytic establishment of the fungi within the plant protects the fungi from UV light, desiccation, and unfavorable temperatures, while harboring the fungi in the very plant tissues they are intended to protect. Introducing fungi to live endophytically within plants requires no genetic modification of the plant or microorganisms, and the fungi themselves can be a source for natural products. In various embodiments, the fungal inoculant can be formulated and applied, for example, as treatment of seeds, in furrow applications, before or during planting, or as foliar application after plant germination, and after inoculation, the fungal endophytes provide season-long protective effects and higher crop yields (approximately 25% higher). In certain embodiments, the increase of yield is about 1%, 2%, 3%, 4%, 5%, 10%, 15%, 20%, 30%, 40%, 45%, 50%, or greater than 50% relative to a crop to which no endophyte composition has been applied. In further embodiments, the increase of yield is the result of reduction of loss that comprises reduction of loss due to insect infestation or drought and the loss is less than 50%, 40%, 30%, 20%, 10%, 5%, or 5% relative to a crop to which no endophyte composition has been applied. In certain embodiments, the crop is cotton and the reduction of loss comprises reduced boll damage.

The fungal endophyte may be present in intercellular spaces within plant tissue, such as the root. Its presence may also occur or may also be maintained within a plant or plant population by means of grafting or other inoculation methods such as treating seeds, plants or parts thereof with endophyte mycelia, or endophyte spores. In certain embodiments, the plant, part of the plant, roots, seed, or leaves are sterilized to remove microorganisms before applying the endophyte. In particular embodiments, seeds are sterilized to remove microorganisms prior to combining the seeds with the endophyte compositions herein described. In certain aspects, the ability of the seed to germinate is not affected by the sterilization. In particular embodiments, the plant surface is sterilized to remove microorganisms prior to applying a foliar treatment with the endophyte compositions herein described.

The invention also provides methods for detecting the presence of the fungal endophyte of the present invention within a host plant. This may be accomplished, for instance, by isolation of total DNA from tissues of a potential plant-endophyte combination, followed by PCR, or alternatively, Southern blotting, western blotting, or other methods known in the art, to detect the presence of specific nucleic or amino acid sequences associated with the presence of a fungal endophyte strain of the present invention. Alternatively, biochemical methods such as ELISA, HPLC, TLC, or fungal metabolite assays may be utilized to determine the presence of an endophyte strain of the present invention in a given sample of crop tissue. Additionally, methods for identification may include microscopic analysis, such as root staining, or culturing methods, such as grow out tests or other methods known in the art (Deshmukh et al. 2006). In particular embodiments, the roots of a potential plant-endophyte combination may be stained with fungal specific stains, such as WGA-Alexa 488, and microscopically assayed to determine fungal root associates.

Metabolomic differences between the plants can be detected using methods known in the art. For example, a biological sample (whole tissue, exudate, phloem sap, xylem sap, root exudate, etc.) from the endophyte-associated and reference agricultural plants can be analyzed essentially as described in Fiehn et al., (2000) Nature Biotechnol., 18, 1157-1161, or Roessner et al., (2001) Plant Cell, 13, 11-29. Such metabolomic methods can be used to detect differences in levels in hormones, nutrients, secondary metabolites, root exudates, phloem sap content, xylem sap content, heavy metal content, and the like.

In another embodiment, the present invention contemplates methods of coating the seed of a plant with a plurality of endophytes, as well as seed compositions comprising a plurality of endophytes on and/or in the seed. In some embodiments, a seed coating comprises at least 1, 2, 3, 4, 5, 6, 7, 8, 9, 10, 11, 12, 13, 14, 15, 16, 17, 18, 19, or 20 endophytes. The methods according to this embodiment can be performed in a manner similar to those described herein for single endophyte coating. In one example, multiple endophytes can be prepared in a single preparation that is coated onto the seed. The endophytes can be from a common origin (i.e., a same plant). Alternatively, the endophytes can be from different plants.

Where multiple endophytes are coated onto the seed, any or all of the endophytes may be capable of conferring a beneficial trait onto the host plant. In some cases, all of the endophytes are capable of conferring a beneficial trait onto the host plant. The trait conferred by each of the endophytes may be the same (e.g., both improve the host plant's tolerance to a particular biotic stress), or may be distinct (e.g., one improves the host plant's tolerance to drought, while another improves phosphate utilization). In other cases, the conferred trait may be the result of interactions between the endophytes.

In certain embodiments, the agronomic qualities may be selected from the group consisting of: increased disease resistance, increased pest resistance, increased herbivore resistance, increased resistance to a fungal pathogen, increased resistance to a bacterial pathogen, increased resistance to a viral pathogen, increased resistance to a nematode, increased insect resistance, increased leaf area in the presence of a biotic stressor, increased yield in the presence of a biotic stressor, or combinations thereof, each of these qualities being rated in comparison to otherwise identical plants grown under the same conditions, and differing only with respect to the presence or absence of a fungal endophyte. The synthetic combinations and methods of the present invention may be applied to respond to actual or anticipated stresses.

Plant-parasitic nematodes are distributed worldwide and parasitize almost all higher plants. They feed and reproduce on living plant cells in roots, and induce formation of giant cells and galls, which leads to disrupted plant water and nutrient uptake that can damage crops and reduce yields. External symptoms due to nematode infection include various degrees of stunting and wilting. In some embodiments, secondary infection by other pathogens may lead to decay of nematode-infected tissues. Non-limiting examples of nematode pests include root knot nematode (*Meloidogyne incognita*) and Reniform nematode (*Rotylenchulus reniformis*).

Current nematode control practices include chemical and cultural control with some use of host plant resistance. Increasing awareness of environmental and human safety has greatly reduced the amount of chemical usage and number of new nematicides approved for use. Studies using nematophagous microbes as biological control agents for nematode management have received more attention as the withdrawal of several nematicides (e.g. methyl bromide, dichloropropene, aldicarb and phenamiphos) from market increases the need for new nematode control strategies. An alternative to the application of fungal biological control agents to the soil for nematode control is the manipulation of the presence of fungal endophytes within the plant.

The present disclosure provides, in one embodiment, fungal endophytes selected from those in Table 3 that negatively affect the reproduction of plant parasitic nematodes attacking roots below ground, including knot nematodes (*Meloidogyne incognita*) and reniform nematodes (*Rotylenchulus reniformis*). Increased resistance to root knot nematodes was demonstrated in cotton, for example, employing *Chaetomium globosum* as an endophyte in greenhouse trials. In some embodiments, improved plant performance and yields in endophyte treated versus control plants can be observed in field trials. In some embodiments, the endophyte treatment is applied to a seed. In some embodiments, the endophyte treatment is a foliar treatment. In some embodiments, the endophyte treatment is a root drench. In some embodiments, an endophyte treatment comprises at least 1, 2, 3, 4, 5, 6, 7, 8, 9, 10, 11, 12, 13, 14, 15, 16, 17, 18, 19, or 20 endophytes. In some embodiments, an endophyte treatment comprises culture filtrate.

The present disclosure provides, in one embodiment, fungal endophytes selected from those in Table 3 that negatively affect the abundance and size of plant pests of the Order Lepidoptera also known as "chewing" insects. The larval stages of several Lepidopteran insects can cause serious to agricultural crops, particularly dicots including cotton and soybean. Defoliation due to excessive herbivory reduces the photosynthetic capacity of crops and is associated with reduced fruit and seed yield. Non-limiting examples of such of Lepidopteran insects include soybean looper (*Chrysodeixis includens* or *Pseudoplusia includens*) and cabbage looper (*Trichoplusia ni*). Increased resistance to soybean and cabbage looper in endophyte treated plants can be demonstrated by increased yield, improved vigor, improved resistance to fungal pathogens, or increased leaf area as compared to a reference plant element not further comprising the endophyte. In some embodiments, improved plant performance and yields in endophyte treated versus control plants can be observed in field trials. In some embodiments, fungal endophytes capable of improving plant performance under chewing insect pressure are selected from the genera *Cladosporium, Alternaria, Bipolaris, Chaetomium, Verticillium, Preussia, Pleospora,* or *Epicoccum*. In some embodiments, fungal endophytes capable of improving plant performance under chewing insect pressure comprises a nucleic acid sequence that is at least 97% identical to a nucleic acid sequence selected from the group consisting of SEQ ID NOs: 26-115.

The present disclosure provides, in one embodiment, fungal endophytes selected from those in Table 3 that negatively affect the affinity of piercing-sucking insects for endophyte treated plant tissue or plants derived from treated seeds or treated plants. Many piercing-sucking insects are of the Order Hemiptera and feed on plants. Non-limiting example of a piercing-sucking insects include aphids, thrips, fleahoppers, *lygus* bugs (members of the genus *Lygus*), and stink bugs including the brown marmorated stink bug (*Halyomorpha halys*) and southern green stink bugs (*Nezara viridula*). In some embodiments, treatment of a plant with one or more fungal endophytes affects piercing-sucking insect behavior by decreasing the amount of time insects spend on plants or plant elements including their reproductive tissue (for example, cotton bolls), decreasing the number of times an insect approaches a plant or plant element, decreasing the number of insects that contact a plant or plant element, or increasing the amount of time before an insect approaches a plant or plant element, compared to a reference plant or plant element not further comprising the endophyte. In some embodiments, reducing the affinity of a piercing-sucking insect for a plant or plant element reduces the damage to the plant or plant element by insect feeding or infection by pathogenic bacteria, fungi or viruses. In some embodiments, reduced damage by piercing-sucking insects can be demonstrated by increased yield, improved vigor, or improved resistance pathogenic bacteria, fungi or viruses. In some embodiments, improved vigor includes a reduction in yellowing, wilting, deformation or stunting of plant tissue as compared to a reference plant tissue. In some embodiments, fungal endophytes capable of improving plant performance under piercing-sucking insect pressure are selected from the genera *Cladosporium, Alternaria, Bipolaris, Chaetomium, Verticillium, Preussia, Pleospora*, or *Epicoccum*. In some embodiments, fungal endophytes capable of improving plant performance under piercing-sucking insect pressure comprises a nucleic acid sequence that is at least 97% identical to a nucleic acid sequence selected from the group consisting of SEQ ID NOs: 26-115.

In some embodiments, the methods of preventing or treating a pest infestation provide a benefit to the treated plant by reducing the abundant of pests on the plants. In some embodiments, the reduced the abundant of pests on the plants is measured by counting the number of immature pests or pest eggs on the endophyte treated plant tissue. In some embodiments, the reduction in pest abundance is due to decreased survival of pests feeding on endophyte treated plants. In some embodiments, the reduction in pest abundance is due to the decreased attractiveness of endophyte treated plants to pests. In some embodiments, the decreased attractiveness of endophyte treated plants to pests is measured by, as non-limiting examples: decreased movement of pests, increased time of pests to move toward endophyte treated plants, decreased frequency of visits by the pest to the plant, or decreased time spent on or feeding on endophyte treated plants. In some embodiments, the methods of preventing or treating a pest infestation provide a benefit to the treated plant by reducing the biomass of feeding pests. In some embodiments, the pests on endophyte treated plants are visibly smaller. In some embodiments, the pests on endophyte treated plants are smaller as determined by measuring the pests' biomass.

A method for preventing pest infestation, comprising inoculating plant elements with a formulation comprising a fungal endophyte heterologously disposed to the plant elements, wherein the fungal endophyte is selected from Table 3, wherein pests are smaller on the plants comprising or derived from the inoculated plant elements compared to plants comprising or derived from reference plant elements not inoculated with the formulation.

In some embodiments, treatment or prevention of a biotic stress condition in a plant caused by a nematode, insect, fungi or bacteria with a fungal endophyte may reduce the frequency or rate of application of chemical nematocides, insecticides, fungicides or bactericides by 1%, 2%, 3%, 4%, 5%, 10%, 15%, 20%, 30%, 40%, 50%, 60%, 70%, 80%, 90% or 100%.

As used herein, a nucleic acid has "homology" or is "homologous" to a second nucleic acid if the nucleic acid sequence has a similar sequence to the second nucleic acid sequence. The terms "identity", "percent identity", "percent sequence identity" or "identical" in the context of nucleic acid sequences refer to the nucleotides in the two sequences that are the same when aligned for maximum correspondence. There are different algorithms known in the art that can be used to measure nucleotide sequence identity. Nucleotide sequence identity can be measured by a local or global alignment, preferably implementing an optimal local or optimal global alignment algorithm. For example, a global alignment may be generated using an implementation of the Needleman-Wunsch algorithm (Needleman, S. B. & Wunsch, C. D. (1970) Journal of Molecular Biology. 48(3): 443-53). For example, a local alignment may be generated using an implementation of the Smith-Waterman algorithm (Smith T. F & Waterman, M. S. (1981) Journal of Molecular Biology. 147(1):195-197). Optimal global alignments using the Needleman-Wunsch algorithm and optimal local alignments using the Smith-Waterman algorithm are implemented in USEARCH, for example USEARCH version v8.1.1756_i86osx32.

A gap is a region of an alignment wherein a sequence does not align to a position in the other sequence of the alignment. In global alignments, terminal gaps are discarded before identity is calculated. For both local and global alignments, internal gaps are counted as differences. A terminal gap is a region beginning at the end of a sequence in an alignment wherein the nucleotide in the terminal position of that sequence does not correspond to a nucleotide position in the other sequence of the alignment and extending for all contiguous positions in that sequence wherein the nucleotides of that sequence do not correspond to a nucleotide position in the other sequence of the alignment. An internal gap is a gap in an alignment which is flanked on the 3' and 5' end by positions wherein the aligned sequences are identical.

The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 76%, 80%, 85%, or at least about 90%, or at least about 95%, 96%, at least 97%, 98%, 99% or 100% of the positions of the alignment, wherein the region of alignment is at least about 50%, 60%, 70%, 75%, 85%, or at least about 90%, or at least about 95%, 96%, 97%, 98%, 99% or 100% of the length of the query sequence. In a preferred embodiment, inference of homology from a sequence alignment is make where the region of alignment is at least 85% of the length of the query sequence. In a preferred embodiment, the region of alignment contains at least 100 positions inclusive of any internal gaps. In some embodiments, the region of alignment comprises at least 100 nucleotides of the query sequence. In some embodiments, the region of alignment comprises at least 200 nucleotides of the query sequence. In some embodiments, the region of alignment comprises at least 300 nucleotides of the query sequence. In some embodiments, the region of alignment comprises at least 400 nucleotides of the query sequence. In some embodiments, the region of alignment comprises at least 500 nucleotides of the query sequence. In some embodiments, the query sequence is selected from the SEQ ID Nos in Table 3.

Historical taxonomic classification of fungi has been according to morphological presentation. Beginning in the mid-1800's, it was recognized that some fungi have a pleomorphic life cycle, and that different nomenclature designations were being used for different forms of the same fungus. With the development of genomic sequencing, it became evident that taxonomic classification based on molecular phylogenetics did not align with morphological-based nomenclature (Shenoy B D, Jeewon R, Hyde K D. Impact of DNA sequence-data on the taxonomy of anamorphic fungi. Fungal Diversity 26(10) 1-54. 2007). Systematics experts have not aligned on common nomenclature for all fungi, nor are all existing databases and information resources inclusive of updated taxonomies. As such, many fungi referenced herein may be described by their anamorph form but it is understood that based on identical genomic sequencing, any pleomorphic state of that fungus may be considered to be the same organism. In some cases, fungal genera have been reassigned due to various reasons, and it is understood that such nomenclature reassignments are within the scope of any claimed taxonomic classification.

For example, the genus *Bipolaris* and the genus *Curvularia* are closely related, but separate anamorphs, although the genus *Cochliobolus* has been described as the teleomorph for both. It is understood that the genus *Acremonium* is also reported in the literature as genus *Sarocladium* as well as genus *Tilachilidium* (Summerbell R. C., C. Gueidan, H-J. Schroers, G. S. de Hoog, M. Starink, Y. Arocha Rosete, J. Guano and J. A. Scott. *Acremonium* phylogenetic overview and revision of *Gliomastix, Sarocladium*, and *Trichothecium*. Studies in Mycology 68: 139-162. 2011). Further, it is understood that the genus *Cladosporium* is an anamorph of the teleomorph genus *Davidiella* (Bensch K, Braun U, Groenewald J Z, Crous P W. The genus *Cladosporium*. Stud Mycol. 2012 Jun. 15; 72(1): 1-401.), and is understood to describe the same organism. *Stemphylium herbarum* has been reported in the literature as the anamorph of *Pleospora herbarum* (Simmons, E. G. (1985). Perfect states of *Stemphylium* II.—Sydowia 38: 284-293). Additionally the literature has suggested that *Verticillium nigrescens* be reassigned to the genus *Gibellulopsis* (Zane, Rasoul & Gams, Walter & Starink-Willemse, Mieke & Summerbell, Richard. (2007). *Gibellulopsis*, a suitable genus for *Verticillium nigrescens*, and *Musicillium*, a new genus for *V. theobromae*. Nova Hedwigia. 85. 463-489. 10.1127/0029-5035/2007/0085-0463).

EXAMPLES

Example 1: Isolation of Endophytic Fungi

Endophytic fungi were obtained from cotton plants as described (Ek-Ramos et al. 2013, PLoS ONE 8(6): e66049. doi:10.1371/journal.pone.0066049), except *Beauveria bassiana* which was cultured from a commercially obtained strain (available from Botanigard, BioWorks). Persons of ordinary skill in the art can obtain endophytes suitable for performing the various embodiments of the present invention by performing the procedures described therein. In short, plant samples were rinsed in tap water and surface sterilized by immersion in 70% ethanol for 5 min, 10% bleach solution for 3 min, and rinsed twice with autoclaved distilled water. Samples were blotted dry using autoclaved paper towels. Five individual surface sterilized leaves, squares and bolls (N=15 total samples) were randomly selected and imprinted onto fresh potato dextrose agar (PDA) and V8 media as a way to monitor surface sterilization efficiency. For endophyte isolation, leaves were cut in small fragments of approximately 1 square cm. Squares and bolls were cut in six pieces. Any fiber present was removed and cut into six smaller pieces. Leaf fragments were placed upside down on PDA and V8 medium plates in triplicate. Each plate contained 3 leaf fragments for a total of 9 fragments assayed per plant. For squares collected early in the season, 3 slices per square were plated on PDA and V8 media as with the leaf fragments. Because of similarity in size and location within a plant, when collected later in the season, squares and bolls from a given plant were plated together on petri dishes containing two square slices, two boll slices and two pieces of fiber. Antibiotics Penicillin G (100 Units/mL) and Streptomycin (100 µg/mL) (Sigma, St Louis, Mo., USA) were added to the media to suppress bacterial growth. All plates were incubated in the dark at room temperature for, in average, two weeks until growth of fungal endophyte hyphae from plant tissues was detected.

An inclusive combination of morphological and molecular fungal endophyte identification was employed for identification. Once fungal hyphae were detected growing from the plant material, samples were taken to obtain pure fungal isolates. Genomic DNA was extracted from mycelium of each isolated fungal strain using DNeasy DNA extraction kit (Qiagen, Hilden, Germany) according to the manufacturer's instructions. The endophytes were characterized by the sequences of genomic regions, these sequences are SEQ ID NOs: 26-115. Primers that amplify genomic regions of the endophytes of the present invention are listed in Table 1 (SEQ ID NOs: 1-25). IUPAC nucleotide ambiguity codes are used in the nucleic acid sequences of the present invention.

TABLE 1

| Primer sequences useful in identifying microbes of the present invention | |
|---|---|
| Primers | Genomic locus |
| ITS_1 (5'-CTTGGTCATTTAGAGGAAGTAA-3') (SEQ ID NO: 1) LR5 (5'-TCCTGAGGGAAACTTCG-3') (SEQ ID NO: 4) | ITS |
| LR0R (5'-ACCCGCTGAACTTAAGC-3') (SEQ ID NO: 18) | LSU |

TABLE 1-continued

Primer sequences useful in identifying
microbes of the present invention

| Primers | Genomic locus |
|---|---|
| LR5 (5'-TCCTGAGGGAAACTTCG-3')<br>(SEQ ID NO: 4) | |
| ITS_2 (5'-GCTGCGTTCTTCATCGATGC-3')<br>(SEQ ID NO: 2)<br>ITS_3 (5'-GCATCGATGAAGAACGCAGC-3')<br>(SEQ ID NO: 3) | ITS |
| 60S-506F (5'-CTTVAVYTGGAACTTGATGGT-3')<br>(SEQ ID NO: 12)<br>60S-908R (5'-GHGACAAGCGTTTCTCNGG-3')<br>(SEQ ID NO: 13) | 60S ribosomal<br>protein L 10 |
| PGK (5'-GTYGAYTTCAAYGTYCC-3')<br>(SEQ ID NO: 10)<br>PGK (5'-ACACCDGGDGGRCCGTTCCA-3')<br>(SEQ ID NO: 11) | Phosphoglycerate<br>kinase |
| RPB1-Af, largest subunit of RNA polymerase<br>II, primer-amplicon F (5'-GARTGYC<br>CDGGDCAYTTYGG-3') (SEQ ID NO: 24)<br>RPB1-Cr, largest subunit of RNA polymerase<br>II, primer-amplicon R (5'-CCNGCDAT<br>NTCRTTRTCCATRTA-3') (SEQ ID NO: 25) | largest subunit<br>of RNA polymerase<br>II |
| fRPB2-5F (5'-GAYGAYMGWGATCAYTTYGG-3')<br>(SEQ ID NO: 9)<br>fRPB2-7R (5'-CCCATWGCYTGCTTMCCCAT-3')<br>(SEQ ID NO: 8)<br>bRPB2-7.1R (5'-CCCATRGCYTGYTTMCCCATDGC-3')<br>(SEQ ID NO: 7) | second largest<br>subunit of RNA<br>polymerase II |
| Btub2Fd (5'-GTBCACCTYCARACCGGYCARTG-3')<br>(SEQ ID NO: 14)<br>Btub4Rd (5'-CCRGAYTGRCCRAARACRAAGTTGTC-3')<br>(SEQ ID NO: 15) | Partial beta-<br>tubulin II |
| ACT512f (5'-ATGTGCAAGGCCGGTTTCG-3')<br>(SEQ ID NO: 16)<br>ACT783r (5'-TACGAGTCCTTCTGGCCCAT-3')<br>(SEQ ID NO: 17) | Actin |
| SSU_NS4 (5'-CTTCCGTCAATTCCTTTAAG-3')<br>(SEQ ID NO: 19)<br>SSU_NS1 (5'-GTAGTCATATGCTTGTCTC-3')<br>(SEQ ID NO: 20) | Partial SSU, small<br>subunit rRNA gene |
| SSU_NS4 (5'-CTTCCGTCAATTCCTTTAAG-3')<br>(SEQ ID NO: 19)<br>SSU_SR1R (5'-TACCTGGTTGATCCTGCCAGT-3')<br>(SEQ ID NO: 21) | Partial SSU, small<br>subunit rRNA gene |
| MIC-76091 (5'-GGTGAATCGCACATGCTAGA-3')<br>(SEQ ID NO: 5)<br>MIC-76091 (5'-CGACCAGACAGAGCGTATGA-3')<br>(SEQ ID NO: 6) | unique genomic<br>region |
| MIC-68178 (5'-CTCCTCCTCCTCCTCCTGAT-3')<br>(SEQ ID NO: 22)<br>MIC-68178 (5'-TCACAGAGCTACGCGACTTG-3')<br>(SEQ ID NO: 23) | unique genomic<br>region |

Example 2: Identification of Endophytes Using Marker Gene Sequences

Classification of the Fungal Strain Using Marker Gene Sequences Other than ITS

The fungal endophytes of the present invention can be identified by the sequence of one or more of the following loci: second largest subunit of RNA polymerase II (RPB2), 60S ribosomal protein L 10, phosphoglycerate kinase (PGK). PCR amplification of the gene encoding second largest subunit of RNA polymerase II (RPB2) using primer sequences fRPB2-5F (SEQ ID NO: 9) and fRPB2-7.1R (SEQ ID NO: 7) is described in Riess K, Oberwinkler F, Bauer R, Garnica S. High genetic diversity at the regional scale and possible speciation in *Sebacina epigaea* and *S. incrustans*. BMC Evolutionary Biology. 2013; 13:102. doi: 10.1186/1471-2148-13-102. PCR amplification of the gene encoding second largest subunit of RNA polymerase II (RPB2) using primer sequences fRPB2-5F (SEQ ID NO: 9) and fRPB2-7R (SEQ ID NO: 8) is described in Liu Y, Whelen S, Hall B. Phylogenetic relationships among ascomycetes: evidence from an RNA polymerase II subunit. Mol. Biol. Evol. 1999. 16(12): 1799-1808. PCR amplification of the gene encoding 60S ribosomal protein L 10 using primer sequences 605-506F (SEQ ID NO: 12) and 60S-908R (SEQ ID NO: 13) is described in Stielow et al. (2015) One fungus, which genes? Development and assessment of universal primers for potential secondary fungal DNA barcodes, Persoonia 35: 242-263. PCR amplification of the gene encoding Beta-tubulin 2 using primer sequences Btub2Fd (SEQ ID NO: 14) and Btub4Rd (SEQ ID NO: 15) is descriebd in Stielow et al. (2015). PCR amplification of the gene encoding phosphoglycerate kinase using primer sequences PGK_533-F (SEQ ID NO: 10) and PGK_533-R (SEQ ID NO: 11) is described in Stielow et al. (2015). PCR amplification of the SSU using primer sequences SR1R (SEQ ID NO: 21) and NS4 (SEQ ID NO: 19) is described in Zhu et al. (2016) *Helminthosporium velutinum* and *H. aquaticum* sp. *nov*. from aquatic habitats in Yunnan Province, China. Phytotaxa 253 (3): 179-190. PCR amplification of the SSU using primer sequences NS1 (SEQ ID NO: 20) and NS4 (SEQ ID NO: 19) is described in White T. J.; Bruns T.; Lee S. H.; Taylor J. W. PCR protocols: a guide to methods and application. San Diego 1990, 315-32210.1016/B978-0-12-372180-8.50042-1. PCR amplification of Actin using primer sequences ACT512f (SEQ ID NO: 16) and ACT783r (SEQ ID NO: 17) is described in Carbone, I. & Kohn, L. M. (1999) A method for designing primer sets for speciation studies in filamentous ascomycetes. Mycologia, 91(3):552-556. PCR amplification of the largest subunit of RNA polymerase I (RPB1) using primer sequences RPB1-Af (SEQ ID NO: 24) and RPB1-Cr (SEQ ID NO: 25) is described in Cendejas-Bueno E, Kolecka A, Alastruey-Izquierdo A, et al. Reclassification of the *Candida haemulonii* Complex as *Candida haemulonii* (*C. haemulonii* Group I), *C. duobushaemulonii* sp. *nov*. (*C. haemulonii* Group II), and *C. haemulonii* var. *vulnera* var. *nov*.: Three Multiresistant Human Pathogenic Yeasts. Journal of Clinical Microbiology. 2012; 50(11):3641-3651.

MIC-76091 can be identified by sequence homology to one or more of the following sequences: second largest subunit of RNA polymerase II (SEQ ID NOs: 53, 55), phosphoglycerate kinase (SEQ ID NO: 54), 60S ribosomal protein L 10 (SEQ ID NO: 56), and a unique genomic region (SEQ ID NO: 57). MIC-67271 can be identified by sequence homology to one or more of the following sequences: second largest subunit of RNA polymerase II (SEQ ID NO: 42), 60S ribosomal protein L 10 (SEQ ID NO: 44), beta-tubulin II (SEQ ID NO: 43), and actin (SEQ ID NO: 45). MIC-68178 can be identified by sequence homology to one or more of the following: beta-tubulin II (SEQ ID NO: 48) and a unique genomic region (SEQ ID NO: 49). MIC-07010 can be identified by sequence homology to SEQ ID NO: 75 which is a partial sequence of the gene encoding phosphoglycerate kinase. MIC-31593 can be identified by sequence homology to one or more of the following: second largest subunit of RNA polymerase II (SEQ ID NO: 79), beta-tubulin II (SEQ ID NO: 80), and a unique genomic region (SEQ ID NO: 81). MIC-96038 can be identified by sequence homology to one or more of the following: actin (SEQ ID NO: 88), beta-tubulin II (SEQ ID NO: 89), second largest subunit of RNA polymerase II (SEQ ID NOs: 90), largest subunit of RNA polymerase II (SEQ ID NO: 91), and a unique genomic region (SEQ ID NO: 92). MIC-33414 can be identified by sequence homology to one or more of the following: actin (SEQ ID NO: 99), large-subunit rRNA (LSU) (SEQ ID NO: 100), largest subunit of RNA polymerase II (SEQ ID NO: 101), small-subunit rRNA (SSU) (SEQ ID NOS:102, 103), beta-tubulin II (SEQ ID NO: 104), and a unique genomic region (SEQ ID NO: 105).

Classification of the Fungal Strain Using ITS Sequences

Total genomic DNA was extracted from individual fungal isolates, using the DNeasy Plant Mini Kit (Qiagen, Germantown, Md.). Polymerase Chain Reaction (PCR) was used to amplify a genomic region including the nuclear ribosomal internal transcribed spacers (ITS) using a primer pair ITS_1 (5'-CTTGGTCATTTAGAGGAAGTAA-3') (SEQ ID NO: 1) and LR5 (5'-TCCTGAGGGAAACTTCG-3') (SEQ ID NO: 4). Each 25 microliter-reaction mixture included 22.5 microliters of Invitrogen Platinum Taq supermix, 0.5 microliter of each primer (10 uM), and 1.5 microliters of DNA template (~2-4ng). Cycling reactions were run with MJ Research PTC thermocyclers and consisted of 94° C. for 5 min, 35 cycles of 94° C. for 30 s, 54° C. for 30 s, and 72° C. for 1 min, and 72° C. for 10 min. Sanger sequencing of was performed at Genewiz (South Plainfield, N.J.) using primers: ITS_1 (5'-CTTGGTCATTTAGAGGAAGTAA-3') (SEQ ID NO: 1), ITS_2 (5'-GCTGCGTTCTTCATC-GATGC-3') (SEQ ID NO: 2), ITS_3 (5'-GCATCGAT-GAAGAACGCAGC-3') (SEQ ID NO: 3), and LR5 (5'-TCCTGAGGGAAACTTCG-3') (SEQ ID NO: 4). Sequencing primers were chosen so that overlapping regions were sequenced. Raw chromatograms were converted to sequences, and corresponding quality scores were assigned using TraceTuner v3.0.6beta (U.S. Pat. No. 6,681,186). These sequences were quality filtered, aligned and a consensus sequence generated using Geneious v 8.1.8 (Biomatters Limited, Auckland NZ).

Taxonomic classifications were assigned to the sequences using the highest probability of assignment based on the results of industry standard taxonomic classification tools: LCA (runs USEARCH (Edgar, R. C. (2010) Bioinformatics. 26(19):2460-2461) with option search_global, then for all best match hits, returns lowest taxonomic rank shared by all best hits for a query), SPINGO (Allard et al. (2015) BMC Bioinformatics. 16: 324), and UTAX (Edgar, R. C., 2016), using the WARCUP Fungal ITS trainset 1 (Deshpande et al. (2016) Mycologia 108(1):1-5) and UNITE (Koljalg et al. (2013) Molecular Ecology, 22: 5271-5277). The classifier and database combinations listed in Table 2 were used to assign taxonomy to fungal sequences. Taxonomic assignments for endophytes of the present invention are listed in Table 3.

TABLE 2

The classifier and database combinations used to classify ITS sequences

| Classifier | Database |
| --- | --- |
| LCA | UNITE, Fungal ITS trainset 07/04/2014 |
| RDP | UNITE, Fungal ITS trainset 07/04/2014 |
|  | WARCUP, Fungal ITS trainset 1 |
| SPINGO | UNITE, Fungal ITS trainset 07/04/2014 |
| UTAX | UNITE, Fungal ITS trainset 07/04/2014 |
|  | WARCUP, Fungal ITS trainset 1 |

TABLE 3

Exemplary taxonomy and microbe identifiers for fungal endophytes useful in the present invention.

| SEQ ID | MIC ID | TAMU ID | Phylum | Class | Order | Family | Genus | Species |
|---|---|---|---|---|---|---|---|---|
| 26, 27 | MIC-91347 | TAM00169 | Ascomycota | Dothideomycetes | Capnodiales | Cladosporiaceae | *Cladosporium* | *cladosporioides* |
| 28 | MIC-12927 | TAM00193 | Ascomycota | Dothideomycetes | Capnodiales | Cladosporiaceae | *Cladosporium* | *cladosporioides* |
| 29 | MIC-31246 | TAM00501 | Ascomycota | Dothideomycetes | Capnodiales | Cladosporiaceae | *Cladosporium* | |
| 30 | MIC-72531 | TAM00517 | Ascomycota | Dothideomycetes | Capnodiales | Cladosporiaceae | *Cladosporium* | *cladosporioides* |
| 31 | MIC-80602 | TAM00249 | Ascomycota | Dothideomycetes | Capnodiales | Cladosporiaceae | *Cladosporium* | *gossypiicola* |
| 32 | MIC-42406 | TAM00190 | Ascomycota | Dothideomycetes | Capnodiales | Cladosporiaceae | *Cladosporium* | *herbarum* |
| 33 | MIC-87929 | TAM00415 | Ascomycota | Dothideomycetes | Capnodiales | Cladosporiaceae | *Cladosporium* | *herbarum* |
| 34 | MIC-50414 | TAM00534 | Ascomycota | Dothideomycetes | Capnodiales | Cladosporiaceae | *Cladosporium* | *oxysporum* |
| 35 | MIC-29439 | TAM00201 | Ascomycota | Dothideomycetes | Capnodiales | Cladosporiaceae | *Cladosporium* | |
| 36 | MIC-10602 | TAM00248 | Ascomycota | Dothideomycetes | Capnodiales | Cladosporiaceae | *Cladosporium* | |
| 37 | MIC-17794 | TAM00304 | Ascomycota | Dothideomycetes | Capnodiales | Cladosporiaceae | *Cladosporium* | |
| 38 | MIC-91557 | TAM00463 | Ascomycota | Dothideomycetes | Capnodiales | Cladosporiaceae | *Cladosporium* | |
| 39 | MIC-26952 | TAM00494 | Ascomycota | Dothideomycetes | Capnodiales | Cladosporiaceae | *Cladosporium* | |
| 40 | MIC-63740 | TAM00504 | Ascomycota | Dothideomycetes | Capnodiales | Mycosphaerellaceae | *Sphaerulina* | *pseudovirgaureae* |
| 41, 42, 43, 44, 45 | MIC-67271 | TAM00089 | Ascomycota | Dothideomycetes | Pleosporales | Didymellaceae | *Epicoccum* | *nigrum* |
| 46, 47, 48, 49 | MIC-68178 | TAM00032 | Ascomycota | Dothideomycetes | Pleosporales | Didymellaceae | *Epicoccum* | *nigrum* |
| 50 | MIC-85555 | TAM00074 | Ascomycota | Dothideomycetes | Pleosporales | Didymellaceae | *Epicoccum* | *nigrum* |
| 51 | MIC-77047 | TAM00100 | Ascomycota | Dothideomycetes | Pleosporales | Didymellaceae | *Epicoccum* | *nigrum* |
| 52 | MIC-62081 | TAM00103 | Ascomycota | Dothideomycetes | Pleosporales | Didymellaceae | *Epicoccum* | *nigrum* |
| 53, 54, 55, 56, 57, 58 | MIC-76091 | TAM00194 | Ascomycota | Dothideomycetes | Pleosporales | Didymellaceae | *Epicoccum* | *nigrum* |
| 59 | MIC-90504 | TAM00497 | Ascomycota | Dothideomycetes | Pleosporales | Didymellaceae | *Epicoccum* | *nigrum* |
| 60 | MIC-16066 | TAM00536 | Ascomycota | Dothideomycetes | Pleosporales | Didymellaceae | *Epicoccum* | *nigrum* |
| 61 | MIC-90694 | TAM00046 | Ascomycota | Dothideomycetes | Pleosporales | Didymellaceae | | |
| 62 | MIC-20571 | TAM00160 | Ascomycota | Dothideomycetes | Pleosporales | Massarinaceae | *Stagonospora* | |
| 63 | MIC-26235 | TAM00452 | Ascomycota | Dothideomycetes | Pleosporales | Pleosporaceae | *Alternaria* | *eichhorniae* |
| 64 | MIC-39830 | TAM00129 | Ascomycota | Dothideomycetes | Pleosporales | Pleosporaceae | *Alternaria* | *eichhorniae* |
| 65 | MIC-31674 | TAM00416 | Ascomycota | Dothideomycetes | Pleosporales | Pleosporaceae | *Alternaria* | *eichhorniae* |
| 66 | MIC-61920 | TAM00529 | Ascomycota | Dothideomycetes | Pleosporales | Pleosporaceae | *Alternaria* | *eichhorniae* |
| 67 | MIC-39233 | TAM00323 | Ascomycota | Dothideomycetes | Pleosporales | Pleosporaceae | *Alternaria* | *planifunda* |
| 68 | MIC-92234 | TAM00013 | Ascomycota | Dothideomycetes | Pleosporales | Pleosporaceae | *Bipolaris* | *spicifera* |
| 69 | MIC-77538 | TAM00439 | Ascomycota | Dothideomycetes | Pleosporales | Pleosporaceae | *Bipolaris* | *spicifera* |
| 70 | MIC-45943 | TAM00362 | Ascomycota | Dothideomycetes | Pleosporales | Pleosporaceae | *Stemphylium* | *herbarum* |
| 71 | MIC-32308 | TAM00473 | Ascomycota | Dothideomycetes | Pleosporales | Pleosporaceae | *Stemphylium* | *herbarum* |
| 72 | MIC-12207 | TAM00296 | Ascomycota | Dothideomycetes | Pleosporales | Pleosporaceae | | |
| 73 | MIC-17815 | TAM00518 | Ascomycota | Dothideomycetes | Pleosporales | Sporormiaceae | *Preussia* | *africana* |
| 74, 75, 76 | MIC-07010 | TAM00105 | Ascomycota | Dothidiomycetes | Pleosporales | Pleosporaceae | *Curvularia* | *protuberata* |
| 77, 78, 79, 80, 81 | MIC-31593 | TAM00189 | Ascomycota | Dothideomycetes | Pleosporales | Pleosporaceae | *Curvularia* | *spicifera* |
| 82 | MIC-50324 | TAM00413 | Ascomycota | Eurotiomycetes | Eurotiales | Aspergillaceae | *Penicillium* | |
| 83 | MIC-95013 | TAM00526 | Ascomycota | Sordariomycetes | Diaporthales | Valsaceae | *Phomopsis* | *liquidambari* |
| 84 | MIC-42665 | TAM00524 | Ascomycota | Sordariomycetes | Glomerellales | Plectosphaerellaceae | *Gibellulopsis* | *nigrescens* |
| 85 | MIC-16714 | TAM00531 | Ascomycota | Sordariomycetes | Glomerellales | Plectosphaerellaceae | *Gibellulopsis* | *nigrescens* |
| 86 | MIC-49739 | TAM00533 | Ascomycota | Sordariomycetes | Glomerellales | Plectosphaerellaceae | *Gibellulopsis* | *nigrescens* |
| 87, 88, 89, 90, 91, 92 | MIC-96038 | TAM00505 | Ascomycota | Sordariomycetes | Hypocreales | Hypocreaceae | *Acremonium* | *alternatum* |
| 93 | MIC-87502 | TAM00340 | Ascomycota | Sordariomycetes | Hypocreales | Nectriaceae | *Fusarium* | |
| 94 | MIC-21610 | TAM00424 | Ascomycota | Sordariomycetes | Hypocreales | Ophiocordycipitaceae | *Purpureocillium* | *lavendulum* |
| 95 | MIC-50989 | TAM00490 | Ascomycota | Sordariomycetes | Sordariales | Cephalothecaceae | *Phialemonium* | *inflatum* |
| 96 | MIC-39959 | TAM00333 | Ascomycota | Sordariomycetes | Sordariales | Chaetomiaceae | *Chaetomium* | *coarctatum* |
| 97, 98, 99, 100, | MIC-33414 | TAM00554 | Ascomycota | Sordariomycetes | Sordariales | Chaetomiaceae | *Chaetomium* | *globosum* |

TABLE 3-continued

Exemplary taxonomy and microbe identifiers for fungal endophytes useful in the present invention.

| SEQ ID | MIC ID | TAMU ID | Phylum | Class | Order | Family | Genus | Species |
|---|---|---|---|---|---|---|---|---|
| 101, | | | | | | | | |
| 102, | | | | | | | | |
| 103, | | | | | | | | |
| 104, | | | | | | | | |
| 105 | | | | | | | | |
| 106 | MIC-22947 | TAM00559 | Ascomycota | Sordariomycetes | Sordariales | Chaetomiaceae | *Chaetomium* | *globosum* |
| 107 | MIC-44512 | TAM00560 | Ascomycota | Sordariomycetes | Sordariales | Chaetomiaceae | *Chaetomium* | *globosum* |
| 108 | MIC-51742 | TAM00251 | Ascomycota | Sordariomycetes | Sordariales | Chaetomiaceae | *Chaetomium* | *piluliferum* |
| 109 | MIC-39772 | TAM00317 | Ascomycota | Sordariomycetes | Sordariales | Chaetomiaceae | *Chaetomium* | |
| 110 | MIC-72092 | TAM00508 | | | | | | |
| 111 | MIC-67609 | TAM00512 | Basidiomycota | Tremellomycetes | Tremellales | Incertae sedis | *Cryptococcus* | |
| 112 | MIC-39051 | TAM00514 | Basidiomycota | Tremellomycetes | Tremellales | Incertae sedis | *Cryptococcus* | |
| 113 | MIC-38632 | TAM00489 | | | | | | |
| 114 | MIC-48747 | TAM00244 | Ascomycota | Dothideomycetes | Capnodiales | Cladosporiaceae | *Cladosporium* | |
| 115 | MIC-20835 | TAM00565 | Ascomycota | Dothideomycetes | Capnodiales | Cladosporiaceae | *Cladosporium* | |

Example 3: Preparation of Fungal Biomass and Seed Treatment

Fungal Biomass Production and Heterologous Disposition on Seeds:

Agar plugs of each fungal endophyte (5×5 mm) were transferred to 400 mL Potato Dextrose Broth (PDB; penicillin 10 IU mL$^{-1}$, streptomycin sulfate 0.1 mg mL$^{-1}$) in 1 liter flasks placed onto a rotary shaker at 150 rpm under 25-27° C. for two to three weeks. Fungal biomass was harvested from the liquid culture media by straining through several layers of sterile cheesecloth and transferring to 50 mL conical tubes. Fresh biomass was lyophilized under −85° C. using the Labconco® FreeZone 6 (Kansas City, Mo., USA) plus for at least 48 hrs. Dry biomass was then manually ground using autoclaved mortar and pestle with dry ice and then kept refrigerated at 4° C.

Dry powdered biomass (50 mg mL$^{-1}$) was mixed with 1 mL methylcellulose solution (2%) as a sticker and applied to seeds at a rate of 1 mL per 200 seeds. Seeds were air-dried on aluminum trays in a laminar flow hood, occasionally mixed to ensure homogeneous coating on each seeds, and then coated with 1 g talc per 200 seeds to prevent sticking. Formulation control seeds were similarly treated, but without the addition of fungal biomass.

Fungal Spore Production and Heterologous Disposition on Seeds:

Fungal isolates were grown on potato dextrose agar (PDA) for four days, 2 plugs were macerated in 0.05% Silwet with 2-3 3 mm glass beads and the resulting suspension plated onto malt extract agar (MEA) slants in 50 mL conical tubes which were then incubated in a 26° C. growth chamber with 16 hour daylight for 17 days. Spores were harvested by scraping cultures flooded with 0.05% Silwet and filtering the resulting suspension through a 60 μm nylon membrane. Spores were quantified with a CytoFlex Flow Cytometer and serial dilutions of the spore suspension were plated onto PDA to quantify the proportion of viable spores.

Fungal spore suspensions were added to seeds at a normalized dose rate of 6×10$^4$ spores per seed. Treated seeds were then coated with a flowability polymer. Control seeds received 0.05% Silwet solution and flowability polymer without spores. On surface spore viability was assessed by agitating treated seeds in 40 mM sodium phosphate buffer and plating serial dilutions of the resulting suspension onto PDA.

Example 4: Greenhouse Cotton Time to Wilt and Time to Death

Relatively small increases of one or two days in seedling time to wilt or time to death under water stress have a substantial and agronomically relevant impact on seedling establishment and cotton stand. Among other things, this example describes a greenhouse assay that mimics environmental conditions of extended water stress during the seedling stage of plant development in field production of cotton. Among other things, this example describes strains of fungal endophytes that provide an improved response to water stress to treated cotton plants.

Seed Inoculation:

Black cotton seeds of varieties Phytogen 499WRF and Delta Pine 1321B2RF were treated with fungal endophyte biomass prepared as described in Example 3. Dry powdered biomass (50 mg mL$^{-1}$) was mixed with 1 mL methylcellulose solution (2%) as a sticker and applied to seeds at a rate of 1 mL per 200 seeds. Seeds were air-dried on aluminum trays in a laminar flow hood, occasionally mixed to ensure homogeneous coating on each seeds, and then coated with 1 g talc per 200 seeds to prevent sticking. Formulation control seeds were similarly treated, but without the addition of fungal biomass.

Plant Production:

Seeds of each treatment combination (inoculated or control seeds) were planted individually in seedling germination trays. Each cell pot measured 4 cm top diameter×6 cm deep and was filled with nonsterile Metro-Mix® 900 soil (Sun Gro Horticulture, Agawam, Mass.; ingredients: bark, vermiculite, peat moss, perlite, dolomitic limestone) watered to saturation prior to planting. Plants were grown in a controlled temperature room at 25° C. under constant overhead illumination (EnviroGro T5 High Output Fluorescent Lighting Systems). Equal amounts of water corresponding to the pot saturation volume were applied to each plant at 7 and 14 days after planting (DAP) by which time they had reached the early 1$^{st}$ true leaf stage. Water was then withheld from all the endophyte-treated and control plants which were monitored daily for the onset of wilting and day of death. Both the time to event, i.e. the day within the evaluation period at which either wilting or death occurred, and the event status, i.e. a binary tally of whether or not the event occurred, were recorded. Tray positions were randomized and rotated daily to control for potential position effects.

Data Analysis:

The survival package (v. 2.40-1) (Therneau T (2015). *A Package for Survival Analysis in S*. version 2.38, available online at CRAN.R-project.org/package=survival; Terry M. Therneau and Patricia M. Grambsch (2000). *Modeling Survival Data: Extending the Cox Model*. Springer, New York. ISBN 0-387-98784-3.) in R (v. 3.2.2) (R Development Core Team (2008). R: A language and environment for statistical computing. R Foundation for Statistical Computing, Vienna, Austria. ISBN 3-900051-07-0, available online at R-project.org.) was used to run the Cox proportional hazards model to generate hazard ratios (HR) and associated p-values for each strain compared to the formulation controls within the same experiment. Both the strain used as a seed treatment and the crop variety were included in the model: coxph(Surv (time to event, event status)~strain+variety)

Figure 32:
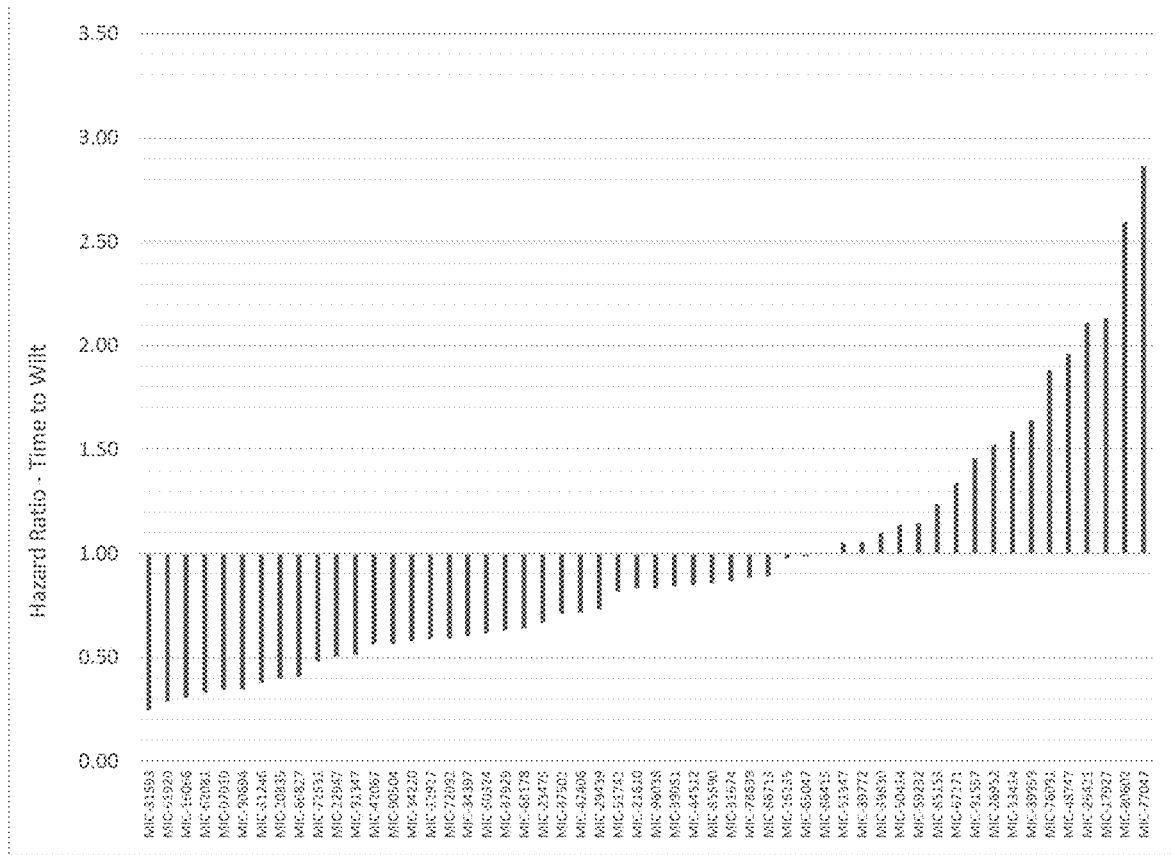
FIG. 32. Hazard ratios derived from the Cox proportional hazards model for time to wilt of cotton seedlings treated with fungal endophyte strains. Hazard ratios are displayed in rank order from strains giving the most effective protection from the measured hazard (HR<1) to strains giving no protection from the measured hazard (HR>1).
Figure 33:
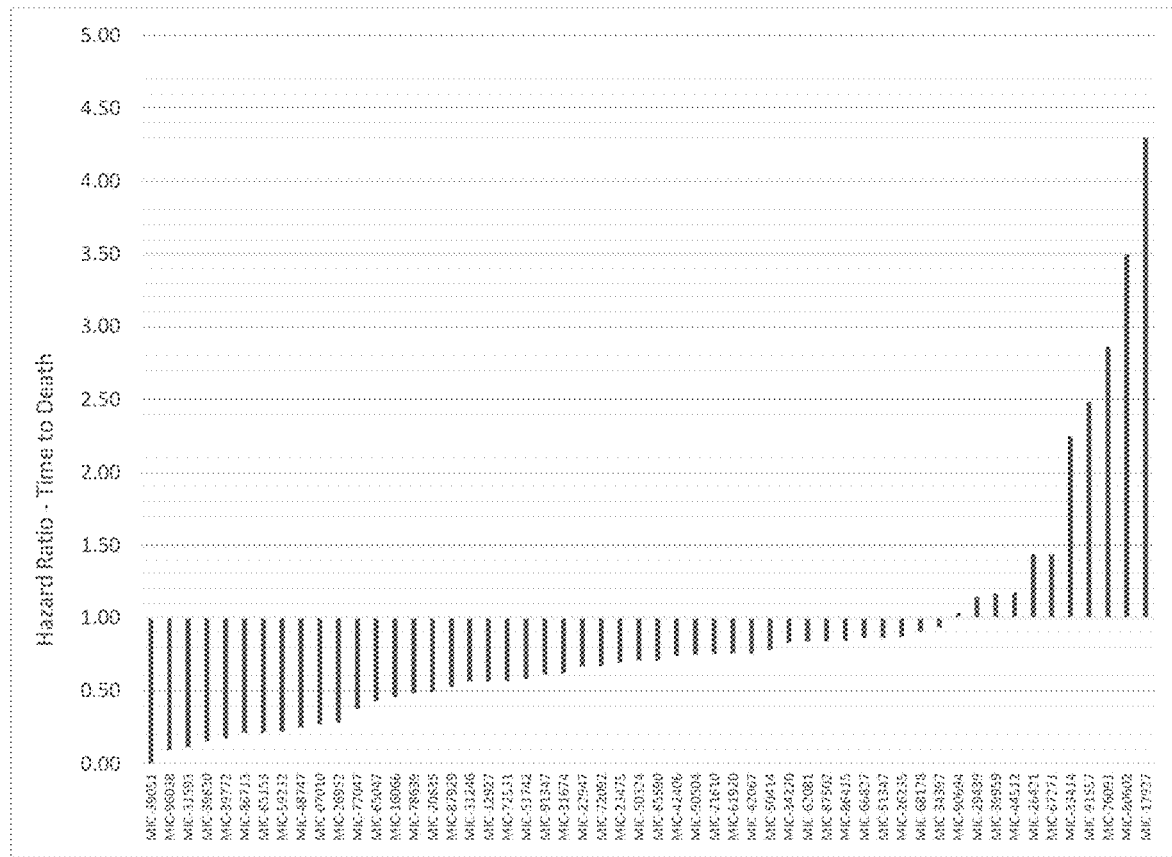
FIG. 33. Hazard ratios derived from the Cox proportional hazards model for time to death of cotton seedlings treated with fungal endophyte strains. Hazard ratios are displayed in rank order from strains giving the most effective protection from the measured hazard (HR<1) to strains giving no protection from the measured hazard (HR>1).
Figure 34:
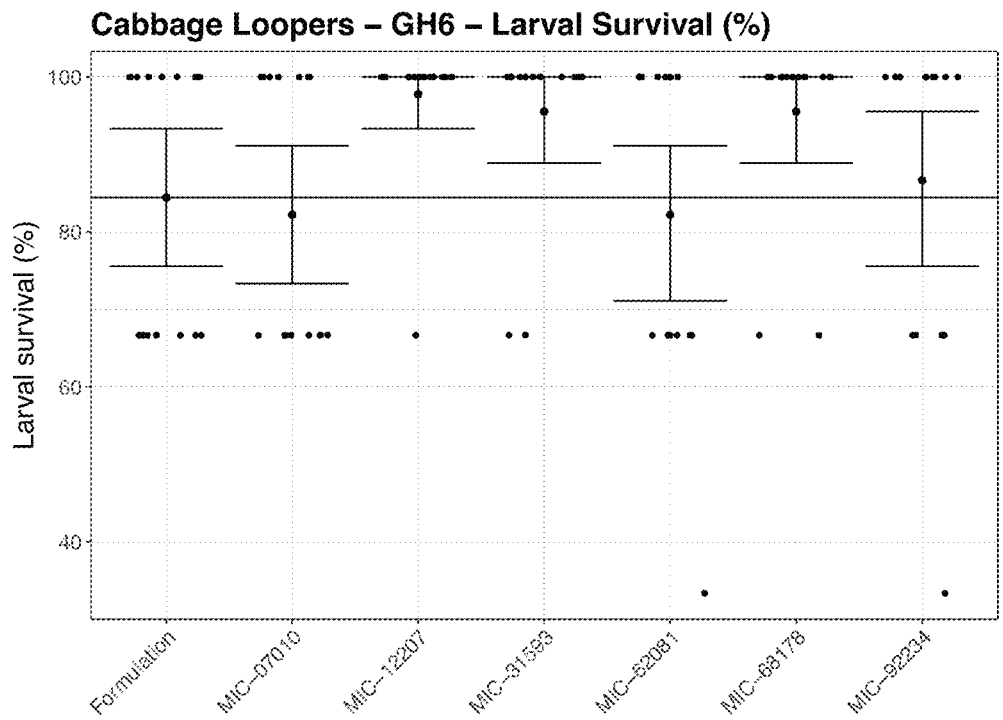
FIG. 34. Larval survival (%) after 7 days of herbivory by cabbage looper larvae on a soy leaflet grown from seeds treated with fungal endophytes MIC-92234 (TAM00013), MIC-68178 (TAM00032), MIC-62081 (TAM00103), MIC-07010 (TAM00105), MIC-31593 (TAM00189), or MIC-12207 (TAM00296). GH6—This round received 3 larvae per leaflet and larvae were transferred to a fresh leaflet from the same plant after 5 days. n=15 plants per treatment.
Figure 35:
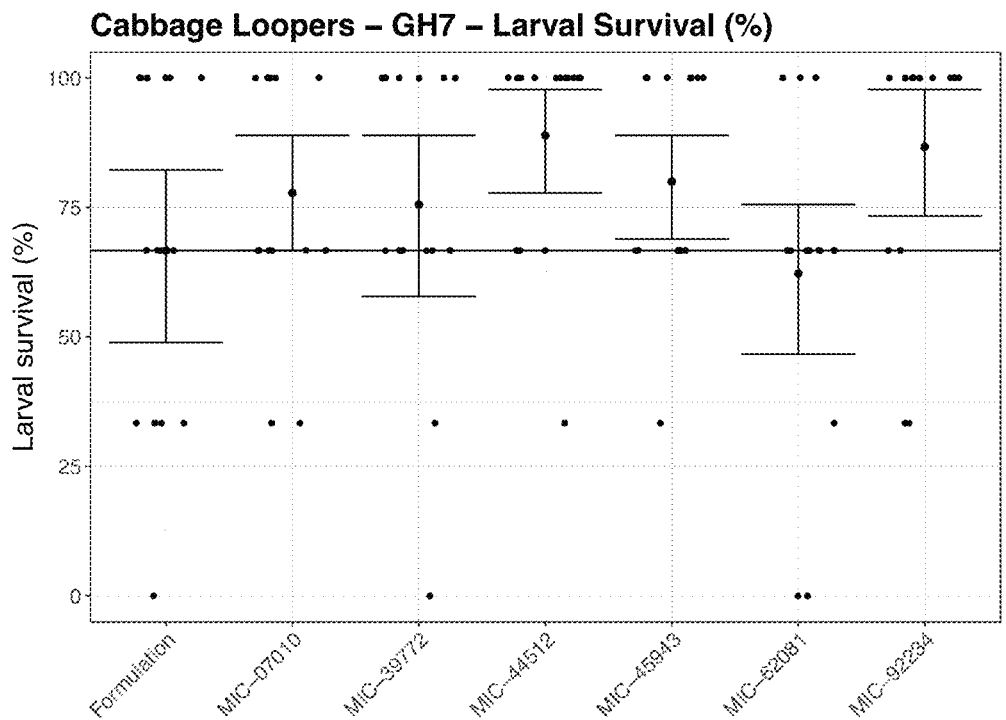
FIG. 35. Larval survival (%) after 7 days of herbivory by cabbage looper larvae on a soy leaflet grown from seeds treated with fungal endophytes MIC-92234 (TAM00013), MIC-62081 (TAM00103), MIC-07010 (TAM00105), MIC-39772 (TAM00317), MIC-45943 (TAM00362), or MIC-44512 (TAM00560). GH7—This round received 3 larvae per leaflet and larvae were transferred to a fresh leaflet from the same plant after 5 days. n=15 plants per treatment.
Figure 36:
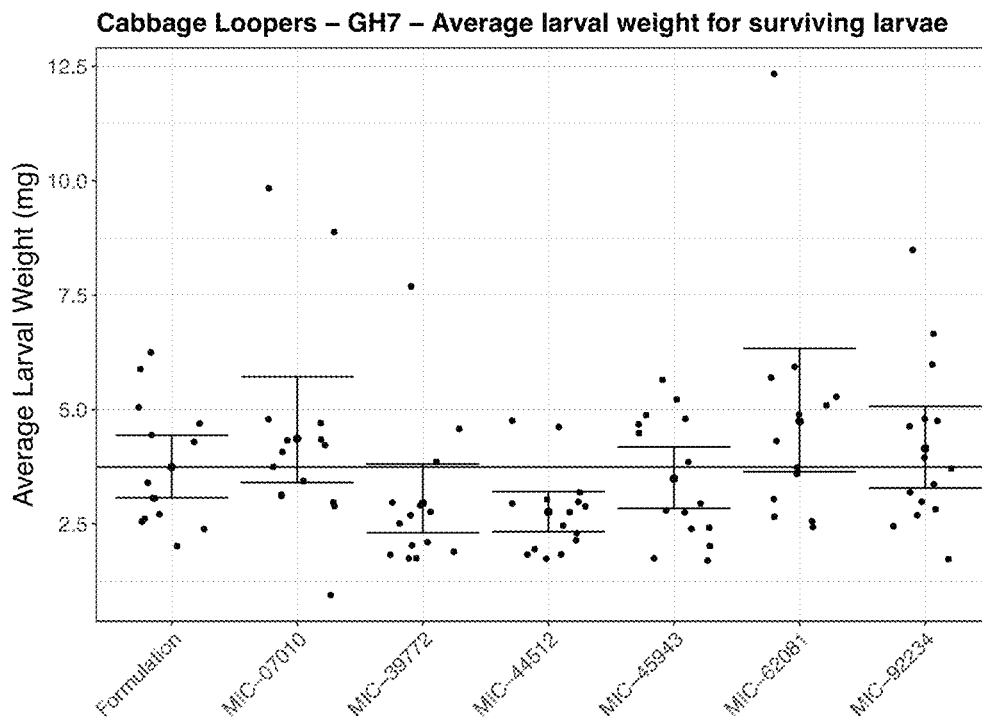
FIG. 36. Average weight of surviving cabbage looper larvae (mg) after 7 days of herbivory on a soy leaflet grown from seeds treated with fungal endophytes MIC-92234 (TAM00013), MIC-62081 (TAM00103), MIC-07010 (TAM00105), MIC-39772 (TAM00317), MIC-45943 (TAM00362), or MIC-44512 (TAM00560). GH7—This round received 3 larvae per leaflet and larvae were transferred to a fresh leaflet from the same plant after 5 days. n=15 plants per treatment.
Figure 37:
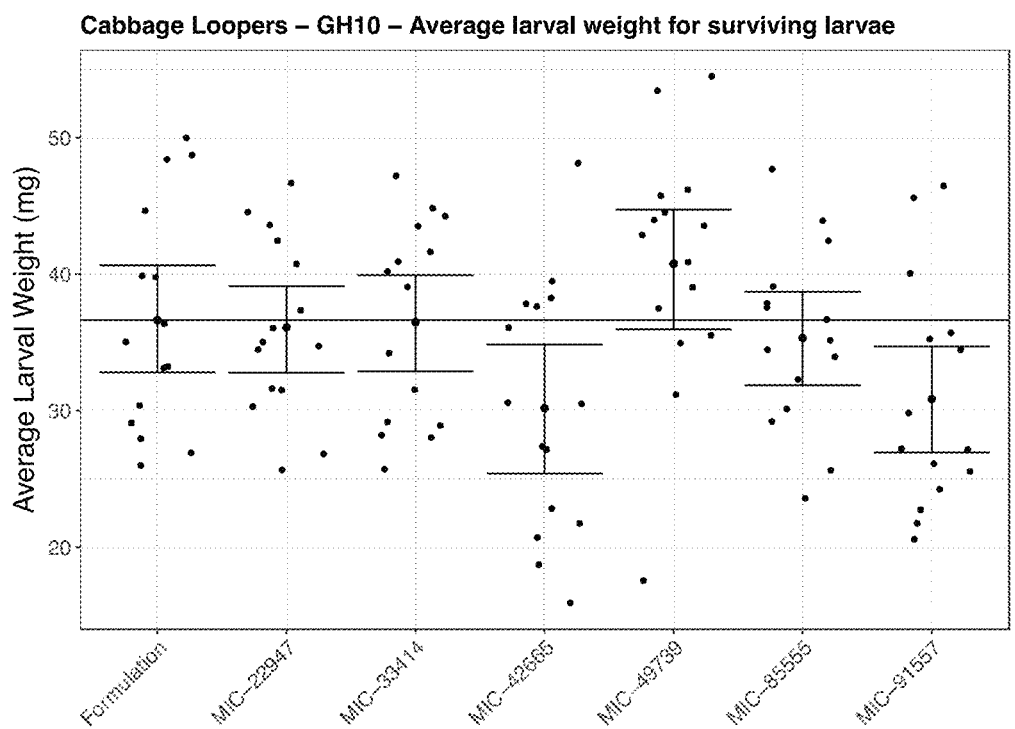
FIG. 37. Average weight of surviving cabbage looper larvae (mg) after 7 days of herbivory on a soy leaflet grown from seeds treated with fungal endophytes MIC-85555 (TAM00074), MIC-91557 (TAM00463), MIC-42665 (TAM00524), MIC-49739 (TAM00533), MIC-33414 (TAM00554), or MIC-22947 (TAM00559). GH10—This round received 3 larvae per leaflet and larvae were transferred to a fresh leaflet from the same plant after 5 days. n=15 plants per treatment.
Figure 38:
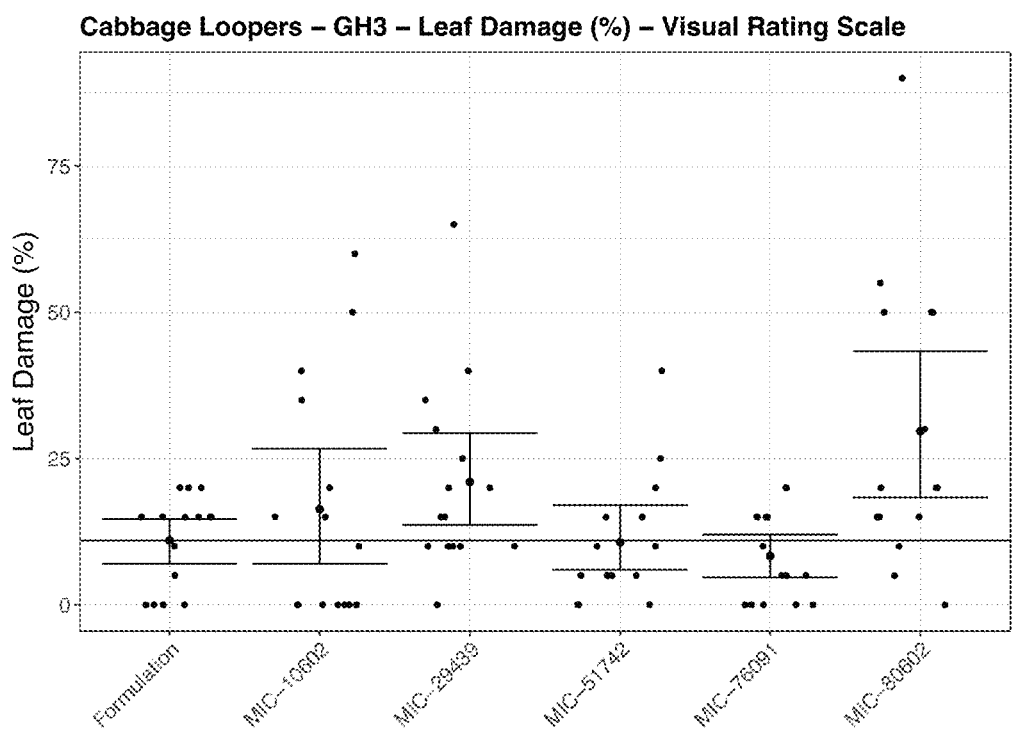
FIG. 38. Leaf damage (%) as assessed via visual rating scale after 7 days of herbivory by cabbage looper larvae on a soy leaflet grown from seeds treated with fungal endophytes MIC-76091 (TAM00194), MIC-29439 (TAM00201), MIC-10602 (TAM00248), MIC-80602 (TAM00249), or MIC-51742 (TAM00251). GH3—This round received 3 larvae per leaflet and larvae were transferred to a fresh leaflet from the same plant after 5 days. n=15 plants per treatment. This batch of cabbage loopers had poor overall herbivory performance.
Figure 39:
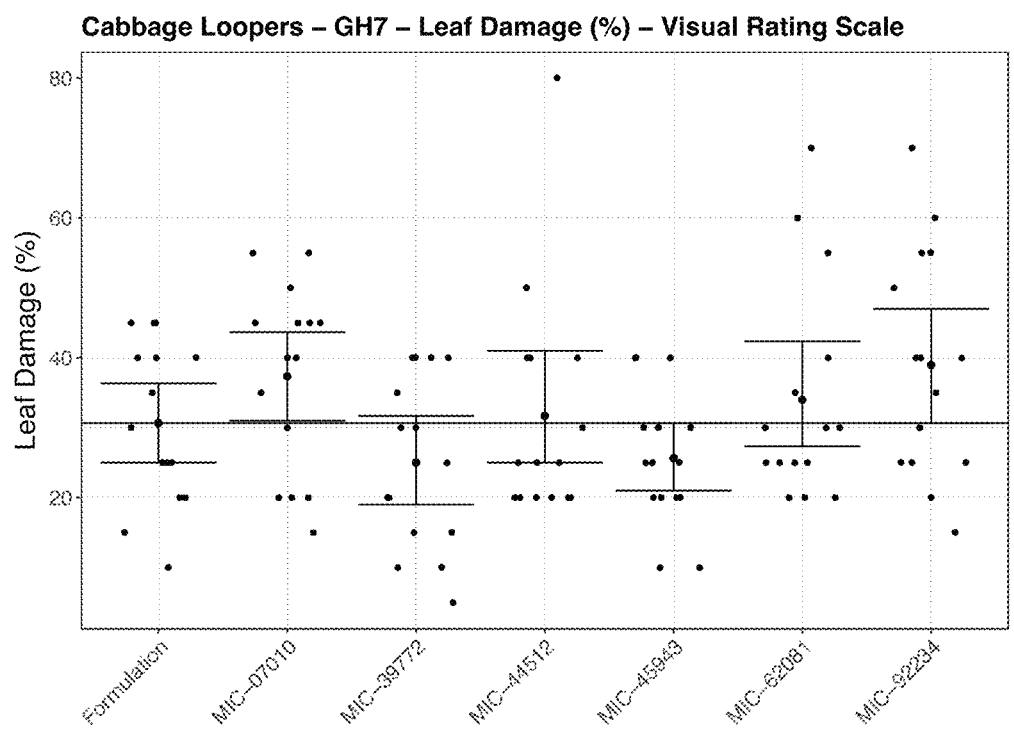
FIG. 39. Leaf damage (%) as assessed via visual rating scale after 7 days of herbivory by cabbage looper larvae on a soy leaflet grown from seeds treated with fungal endophytes MIC-92234 (TAM00013), MIC-62081 (TAM00103), MIC-07010 (TAM00105), MIC-39772 (TAM00317), MIC-45943 (TAM00362), or MIC-44512 (TAM00560). GH7—This round received 3 larvae per leaflet and larvae were transferred to a fresh leaflet from the same plant after 5 days. n=15 plants per treatment.
Figure 40:
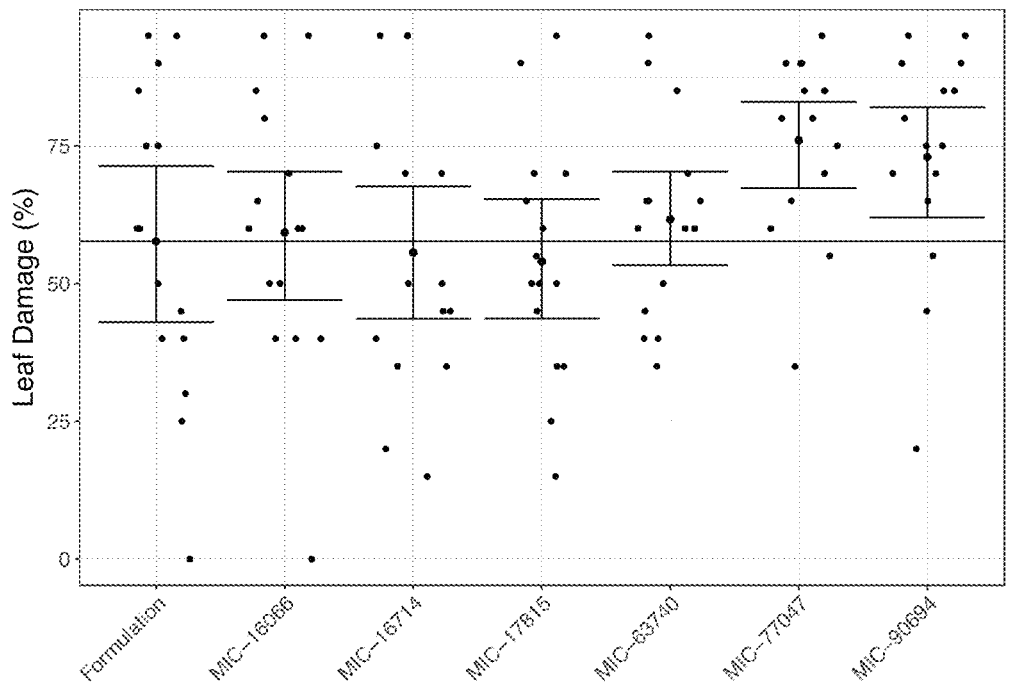
FIG. 40. Leaf damage (%) as assessed via visual rating scale after 7 days of herbivory by cabbage looper larvae on a soy leaflet grown from seeds treated with fungal endophytes MIC-90694 (TAM00046), MIC-77047 (TAM00100), MIC-63740 (TAM00504), MIC-17815 (TAM00518), MIC-16714 (TAM00531), or MIC-16066 (TAM00536). GH8—This round received 3 larvae per leaflet and larvae were transferred to a fresh leaflet from the same plant after 5 days. n=15 plants per treatment.
Figure 41:
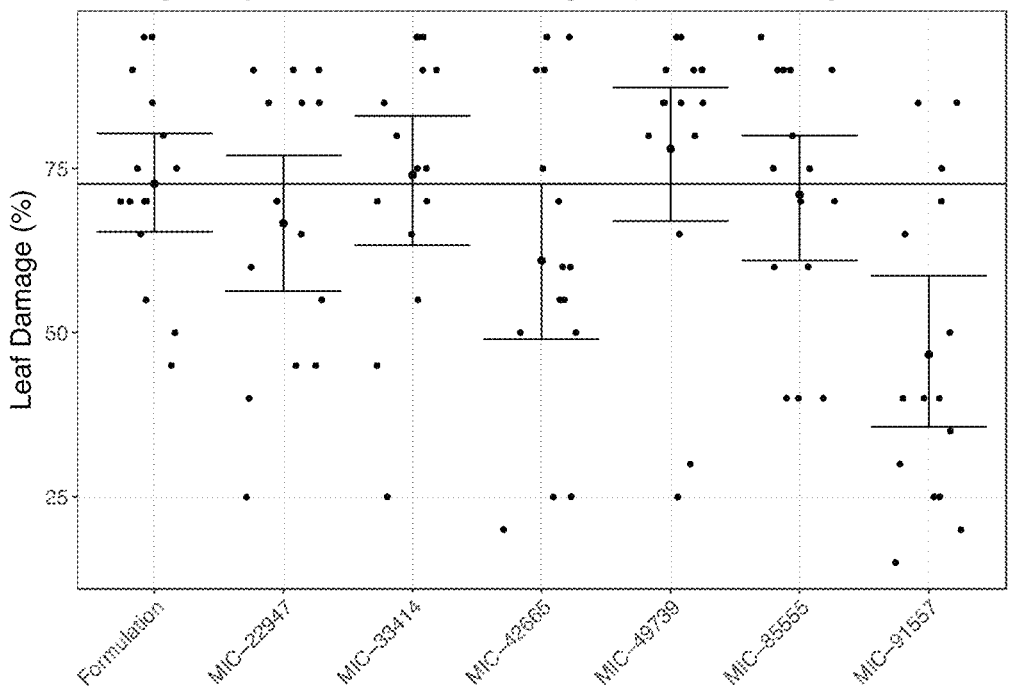
FIG. 41. Leaf damage (%) as assessed via visual rating scale after 7 days of herbivory by cabbage looper larvae on a soy leaflet grown from seeds treated with fungal endophytes MIC-85555 (TAM00074), MIC-91557 (TAM00463), MIC-42665 (TAM00524), MIC-49739 (TAM00533), MIC-33414 (TAM00554), or MIC-22947 (TAM00559). GH10—This round received 3 larvae per leaflet and larvae were transferred to a fresh leaflet from the same plant after 5 days. n=15 plants per treatment.
Figure 42:
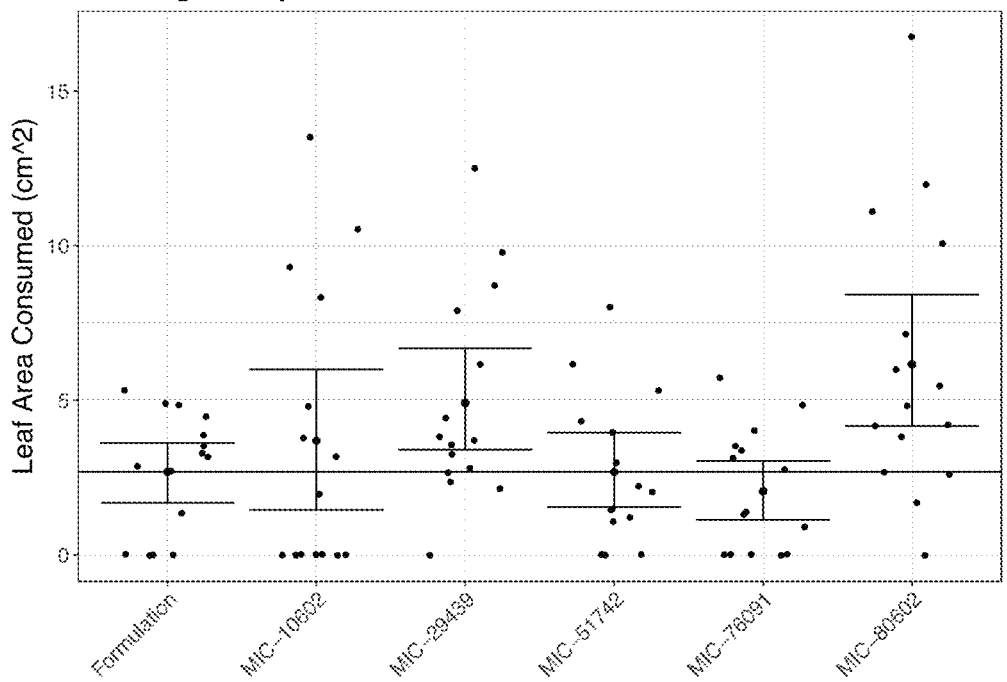
FIG. 42. Leaf area consumed (cm^2) as calculated from starting leaf area and percent leaf damage assessed via visual rating scale after 7 days of herbivory by cabbage looper larvae on a soy leaflet grown from seeds treated with fungal endophytes MIC-76091 (TAM00194), MIC-29439 (TAM00201), MIC-10602 (TAM00248), MIC-80602 (TAM00249), or MIC-51742 (TAM00251). GH3—This round received 3 larvae per leaflet and larvae were transferred to a fresh leaflet from the same plant after 5 days. n=15 plants per treatment. This batch of cabbage loopers had poor overall herbivory performance.
Figure 43:
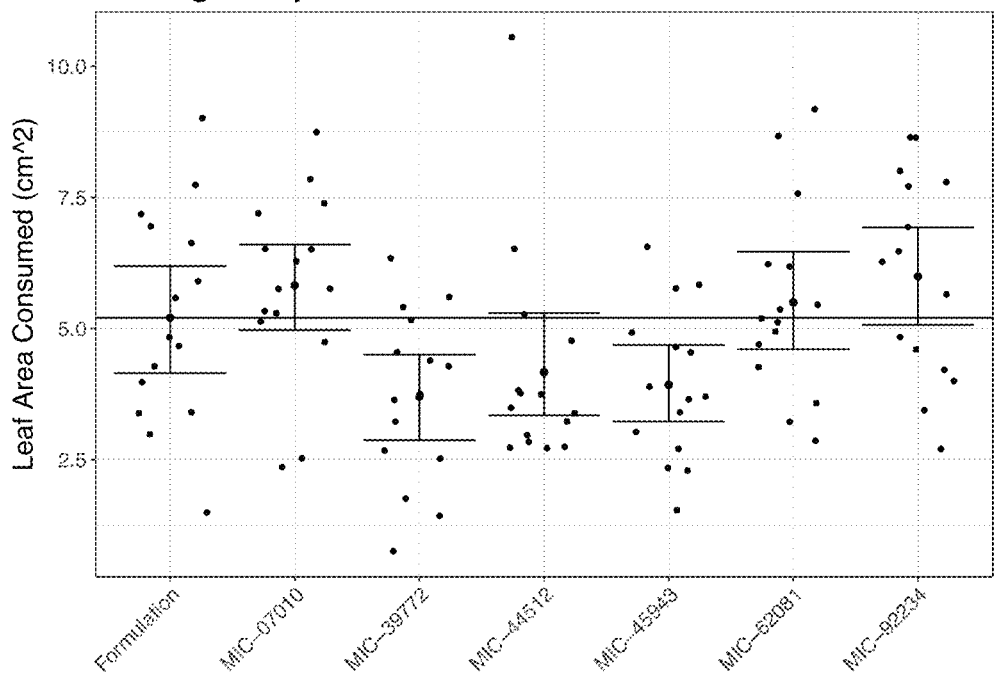
FIG. 43. Leaf area consumed (cm^2) as calculated from starting leaf area and percent leaf damage assessed via visual rating scale after 7 days of herbivory by cabbage looper larvae on a soy leaflet grown from seeds treated with fungal endophytes MIC-92234 (TAM00013), MIC-62081 (TAM00103), MIC-07010 (TAM00105), MIC-39772 (TAM00317), MIC-45943 (TAM00362), or MIC-44512 (TAM00560). GH7—This round received 3 larvae per leaflet and larvae were transferred to a fresh leaflet from the same plant after 5 days. n=15 plants per treatment.
Figure 44:
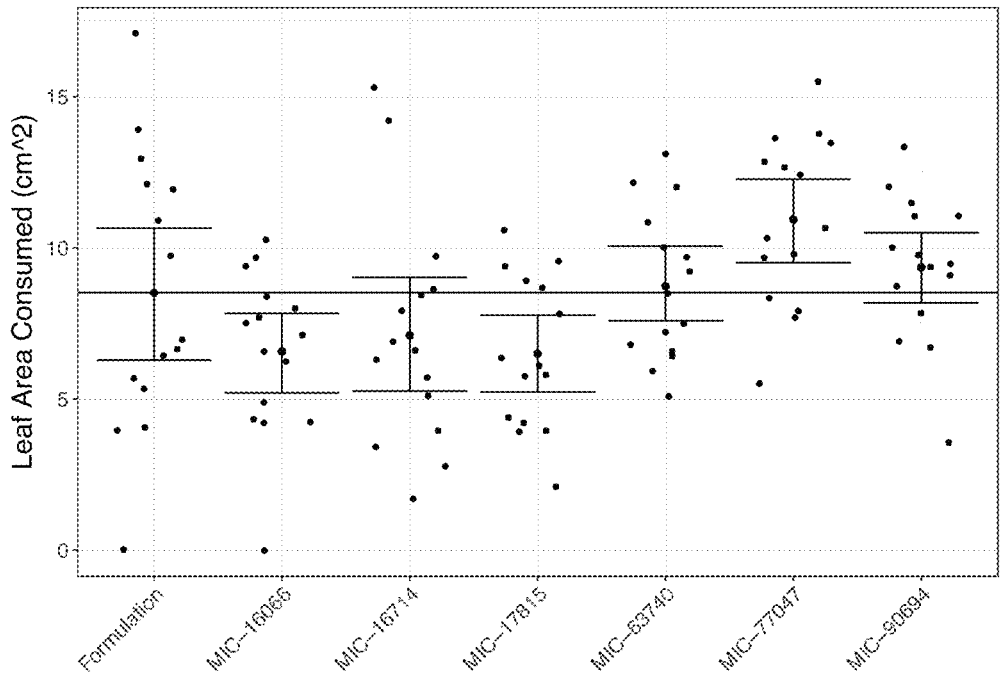
FIG. 44. Leaf area consumed (cm^2) as calculated from starting leaf area and percent leaf damage assessed via visual rating scale after 7 days of herbivory by cabbage looper larvae on a soy leaflet grown from seeds treated with fungal endophytes MIC-90694 (TAM00046), MIC-77047 (TAM00100), MIC-63740 (TAM00504), MIC-17815 (TAM00518), MIC-16714 (TAM00531), or MIC-16066 (TAM00536). GH8—This round received 3 larvae per leaflet and larvae were transferred to a fresh leaflet from the same plant after 5 days. n=15 plants per treatment.
Figure 45:
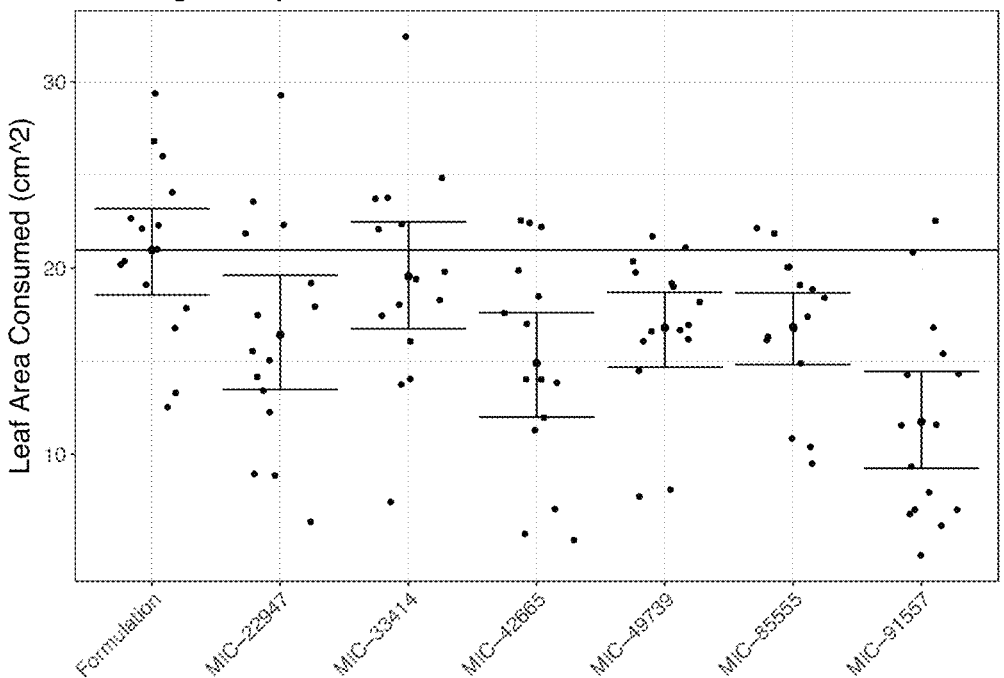
FIG. 45. Leaf area consumed (cm^2) as calculated from starting leaf area and percent leaf damage assessed via visual rating scale after 7 days of herbivory by cabbage looper larvae on a soy leaflet grown from seeds treated with fungal endophytes MIC-85555 (TAM00074), MIC-91557 (TAM00463), MIC-42665 (TAM00524), MIC-49739 (TAM00533), MIC-33414 (TAM00554), or MIC-22947 (TAM00559). GH10—This round received 3 larvae per leaflet and larvae were transferred to a fresh leaflet from the same plant after 5 days. n=15 plants per treatment.
Figure 46:
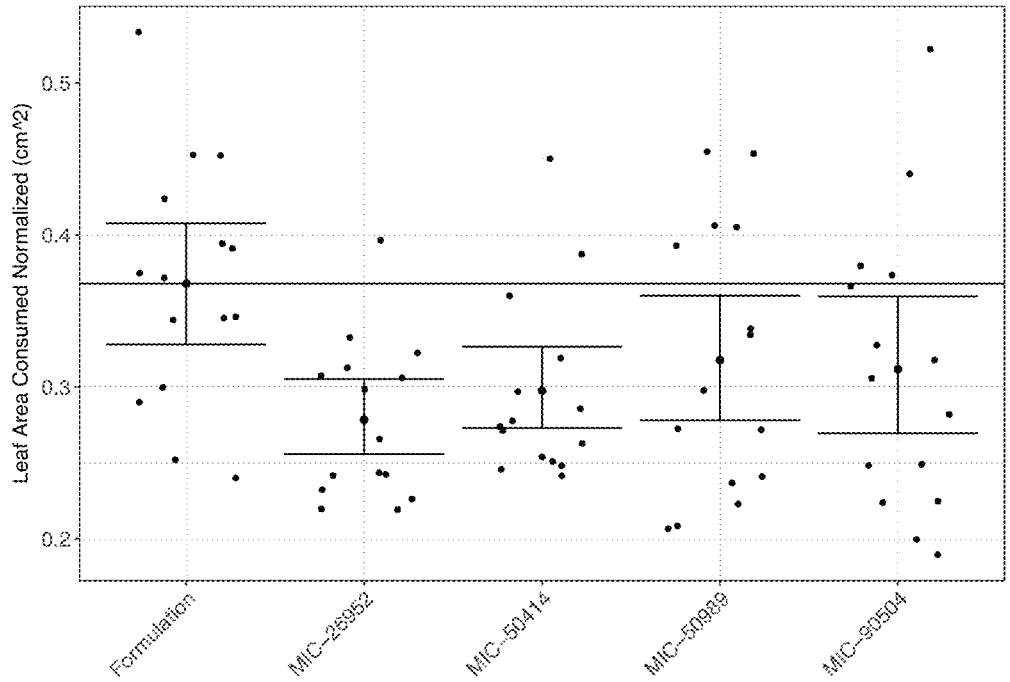
FIG. 46. Leaf area consumed (cm^2) as assessed normalized by average larval weight (mg) after 7 days of herbivory by cabbage looper larvae on a soy leaflet grown from seeds treated with fungal endophytes MIC-50989 (TAM00490), MIC-26952 (TAM00494), MIC-90504 (TAM00497), or MIC-50414 (TAM00534). GH2—This round received 3 larvae per leaflet and larvae were transferred to a fresh leaflet from the same plant after 5 days. n=15 plants per treatment.
Figure 47:
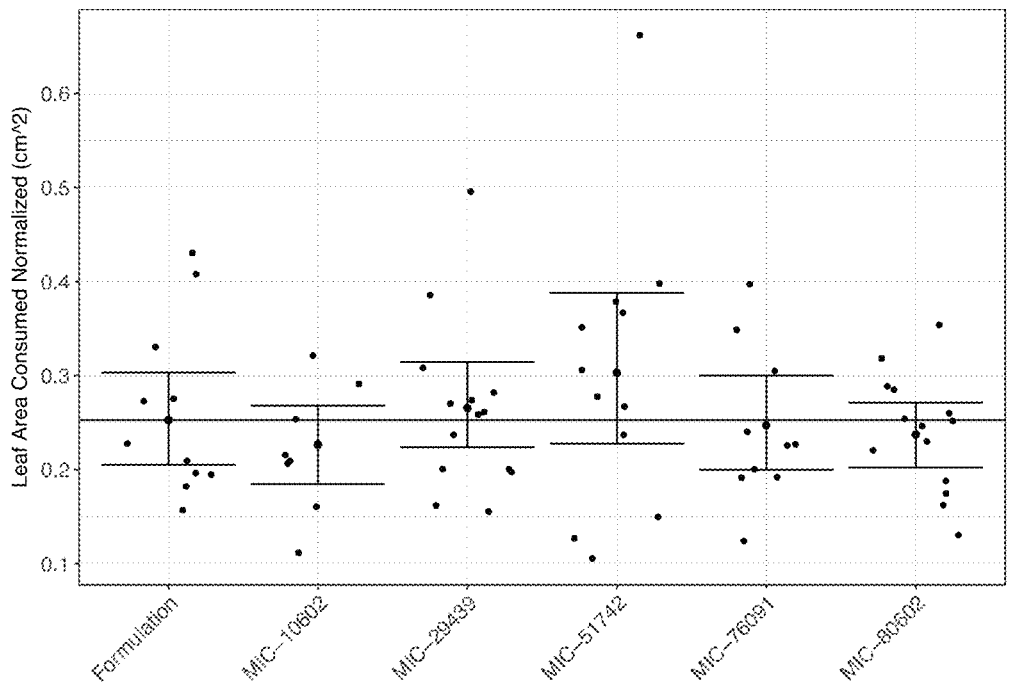
FIG. 47. Leaf area consumed (cm^2) as assessed normalized by average larval weight (mg) after 7 days of herbivory by cabbage looper larvae on a soy leaflet grown from seeds treated with fungal endophytes MIC-76091 (TAM00194), MIC-29439 (TAM00201), MIC-10602 (TAM00248), MIC-80602 (TAM00249), or MIC-51742 (TAM00251). GH3—This round received 3 larvae per leaflet and larvae were transferred to a fresh leaflet from the same plant after 5 days. n=15 plants per treatment. This batch of cabbage loopers had poor overall herbivory performance.
Figure 48:
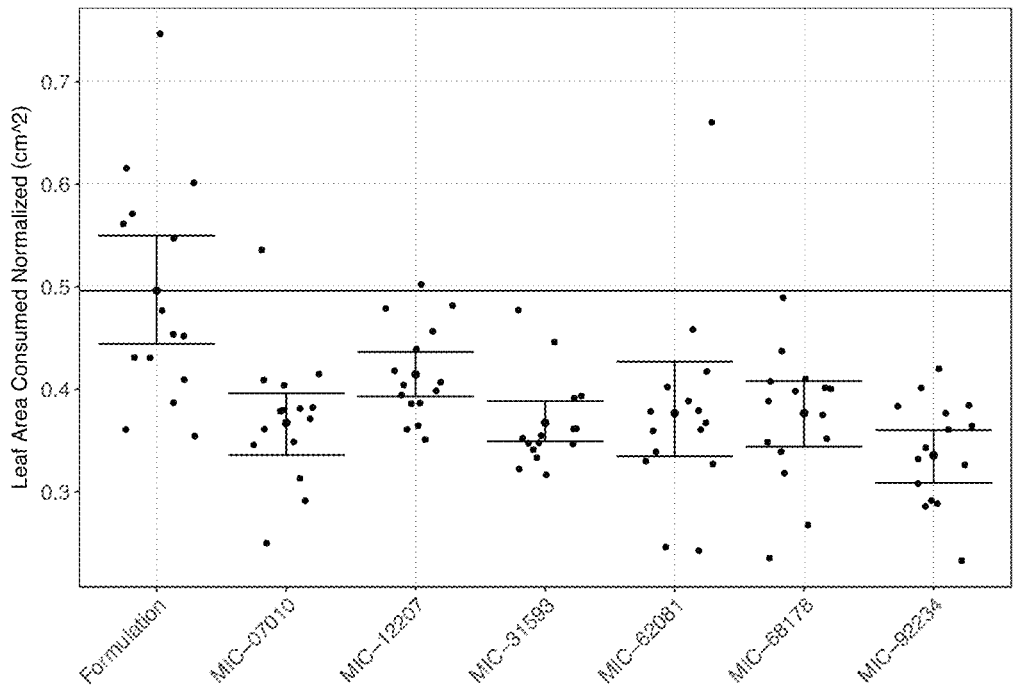
FIG. 48. Leaf area consumed (cm^2) as assessed normalized by average larval weight (mg) after 7 days of herbivory by cabbage looper larvae on a soy leaflet grown from seeds treated with fungal endophytes MIC-92234 (TAM00013), MIC-68178 (TAM00032), MIC-62081 (TAM00103), MIC-07010 (TAM00105), MIC-31593 (TAM00189), or MIC-12207 (TAM00296). GH6—This round received 3 larvae per leaflet and larvae were transferred to a fresh leaflet from the same plant after 5 days. n=15 plants per treatment.
Figure 49:
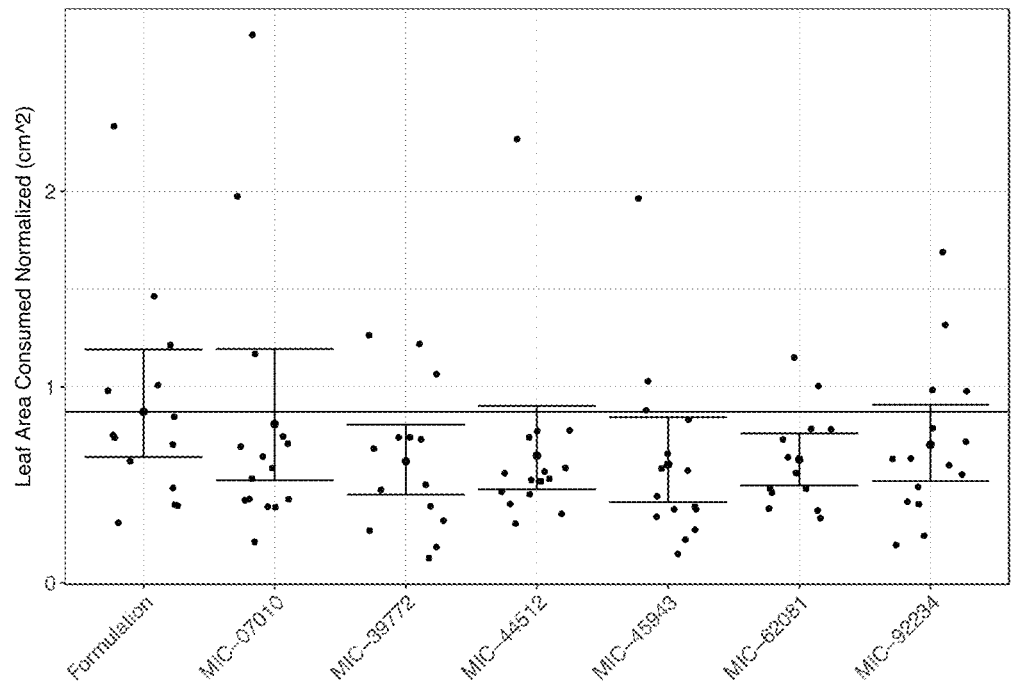
FIG. 49. Leaf area consumed (cm^2) as assessed normalized by average larval weight (mg) after 7 days of herbivory by cabbage looper larvae on a soy leaflet grown from seeds treated with fungal endophytes MIC-92234 (TAM00013), MIC-62081 (TAM00103), MIC-07010 (TAM00105), MIC-39772 (TAM00317), MIC-45943 (TAM00362), or MIC-44512 (TAM00560). GH7—This round received 3 larvae per leaflet and larvae were transferred to a fresh leaflet from the same plant after 5 days. n=15 plants per treatment.
Figure 50:
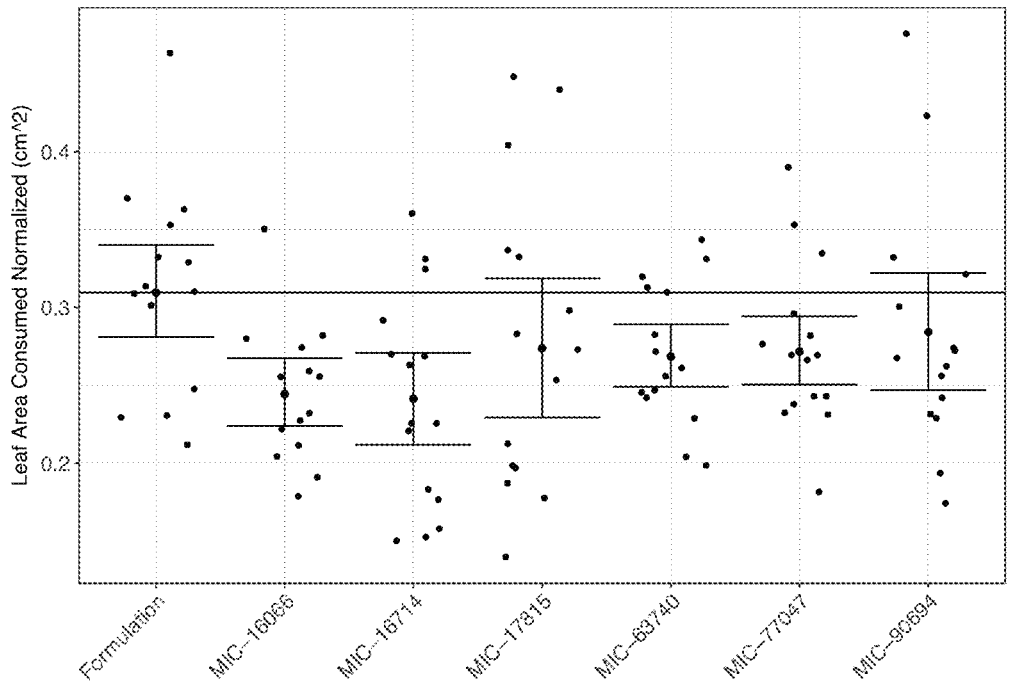
FIG. 50. Leaf area consumed (cm^2) as assessed normalized by average larval weight (mg) after 7 days of herbivory by cabbage looper larvae on a soy leaflet grown from seeds treated with fungal endophytes MIC-90694 (TAM00046), MIC-77047 (TAM00100), MIC-63740 (TAM00504), MIC-17815 (TAM00518), MIC-16714 (TAM00531), or MIC-16066 (TAM00536). GH8—This round received 3 larvae per leaflet and larvae were transferred to a fresh leaflet from the same plant after 5 days. n=15 plants per treatment.
Figure 51:
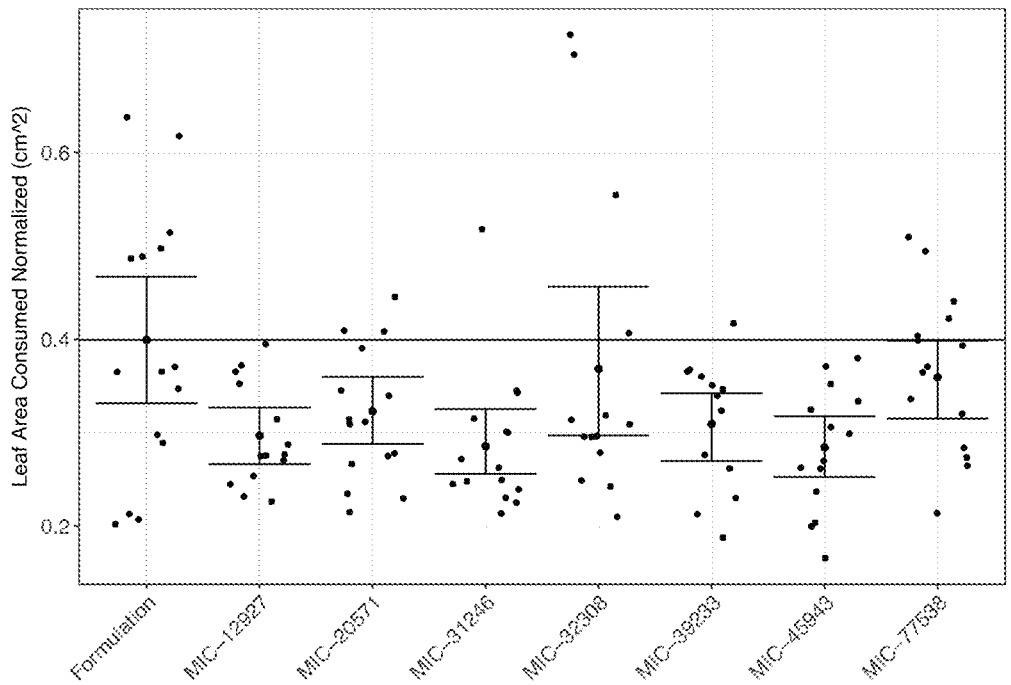
FIG. 51. Leaf area consumed (cm^2) as assessed normalized by average larval weight (mg) after 7 days of herbivory by cabbage looper larvae on a soy leaflet grown from seeds treated with fungal endophytes MIC-20571 (TAM00160), MIC-12927 (TAM00193), MIC-39233 (TAM00323), MIC-45943 (TAM00362), MIC-77538 (TAM00439), MIC-32308 (TAM00473), or MIC-31246 (TAM00501). GH9—This round received 3 larvae per leaflet and larvae were transferred to a fresh leaflet from the same plant after 5 days. n=15 plants per treatment.
Figure 52:
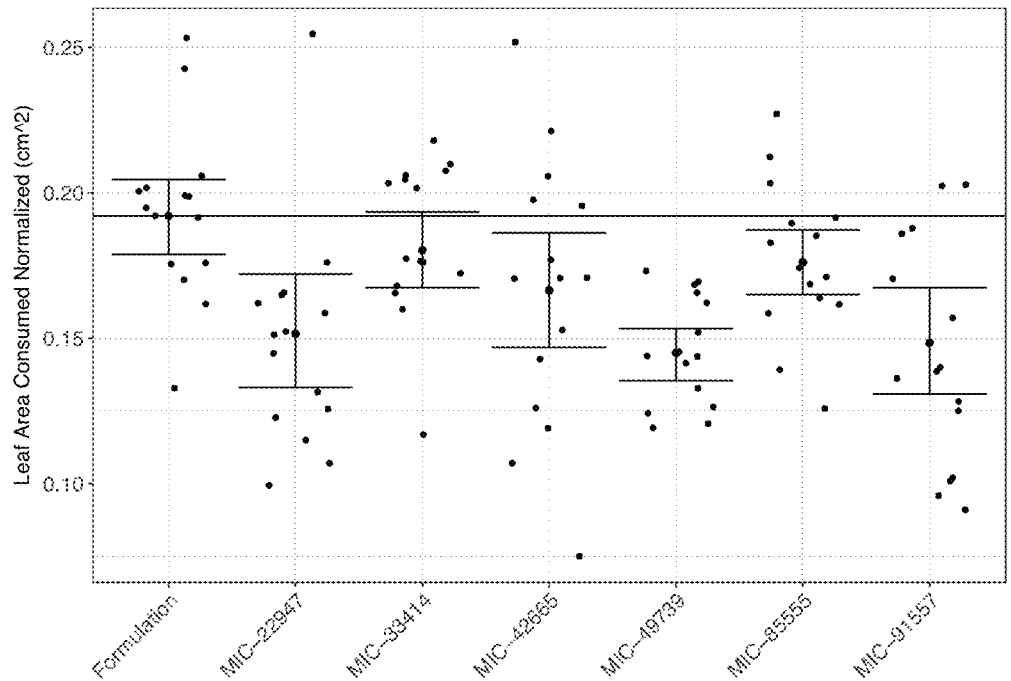
FIG. 52. Leaf area consumed (cm^2) as assessed normalized by average larval weight (mg) after 7 days of herbivory by cabbage looper larvae on a soy leaflet grown from seeds treated with fungal endophytes MIC-85555 (TAM00074), MIC-91557 (TAM00463), MIC-42665 (TAM00524), MIC-49739 (TAM00533), MIC-33414 (TAM00554), or MIC-22947 (TAM00559). GH10—This round received 3 larvae per leaflet and larvae were transferred to a fresh leaflet from the same plant after 5 days. n=15 plants per treatment.

Hazard ratios>1 indicate that the endophyte treated plants experience a higher risk of the modeled hazard (wilt or death) and a lower survival rate under water stress compared to formulation controls. Conversely, hazard ratios<1 indicate that the endophyte treated plants experience a lower risk of the modeled hazard (wilt or death) and a higher survival rate under water stress compared to formulation controls (FIGS. 32-34). Kaplan Meier survival curves were generated for each strain using the rms package (v. 5.0-0) (Frank E Harrell Jr (2016). rms: Regression Modeling Strategies. R package version 5.0-0. available online at CRAN.R-project.org/package=rms) in R. Exemplary Kaplan Meier survival curves for exemplary endophyte treated plants relative to formulation controls are shown in FIGS. 3-31, hazard ratios are summarized in FIGS. 32-34.

Results:

For time to wilt, 15 of 54 strains evaluated showed a statistically significant increase in time to wilt under water stress compared to formulation control treated plants (Table 4). For time to death, 18 of 54 strains evaluated showed a statistically significant increase in time to death under water stress compared to formulation control treated plants (Table 5); these endophytes may be identified by sequence homology to one or more sequence selected from the group consisting of SEQ ID NOs: 30, 33, 39, 51, 64, 74, 75, 76, 77, 78, 79, 80, 81, 87, 88, 89, 90, 91, 92, 109, and 114.

TABLE 4

Of 54 strains evaluated as seed treatments for two varieties of cotton, 15 showed a statistically significant increase in time to wilt under water stress compared to formulation control treated plants.

| Taxonomic ID | Strain ID | HR Wilt | Pr (>|z|) Wilt |
|---|---|---|---|
| Didymellaceae | MIC-90694 | 0.35 | 0.000173 |
| Epicoccum nigrum | MIC-62081 | 0.33 | 6.63E-05 |
| Curvularia protuberata | MIC-07010 | 0.34 | 3.90E-05 |
| Chaetomium sp. | MIC-66827 | 0.41 | 0.002422 |
| Chaetomium globosum | MIC-23475 | 0.67 | 0.040085 |
| Diaporthe sp. | MIC-42067 | 0.56 | 0.040736 |
| Cladosporium cladosporioides | MIC-91347 | 0.51 | 0.016866 |
| Alternaria sp. | MIC-86713 | 0.46 | 0.006176 |
| Curvularia spicifera | MIC-31593 | 0.24 | 1.11E-06 |
| Cladosporium sp. | MIC-31246 | 0.38 | 0.001339 |
| Cladosporium cladosporioides | MIC-72531 | 0.48 | 0.004828 |
| Alternaria eichhorniae | MIC-61920 | 0.29 | 0.000123 |
| Epicoccum nigrum | MIC-16066 | 0.31 | 2.73E-05 |
| Chaetomium globosum | MIC-22947 | 0.50 | 0.005774 |
| Cladosporium cladosporioides | MIC-20835 | 0.40 | 0.002042 |

TABLE 5

Of 54 strains evaluated as seed treatments for two varieties of cotton, 15 showed a statistically significant increase in time to death under water stress compared to formulation control treated plants.

| Taxonomic ID | Strain ID | HR Death | Pr(>|z|) Death |
|---|---|---|---|
| Epicoccum nigrum | MIC-77047 | 0.38 | 0.002237 |
| Curvularia protuberata | MIC-07010 | 0.27 | 0.012087 |
| Epicoccum nigrum | MIC-65047 | 0.43 | 0.033795 |
| Alternaria eichhorniae | MIC-39830 | 0.15 | 2.71E-06 |
| Alternaria sp. | MIC-86713 | 0.21 | 0.000604 |
| Curvularia spicifera | MIC-31593 | 0.11 | 0.004091 |
| Cladosporium sp. | MIC-48747 | 0.25 | 3.94E-05 |
| Chaetomium sp. | MIC-39772 | 0.17 | 0.028894 |
| Chaetomium globosum | MIC-59232 | 0.22 | 9.32E-05 |
| Cladosporium herbarum | MIC-87929 | 0.53 | 0.032516 |
| Epicoccum nigrum | MIC-85153 | 0.21 | 1.39E-05 |
| Cladosporium sp. | MIC-26952 | 0.28 | 0.000146 |
| Acremonium alternatum | MIC-96038 | 0.09 | 0.02573 |
| Cladosporium cladosporioides | MIC-72531 | 0.57 | 0.044338 |
| Cladosporium cladosporioides | MIC-20835 | 0.49 | 0.033986 |

Example 5: In Vitro Antibiosis

This example describes an exemplary method of in vitro antibiosis screenings of microbes against the crop pathogen *Fusarium oxysporum*, using the non-pathogenic *Fusarium oxysporum* Fo47 (ATCC, MYA-1198). Caspofungin diacetate (Sigma, SML0425-5MG) is a compound with antifungal activity that is used as a positive control. Caspofungin inhibits β-1,3-D-glucan synthase and thereby disrupting fungal cell wall integrity. Amphotericin B is a compound with antifungal activity that is used as a positive control. All stock compounds are prepared in DMSO at a concentration of 5,120 μg/ml.

Preparation of Fo47 Spores

Fo47 is cultured on 2% potato dextrose agar (PDA) plates for 14 days at room temperature in a weak light condition. Three ml of 0.05% Silwett L-77 in 1× phosphate buffered saline (PBS) is added to each plate, then mycelium are scraped off and filtered through glass wool into a new 50 ml Falcon tube. Spores are then counted using a hemocytometer and adjusted to 5×106 CFU/ml with sterile 1×PBS.

Preparation of Endophytic Fungal Culture

Five glass beads (3 mm) are added to each well of a 24-deep well plate (VWR, Cat. No. 89080-534) and autoclaved. Fungal cultures are started by adding 5 μl of spore suspension normalized to 1×106 cfu/ml into 3 ml PDB culture into each well. The plates are incubated for 3 days at room temperature with vigorous shaking at 500 rpm.

Antibiosis Assay

Prepare PDA plates: PDA with 1% agar are autoclaved in a liquid cycle for 20 minutes with a magnetic stir bar in the flask and kept in a 50° C. water bath. When ready the PDA flask is taken to a sterile environment such as a biosafety cabinet and cooled at room temperature for 15-20 min. Then 2 ml of the prepared *Fusarium* spores are added per 1 liter of PDA. OmniTrays (ThermoFisher, Cat. No. 264728) are filled with 60 ml of the PDA/spore mixture. After the plates solidify, the plates are air dried for 30 min before covering with the lid.

For each OmniTray, 24 wells are drilled at once using the liquid handling system, BioMek Fx with the following setting: load pod1 (96 pin head) with 24 200-μl wide bore barrier tips (Beckman Coulter, Cat. No. B01110-AA), draw 165 μl well contents using the "Bacterial culture 100 μl technique" at 1.5 mm from the bottom of OmniTray using the "override technique", dispense tips contents to reservoir plate using the "Reservoir technique" at 6 mm from bottom of OmniTray using "override technique".

For each OmniTray, 7.5 µl of the prepared bacterial cultures are added into each of the 24 wells using BioMek Fx system, 3 replicated plates are prepared. A negative control (nothing added), a medium control, a DMSO control, a positive compound control (e.g. Caspofungin diacetate, or Amphotericin B) and a positive biological control of the same volume are included on each plate. The plates are then incubated at room temperature in sterile conditions for 4 days. Photographs are taken of each plate and the zone of inhibition between the cultures and *Fusarium* growth are qualitatively scored using a 0-3 scale (3 denotes a strong inhibition) and quantitatively measured using the ImageJ program.

Example 6: Greenhouse Assessment of Improved Plant Characteristics Under Biotic Stress This example describes an exemplary method of greenhouse screening of microbes against a crop pathogen *Rhizoctonia solani*, one of the causal agents of seedling damping off disease.
Preparation of *Rhizoctonia* R9 inoculum A permanent stock of R9 is maintained on corn meal agar slants at room temperature. R9 is sub-cultured in a PDA plate for a week, then 5 plugs of mycelium are transferred into one liter of PDB broth in a 3-liter flask. The culture is grown at room temperature with vigorous shaking for 5 days. The entire one liter of the culture is poured into and mixed well 4 pounds of doubly autoclaved millet seeds. The mixture is sealed in a large plastic bag and incubated for 2 weeks at room temperature with gentle mixing every other day followed by a 2-day air drying inside a biosafety cabinet. Dried infected millet seeds are aliquoted into smaller bags and are usually used to set up disease assay in greenhouse within a week.
Greenhouse Assay Setup This greenhouse assay is conducted in 6.5 inch diameter plastic pots. The pots are first filled with 400 cc of mildly moistured Sunshine potting mix, followed by another layer of 400 cc potting mix uniformly blended with 2 tablespoons of R9-infected millet seeds. The pots are generally two third full with 800 cc of potting mix. The pots are left sitting at room temperature under dark condition for two nights before placing seeds to ensure a thick layer of aggressively grown pathogen mycelium in the soil.

This greenhouse assay is conducted using chemically treated soy seeds coated with fungal endophytes described herein and formulation control (no endophyte) and untreated controls (no endophyte and no formulation) as described in Example 3. Five seeds are evenly placed onto each pot on top of the inoculum layer and the pots are filled up with another 400 cc potting mix. Ten replicated pots of each treatment are set up and placed on a greenhouse bench using a random block design. The following growth and vigor metrics are measured: percentage emergence at Day 7 and percentage standing at Days 14 and 21, top view images at Day 7 and side view images of pulled and washed seedlings at Day 21, plant height at Day 21, plant dry weight at Day 21, and root crown disease rating at Day 21 using a 0-5 scale with 5 denotes the strongest necrosis and collapse of stem at the root crown region.

At Day 21 post planting, seedlings are gently pulled off the pot, washed with tap water to remove dirt, and kept in plastic bags at 4° C. for further data measurement. The severity of root crown necrosis is first independently rated by multiple persons using the scale described above, followed by plant height measurement before being laid on to a fluted plastic board for side view imaging. After side view imaging, seedlings from the same pot are put into a paper bag and dried in an oven. Plant dry weight of each individual seedling is recorded.

Example 7: Treatment of Nematode Infestation

A two-tiered approach was used to evaluate the efficacy and repeatability of 56 strains of fungi originally isolated as foliar endophytes from cotton (*Gossypium hirsutum*) for antagonistic effects on root-knot nematodes (*Meloidogyne incognita*). All fungi were inoculated to cotton using a seed treatment. A majority of the fungi tested had negative effects on root-knot nematode galling three weeks after egg inoculation of cotton seedlings. Across replicated greenhouse assays, 40% percent of the strains exhibited consistent statistically significant negative effects. Strains with consistent negative effects belonged to the genera *Chaetomium*, *Cladosporium, Epicoccum*, and *Phomopsis*. Three strains in the genera *Bipolaris, Chaetomium*, and *Phomopsis* had an opposite effect and significantly increased gall numbers. This example describes that a large proportion of cotton fungal endophytes are capable of conferring some degree of resistance to the plant from root-knot nematode infection.

Seed inoculation: Seeds of a nematode susceptible cotton cultivar PhytoGen PHY499WRF were treated with fungal endophyte biomass prepared as described in Example 3. 50 mg of ground dry-biomass was mixed with 1 mL of 2% Methyl cellulose (MC) solution (Sigma-Aldrich®, M7140-250G, 15 cP viscosity), which was finalized to the concentration of $10^5$ CFUs $mL^{-1}$. Approximately 200 seeds (delinted black seed without fungicides or insecticides) were coated using 1 mL of either the sticker solution alone (Control) or the fungus-containing sticker solution, and then dried at room temperature and finished with talc powder (Sigma-Aldrich®, Prod. No. 18654) to prevent sticking.

Host plants: Inoculated seeds were planted and germinated in pasteurized sand (steamed for eight hours at 72° C.) in seed starter trays (each cell pot measured 4 cm top diameter×6 cm deep) in a plant growth facility at 24° C. (12L:12D photoperiod) until first true-leaf stage.

Nematode preparation and infection: *M. incognita* eggs were extracted from infected tomato plants by agitating the roots in 0.6% NaOCl for 4 min, and collected on a sieve with a pore size of 25 µm (Hussey and Barker, 1973). Egg concentration in the extraction solution was quantified under a microscope using a Neubauer hemocytometer (a modified method of Gordon and Whitlock (1939)). Cotton seedlings at the first true-leaf stage were inoculated by pipetting a volume of egg suspension containing approximately 2000 eggs directly to the soil at the base of the plant.

Evaluation of nematode infection: Plants were maintained in the greenhouse for three weeks after nematode inoculation (WAI), then carefully removed from pots and washed free of soil from the roots. Root fresh weight was measured and the total number of galls per root system was quantified for each plant. A total of 15 replicate plants per treatment group were sampled.

A two-tiered approach was used to evaluate the repeatability of observed negative effects on nematode galling. First, an initial series of assays was performed as described herein on all 56 fungal strains. A second series of replicate follow-up assays was then performed on a reduced endophyte set consisting only of strains that exhibited statistically significant reductions in nematode galls in the first assay.

Bioassays were conducted across eight different rounds, each with a corresponding control treatment grown at the same time, in order to cycle all strains through the assay. All comparisons between treatment and control plants were made only among plants grown within the same bioassay round. The strains tested within each round are listed in Table 6.

Statistical analysis: All statistical analyses were performed using IMP® Pro, Version 12.0.1 (SAS Institute Inc., Cary, N.C., USA). All data were tested for normality and equality of variances. One-way ANOVA was performed to analyze the impact of endophyte treatment on gall numbers per gram of root tissue ($\alpha=0.05$). If a significant overall treatment effect was detected, post-hoc Dunnett's tests were used to compare the mean of the control against all the other treatments ($\alpha=0.05$).

Significant overall effects of fungal treatments on nematode on gall numbers were found within each of the eight separate rounds of bioassays conducted (ANOVA Round 1: $F_{4, 70}=7.63$, $p<0.0001$; Round 2: $F_{5, 84}=7.10$, $p<0.0001$; Round 3: $F_{12,182}=4.84$, $p<0.0001$; Round 4: $F_{10, 154}=10.38$, $p<0.0001$; Round 5: $F_{10, 154}=8.93$, $p<0.0001$; Round 6: $F_{15, 224}=4.05$, $p<0.0001$; Round 7: $F_{11, 168}=16.75$, $p<0.0001$; Round 8: $F_{11, 168}=17.38$, $p<0.0001$). Result of pairwise comparisons between the treatment and control groups are reported separately in Table 1 for each of the eight rounds of bioassays conducted.

Figure 1:
FIG. 1. Percentage change in mean number of root-knot nematode galls in endophyte treated cotton plants relative to the control treatment; plants were treated and grown as described in Example 7. Symbol on each bar indicates a significant difference in number of galls relative to the control treatment, * indicates p-value of <0.05.

Endophytic fungi from cotton exhibited repeatable negative effects on nematode galling. A majority of the fungi endophytes reduced the number of galls in treated relative to control plants in the first round of assays (FIG. 1). The number of strains with negative effects on nematodes (77%) was significantly higher than would have been expected under the null hypothesis of no effect of the fungal treatments (50%) (Fisher's exact test, $p=0.0029$). Of the 56 strains initially assayed, 22 (39%) exhibited statistically significant reductions in nematode galling (FIG. 1; Table 6). These 22 strains were selected for further evaluation in the second series of replicate follow-up assays.

Figure 2:
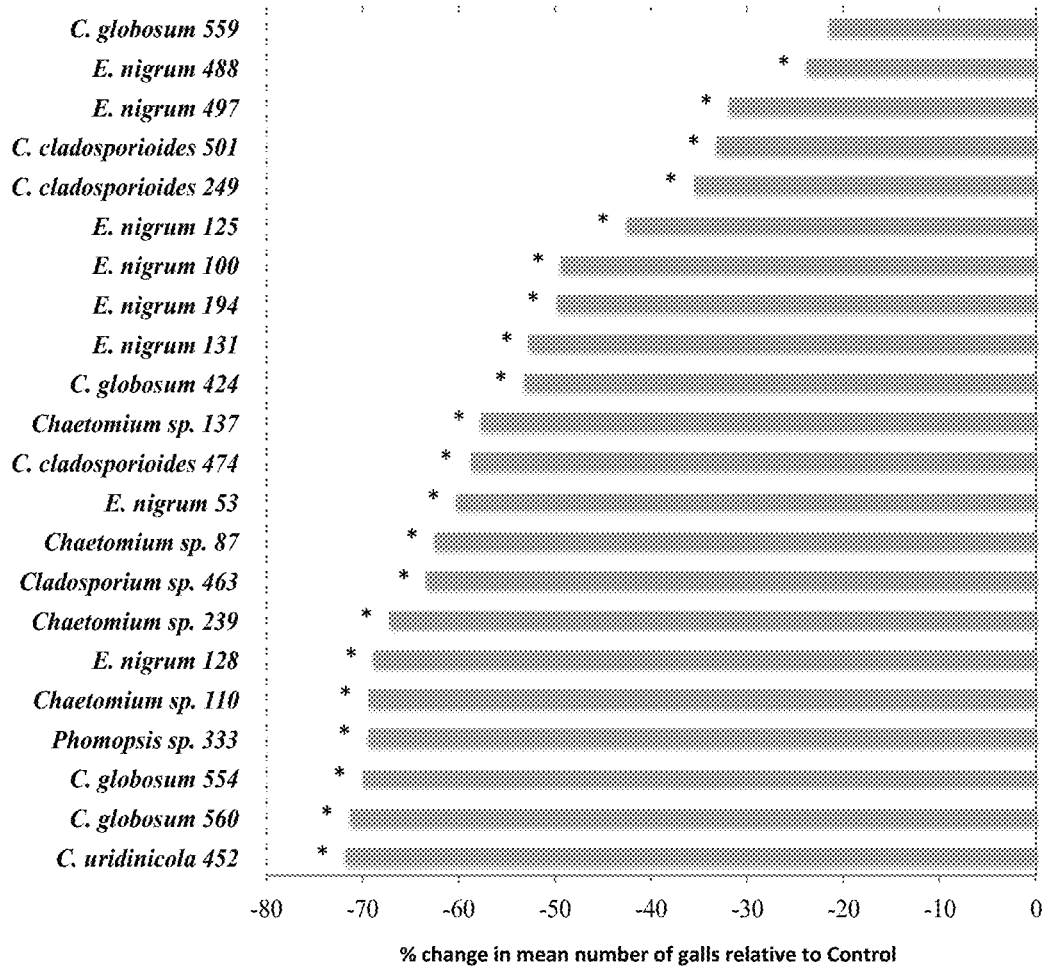
FIG. 2. Percentage change in mean number of root-knot nematode galls in endophyte treated cotton plants relative to the control treatment; plants were treated and grown as described in Example 7. Symbol on each bar indicates a significant difference in number of galls relative to the control treatment, * indicates p-value of <0.05.
Figure 3:
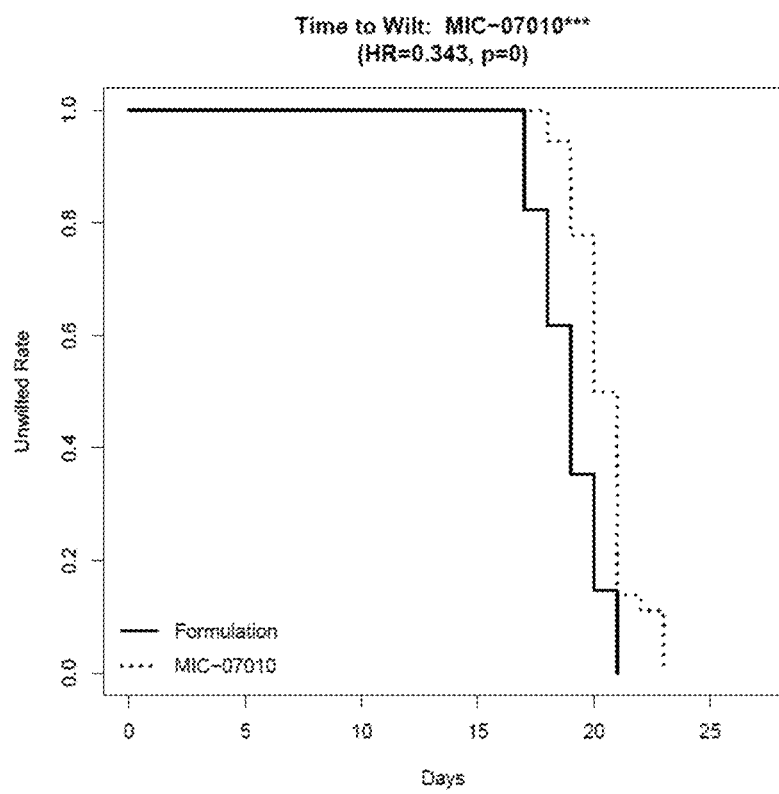
FIG. 3. Kaplan Meier survival curve of output of the Cox proportional hazards model for time to wilt of cotton seedlings treated with fungal endophyte strain MIC-07010. Day 0 represents sowing, plants were watered to saturation at day 7 and day 14, after which time water was withheld and wilting was scored on a daily basis; plants were treated and grown as described in Example 4.
Figure 4:
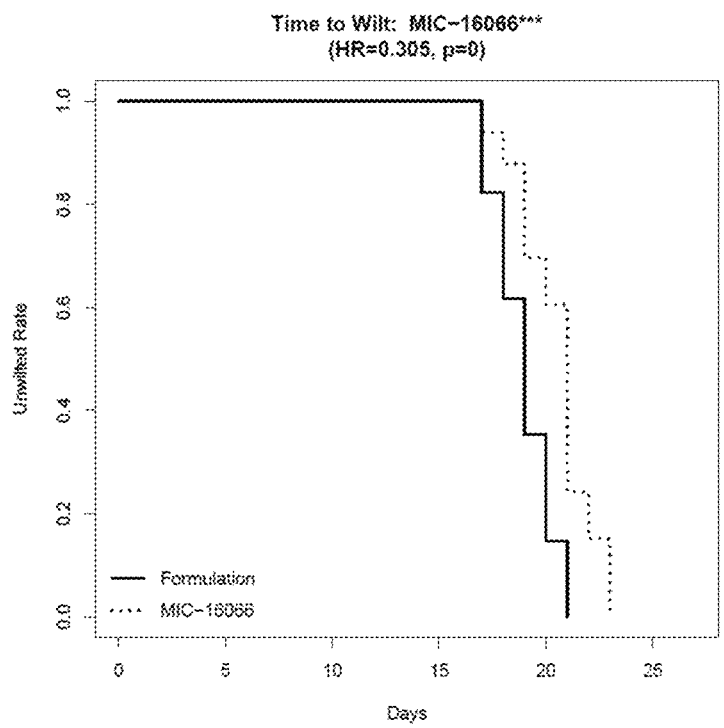
FIG. 4. Kaplan Meier survival curve of output of the Cox proportional hazards model for time to wilt of cotton seedlings treated with fungal endophyte strain MIC-16066. Day 0 represents sowing, plants were watered to saturation at day 7 and day 14, after which time water was withheld and wilting was scored on a daily basis; plants were treated and grown as described in Example 4.
Figure 5:
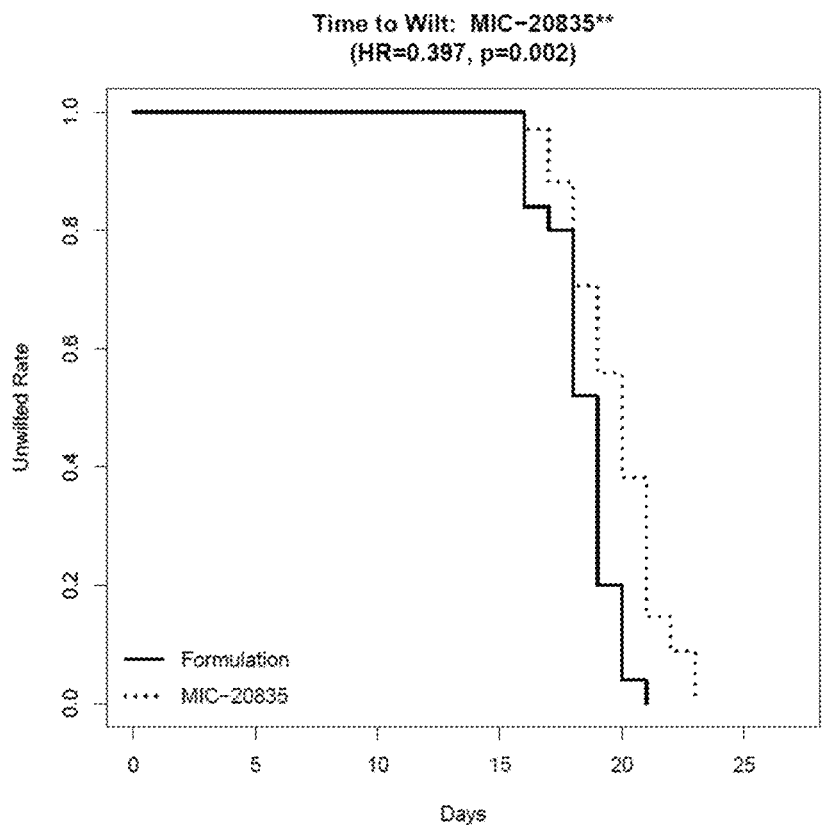
FIG. 5. Kaplan Meier survival curve of output of the Cox proportional hazards model for time to wilt of cotton seedlings treated with fungal endophyte strain MIC-20835. Day 0 represents sowing, plants were watered to saturation at day 7 and day 14, after which time water was withheld and wilting was scored on a daily basis; plants were treated and grown as described in Example 4.
Figure 6:
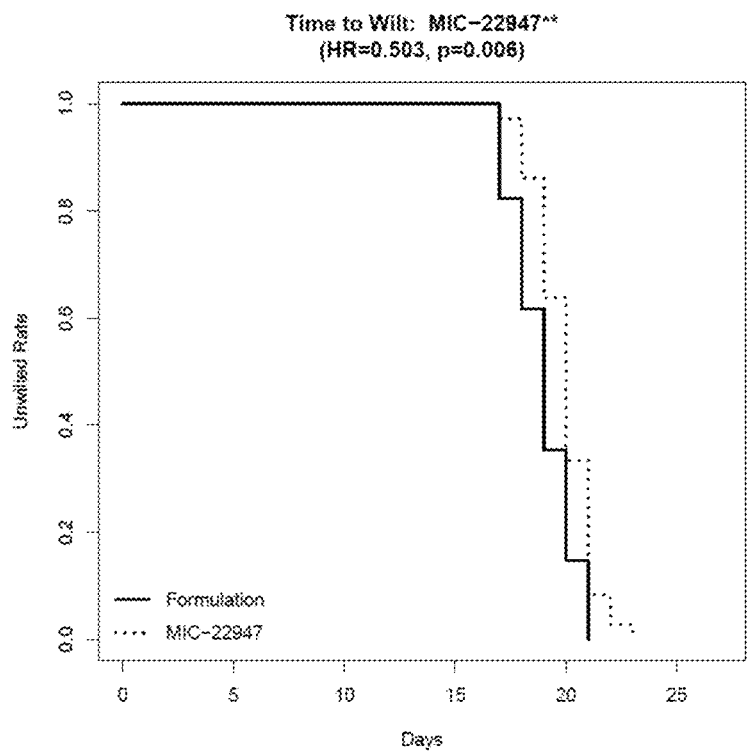
FIG. 6. Kaplan Meier survival curve of output of the Cox proportional hazards model for time to wilt of cotton seedlings treated with fungal endophyte strain MIC-22947. Day 0 represents sowing, plants were watered to saturation at day 7 and day 14, after which time water was withheld and wilting was scored on a daily basis; plants were treated and grown as described in Example 4.
Figure 7:
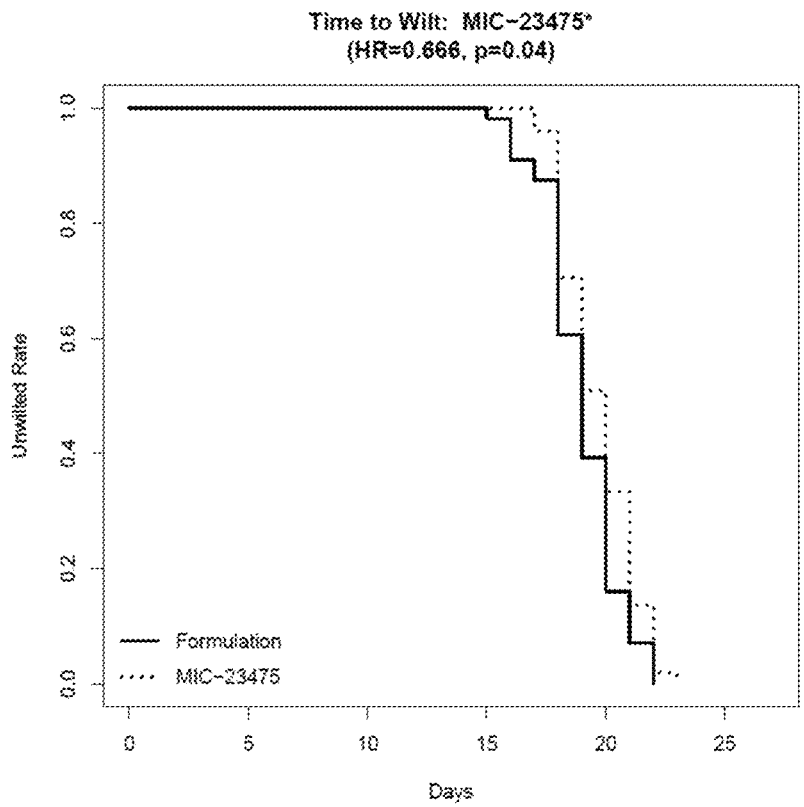
FIG. 7. Kaplan Meier survival curve of output of the Cox proportional hazards model for time to wilt of cotton seedlings treated with fungal endophyte strain MIC-23475. Day 0 represents sowing, plants were watered to saturation at day 7 and day 14, after which time water was withheld and wilting was scored on a daily basis; plants were treated and grown as described in Example 4.
Figure 8:
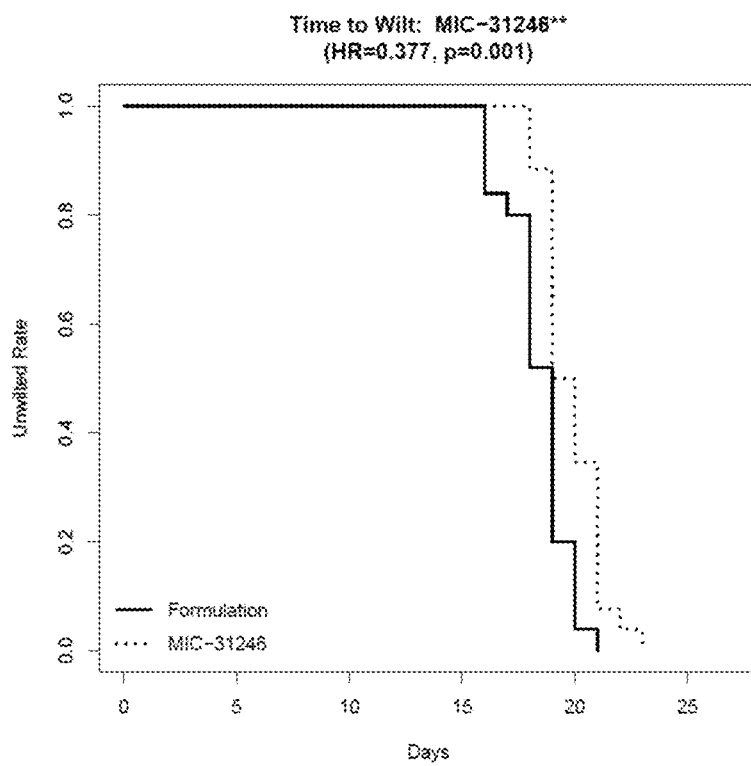
FIG. 8. Kaplan Meier survival curve of output of the Cox proportional hazards model for time to wilt of cotton seedlings treated with fungal endophyte strain MIC-31246. Day 0 represents sowing, plants were watered to saturation at day 7 and day 14, after which time water was withheld and wilting was scored on a daily basis; plants were treated and grown as described in Example 4.
Figure 9:
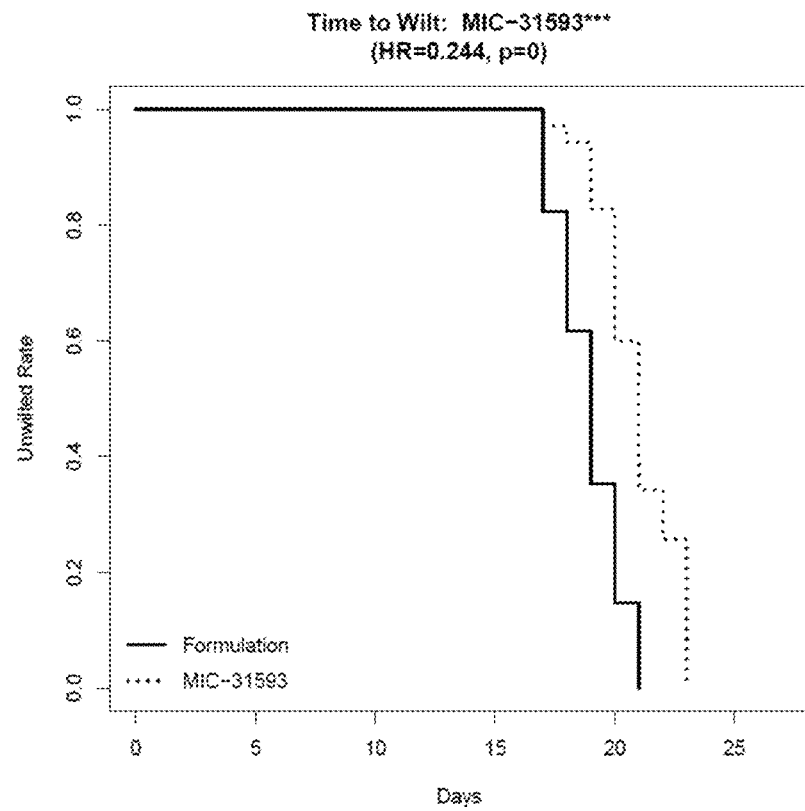
FIG. 9. Kaplan Meier survival curve of output of the Cox proportional hazards model for time to wilt of cotton seedlings treated with fungal endophyte strain MIC-31593. Day 0 represents sowing, plants were watered to saturation at day 7 and day 14, after which time water was withheld and wilting was scored on a daily basis; plants were treated and grown as described in Example 4.
Figure 10:
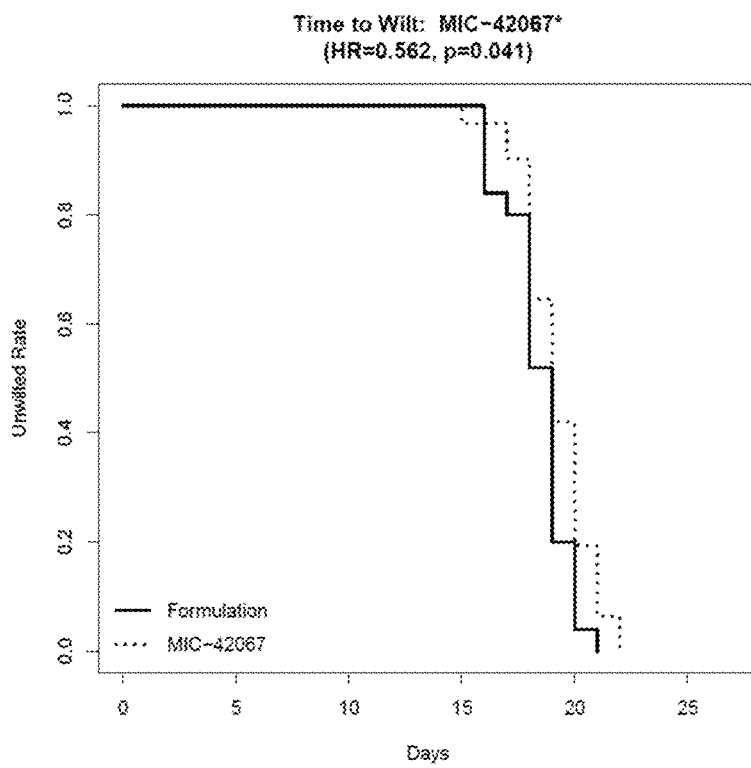
FIG. 10. Kaplan Meier survival curve of output of the Cox proportional hazards model for time to wilt of cotton seedlings treated with fungal endophyte strain MIC-42067. Day 0 represents sowing, plants were watered to saturation at day 7 and day 14, after which time water was withheld and wilting was scored on a daily basis; plants were treated and grown as described in Example 4.
Figure 11:
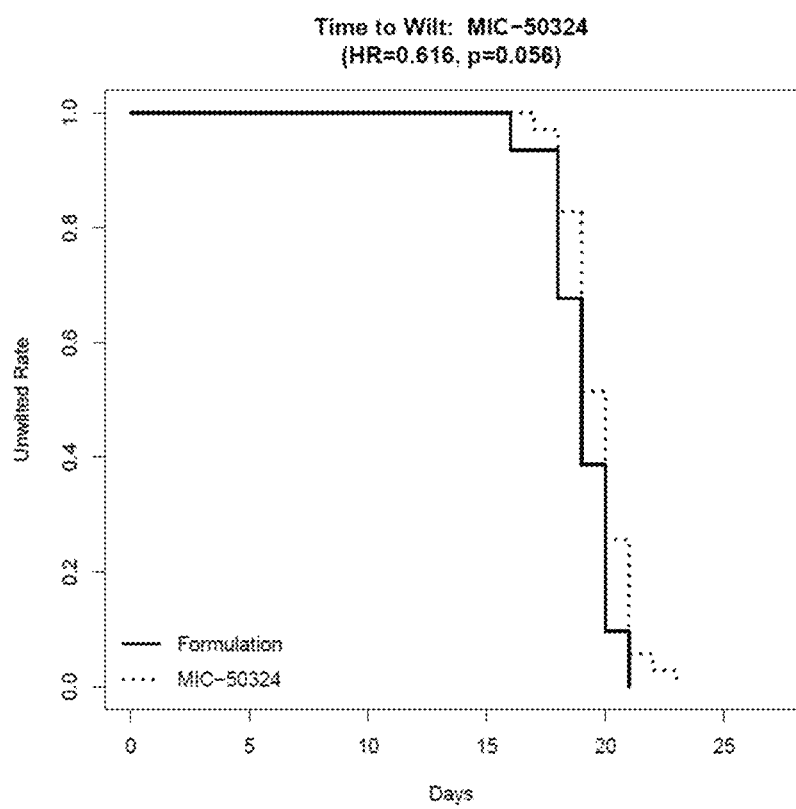
FIG. 11. Kaplan Meier survival curve of output of the Cox proportional hazards model for time to wilt of cotton seedlings treated with fungal endophyte strain MIC-50324. Day 0 represents sowing, plants were watered to saturation at day 7 and day 14, after which time water was withheld and wilting was scored on a daily basis; plants were treated and grown as described in Example 4.
Figure 12:
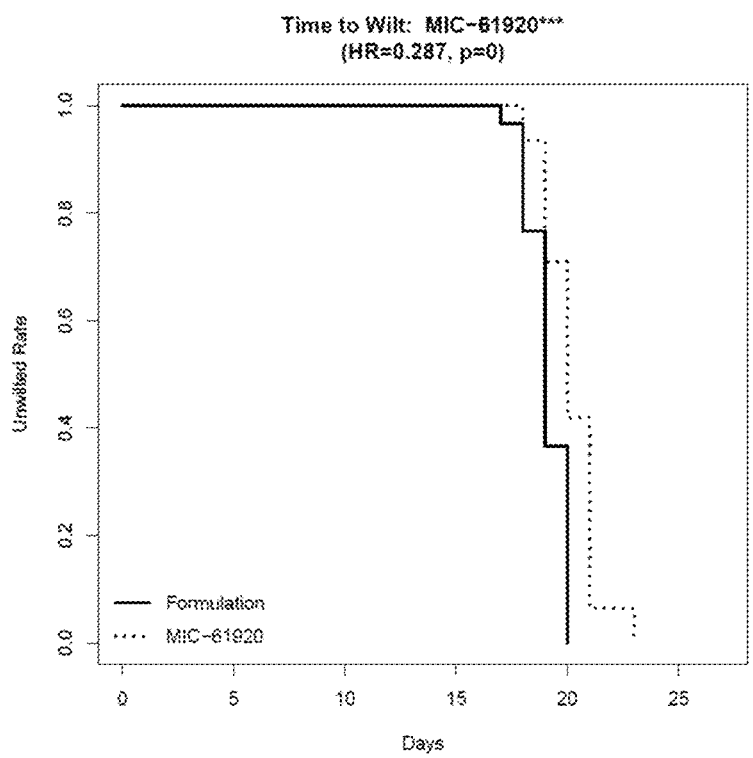
FIG. 12. Kaplan Meier survival curve of output of the Cox proportional hazards model for time to wilt of cotton seedlings treated with fungal endophyte strain MIC-61920. Day 0 represents sowing, plants were watered to saturation at day 7 and day 14, after which time water was withheld and wilting was scored on a daily basis; plants were treated and grown as described in Example 4.
Figure 13:
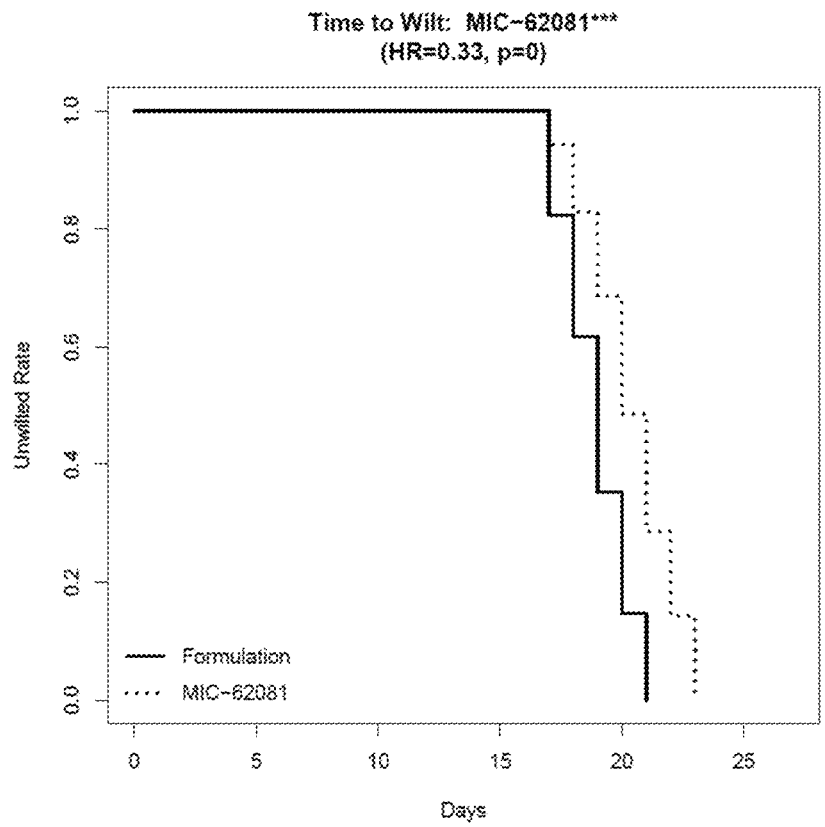
FIG. 13. Kaplan Meier survival curve of output of the Cox proportional hazards model for time to wilt of cotton seedlings treated with fungal endophyte strain MIC-62081. Day 0 represents sowing, plants were watered to saturation at day 7 and day 14, after which time water was withheld and wilting was scored on a daily basis; plants were treated and grown as described in Example 4.
Figure 14:
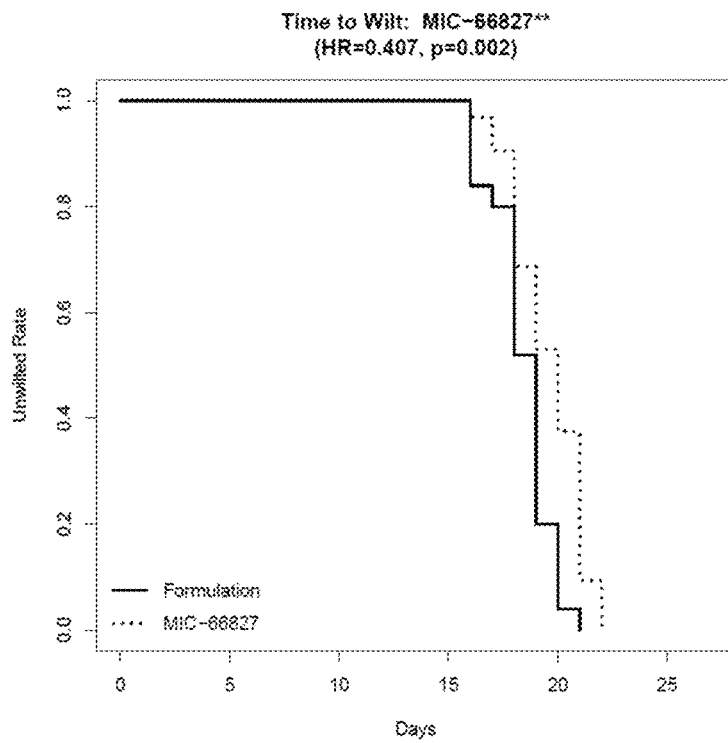
FIG. 14. Kaplan Meier survival curve of output of the Cox proportional hazards model for time to wilt of cotton seedlings treated with fungal endophyte strain MIC-66827. Day 0 represents sowing, plants were watered to saturation at day 7 and day 14, after which time water was withheld and wilting was scored on a daily basis; plants were treated and grown as described in Example 4.
Figure 15:
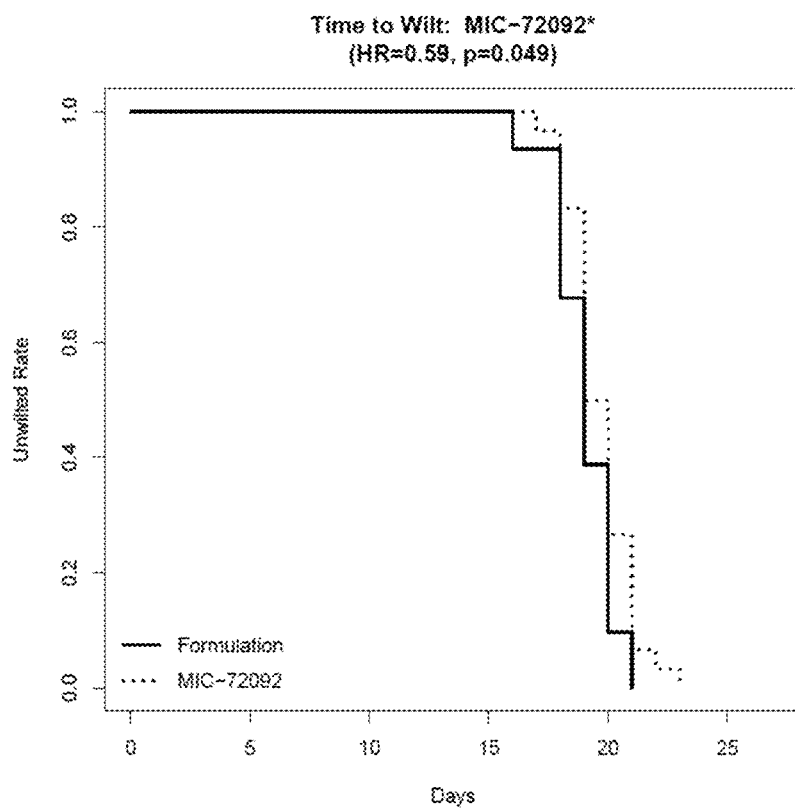
FIG. 15. Kaplan Meier survival curve of output of the Cox proportional hazards model for time to wilt of cotton seedlings treated with fungal endophyte strain MIC-72092. Day 0 represents sowing, plants were watered to saturation at day 7 and day 14, after which time water was withheld and wilting was scored on a daily basis; plants were treated and grown as described in Example 4.
Figure 16:
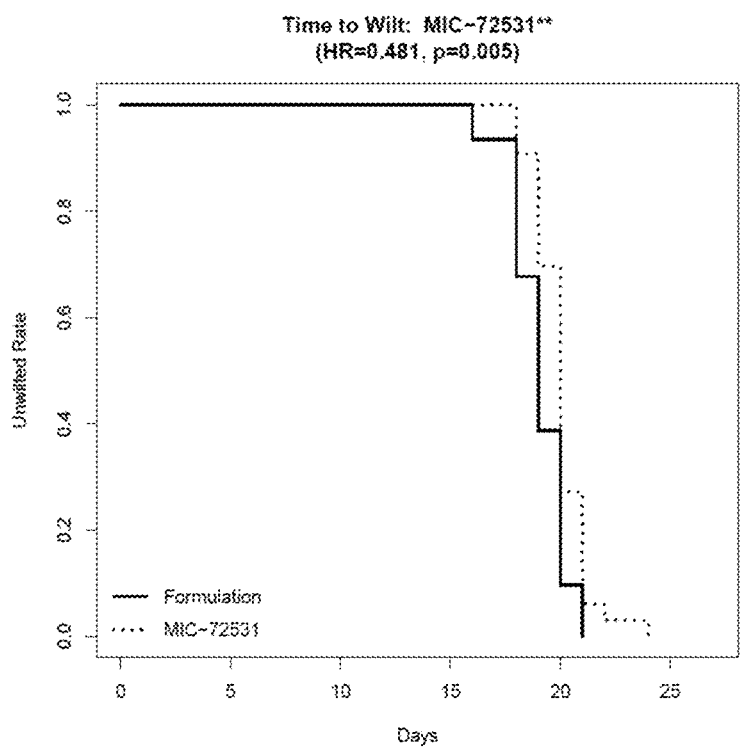
FIG. 16. Kaplan Meier survival curve of output of the Cox proportional hazards model for time to wilt of cotton seedlings treated with fungal endophyte strain MIC-72531. Day 0 represents sowing, plants were watered to saturation at day 7 and day 14, after which time water was withheld and wilting was scored on a daily basis; plants were treated and grown as described in Example 4.
Figure 17:
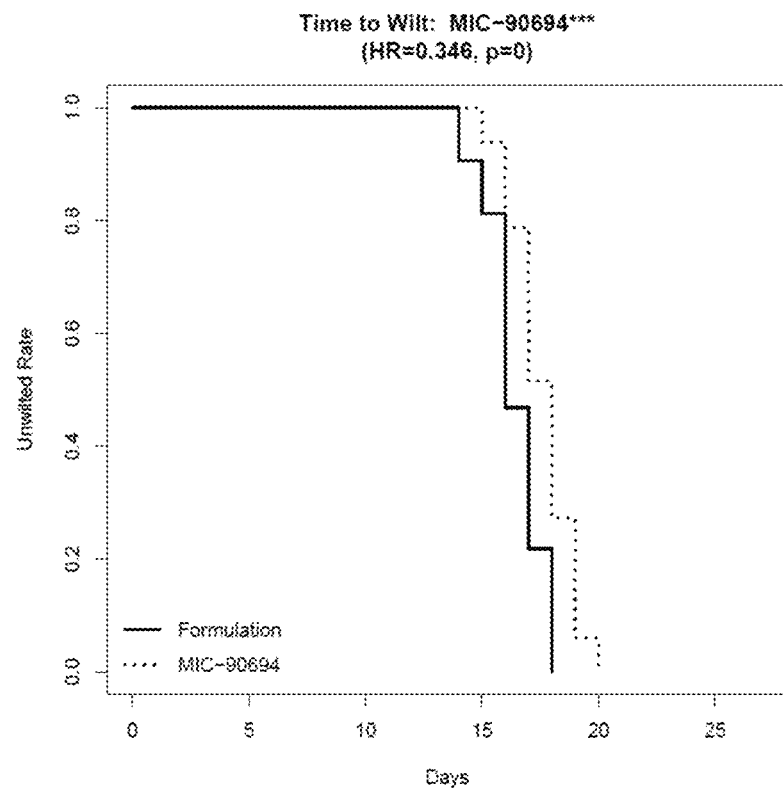
FIG. 17. Kaplan Meier survival curve of output of the Cox proportional hazards model for time to wilt of cotton seedlings treated with fungal endophyte strain MIC-90694. Day 0 represents sowing, plants were watered to saturation at day 7 and day 14, after which time water was withheld and wilting was scored on a daily basis; plants were treated and grown as described in Example 4.
Figure 18:
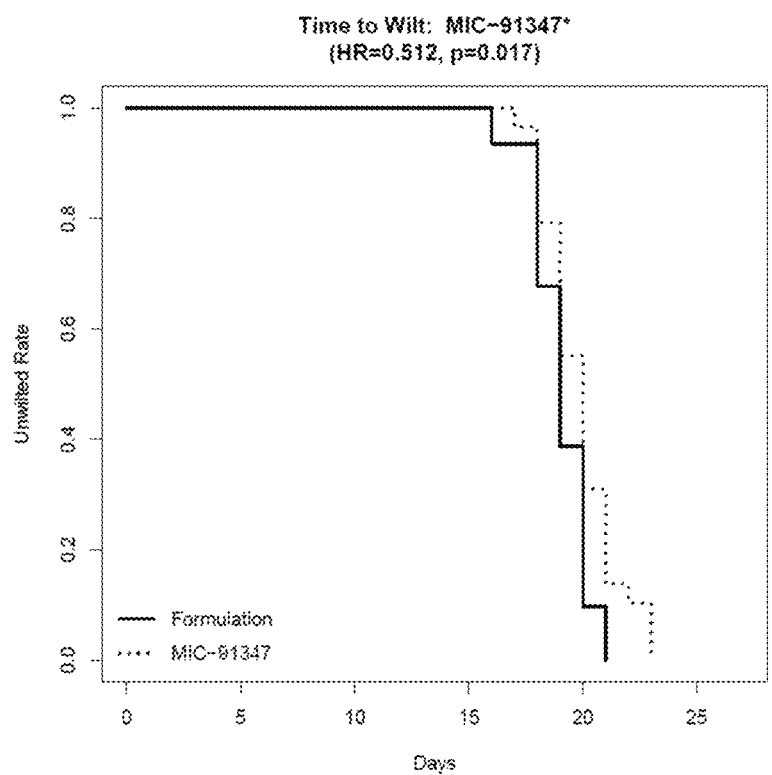
FIG. 18. Kaplan Meier survival curve of output of the Cox proportional hazards model for time to wilt of cotton seedlings treated with fungal endophyte strain MIC-91347. Day 0 represents sowing, plants were watered to saturation at day 7 and day 14, after which time water was withheld and wilting was scored on a daily basis; plants were treated and grown as described in Example 4.
Figure 19:
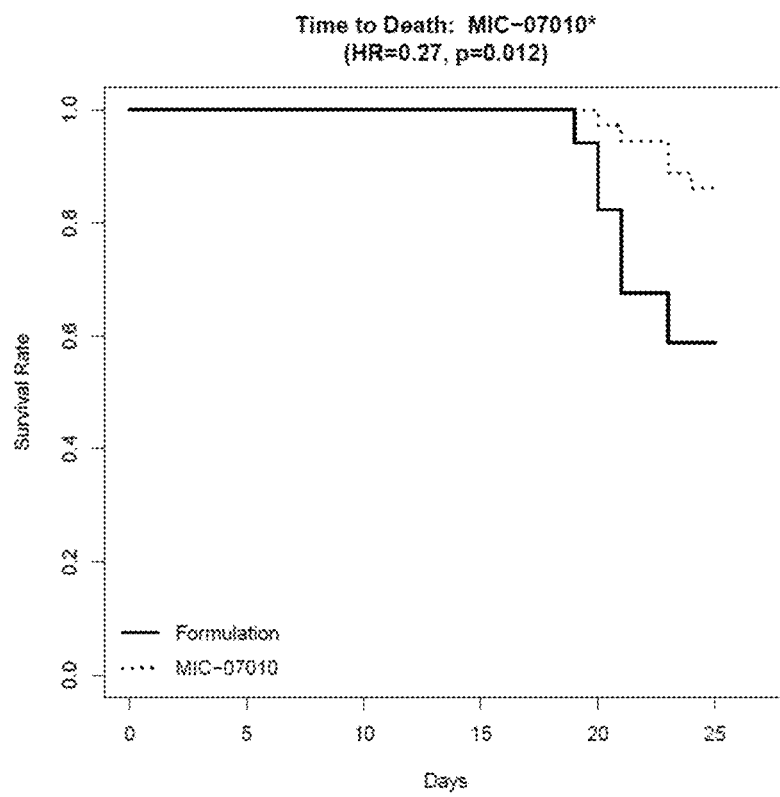
FIG. 19. Kaplan Meier survival curve of output of the Cox proportional hazards model for time to death of cotton seedlings treated with fungal endophyte strain MIC-07010. Day 0 represents sowing, plants were watered to saturation at day 7 and day 14, after which time water was withheld and death was scored on a daily basis; plants were treated and grown as described in Example 4.
Figure 20:
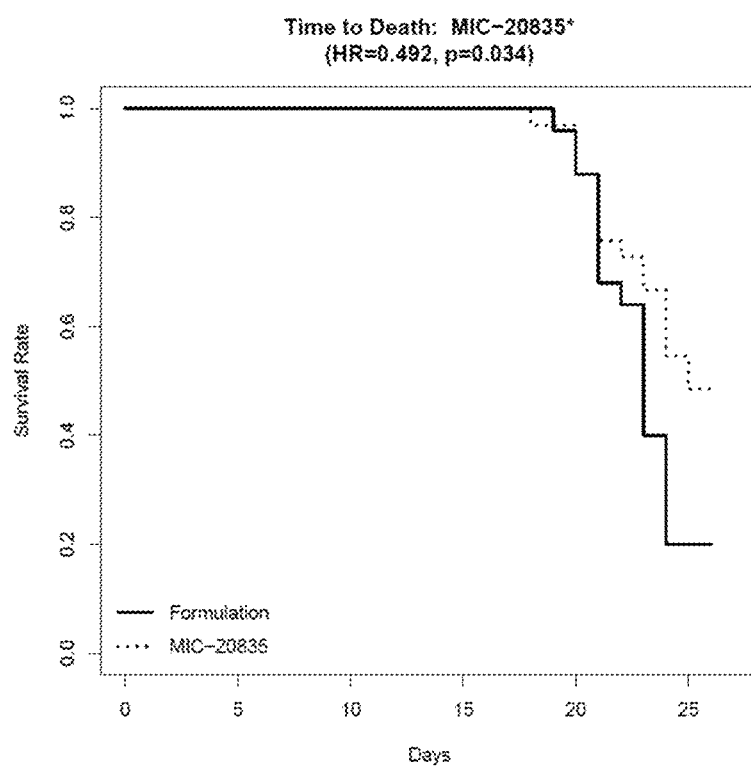
FIG. 20. Kaplan Meier survival curve of output of the Cox proportional hazards model for time to death of cotton seedlings treated with fungal endophyte strain MIC-20835. Day 0 represents sowing, plants were watered to saturation at day 7 and day 14, after which time water was withheld and death was scored on a daily basis; plants were treated and grown as described in Example 4.
Figure 21:
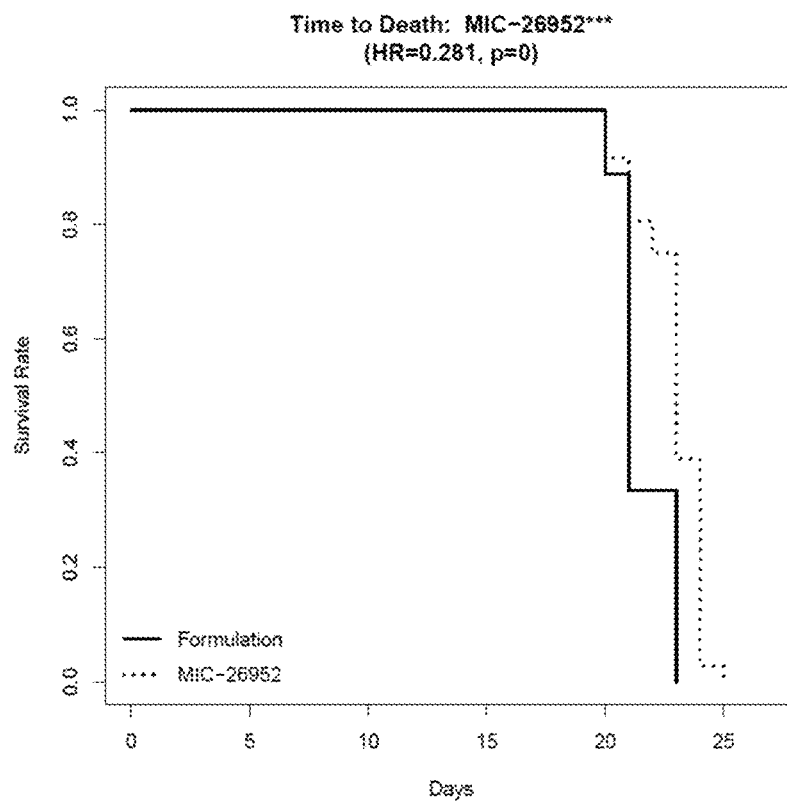
FIG. 21. Kaplan Meier survival curve of output of the Cox proportional hazards model for time to death of cotton seedlings treated with fungal endophyte strain MIC-26952. Day 0 represents sowing, plants were watered to saturation at day 7 and day 14, after which time water was withheld and death was scored on a daily basis; plants were treated and grown as described in Example 4.
Figure 22:
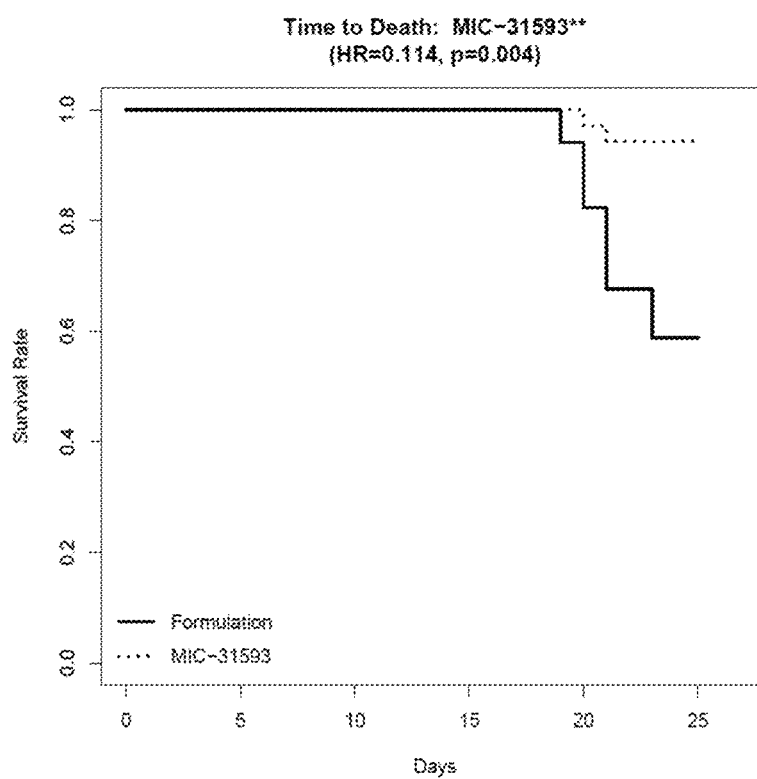
FIG. 22. Kaplan Meier survival curve of output of the Cox proportional hazards model for time to death of cotton seedlings treated with fungal endophyte strain MIC-31593. Day 0 represents sowing, plants were watered to saturation at day 7 and day 14, after which time water was withheld and death was scored on a daily basis; plants were treated and grown as described in Example 4.
Figure 23:
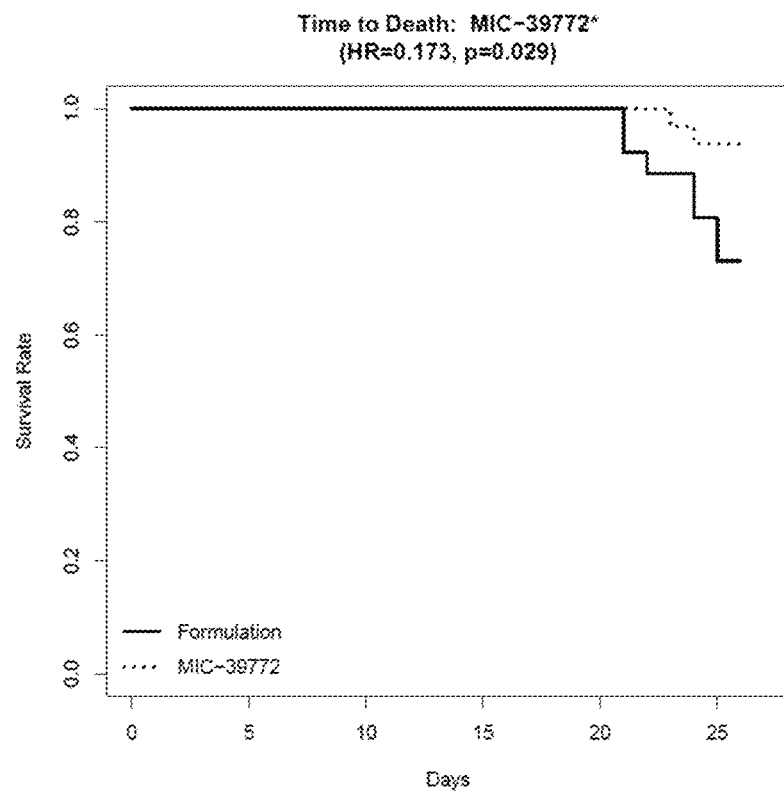
FIG. 23. Kaplan Meier survival curve of output of the Cox proportional hazards model for time to death of cotton seedlings treated with fungal endophyte strain MIC-39772. Day 0 represents sowing, plants were watered to saturation at day 7 and day 14, after which time water was withheld and death was scored on a daily basis; plants were treated and grown as described in Example 4.
Figure 24:
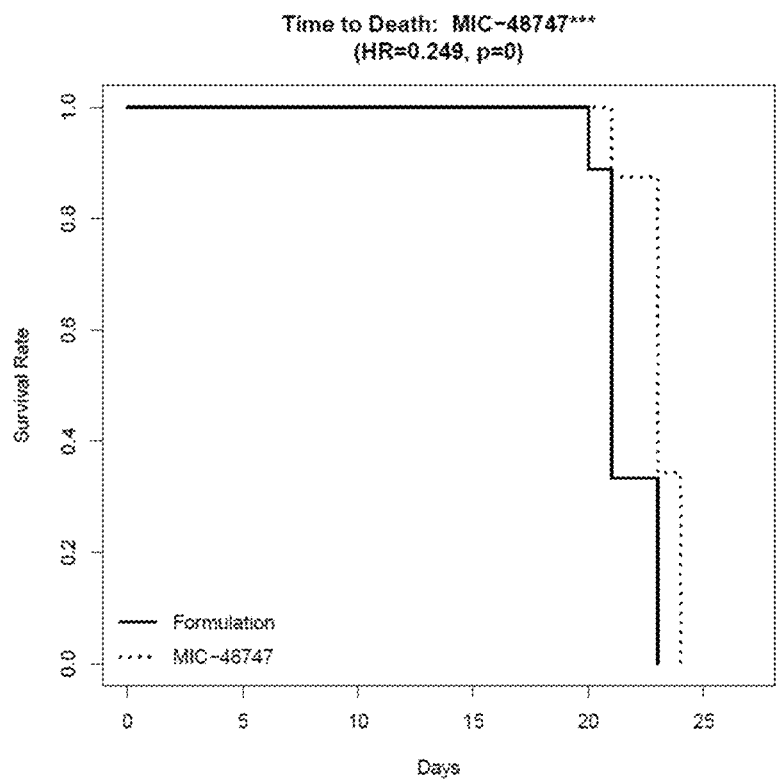
FIG. 24. Kaplan Meier survival curve of output of the Cox proportional hazards model for time to death of cotton seedlings treated with fungal endophyte strain MIC-48747. Day 0 represents sowing, plants were watered to saturation at day 7 and day 14, after which time water was withheld and death was scored on a daily basis; plants were treated and grown as described in Example 4.
Figure 25:
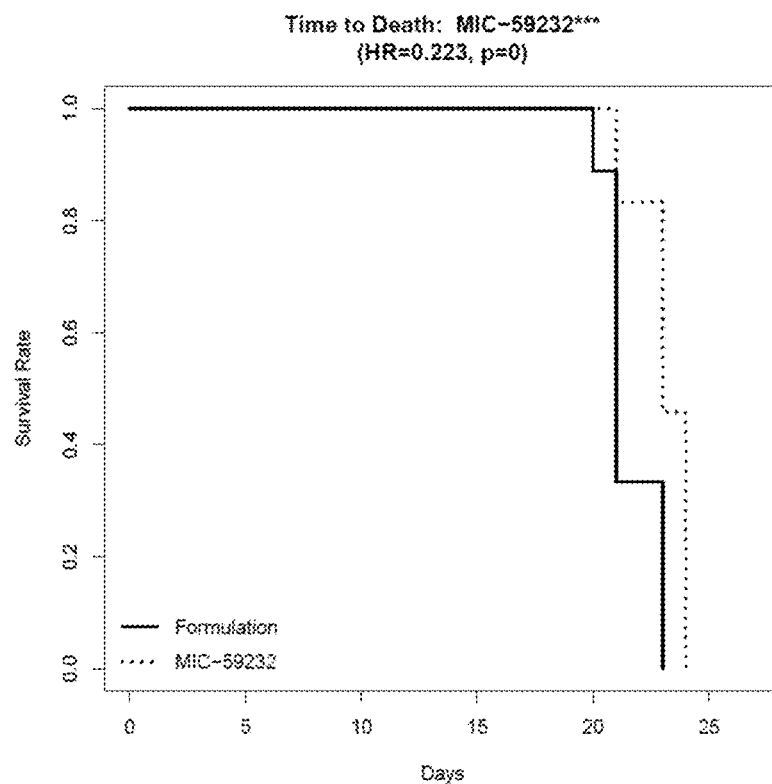
FIG. 25. Kaplan Meier survival curve of output of the Cox proportional hazards model for time to death of cotton seedlings treated with fungal endophyte strain MIC-59232. Day 0 represents sowing, plants were watered to saturation at day 7 and day 14, after which time water was withheld and death was scored on a daily basis; plants were treated and grown as described in Example 4.
Figure 26:
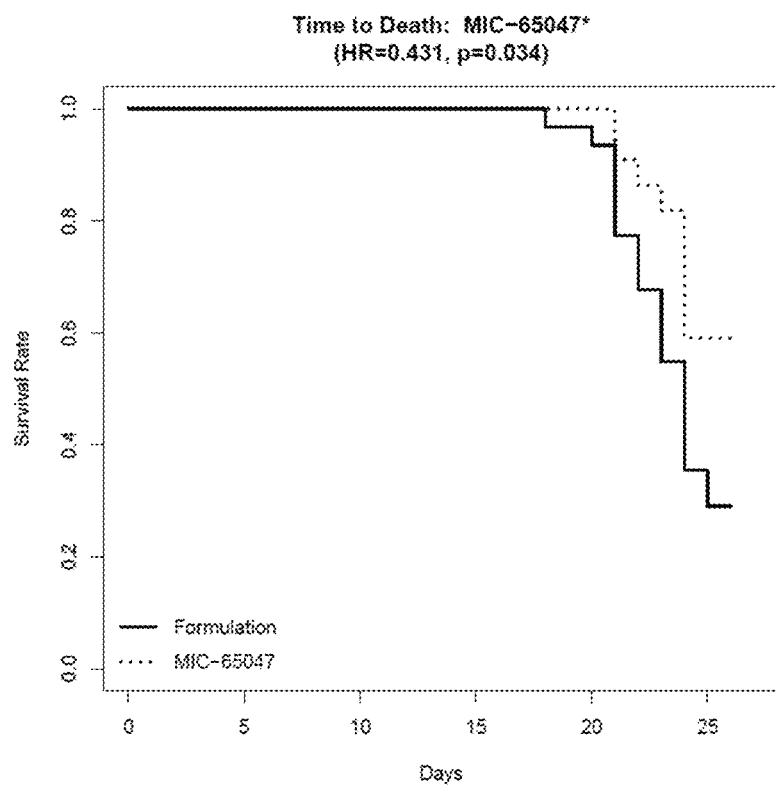
FIG. 26. Kaplan Meier survival curve of output of the Cox proportional hazards model for time to death of cotton seedlings treated with fungal endophyte strain MIC-65047. Day 0 represents sowing, plants were watered to saturation at day 7 and day 14, after which time water was withheld and death was scored on a daily basis; plants were treated and grown as described in Example 4.
Figure 27:
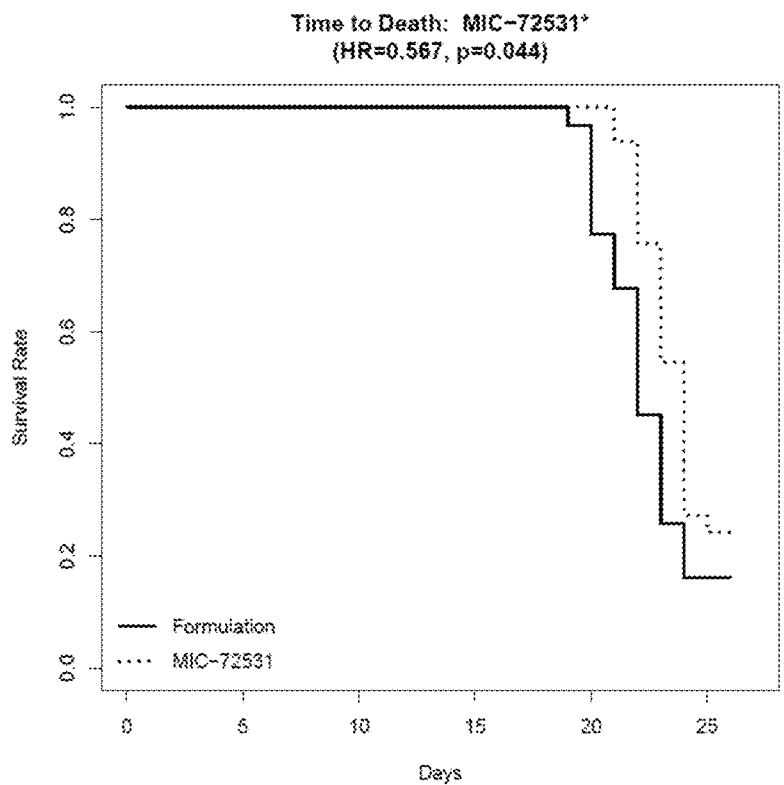
FIG. 27. Kaplan Meier survival curve of output of the Cox proportional hazards model for time to death of cotton seedlings treated with fungal endophyte strain MIC-72531. Day 0 represents sowing, plants were watered to saturation at day 7 and day 14, after which time water was withheld and death was scored on a daily basis; plants were treated and grown as described in Example 4.
Figure 28:
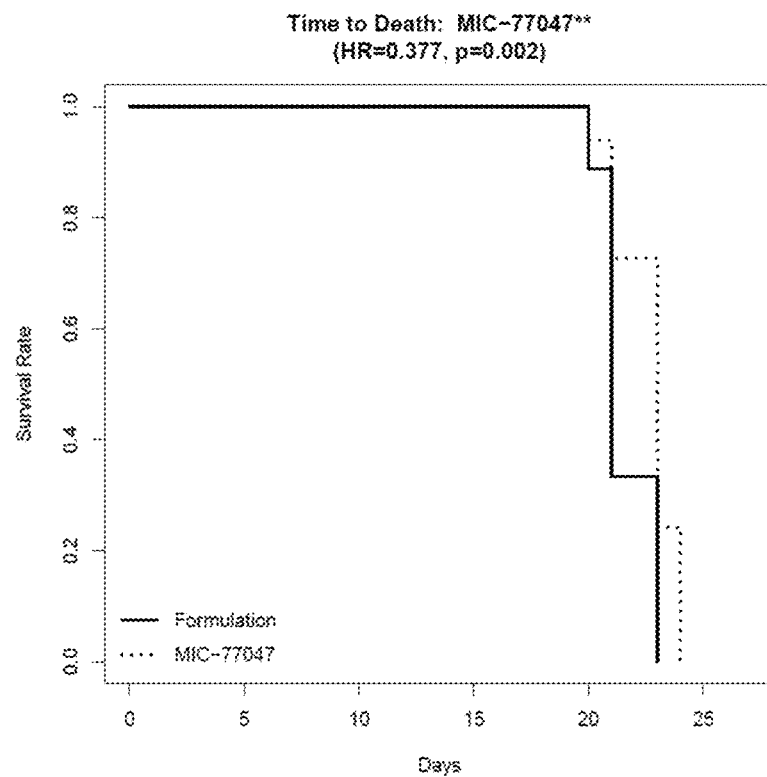
FIG. 28. Kaplan Meier survival curve of output of the Cox proportional hazards model for time to death of cotton seedlings treated with fungal endophyte strain MIC-77047. Day 0 represents sowing, plants were watered to saturation at day 7 and day 14, after which time water was withheld and death was scored on a daily basis; plants were treated and grown as described in Example 4.
Figure 29:
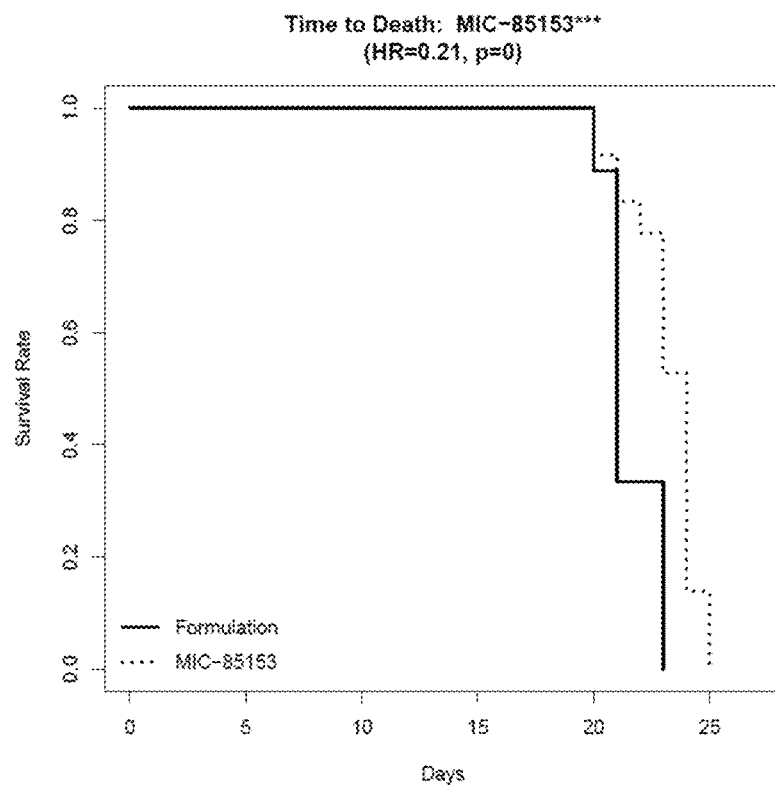
FIG. 29. Kaplan Meier survival curve of output of the Cox proportional hazards model for time to death of cotton seedlings treated with fungal endophyte strain MIC-85153. Day 0 represents sowing, plants were watered to saturation at day 7 and day 14, after which time water was withheld and death was scored on a daily basis; plants were treated and grown as described in Example 4.
Figure 30:
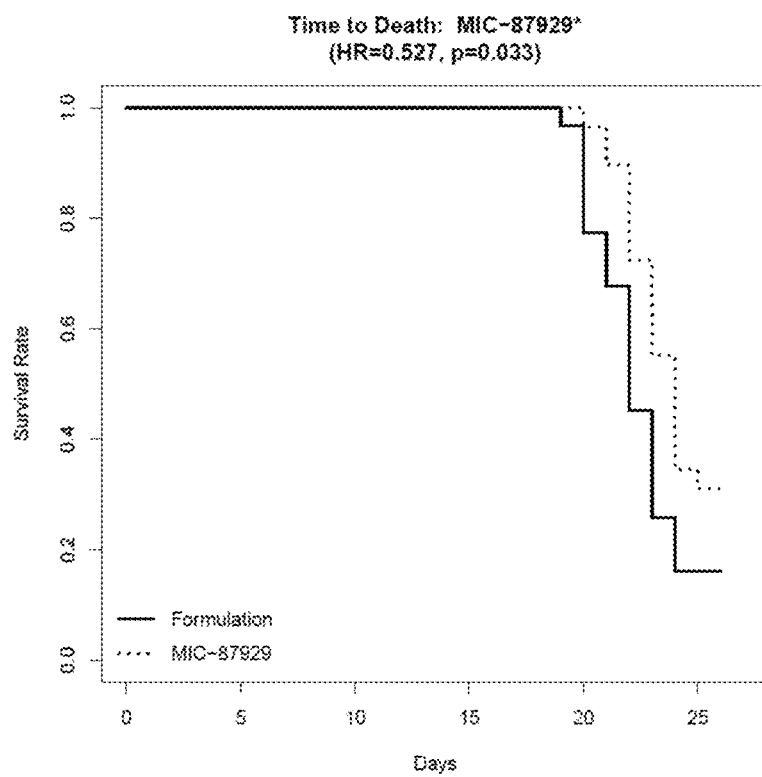
FIG. 30. Kaplan Meier survival curve of output of the Cox proportional hazards model for time to death of cotton seedlings treated with fungal endophyte strain MIC-87929. Day 0 represents sowing, plants were watered to saturation at day 7 and day 14, after which time water was withheld and death was scored on a daily basis; plants were treated and grown as described in Example 4.
Figure 31:
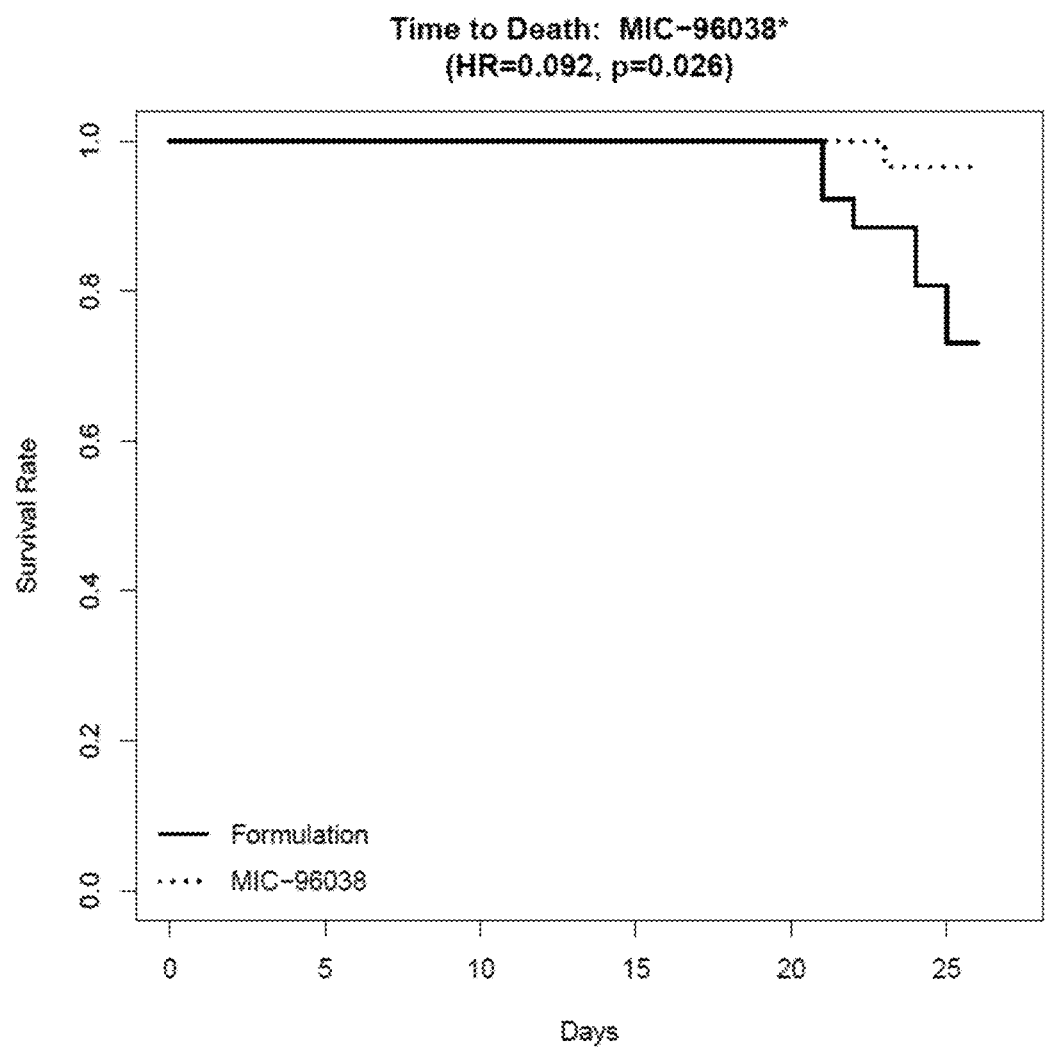
FIG. 31. Kaplan Meier survival curve of output of the Cox proportional hazards model for time to death of cotton seedlings treated with fungal endophyte strain MIC-96038. Day 0 represents sowing, plants were watered to saturation at day 7 and day 14, after which time water was withheld and death was scored on a daily basis; plants were treated and grown as described in Example 4.

The reductions in nematode galling observed in the first series of assays were highly repeatable. All of strains selected for follow up evaluation in the second series of assays reduced galling relative to the control plants. Of the 22 strains tested, 21 (95%) significantly reduced root-knot nematode galling across both replicate trials (FIG. 2; Table 6). Examples of endophytes which consistently reduced root-knot nematode galling include, those identified by sequence homology to one or more sequence selected from the group consisting of SEQ ID NOs: 29, 31, 38, 51, 53, 54, 55, 56, 57, 58, 59, 63, 94, 96, 97, 98, 99, 100, 101, 102, 103, 104, 105, and 107.

A taxonomic summary of the observed negative and positive effects on nematode galling based on the genera of fungi tested is provided in Table 7.

This example describes that cotton fungal endophytes are capable of conferring some degree of resistance to the plant from root-knot nematode infection. In some embodiments, endophytic fungal strains described herein reduced root-knot nematode galling of cotton seedlings. Importantly, this effect was highly repeatable, with 95% of the isolates that exhibited a significant reduction in galling in the first assay, again doing so in a second replicate assay. To our knowledge, this study provides the first examples negative effects on root-knot nematodes by endophytic isolates of *Epicoccum* and *Phomopsis* fungi.

TABLE 6

Number of galls produced by root-knot nematode per gram of root tissue (mean ± SE) in each treatment. Statistical differences between treatments and the Control group were compared using Dunnett's test ($\alpha = 0.05$)

| Bioassay | Treatment | Mean ± S.E. | P - value |
|---|---|---|---|
| Round 1 | Control | 28.02 ± 2.81 | — |
| | *Curvularia spicifera* TAMU189 (MIC-31593) | 51.19 ± 6.03 | 0.0002 |
| | *Acremonium alternatum* TAMU505 (MIC-96038) | 36.97 ± 3.51 | 0.29 |
| | *Cladosporium oxysporum* TAMU534 (MIC-50414) | 29.01 ± 2.24 | 1.00 |
| | *Curvularia protuberata* TAMU105 (MIC-07010) | 25.23 ± 3.29 | 0.96 |
| Round 2 | Control | 81.17 ± 14.90 | — |
| | Didymellaceae TAMU46 (MIC-90694) | 69.96 ± 23.48 | 0.94 |
| | *Cladosporium gossypiicola* TAMU249 (MIC-80602) | 39.01 ± 3.64 | 0.047 |
| | *Cladosporium* sp. TAMU463 (MIC-91557) | 30.27 ± 2.37 | 0.011 |
| | *Epicoccum nigrum* TAMU194 (MIC-76091) | 8.47 ± 1.28 | 0.0001 |
| | *Chaetomium globosum* TAMU554 (MIC-33414) | 8.00 ± 1.24 | 0.0001 |
| Round 3 | Control | 54.76 ± 5.31 | — |
| | *Epicoccum nigrum* TAMU89 (MIC-67271) | 48.02 ± 4.16 | 0.74 |
| | *Epicoccum nigrum* TAMU103 (MIC-62081) | 46.57 ± 3.42 | 0.51 |
| | *Alternaria* sp. TAMU53 (MIC-34397) | 40.77 ± 8.09 | 0.042 |
| | *Epicoccum nigrum* TAMU125 (MIC-51347) | 39.81 ± 1.96 | 0.024 |
| | *Purpureocillium lilacinum* TAMU239 (MIC-86415) | 39.71 ± 2.81 | 0.022 |
| | *Chaetomium coarctatum* TAMU333 (MIC-39959) | 38.48 ± 4.59 | 0.010 |
| | *Chaetomium* sp. TAMU87 (MIC-78639) | 37.32 ± 3.44 | 0.0047 |
| | *Epicoccum nigrum* TAMU131 (MIC-85590) | 36.74 ± 2.41 | 0.0031 |
| | *Diaporthe* sp. TAMU137 (MIC-42067) | 31.76 ± 3.61 | <0.0001 |
| | *Epicoccum nigrum* TAMU497 (MIC-90504) | 31.54 ± 3.71 | <0.0001 |
| | *Alternaria eichhorniae* TAMU452 (MIC-26235) | 29.85 ± 2.37 | <0.0001 |
| | *Chaetomium globosum* TAMU560 (MIC-44512) | 28.94 ± 3.24 | <0.0001 |
| Round 4 | Control | 42.18 ± 4.32 | — |
| | *Chaetomium globosum* TAMU117 (MIC-23475) | 52.32 ± 4.64 | 0.20 |
| | *Chaetomium piluliferum* TAMU251 (MIC-51742) | 48.23 ± 3.30 | 0.76 |
| | *Beauveria bassiana* | 39.49 ± 3.08 | 1.00 |
| | *Epicoccum nigrum* TAMU58 (MIC-26421) | 38.41 ± 2.95 | 0.98 |
| | *Alternaria eichhorniae* TAMU129 (MIC-39830) | 35.54 ± 4.51 | 0.67 |
| | *Chaetomium globosum* TAMU356 (MIC-59232) | 31.50 ± 3.36 | 0.16 |

TABLE 6-continued

Number of galls produced by root-knot nematode per
gram of root tissue (mean ± SE) in each treatment.
Statistical differences between treatments and the Control
group were compared using Dunnett's test (α = 0.05)

| Bioassay | Treatment | Mean ± S.E. | P - value |
|---|---|---|---|
| | *Chaetomium globosum* TAMU559 (MIC-22947) | 28.57 ± 1.98 | 0.035 |
| | *Epicoccum nigrum* TAMU488 (MIC-85153) | 24.30 ± 1.58 | 0.0020 |
| | *Epicoccum nigrum* TAMU100 (MIC-77047) | 21.19 ± 2.88 | 0.0002 |
| | *Epicoccum nigrum* TAMU128 (MIC-65047) | 19.43 ± 2.66 | <0.0001 |
| Round 5 | Control | 53.08 ± 4.27 | — |
| | *Alternaria* sp. TAMU179 (MIC-86713) | 74.84 ± 6.00 | 0.018 |
| | *Alternaria eichhorniae* TAMU416 (MIC-31674) | 74.42 ± 5.62 | 0.021 |
| | *Cladosporium* sp. TAMU494 (MIC-26952) | 70.22 ± 5.09 | 0.10 |
| | *Epicoccum nigrum* TAMU536 (MIC-16066) | 58.21 ± 5.61 | 0.99 |
| | *Alternaria eichhorniae* TAMU529 (MIC-61920) | 57.99 ± 5.38 | 1.00 |
| | *Cryptococcus* sp. TAMU514 (MIC-39051) | 51.61 ± 5.89 | 1.00 |
| | *Cladosporium* sp. TAMU244 (MIC-48747) | 50.35 ± 3.57 | 1.00 |
| | *Epicoccum nigrum* TAMU32 (MIC-68178) | 45.99 ± 4.80 | 0.92 |
| | *Chaetomium* sp. TAMU110 (MIC-66827) | 32.61 ± 3.56 | 0.030 |
| | *Cladosporium cladosporioides* TAMU474 (MIC-34220) | 31.86 ± 3.56 | 0.022 |
| Round 6 | Control | 57.47 ± 3.25 | — |
| | *Cladosporium* sp. TAMU201 (MIC-29439) | 76.87 ± 8.38 | 0.13 |
| | *Cladosporium herbarum* TAMU190 (MIC-42406) | 63.82 ± 7.13 | 1.00 |
| | *Cladosporium cladosporioides* TAMU169 (MIC-91347) | 58.46 ± 6.34 | 1.00 |
| | *Cladosporium cladosporioides* TAMU193 (MIC-12927) | 54.84 ± 8.24 | 1.00 |
| | Nectriaceae TAMU355 (MIC-17927) | 48.91 ± 4.72 | 0.95 |
| | *Chaetomium* sp. TAMU317 (MIC-39772) | 46.16 ± 3.98 | 0.75 |
| | *Cladosporium herbarum* TAMU415 (MIC-87929) | 45.99 ± 2.96 | 0.75 |
| | *Cladosporium cladosporioides* TAMU565 (MIC-20835) | 44.70 ± 6.76 | 0.60 |
| | *Cladosporium cladosporioides* TAMU517 (MIC-72531) | 44.65 ± 4.36 | 0.60 |
| | TAMU508 (MIC-72092) | 44.60 ± 4.17 | 0.60 |
| | *Fusarium* sp. TAMU340 (MIC-87502) | 43.40 ± 5.62 | 0.48 |
| | *Chaetomium globosum* (TAMU353) | 42.75 ± 4.36 | 0.42 |
| | *Penicillium* sp. TAMU413 (MIC-50324) | 40.24 ± 5.52 | 0.24 |
| | *Cladosporium* sp. TAMU501 (MIC-31246) | 34.34 ± 3.46 | 0.038 |
| | *Purpureocillium lavendulum* TAMU424 (MIC-21610) | 33.60 ± 5.41 | 0.029 |
| Round 7 | Control | 44.49 ± 3.88 | — |
| | *Chaetomium globosum* TAMU559 (MIC-22947) | 34.86 ± 2.08 | 0.056 |
| | *Epicoccum nigrum* TAMU488 (MIC-85153) | 33.86 ± 1.93 | 0.026 |
| | *Epicoccum nigrum* TAMU497 (MIC-90504) | 30.26 ± 2.28 | 0.0008 |
| | *Cladosporium gossypiicola* TAMU249 (MIC-80602) | 28.69 ± 2.54 | 0.0001 |
| | *Epicoccum nigrum* TAMU100 (MIC-77047) | 22.49 ± 2.59 | <0.0001 |
| | *Epicoccum nigrum* TAMU194 (MIC-76091) | 22.35 ± 2.63 | <0.0001 |
| | *Diaporthe* sp. TAMU137 (MIC-42067) | 18.82 ± 2.70 | <0.0001 |
| | *Cladosporium* sp. TAMU463 (MIC-91557) | 16.27 ± 2.05 | <0.0001 |
| | *Epicoccum nigrum* TAMU128 (MIC-65047) | 13.85 ± 1.95 | <0.0001 |
| | *Chaetomium globosum* TAMU560 (MIC-44512) | 12.79 ± 2.89 | <0.0001 |
| | *Alternaria eichhorniae*. TAMU452 (MIC-26235) | 12.55 ± 1.62 | <0.0001 |
| Round 8 | Control | 47.03 ± 3.57 | — |
| | *Cladosporium* sp. TAMU501 (MIC-31246) | 31.37 ± 2.70 | <0.0001 |
| | *Epicoccum nigrum* TAMU125 (MIC-51347) | 27.00 ± 2.16 | <0.0001 |
| | *Epicoccum nigrum* TAMU131 (MIC-85590) | 22.25 ± 2.43 | <0.0001 |
| | *Purpureocillium lavendulum* TAMU424 (MIC-21610) | 22.03 ± 3.14 | <0.0001 |
| | *Cladosporium cladosporioides* TAMU474 (MIC-34220) | 19.41 ± 1.83 | <0.0001 |
| | *Alternaria* sp. TAMU53 (MIC-34397) | 18.66 ± 2.39 | <0.0001 |
| | *Chaetomium* sp. TAMU87 (MIC-78639) | 17.60 ± 1.94 | <0.0001 |
| | *Purpureocillium lilacinum* TAMU239 (MIC-86415) | 15.45 ± 1.64 | <0.0001 |
| | *Chaetomium* sp. TAMU110 (MIC-66827) | 14.44 ± 1.31 | <0.0001 |
| | *Chaetomium coarctatum* TAMU333 (MIC-39959) | 14.40 ± 1.55 | <0.0001 |
| | *Chaetomium globosum* TAMU554 (MIC-33414) | 14.14 ± 1.57 | <0.0001 |

TABLE 7

The effects of 56 endophytic fungal isolates from cotton on root-knot nematode gall production summarized by genera. Increased resistance was defined as a statistically significant decrease in the number of galls produced by root-knot nematode per gram of root tissue compared to the corresponding control treatment. Decreased resistance was defined as a statistically significant increase in the number of galls produced by root-knot nematode per gram of root tissue compared to the corresponding control treatment. Where an endophyte treatement was tested in more than one round of the experiment, increased or decreased resistance was counted in this table only if results were consistent in direction and significance between the rounds.

| Fungal Taxonomic ID | Increased Resistance | No effect | Decreased Resistance | Sub-Total |
|---|---|---|---|---|
| Acremonium | 0 | 1 | 0 | 1 |
| Alternaria | 2 | 2 | 2 | 6 |
| Beauveria | 0 | 1 | 0 | 1 |
| Chaetomium | 5 | 6 | 0 | 11 |
| Cladosporium | 4 | 10 | 0 | 14 |
| Cryptococcus | 0 | 1 | 0 | 1 |
| Curvularia | 0 | 1 | 1 | 2 |
| Diaporthe | 1 | 0 | 0 | 1 |
| Didymellaceae | 0 | 1 | 0 | 1 |
| Epicoccum | 7 | 5 | 0 | 12 |
| Fusarium | 0 | 1 | 0 | 1 |
| Nectriaceae | 0 | 1 | 0 | 1 |
| Penicillium | 0 | 1 | 0 | 1 |
| Purpureocillium | 2 | 0 | 0 | 2 |
| Unknown | 0 | 1 | 0 | 1 |
| Total | 21 | 32 | 3 | 56 |

Example 8: Fungal Endophytes Reduce Nematode Reproduction

Plants are germinated from treated and untreated control seeds in an environment chamber and then transplanted to soil in pots 11 days after planting. Two replicate seedlings per treatment are sampled to examine the endophyte colonization efficiency by surface sterilization and plating on PDA agar. Nematode treatment group seedlings are treated with either 2,000 or 10,000 eggs/plant at day six after transplanting. Plants are harvested and processed 6 weeks after nematode inoculation. The numbers of galls per gram of root tissue and total egg numbers in the population for each plant are quantified to compare nematode performance between endophyte-treated and untreated (control) plants.

Example 9: Herbivory Assays: Soy and Cabbage Looper on Soybean Plants

Endophyte treatments and untreated controls (no endophyte) were prepared as described in Example 3. Thirty-six fungal endophyte isolates were screened with the detached leaf herbivory assay.

Plant Management:

Two soybean seeds were planted in each 4 cm top diameter×6 cm deep pot, with 15 pots for each treatment. Potting media consists of bark, vermiculite, peat moss, perlite, and dolomitic limestone (non-sterile Metro-Mix® 900 soil, Sun Gro Horticulture, Agawam, Mass.). Soybean seedlings in individual pot were thinned to one plant per plot after the unifoliate leaves have unfolded. Plants were caged and maintained in the greenhouse.

Detached Leaf Assay:

The first trifoliate leaves were collected from each soybean plant when fully expanded. The two lateral leaflets were separated and distributed to 1.5% agar plates for insect infestation, with one leaflet per Petri dish per insect species; soybean looper (*Chrysodeixis includens*) and cabbage looper (*Trichoplusia ni*). Both the plants and plates were labeled to ensure the insects received leaf tissues from the same plant throughout each assay. The eggs of both soybean loopers and cabbage loopers were hatched in zipper bags in an incubating room (under 25±3° C. with 12 hours light: 12 hours dark). Three neonates of each species were transferred onto each 1.5% agar plate with one piece of dissected leaflet. Petri dishes were sealed and stored in a Thermo incubator at 27.5±0.5° C.

Figure 53:
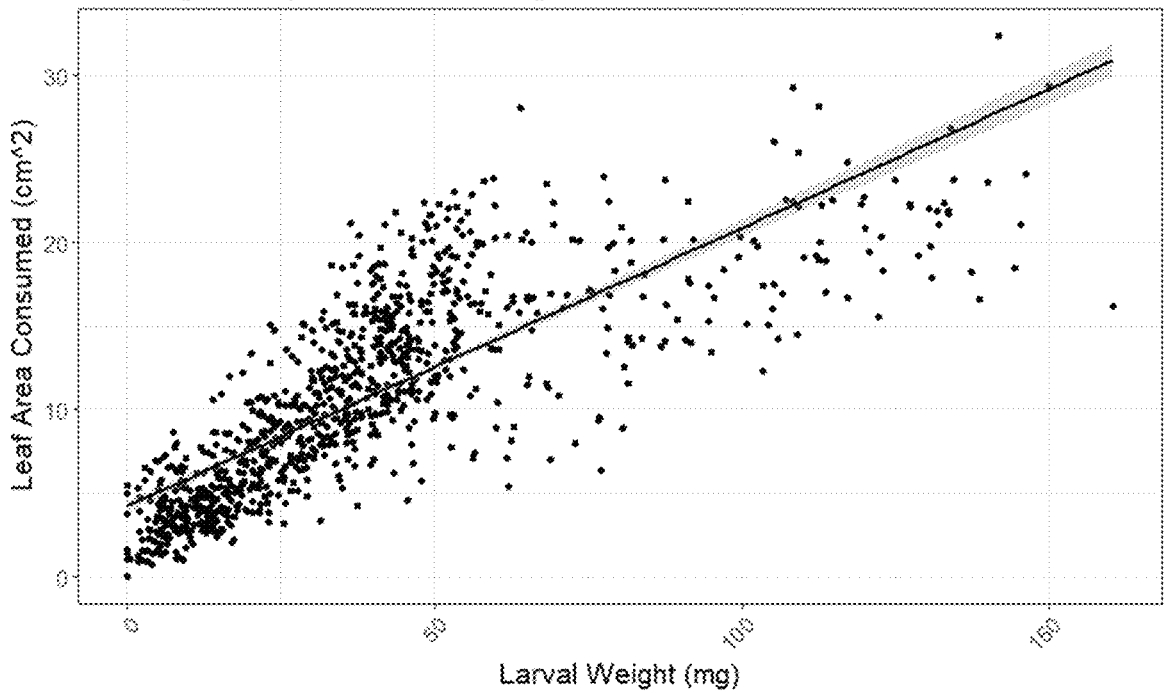
FIG. 53. Relationship between cabbage looper larval weight and leaf area consumed, data from all rounds of the assay are shown.
Figure 54:
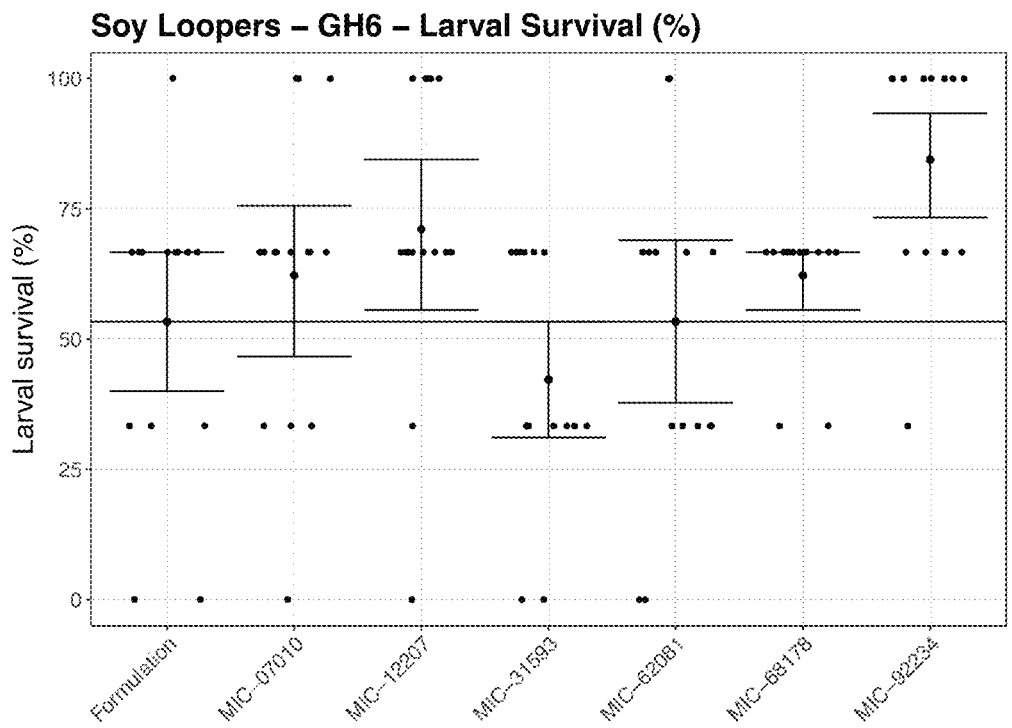
FIG. 54. Larval survival (%) after 7 days of herbivory by soy looper larvae on a soy leaflet grown from seeds treated with fungal endophytes MIC-62081 (TAM00103), MIC-68178 (TAM00032), MIC-62081 (TAM00103), MIC-07010 (TAM00105), MIC-31593 (TAM00189), or MIC-12207 (TAM00296). GH6—This round received 3 larvae per leaflet and larvae were transferred to a fresh leaflet from the same plant after 5 days. n=15 plants per treatment.
Figure 55:
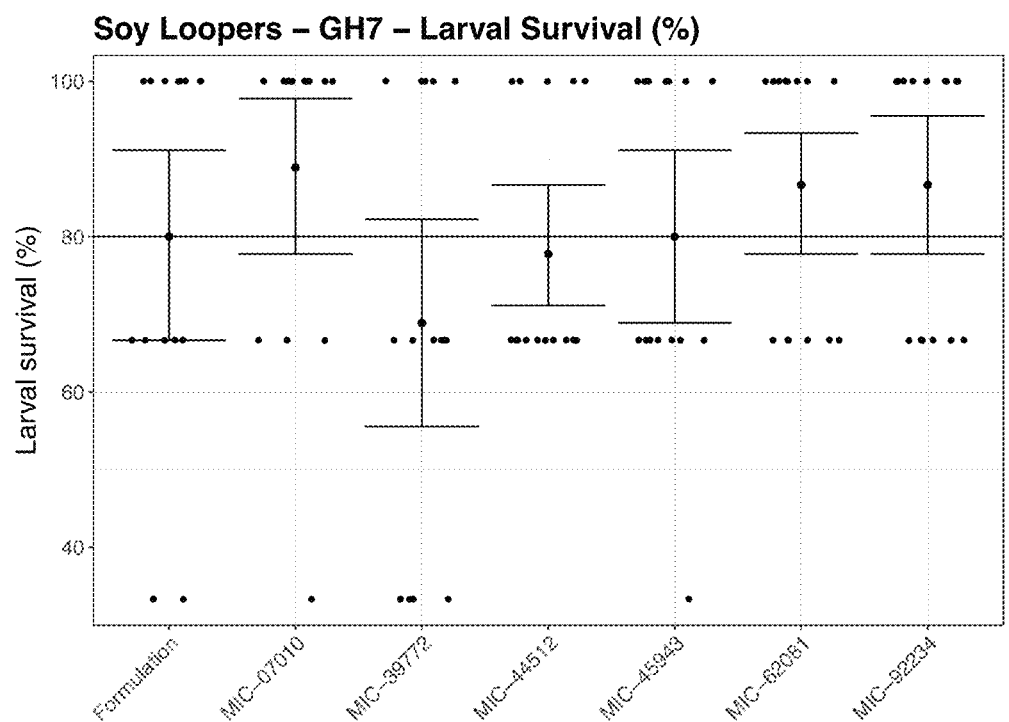
FIG. 55. Larval survival (%) after 7 days of herbivory by soy looper larvae on a soy leaflet grown from seeds treated with fungal endophytes MIC-92234 (TAM00013), MIC-62081 (TAM00103), MIC-07010 (TAM00105), MIC-39772 (TAM00317), MIC-45943 (TAM00362), or MIC-44512 (TAM00560). GH7—This round received 3 larvae per leaflet and larvae were transferred to a fresh leaflet from the same plant after 5 days. n=15 plants per treatment.
Figure 56:
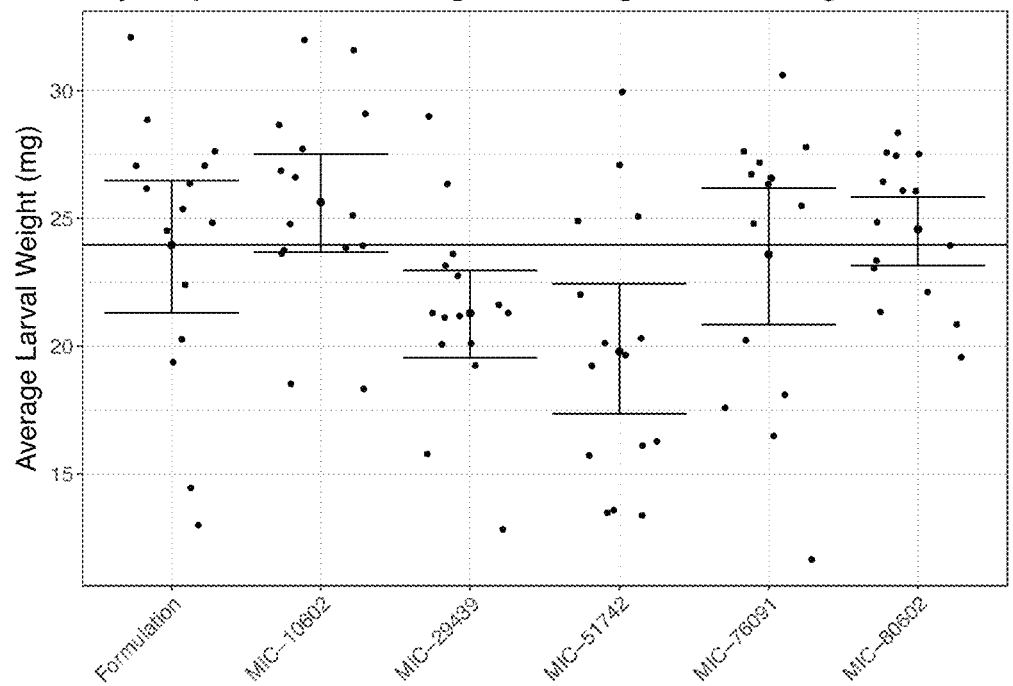
FIG. 56. Average weight of surviving larvae (mg) after 7 days of herbivory by soy looper larvae on a soy leaflet grown from seeds treated with fungal endophytes MIC-76091 (TAM00194), MIC-29439 (TAM00201), MIC-10602 (TAM00248), MIC-80602 (TAM00249), or MIC-51742 (TAM00251). GH3—This round received 3 larvae per leaflet and larvae were transferred to a fresh leaflet from the same plant after 5 days. n=15 plants per treatment.
Figure 57:
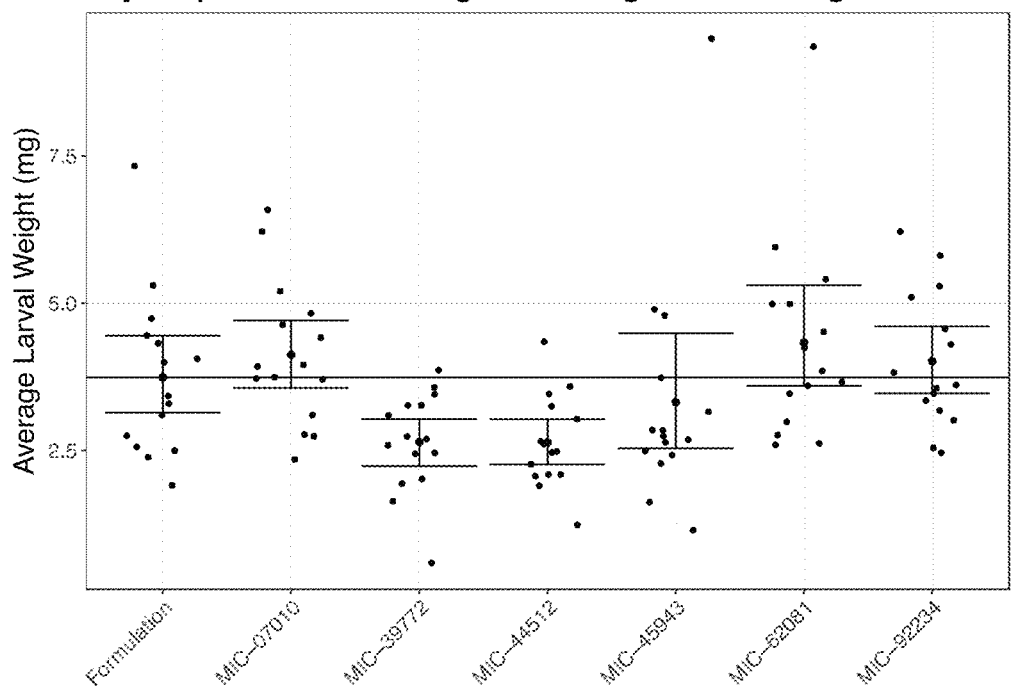
FIG. 57. Average weight of surviving larvae (mg) after 7 days of herbivory by soy looper larvae on a soy leaflet grown from seeds treated with fungal endophytes MIC-92234 (TAM00013), MIC-62081 (TAM00103), MIC-07010 (TAM00105), MIC-39772 (TAM00317), MIC-45943 (TAM00362), or MIC-44512 (TAM00560). GH7—This round received 3 larvae per leaflet and larvae were transferred to a fresh leaflet from the same plant after 5 days. n=15 plants per treatment.
Figure 58:
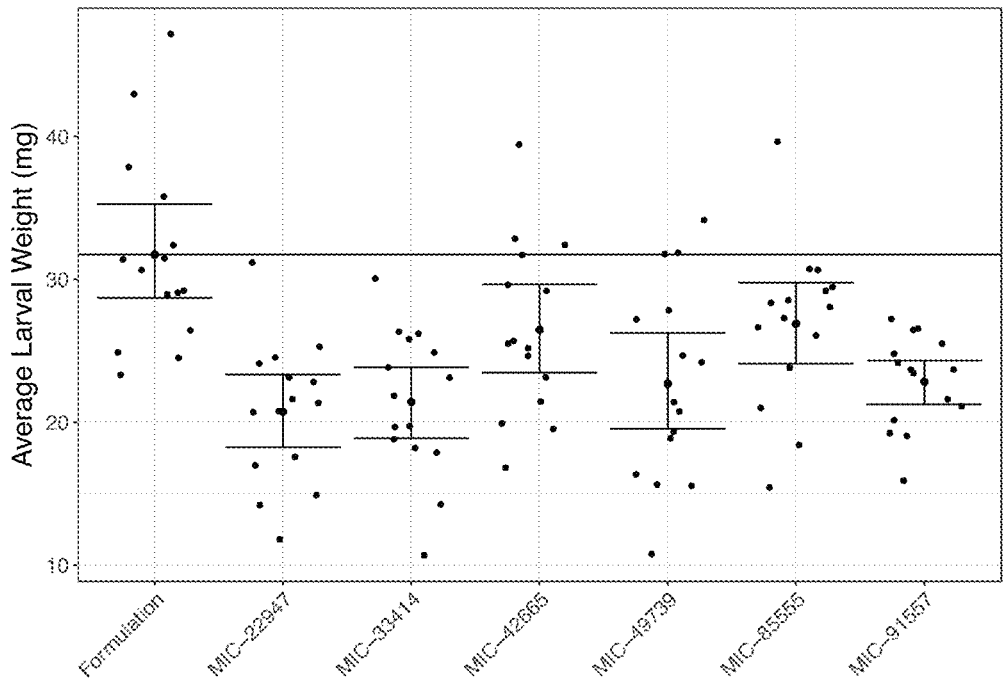
FIG. 58. Average weight of surviving larvae (mg) after 7 days of herbivory by soy looper larvae on a soy leaflet grown from seeds treated with fungal endophytes MIC-85555 (TAM00074), MIC-91557 (TAM00463), MIC-42665 (TAM00524), MIC-49739 (TAM00533), MIC-33414 (TAM00554), or MIC-22947 (TAM00559). GH10—This round received 3 larvae per leaflet and larvae were transferred to a fresh leaflet from the same plant after 5 days. n=15 plants per treatment.
Figure 59:
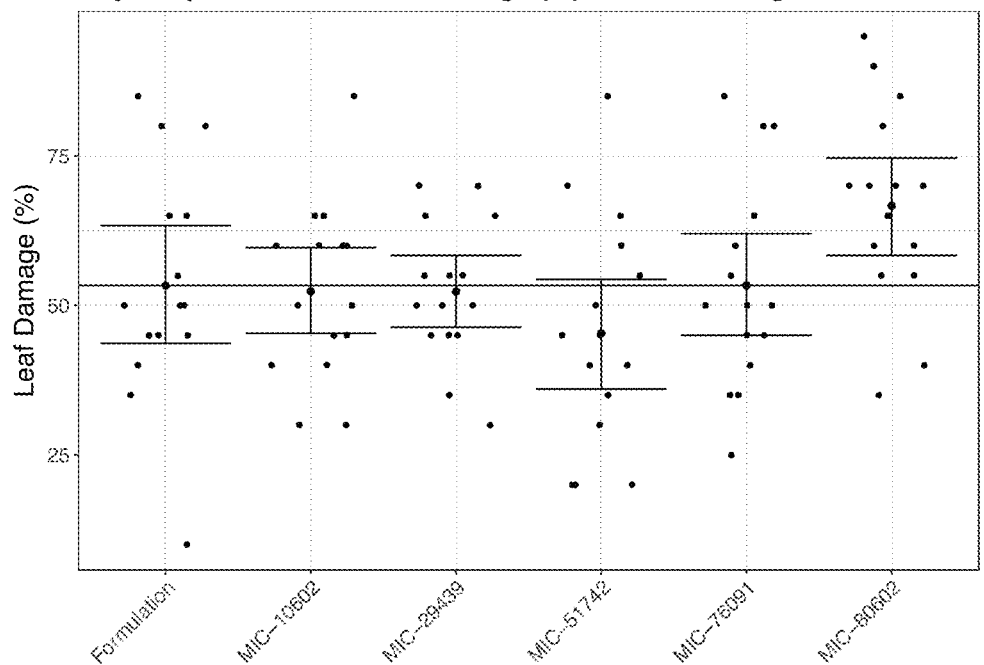
FIG. 59. Leaf damage (%) as assessed via visual rating scale after 7 days of by soy looper larvae herbivory on a soy leaflet grown from seeds treated with fungal endophytes MIC-76091 (TAM00194), MIC-29439 (TAM00201), MIC-10602 (TAM00248), MIC-80602 (TAM00249), or MIC-51742 (TAM00251). GH3—This round received 3 larvae per leaflet and larvae were transferred to a fresh leaflet from the same plant after 5 days. n=15 plants per treatment.
Figure 60:
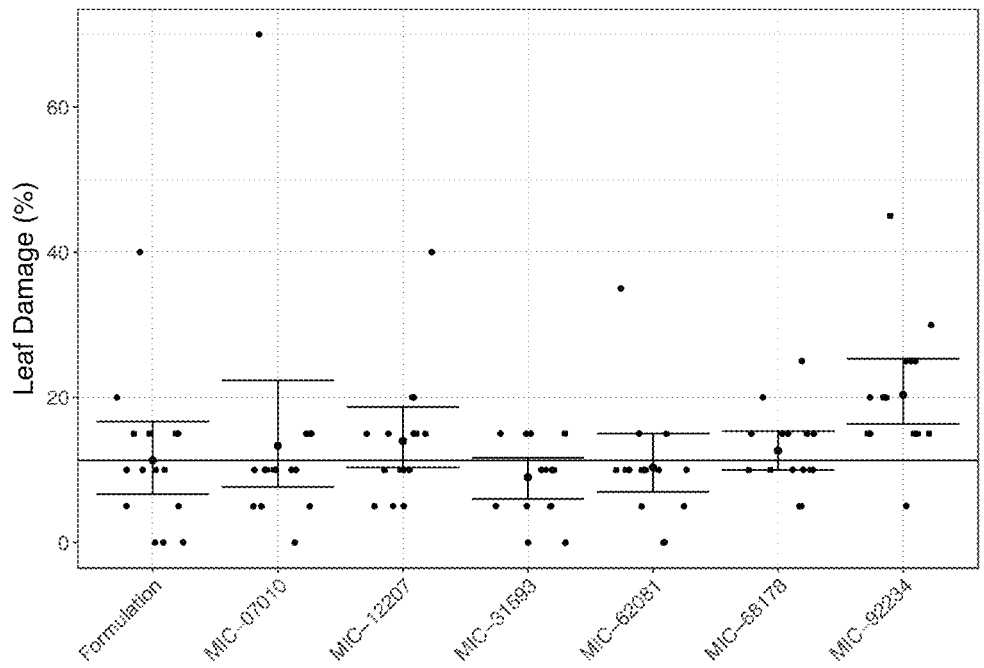
FIG. 60. Leaf damage (%) as assessed via visual rating scale after 7 days of by soy looper larvae herbivory on a soy leaflet grown from seeds treated with fungal endophytes MIC-92234 (TAM00013), MIC-68178 (TAM00032), MIC-62081 (TAM00103), MIC-07010 (TAM00105), MIC-31593 (TAM00189), or MIC-12207 (TAM00296). GH6—This round received 3 larvae per leaflet and larvae were transferred to a fresh leaflet from the same plant after 5 days. n=15 plants per treatment.
Figure 61:
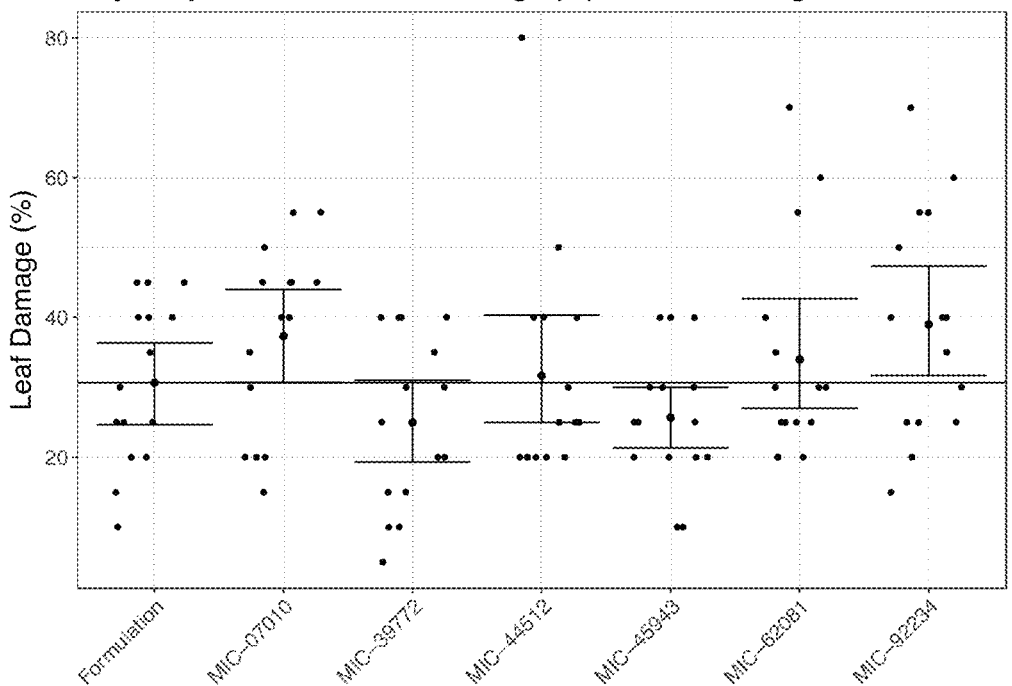
FIG. 61. Leaf damage (%) as assessed via visual rating scale after 7 days of by soy looper larvae herbivory on a soy leaflet grown from seeds treated with fungal endophytes MIC-92234 (TAM00013), MIC-62081 (TAM00103), MIC-07010 (TAM00105), MIC-39772 (TAM00317), MIC-45943 (TAM00362), or MIC-44512 (TAM00560). GH7—This round received 3 larvae per leaflet and larvae were transferred to a fresh leaflet from the same plant after 5 days. n=15 plants per treatment.
Figure 62:
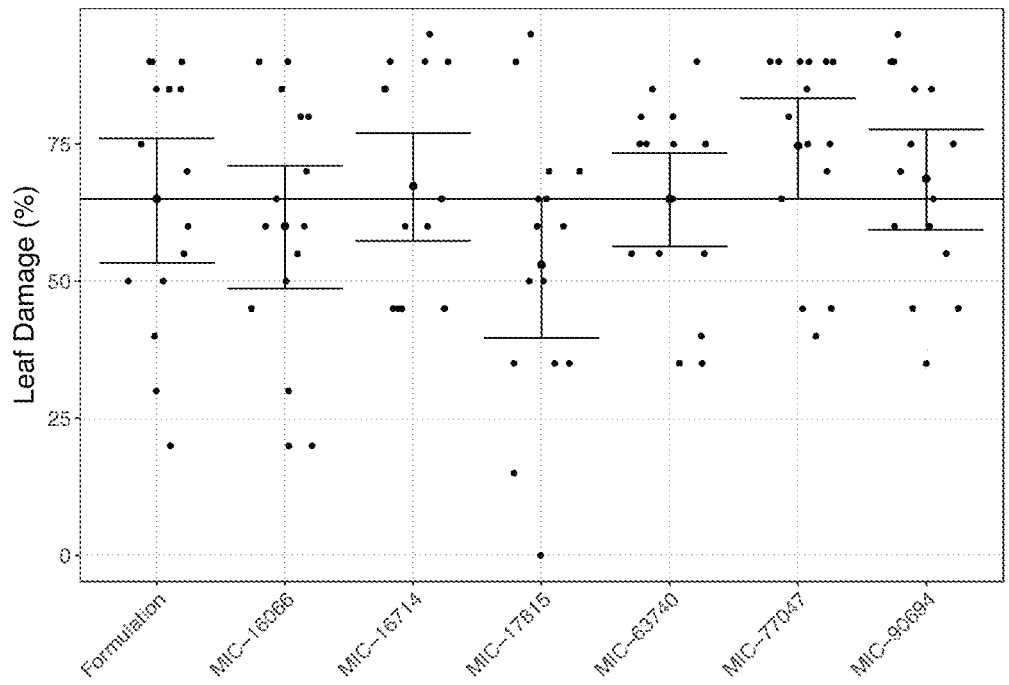
FIG. 62. Leaf damage (%) as assessed via visual rating scale after 7 days of by soy looper larvae herbivory on a soy leaflet grown from seeds treated with fungal endophytes MIC-90694 (TAM00046), MIC-77047 (TAM00100), MIC-63740 (TAM00504), MIC-17815 (TAM00518), MIC-16714 (TAM00531), or MIC-16066 (TAM00536). GH8—This round received 3 larvae per leaflet and larvae were transferred to a fresh leaflet from the same plant after 5 days. n=15 plants per treatment.
Figure 63:
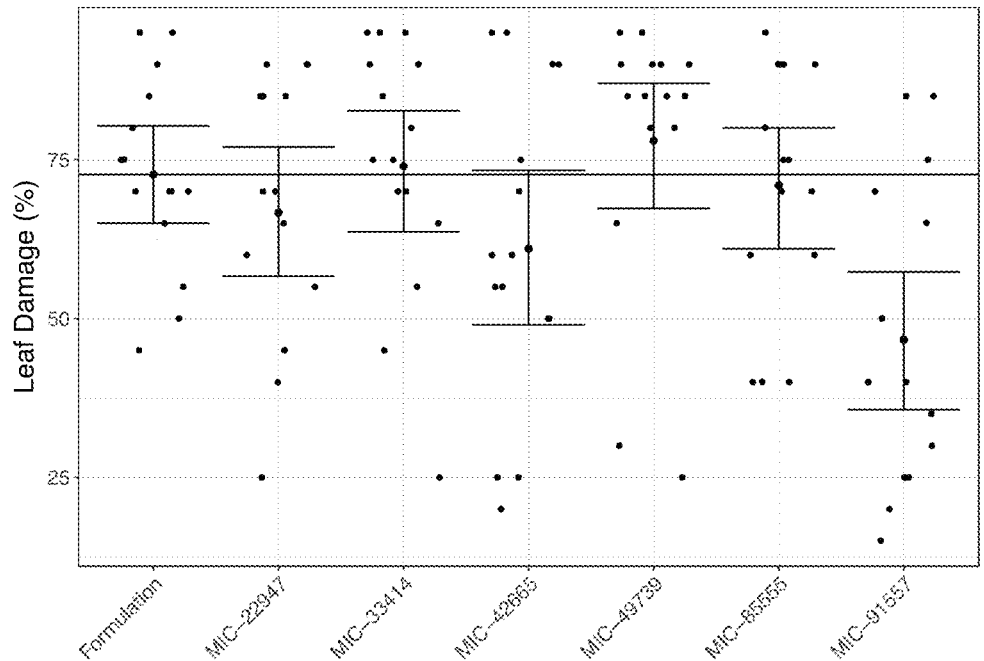
FIG. 63. Leaf damage (%) as assessed via visual rating scale after 7 days of by soy looper larvae herbivory on a soy leaflet grown from seeds treated with fungal endophytes MIC-85555 (TAM00074), MIC-91557 (TAM00463), MIC-42665 (TAM00524), MIC-49739 (TAM00533), MIC-33414 (TAM00554), or MIC-22947 (TAM00559). GH10—This round received 3 larvae per leaflet and larvae were transferred to a fresh leaflet from the same plant after 5 days. n=15 plants per treatment.
Figure 64:
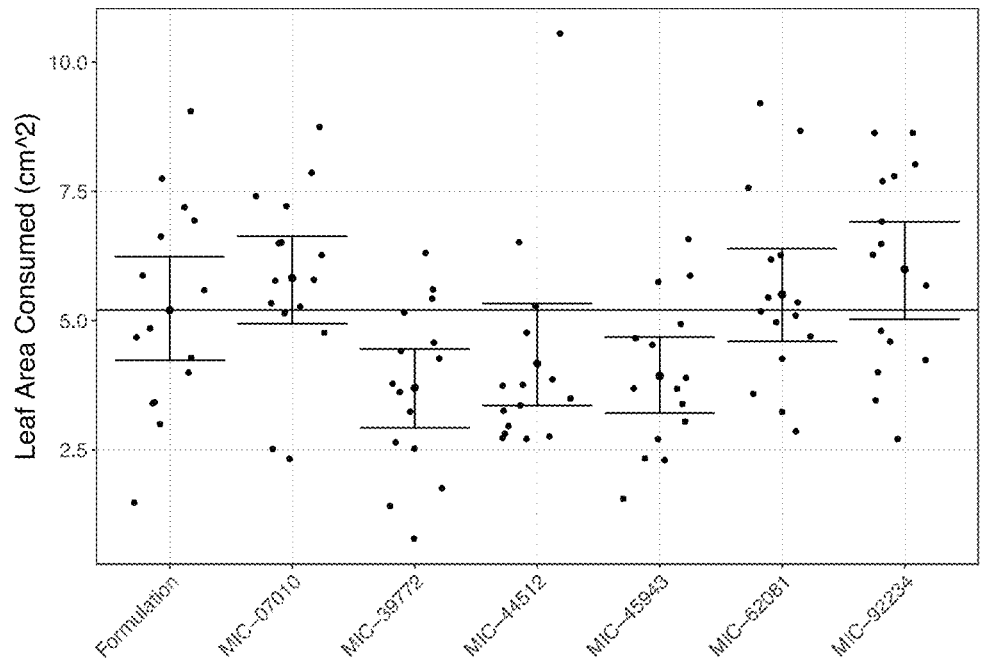
FIG. 64. Leaf area consumed (cm^2) as calculated from starting leaf area and percent leaf damage assessed via visual rating scale after 7 days of herbivory by soy looper larvae on a soy leaflet grown from seeds treated with fungal endophytes MIC-92234 (TAM00013), MIC-62081 (TAM00103), MIC-07010 (TAM00105), MIC-39772 (TAM00317), MIC-45943 (TAM00362), or MIC-44512 (TAM00560). GH7—This round received 3 larvae per leaflet and larvae were transferred to a fresh leaflet from the same plant after 5 days. n=15 plants per treatment.
Figure 65:
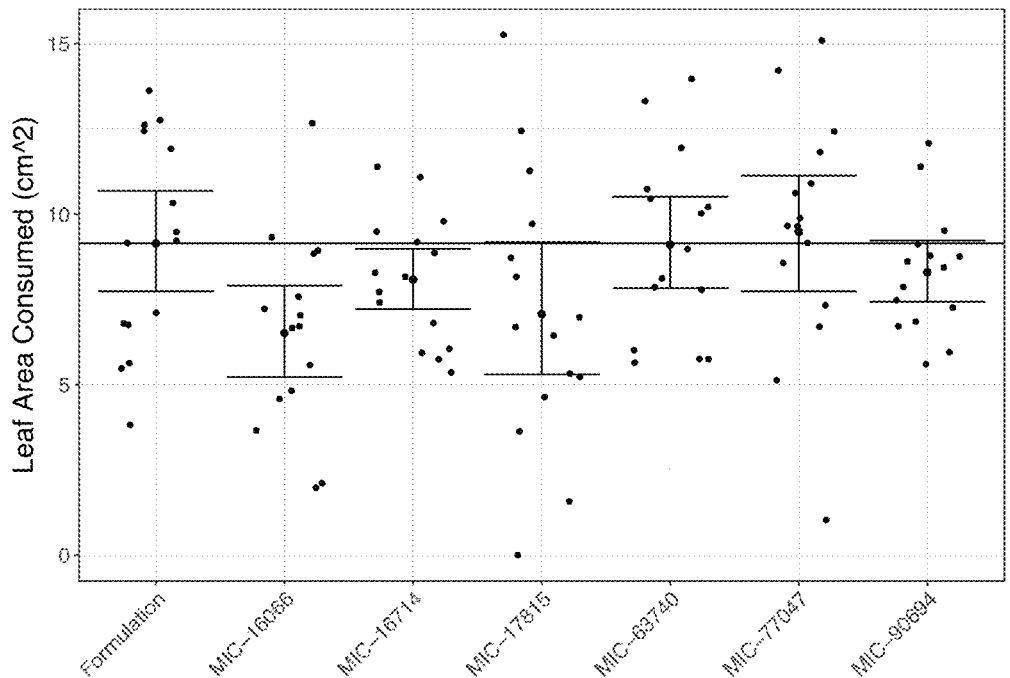
FIG. 65. Leaf area consumed (cm^2) as calculated from starting leaf area and percent leaf damage assessed via visual rating scale after 7 days of herbivory by soy looper larvae on a soy leaflet grown from seeds treated with fungal endophytes MIC-90694 (TAM00046), MIC-77047 (TAM00100), MIC-63740 (TAM00504), MIC-17815 (TAM00518), MIC-16714 (TAM00531), or MIC-16066 (TAM00536). GH8—This round received 3 larvae per leaflet and larvae were transferred to a fresh leaflet from the same plant after 5 days. n=15 plants per treatment.
Figure 66:
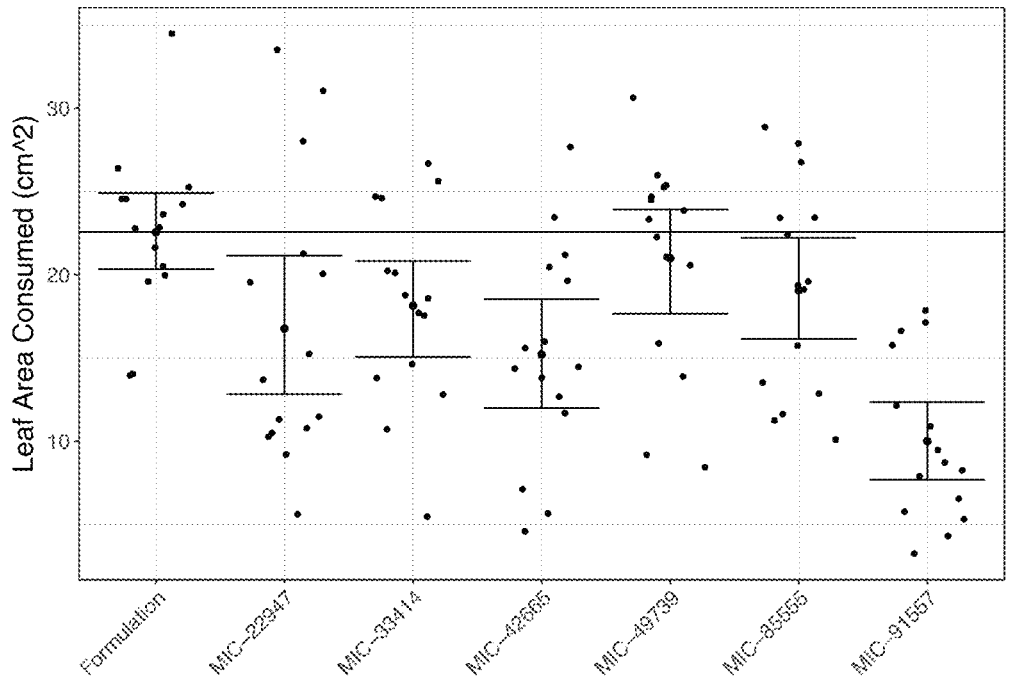
FIG. 66. Leaf area consumed (cm^2) as calculated from starting leaf area and percent leaf damage assessed via visual rating scale after 7 days of herbivory by soy looper larvae on a soy leaflet grown from seeds treated with fungal endophytes MIC-85555 (TAM00074), MIC-91557 (TAM00463), MIC-42665 (TAM00524), MIC-49739 (TAM00533), MIC-33414 (TAM00554), or MIC-22947 (TAM00559). GH10—This round received 3 larvae per leaflet and larvae were transferred to a fresh leaflet from the same plant after 5 days. n=15 plants per treatment.
Figure 67:
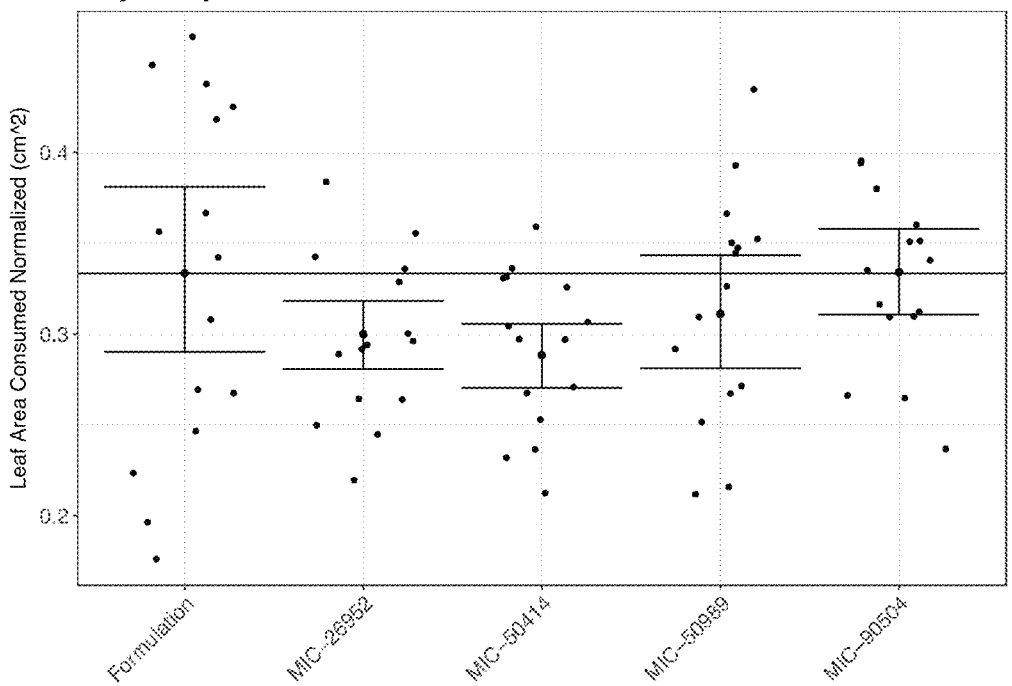
FIG. 67. Leaf area consumed (cm^2) as assessed normalized by average larval weight (mg) after 7 days of herbivory by soy looper larvae on a soy leaflet grown from seeds treated with fungal endophytes MIC-50989 (TAM00490), MIC-26952 (TAM00494), MIC-90504 (TAM00497), or MIC-50414 (TAM00534). GH2—This round received 3 larvae per leaflet and larvae were transferred to a fresh leaflet from the same plant after 5 days. n=15 plants per treatment.

Five days after the initial set up, the old leaf tissues were replaced by one lateral leaflet of the second fully expanded trifoliate leave per Petri dish. All leaf tissues were freshly obtained from the soybean plants described above. Petri dishes were sealed and stored in a Thermo incubator at 27.5±0.5° C. for two days. To terminate the assay, the remaining leaf tissues were removed from each Petri dish and placed on a log sheet for image collections. The percentage of leaf area consumed (FIGS. 42-45 and FIGS. 64-66) was estimated using a soybean leaf defoliation chart as the reference (Ortega et al., Pyramids of QTLs enhance host-plant resistance and Bt-mediated resistance to leaf-chewing insects in soybean. Theor Appl Genet. 2016 April; 129(4):703-715.). Whole leaf area (cm2) was calculated in Image J (Abramoff, M. D., Magalhaes, P. J., Ram, S. J. "Image Processing with ImageJ". Biophotonics International, volume 11, issue 7, pp. 36-42, 2004). Larval survivorship was recorded for each Petri dish (FIGS. 34-35 and FIGS. 54-55). Larval size was recorded as the total larval weight (mg) of all survivors from each Petri dish (FIGS. 36-37, FIGS. 56-58). The percentage leaf area was normalized for larval weight (FIGS. 46-52 and FIGS. 67-72). Larval weight and leaf area consumed for the whole data set was compiled (FIG. 53).

Each round of the experiment (indicated by trial id) contained internal controls. For cabbage looper formulation treated controls, larval survival ranged from roughly 70-100% with poor survival for a single round (GH3—30%), larval weight ranged from roughly 8-15 mg with two rounds showing extreme results (GH7—3 mg, GH10—37 mg), leaf area consumed ranged from roughly 5-11 cm^2 with two rounds showing extreme results (GH3—3 cm^2, GH10—21 cm^2). For soy looper formulation treated controls, larval survival ranged from roughly 80-100% with poor survival for a single round (GH6—53%), larval weight ranged from roughly 11-23 mg with three rounds showing extreme results (GH6—2.5 mg, GH7—4 mg, GH10—33 mg), leaf area consumed ranged from roughly 5-13 cm^2 with two rounds showing extreme results (GH6—3 cm^2, GH10—22 cm^2).

In the cabbage looper assays, fifteen isolates reduced caterpillar defoliation by 15% or more compared to controls, twelve of which also reduced larval growth compared to controls. All fifteen isolates reduced defoliation standardized by larval weight compared to controls. In the soybean looper assays, ten fungal isolates reduced caterpillar defoliation by 15% (Table 10) or more as well as reducing larval growth (Tables 8). When comparing performance across insect species, 22 (77%) of the fungal isolates showed the same trend, either positive or negative, in impact on leaf area consumed. Only 8 fungal isolates (22%) showed a variable response across the two insect species with a reduction in leaf area consumed for one insect and an increase in leaf area consumed for the other (Table 10).

For fungal taxa with multiple isolates included in the experiment, it was possible to compare performance across isolates. In the case of *Bipolaris spicifera*, two isolates (TAM00189 and TAM00013) consistently increased herbivory as measured by increased larval weight and leaf area consumption while one isolate (TAM00439) had a variable response. For *Chaetomium globosum*, all isolates showed a decrease in herbivory with two isolates (TAM00560 and TAM559) showing a decrease in leaf area consumption of well over 15% for both cabbage and soy loopers (Table 10). For *Cladosporium herbarum*, 5 isolates showed an increase in herbivory with 3 isolates showing over an 80% increase in leaf area consumed for cabbage looper compared to formulation controls (Table 10). One *C. herbarum* isolate showed a variable response in leaf area consumption across insect species and two isolates (TAM00494 and TAM00463) consistently decreased herbivory with one of the isolates (TAM00463) showing a decrease in herbivory over 40% in both insect species as the top performer in the experiment as a whole (Table 10). In the case of *Gibellulopsis nigrescens*, all three isolates (TAM00531, TAM00533 and TAM00524) decreased herbivory across both insects (Table 10). And for *Epicoccum nigrum*, 2 isolates (TAM00074 and TAM00536) showed consistent reduction in herbivory across both insects, 2 showed a variable response in each insect and 3 isolates consistently increased herbivory across both insects.

TABLE 8

Effect of fungal endophyte treatment on cabbage and soybean looper larvae weight in soybean detached leaf assay.

| Round | TAMID | TAXID | MICID | Cabbage Looper (*Trichoplusia ni*) % Change in Average Larval Weight | Soybean Looper (*Chrysodeixis includens*) % Change in Average Larval Weight |
|---|---|---|---|---|---|
| GH9 | TAM00323 | *Alternaria planifunda* | MIC-39233 | −43.1 | 23.9 |
| GH6 | TAM00189 | *Curvularia spicifera* | MIC-31593 | 140.3 | 12.6 |
| GH7 | TAM00013 | *Bipolaris spicifera* | MIC-92234 | 42.8 | 17.5 |
| GH9 | TAM00439 | *Bipolaris spicifera* | MIC-77538 | −39.5 | 4.4 |
| GH10 | TAM00554 | *Chaetomium globosum* | MIC-33414 | −2.1 | −33.0 |
| GH10 | TAM00559 | *Chaetomium globosum* | MIC-22947 | −3.4 | −43.2 |
| GH7 | TAM00560 | *Chaetomium globosum* | MIC-44512 | −3.8 | −29.4 |
| GH7 | TAM00317 | *Chaetomium* sp. | MIC-39772 | −8.1 | −35.2 |
| GH9 | TAM00501 | *Cladosporium* sp. | MIC-31246 | 126.6 | 84.7 |
| GH3 | TAM00249 | *Cladosporium gossypiicola* | MIC-80602 | 82.0 | 5.8 |
| GH3 | TAM00201 | *Cladosporium* sp. | MIC-29439 | 66.5 | −8.1 |
| GH3 | TAM00248 | *Cladosporium* sp. | MIC-10602 | 38.4 | 7.1 |
| GH9 | TAM00193 | *Cladosporium cladosporioides* | MIC-12927 | 32.9 | 8.6 |
| GH2 | TAM00534 | *Cladosporium oxysporum* | MIC-50414 | 30.6 | 13.6 |
| GH2 | TAM00494 | *Cladosporium* sp. | MIC-26952 | 19.3 | 2.9 |
| GH10 | TAM00463 | *Cladosporium* sp. | MIC-91557 | −30.4 | −24.6 |
| GH6 | TAM00105 | *Curvularia protuberata* | MIC-07010 | 76.9 | 49.5 |
| GH7 | TAM00105 | *Curvularia protuberata* | MIC-07010 | 29.6 | 21.9 |
| GH6 | TAM00032 | *Epicoccum nigrum* | MIC-68178 | 107.0 | 43.1 |
| GH8 | TAM00100 | *Epicoccum nigrum* | MIC-77047 | 41.8 | 23.4 |
| GH8 | TAM00046 | *Didymellaceae* | MIC-90694 | 22.3 | 6.2 |
| GH7 | TAM00103 | *Epicoccum nigrum* | MIC-62081 | 15.5 | 21.5 |
| GH8 | TAM00536 | *Epicoccum nigrum* | MIC-16066 | −2.4 | −3.3 |
| GH2 | TAM00497 | *Epicoccum nigrum* | MIC-90504 | −3.0 | 6.7 |
| GH10 | TAM00074 | *Epicoccum nigrum* | MIC-85555 | −12.8 | −11.1 |
| GH8 | TAM00531 | *Gibellulopsis nigrescens* | MIC-16714 | 15.5 | 10.2 |
| GH10 | TAM00533 | *Gibellulopsis nigrescens* | MIC-49739 | 6.1 | −24.6 |
| GH10 | TAM00524 | *Gibellulopsis nigrescens* | MIC-42665 | −20.0 | −16.3 |
| GH3 | TAM00251 | *Chaetomium piluliferum* | MIC-51742 | −15.8 | −17.0 |
| GH2 | TAM00490 | *Phialemonium inflatum* | MIC-50989 | 34.6 | 7.2 |
| GH3 | TAM00194 | *Epicoccum nigrum* | MIC-76091 | −18.1 | 4.0 |
| GH6 | TAM00296 | *Pleosporaceae* sp. | MIC-12207 | 126.1 | 57.0 |
| GH8 | TAM00518 | *Preussia africana* | MIC-17815 | −8.0 | −6.9 |
| GH8 | TAM00504 | *Sphaerulina pseudovirgaureae* | MIC-63740 | 14.3 | 9.2 |
| GH9 | TAM00160 | *Stagonospora* sp. | MIC-20571 | 72.1 | 35.3 |
| GH9 | TAM00473 | *Stemphylium herbarum* | MIC-32308 | 19.4 | 0.9 |
| GH9 | TAM00362 | *Stemphylium herbarum* | MIC-45943 | 7.2 | 29.6 |

TABLE 9

Effect of fungal endophyte treatment on cabbage and soybean looper larvae survival in soybean detached leaf assay.

| Round | TAMID | TAXID | MICID | Cabbage Looper (*Trichoplusia ni*) % Change in Surviving Larvae Percent | Soybean Looper (*Chrysodeixis includens*) % Change in Surviving Larvae Percent |
|---|---|---|---|---|---|
| GH9 | TAM00323 | *Alternaria planifunda* | MIC-39233 | −3.45 | 4.65 |
| GH7 | TAM00013 | *Bipolaris spicifera* | MIC-92234 | 30 | 8.33 |
| GH6 | TAM00189 | *Curvularia spicifera* | MIC-31593 | 13.16 | −20.83 |
| GH9 | TAM00439 | *Bipolaris spicifera* | MIC-77538 | 3.45 | 2.33 |
| GH7 | TAM00560 | *Chaetomium globosum* | MIC-44512 | 33.33 | −2.78 |

TABLE 9-continued

Effect of fungal endophyte treatment on cabbage and soybean looper larvae survival in soybean detached leaf assay.

| Round | TAMID | TAXID | MICID | Cabbage Looper (*Trichoplusia ni*) % Change in Surviving Larvae Percent | Soybean Looper (*Chrysodeixis includens*) % Change in Surviving Larvae Percent |
|---|---|---|---|---|---|
| GH10 | TAM00554 | *Chaetomium globosum* | MIC-33414 | −2.22 | 0 |
| GH10 | TAM00559 | *Chaetomium globosum* | MIC-22947 | −2.22 | −11.9 |
| GH7 | TAM00317 | *Chaetomium* sp. | MIC-39772 | 13.33 | −13.89 |
| GH3 | TAM00201 | *Cladosporium* sp. | MIC-29439 | 53.33 | 4.76 |
| GH9 | TAM00501 | *Cladosporium* sp. | MIC-31246 | 34.48 | 0 |
| GH9 | TAM00193 | *Cladosporium cladosporioides* | MIC-12927 | 20.69 | 0 |
| GH3 | TAM00249 | *Cladosporium gossypiicola* | MIC-80602 | 20 | 4.76 |
| GH2 | TAM00494 | *Cladosporium* sp. | MIC-26952 | 10 | 4.76 |
| GH3 | TAM00248 | *Cladosporium* sp. | MIC-10602 | 6.67 | 2.38 |
| GH2 | TAM00534 | *Cladosporium oxysporum* | MIC-50414 | 2.5 | 4.76 |
| GH10 | TAM00463 | *Cladosporium* sp. | MIC-91557 | −13.33 | 4.76 |
| GH7 | TAM00105 | *Curvularia protuberata* | MIC-07010 | 16.67 | 11.11 |
| GH6 | TAM00105 | *Curvularia protuberata* | MIC-07010 | −2.63 | 16.67 |
| GH8 | TAM00100 | *Epicoccum nigrum* | MIC-77047 | 36.67 | −4.65 |
| GH8 | TAM00046 | Didymellaceae | MIC-90694 | 23.33 | −2.33 |
| GH8 | TAM00536 | *Epicoccum nigrum* | MIC-16066 | 16.67 | −4.65 |
| GH6 | TAM00032 | *Epicoccum nigrum* | MIC-68178 | 13.16 | 16.67 |
| GH2 | TAM00497 | *Epicoccum nigrum* | MIC-90504 | 7.5 | 4.76 |
| GH7 | TAM00103 | *Epicoccum nigrum* | MIC-62081 | −6.67 | 8.33 |
| GH10 | TAM00074 | *Epicoccum nigrum* | MIC-85555 | −8.89 | 4.76 |
| GH8 | TAM00531 | *Gibellulopsis nigrescens* | MIC-16714 | 23.33 | −6.98 |
| GH10 | TAM00524 | *Gibellulopsis nigrescens* | MIC-42665 | −2.22 | 0 |
| GH10 | TAM00533 | *Gibellulopsis nigrescens* | MIC-49739 | −4.44 | 4.76 |
| GH3 | TAM00251 | *Chaetomium piluliferum* | MIC-51742 | 20 | 2.38 |
| GH2 | TAM00490 | *Phialemonium inflatum* | MIC-50989 | 10 | 4.76 |
| GH3 | TAM00194 | *Epicoccum nigrum* | MIC-76091 | 20 | 7.14 |
| GH6 | TAM00296 | Pleosporaceae sp. | MIC-12207 | 15.79 | 33.33 |
| GH8 | TAM00518 | *Preussia africana* | MIC-17815 | 30 | −6.98 |
| GH8 | TAM00504 | *Sphaerulina pseudovirgaureae* | MIC-63740 | 36.67 | 4.65 |
| GH9 | TAM00160 | *Stagonospora* sp. | MIC-20571 | 41.38 | 4.65 |
| GH9 | TAM00362 | *Stemphylium herbarum* | MIC-45943 | 24.14 | −4.65 |
| GH9 | TAM00473 | *Stemphylium herb arum* | MIC-32308 | 17.24 | −9.3 |

TABLE 10

Effect of fungal endophyte treatment on cabbage and soybean looper larvae leaf area consumption in soybean detached leaf assay.

| Round | TAMID | TAXID | MICID | Cabbage Looper (*Trichoplusia ni*) % Change in Leaf Area Consumed | Soybean Looper (*Chrysodeixis includens*) % Change in Leaf Area Consumed |
|---|---|---|---|---|---|
| GH9 | TAM00323 | *Alternaria planifunda* | MIC-39233 | −48.9 | 18.87 |
| GH6 | TAM00189 | *Curvularia spicifera* | MIC-31593 | 81.24 | 1.83 |
| GH7 | TAM00013 | *Bipolaris spicifera* | MIC-92234 | 15.14 | 15.14 |
| GH9 | TAM00439 | *Bipolaris spicifera* | MIC-77538 | −39.22 | 4.79 |
| GH10 | TAM00554 | *Chaetomium globosum* | MIC-33414 | −6.71 | −19.62 |
| GH7 | TAM00560 | *Chaetomium globosum* | MIC-44512 | −19.85 | −19.85 |
| GH10 | TAM00559 | *Chaetomium globosum* | MIC-22947 | −21.73 | −25.66 |
| GH7 | TAM00317 | *Chaetomium* sp. | MIC-39772 | −28.92 | −28.92 |
| GH9 | TAM00501 | *Cladosporium* sp. | MIC-31246 | 86.48 | 42.88 |
| GH3 | TAM00201 | *Cladosporium* sp. | MIC-29439 | 82.67 | 1.91 |
| GH3 | TAM00249 | *Cladosporium gossypiicola* | MIC-80602 | 80 | 12.44 |
| GH3 | TAM00248 | *Cladosporium* sp. | MIC-10602 | 37.3 | −5.49 |
| GH9 | TAM00193 | *Cladosporium cladosporioides* | MIC-12927 | 16.22 | 11.88 |
| GH2 | TAM00534 | *Cladosporium oxysporum* | MIC-50414 | 5.91 | 4.71 |
| GH2 | TAM00494 | *Cladosporium* sp. | MIC-26952 | −9.13 | −4.49 |
| GH10 | TAM00463 | *Cladosporium* sp. | MIC-91557 | −43.98 | −55.69 |
| GH6 | TAM00105 | *Curvularia protuberata* | MIC-07010 | 32.63 | 15.28 |
| GH7 | TAM00105 | *Curvularia protuberata* | MIC-07010 | 11.9 | 11.9 |
| GH6 | TAM00032 | *Epicoccum nigrum* | MIC-68178 | 63.45 | 10.16 |
| GH8 | TAM00100 | *Epicoccum nigrum* | MIC-77047 | 28.42 | 3.69 |

TABLE 10-continued

Effect of fungal endophyte treatment on cabbage and soybean looper larvae leaf area consumption in soybean detached leaf assay.

| Round | TAMID | TAXID | MICID | Cabbage Looper (*Trichoplusia ni*) % Change in Leaf Area Consumed | Soybean Looper (*Chrysodeixis includens*) % Change in Leaf Area Consumed |
|---|---|---|---|---|---|
| GH8 | TAM00046 | *Didymellaceae* | MIC-90694 | 9.85 | −9.27 |
| GH7 | TAM00103 | *Epicoccum nigrum* | MIC-62081 | 5.72 | 5.72 |
| GH2 | TAM00497 | *Epicoccum nigrum* | MIC-90504 | −18.92 | 13.48 |
| GH10 | TAM00074 | *Epicoccum nigrum* | MIC-85555 | −19.67 | −15.5 |
| GH8 | TAM00536 | *Epicoccum nigrum* | MIC-16066 | −22.85 | −28.8 |
| GH8 | TAM00531 | *Gibellulopsis nigrescens* | MIC-16714 | −16.55 | −11.6 |
| GH10 | TAM00533 | *Gibellulopsis nigrescens* | MIC-49739 | −19.85 | −6.98 |
| GH10 | TAM00524 | *Gibellulopsis nigrescens* | MIC-42665 | −28.9 | −32.53 |
| GH3 | TAM00251 | *Chaetomium piluliferum* | MIC-51742 | −0.26 | −13.41 |
| GH2 | TAM00490 | *Phialemonium inflatum* | MIC-50989 | 11.69 | 3.91 |
| GH3 | TAM00194 | *Epicoccum nigrum* | MIC-76091 | −23.32 | −6.34 |
| GH6 | TAM00296 | *Pleosporaceae* sp. | MIC-12207 | 93.94 | 41.02 |
| GH8 | TAM00518 | *Preussia africana* | MIC-17815 | −23.68 | −22.66 |
| GH8 | TAM00504 | *Sphaerulina pseudovirgaureae* | MIC-63740 | 2.51 | −0.41 |
| GH9 | TAM00160 | *Stagonospora* sp. | MIC-20571 | 62.35 | 32.82 |
| GH9 | TAM00473 | *Stemphylium herbarum* | MIC-32308 | 10.58 | −4.74 |
| GH9 | TAM00362 | *Stemphylium herbarum* | MIC-45943 | −10.54 | 17.71 |

Example 10: Treatment of Aphid Infestation

Seed Treatment:

Fungal endophyte biomass was prepared and heterologously disposed on black cotton seeds of varieties Phytogen 499WRF and Delta Pine 1321B2RF as described in Example 3.

Plant Production:

Seeds of each treatment combination were planted individually in seedling germination trays. Each cell pot measured 4 cm top diameter×6 cm deep and was filled with nonsterile Metro-Mix® 900 soil (Sun Gro Horticulture, Agawam, Mass.; ingredients: bark, vermiculite, peat moss, perlite, dolomitic limestone) watered to saturation prior to planting. Plants were grown in a controlled temperature room at 25° C. under constant overhead illumination (EnviroGro T5 High Output Fluorescent Lighting Systems).

Aphid Infestation:

Five 4th instar cotton aphids (*Aphis gossypii*) were applied to each plant at 14 days after planting on the 1st true leaf and allowed to reproduce for 7 days. N=18 per endophyte*variety combination. The total number of aphids and the number of winged adult aphids (termed alates) on each plant 7 days after infestation were recorded, exemplary results are shown in FIGS. 81-85.

Results:

Total number of aphids on each plant was used as a measure of reproductive success, presumably reflecting the quality of the host to support aphid development and reproduction. The number of winged adults (alates) was also counted. Wing polymorphism is very common in aphids and has been shown to increase in frequency in response to stressful conditions, including changes in host quality. Thus, the number of alates per plant can be interpreted as a potential indicator of the quality of the plant to act as a host to the insect, with a reduction of the host quality of the plants predicted to induce the production of more alates. In the endophyte-aphid experiments, some endophyte treatments clearly reduced total aphid numbers on the plant relative to control, indicating that the endophyte treatment negatively affected aphid reproductive capacity on the plant. Alternatively, some endophyte treatments resulted in an increase in the total number of aphids per plant, suggesting a positive effect of the treatment on the quality of the plant as a host. Some endophyte treatments increased the number of alates produced on the plant, consistent with the prediction of a higher number of alates produced on plants that were less amenable hosts relative to the untreated controls.

Plants treated with the *Alternaria eichorniae* endophytes TAM00179 (MIC-86713) and TAM00053 (MIC-34397), the *Cladosporium cladosporioides* endophyte TAM00474 (MIC-34220), *Epicoccum nigrum* endophyte TAM00089 (MIC-67271), the *Chaetomium globosum* endophyte TAM00117 (MIC-23475), and *Purpureocillium lavendulum* endophyte TAM00424 (MIC-21610) had a greater than 15% reductions in the number of aphids relative to formulation controls indicating negative affects on aphid reproductive capacity and a greater than 12% increase in the number of alates relative to formulation controls indicating reduced attractiveness of the treated plants as aphid hosts. Plants treated with *Purpureocillium lavendulum* TAM00424 (MIC-21610) had greater than 70% reductions in the number of aphids relative to formulation controls and greater than 70% increase in the number of alates. Plants treated with *Purpureocillium lavendulum* TAM00239 (MIC-86415) also a greater than 30% increase in the number of alates.

TABLE 11

Effect of fungal endophyte treatment on the average number of aphids and alates on cotton plants as a percent change compared to the formulation control for that round. The number of alates and aphids were recorded after 7 days of reproduction on the cotton plants, n = 18 plants per treatment.

| Round | TAMID | TAXID | MICID | Aphid Number | Alates Number |
|---|---|---|---|---|---|
| GH3 | TAM00100 | *Epicoccum nigrum* | MIC-77047 | 39.73 | −17.65 |
| GH3 | TAM00129 | *Alternaria eichorniae* | MIC-39830 | 39.21 | −2.48 |
| GH3 | TAM00179 | *Alternaria eichorniae* | MIC-86713 | 37.64 | 9.38 |
| GH3 | TAM00244 | *Cladosporium* sp. | MIC-48747 | 18.9 | −27.94 |
| GH3 | TAM00356 | *Chaetomium coarctatum* | MIC-59232 | 41.66 | −17.65 |
| GH3 | TAM00488 | *Gibellulopsis nigrescens* | MIC-85153 | 13.1 | −28.32 |
| GH3 | TAM00494 | *Cladosporium* sp. | MIC-26952 | 34.88 | −38.24 |
| GH3 | TAM00534 | *Chaetomium globosum* | MIC-33414 | 36.91 | −25.27 |
| GH4 | TAM00089 | *Epicoccum nigrum* | MIC-67271 | −16.15 | 62.54 |
| GH4 | TAM00129 | *Alternaria eichorniae* | MIC-39830 | 2.14 | 171.62 |
| GH4 | TAM00317 | *Chaetomium* sp. | MIC-39772 | −17.62 | −23.8 |
| GH4 | TAM00333 | *Chaetomium coarctatum* | MIC-39959 | 14.08 | 141.35 |
| GH4 | TAM00340 | *Fusarium* sp. | MIC-87502 | 22.46 | 139.73 |
| GH4 | TAM00452 | *Alternaria eichorniae* | MIC-26235 | −56.46 | −33.71 |
| GH4 | TAM00505 | *Acremonium alternatum* | MIC-96038 | 2.02 | 9.11 |
| GH4 | TAM00514 | *Cryptococcus* sp. | MIC-39051 | 9.34 | 10.73 |
| GH4 | TAM00560 | *Chaetomium globosum* | MIC-44512 | −34.2 | −23.21 |
| GH5 | TAM00110 | *Chaetomium* sp. | MIC-66827 | 8.87 | −18.11 |
| GH5 | TAM00117 | *Chaetomium globosum* | MIC-23475 | −24.56 | 12.28 |
| GH5 | TAM00137 | *Diaporthe* sp. | MIC-42067 | 53.98 | 5.77 |
| GH5 | TAM00179 | *Alternaria eichorniae* | MIC-86713 | −32.68 | 85.5 |
| GH5 | TAM00248 | *Cladosporium* sp. | MIC-10602 | −32.7 | −32.01 |
| GH5 | TAM00340 | *Fusarium* sp. | MIC-87502 | 37.43 | −38.73 |
| GH5 | TAM00474 | *Cladosporium cladosporioides* | MIC-34220 | −15.47 | 47.39 |
| GH5 | TAM00501 | *Cladosporium* sp. | MIC-31246 | −26.8 | −80.77 |
| GH5 | TAM00565 | *Cladosporium herbarum* | MIC-20835 | 39.67 | 44.43 |
| GH6 | TAM00033 | *Epicoccum nigrum* | MIC-16895 | 27.7 | 92.12 |
| GH6 | TAM00053 | *Alternaria eichorniae* | MIC-34397 | −16.86 | 41.06 |
| GH6 | TAM00072 | *Epicoccum nigrum* | MIC-55629 | 22.03 | 5.58 |
| GH6 | TAM00087 | *Alternaria eichorniae* | MIC-78639 | 35 | 51.78 |
| GH6 | TAM00117 | *Chaetomium globosum* | MIC-23475 | 56.14 | 114.18 |
| GH6 | TAM00125 | *Epicoccum nigrum* | MIC-51347 | 126.35 | 287.06 |
| GH6 | TAM00128 | *Epicoccum nigrum* | MIC-65047 | 9.09 | 32.03 |
| GH6 | TAM00131 | *Epicoccum nigrum* | MIC-85590 | 76.01 | 247.35 |
| GH6 | TAM00239 | *Purpureocillium lavendulum* | MIC-86415 | 0.23 | 36.54 |
| GH6 | TAM00251 | *Chaetomium piluliferum* | MIC-51742 | 8.93 | 81.73 |
| GH7 | TAM00169 | *Cladosporium herbarum* | MIC-91347 | −4.43 | 52.31 |
| GH7 | TAM00190 | *Cladosporium herbarum* | MIC-42406 | −6.28 | 4.32 |
| GH7 | TAM00193 | *Cladosporium cladosporioides* | MIC-12927 | −21 | −7.27 |
| GH7 | TAM00413 | *Penicillium* sp. | MIC-50324 | −71.18 | −57.35 |
| GH7 | TAM00415 | *Cladosporium herbarum* | MIC-87929 | −19.39 | −15.7 |
| GH7 | TAM00416 | *Alternaria eichorniae* | MIC-31674 | 11.46 | 67.4 |
| GH7 | TAM00424 | *Purpureocillium lavendulum* | MIC-21610 | −70.47 | 74.22 |
| GH7 | TAM00508 | | MIC-72092 | −11.96 | −25.18 |
| GH7 | TAM00517 | *Cladosporium cladosporioides* | MIC-72531 | 9.32 | −4.82 |
| GH8 | TAM00032 | *Epicoccum nigrum* | MIC-68178 | −34.43 | −21.75 |
| GH8 | TAM00057 | *Drechslerella dactyloides* | MIC-65885 | −47.62 | −28.01 |
| GH8 | TAM00201 | *Cladosporium* sp. | MIC-29439 | −44.47 | −32.68 |
| GH8 | TAM00304 | *Cladosporium* sp. | MIC-17794 | −38.12 | −50.03 |
| GH8 | TAM00489 | | MIC-38632 | −31.33 | −47.54 |
| GH8 | TAM00497 | *Epicoccum nigrum* | MIC-90504 | −23.58 | 2.06 |
| GH8 | TAM00512 | *Crytpococcus* | MIC-67609 | −32.31 | −33.94 |
| GH8 | TAM00526 | *Phomopsis liquidambari* | MIC-95013 | −33.01 | −30.06 |
| GH8 | TAM00529 | *Alternaria eichorniae* | MIC-61920 | −57.6 | −51.91 |

Example 11: Southern Green Stink Bug Behavior Assay

Fungal spore suspensions were produced and Phytogen 499 seeds were treated according to the methods of Example 3.

Detached Boll Assay

No-choice behavioral assays were conducted to compare the response of Southern green stink bug (*Nezara viridula*) individuals to fruits (bolls) from field grown endophyte-treated and untreated cotton plants. The assays were conducted in a temperature controlled observation room at 30° C. in 10 cm diameter Petri dishes with a thin layer of 2% agar on the bottom to provide moisture for the bolls used during the observations. The agar was covered with parafilm to create a dry surface for the insects. For no-choice assays, a single boll was removed from the source plant and pressed into the center of the dish. A single young adult (1-7 d post molt) insect was placed in each dish and covered with the lid. Video tracking software was used to define a "zone" around the boll and tracks insect as it moves in and out of the zone. FIG. 79 shows an exemplary photo of a petri plate "arena" used in this assay and the computer defined zone around each boll. FIG. 80 shows an example of the output of the video tracking software (Ethovision XT version 8.0, Noldus Information Technology, Inc. Leesburg, Va.), a visualization of the path over which the insect in that arena has traveled over the observation period. In each trial, 20 insects were observed for each endophyte and control treatment. Petri dish positions were randomized to avoid any positional bias during the observations. The *N. viridula* no-choice trials were replicated 4 times (total n=20 per treatment) with bolls from field-grown plants. Balanced sex ratios were used in all experiments. No difference between the sexes was observed and data were pooled for final analysis.

Insects in the no-choice assay were observed for 6 hours per trial using video tracking software. For each insect in each trial, the software recorded the insect's movement and the amount of time, if any, spent in the zone surrounding the boll.

Out of 36 fungal endophyte isolates screened in this assay, 10 strains showed greater than 20% reduction in the average amount of time *N. viridula* spent in contact with bolls compared to bolls collected from formulation treated plants. Two of those strains showed greater than 60% reduction in average boll time compared to formulation controls (Table 12).

Where multiple isolates of the same species were screened, the following patterns were observed. Very few species showed a consistent response across all isolates. For *Bipolaris spicifera,* 2 isolates showed a decrease in total boll time, while 2 showed an increase in total boll time. For *Chaetomium globosum*, both isolates showed an increase in total boll time compared to controls. In the case of *Cladosporium herbarum,* 5 isolates showed a decrease in total boll time while 3 isolates showed an increase in total boll time. *Epicoccum nigrum* showed 4 isolates that decreased, 2 that had no change and 1 that increased total boll time compared to controls. *Gibellulopsis nigrescens* showed one isolate decreased and 2 isolates increased boll time. Both *Stemphylium herbarum* isolates increased total boll time relative to controls. Of the 36 isolates tested, 9 showed a decrease in latency to first contact compared to the formulation controls with 4 of those showing over 100% increase in the amount of time that passed before the insects made first contact with the boll.

FIG. 76 shows a reduction in the average frequency of visits of *N. viridula* to bolls from field grown cotton treated with TAM00013 (MIC-92234), TAM00046 (MIC-90694) or TAM00032 (MIC-68178). FIG. 78 shows a reduction in the cumulative time *N. viridula* spent on bolls from field grown cotton treated with TAM00013 (MIC-92234), TAM00046 (MIC-90694) or TAM00032 (MIC-68178) as a percentage of the total observation period. FIG. 77 shows an increase in the average latency of first contact of *N. viridula* to bolls from field grown cotton treated with TAM00013 (MIC-92234). FIG. 74 shows a reduction in the mean distance moved by *N. viridula* in arenas with bolls from field grown cotton treated with TAM00013 (MIC-92234) and TAM00032 (MIC-68178) relative to bolls from untreated reference plants. FIG. 75 shows that on average *N. viridula* are a greater distance from bolls treated with TAM00013 (MIC-92234) during the observation period relative to bolls from plants not treated with an endophyte.

TABLE 12

Aggregated metrics for a detached cotton boll behavior assay with *Nezara viridula* expressed for each fungal endophyte as a percent change compared to the formulation control included in each round. Video tracking software was used to record time spent on the boll, latency to first contact, and frequency of boll visits during the 6 hour no choice assay. n = 20 bolls per treatment.

| Round | TAMID | TAXID | MICID | % Change in Boll Time | % Change in Latency to First Contact | % Change in Boll Frequency |
|---|---|---|---|---|---|---|
| 6 | TAM00323 | *Alternaria planifunda* | MIC-39233 | 2.75 | 92.77 | 1.58 |
| 7 | TAM00439 | *Bipolaris spicifera* | MIC-77538 | −29.87 | 12.35 | −15.65 |
| 1 | TAM00013 | *Bipolaris spicifera* | MIC-92234 | −23.96 | −191.48 | −64.95 |
| 4 | TAM00189 | *Curvularia spicifera* | MIC-31593 | 95.98 | 91.61 | −0.05 |
| 12 | TAM00560 | *Chaetomium globosum* | MIC-44512 | 52.41 | 19.48 | −12.31 |
| 12 | TAM00554 | *Chaetomium globosum* | MIC-33414 | 90.61 | 47.46 | −20.47 |
| 6 | TAM00317 | *Chaetomium* sp. | MIC-39772 | −17.36 | 10.87 | 9.24 |
| 3 | TAM00249 | *Cladosporium gossypiicola* | MIC-80602 | −68.43 | −45.36 | 35.29 |
| 3 | TAM00248 | *Cladosporium* sp. | MIC-10602 | −59.64 | 22.88 | −53.27 |
| 11 | TAM00534 | *Cladosporium oxysporum* | MIC-50414 | −32.02 | 69.25 | 69.67 |
| 5 | TAM00201 | *Cladosporium* sp. | MIC-29439 | −28.94 | 29.24 | −48.87 |
| 10 | TAM00463 | *Cladosporium* sp. | MIC-91557 | −23.63 | 17.18 | −49.48 |
| 9 | TAM00501 | *Cladosporium* sp. | MIC-31246 | 2.37 | 5.87 | −43.57 |
| 8 | TAM00494 | *Cladosporium* sp. | MIC-26952 | 16.34 | 18.47 | 43.41 |
| 5 | TAM00193 | *Cladosporium cladosporioides* | MIC-12927 | 30.09 | −44.71 | −50.81 |
| 3 | TAM00105 | *Curvularia protuberata* | MIC-07010 | −61.37 | −145.98 | −46.06 |
| 2 | TAM00100 | *Epicoccum nigrum* | MIC-77047 | −30.2 | 72.93 | 69.78 |
| 2 | TAM00103 | *Epicoccum nigrum* | MIC-62081 | −22.17 | 77.07 | −34.56 |
| 1 | TAM00046 | Didymellaceae | MIC-90694 | −7.19 | −113.06 | −40.24 |
| 2 | TAM00074 | *Epicoccum nigrum* | MIC-85555 | −0.4 | 33.39 | −30.76 |
| 1 | TAM00032 | *Epicoccum nigrum* | MIC-68178 | 0.02 | 3.83 | −55.03 |
| 9 | TAM00497 | *Epicoccum nigrum* | MIC-90504 | −8.09 | −22.54 | −63.08 |
| 12 | TAM00536 | *Epicoccum nigrum* | MIC-16066 | 30.96 | 57.69 | −13.33 |
| 11 | TAM00531 | *Gibellulopsis nigrescens* | MIC-16714 | −18.04 | −46.63 | 3.28 |
| 11 | TAM00533 | *Gibellulopsis nigrescens* | MIC-49739 | 18.27 | 16.95 | 29.6 |
| 10 | TAM00524 | *Gibellulopsis nigrescens* | MIC-42665 | 44.66 | 40.69 | −44.83 |
| 4 | TAM00251 | *Chaetomium piluliferum* | MIC-51742 | 28.49 | 24.78 | −26 |
| 8 | TAM00490 | *Phialemonium inflatum* | MIC-50989 | −10.03 | −105.57 | 52.02 |
| 5 | TAM00194 | *Epicoccum nigrum* | MIC-76091 | 55.67 | −6.63 | −73.85 |
| 6 | TAM00296 | Pleosporaceae sp. | MIC-12207 | 30.44 | 75.85 | 29.2 |
| 10 | TAM00518 | *Preussia africana* | MIC-17815 | 43.73 | 38.73 | −15.33 |
| 7 | TAM00402 | *Schizothecium inaequale* | MIC-39100 | −17.95 | 30.02 | 135.67 |
| 9 | TAM00504 | *Sphaerulina pseudovirgaureae* | MIC-63740 | −8.43 | 23.89 | −54.79 |
| 4 | TAM00160 | *Stagonospora* sp. | MIC-20571 | 64.42 | 58.77 | 30.77 |

TABLE 12-continued

Aggregated metrics for a detached cotton boll behavior assay with *Nezara viridula* expressed for each fungal endophyte as a percent change compared to the formulation control included in each round. Video tracking software was used to record time spent on the boll, latency to first contact, and frequency of boll visits during the 6 hour no choice assay. n = 20 bolls per treatment.

| Round | TAMID | TAXID | MICID | % Change in Boll Time | % Change in Latency to First Contact | % Change in Boll Frequency |
|---|---|---|---|---|---|---|
| 7 | TAM00362 | *Stemphylium herbarum* | MIC-45943 | −16.91 | 64.14 | 43.63 |
| 8 | TAM00473 | *Stemphylium herbarum* | MIC-32308 | −11.11 | 60.3 | 22.3 |

Example 12: Effect of Fungal Endophytes on Hemiptera Insects

Endophyte-treated and control plants are grown from cotton seeds (*Gossypium hirsutum*) that are inoculated with one or more candidate endophytes (such as *Chaetomium globosum* e.g., TAM00554 (MIC-33414), *Epicoccum nigrum* e.g., TAM00194 (MIC-76091), *Cladosporium* sp. e.g., TAM00463 (MIC-91557)). The plants may be grown under greenhouse and field conditions. Greenhouse plants are first germinated in seedling trays and then transferred to pots. Field grown plants are directly sown in the soil.

Behavioral assays: No-choice and choice behavioral assays are conducted to compare the response of western tarnished plant bugs (*Lygus hesperus*) and green stink bugs (*Nezara viridula*) to squares and bolls from endophyte-treated and untreated plants. The assays are conducted at 30° C. in 10 cm diameter petri dishes with a thin layer of 2% agar on the bottom to provide moisture for the squares (*L. hesperus* assays) and bolls (*N. viridula* assays) from experimental plants offered to the insects during the observations. For no-choice assays, a single square or boll is inserted by the base into the agar in the center of the dish. A single young adult (1-7 days post molt) insect is placed in each dish and the dish covered with the top. At least 10 insects are observed for each control may be from greenhouse or field grown plants.

Choice assays are conducted in plates as above, but with two equal sized squares (*L. hesperus*) or bolls (*N. viridula*) placed 4 ncm apart in the center of the petri dish. One of the two squares or bolls is from an untreated control plant and the other square or boll is from an endophyte treated plant. At least 10 insects are observed for each control and treatment group. served either feeding or resting upon cotton squares (*L. hesperus*) or bolls (*N. viridula*) is compared between treatment groups at each observation point across the duration of the assay using the Wilcoxon Signed Ranks Test. To test for variation in responses over time, for each individual the proportion of observations either feeding or upon the plant sample is calculated for early (0-60 min), middle (61-180 min) and late (181-360 min) periods of the assay and compared across treatment groups using a repeated measures analysis of variance (ANOVA) with the endophyte treatment group as the main factor and time as the repeat effect. The observed frequency of individuals failing to make contact with squares or bolls from endophyte-treated plants is compared to the expected frequency of individuals failing to do so based on the control group using a Chi-squared test. Among the insects that did make contact with either a square or boll, the time to first contact (latency) is compared among treatment groups using a one-way ANOVA.

Example 13: Assessment of Improved Biotic Stress Tolerance of Soy in Field Conditions Field trials are conducted using chemically treated soy seeds coated with fungal endophytes described herein and formulation control (no endophyte) and untreated controls (no endophyte and no formulation) as described in Example 3. Plots for in-field assessment harbor populations of root knot nematode (*Meloidogyne incognita*) and Reniform nematode (*Rotylenchulus reniformis*), respectively, at an approximately 1.0+E04 eggs per gram of fresh root weight. Opportunistically, these plots are infected with natural inoculum of *Fusarium virguliforme*, the causal agent of *Fusarium* Sudden Death Syndrome (SDS). Replicate plots, preferably at least 4 replicate plots, are planted per endophyte or control treatment in a randomized complete block design. Each plot consists of a 7.62 m (25 ft.) by 0.76 m (2.5 ft) row. The following early growth metrics are measured: percent emergence at 14 days post planting, standing count at 28 and 45 days post planting, plant vigor at 14, 28, and 45 days post planting, plant height at 45 days post planting, fresh shoot weight, fresh root weight, disease rating at a 0-3 scale (3 denotes strong disease symptoms) using the split-root scoring system at 45 days post planting, nematode count at 45 days post planting, and yield parameters. An exemplary photo of roots receiving scores of 0, 1, 2 and 3 are each shown in FIGS. 85 A-D.

At the end of the field trial employing endophyte treatment and control treatment plants, plants (preferably at least 4 plants) are randomly dig out from each row, kept in a plastic bag, and brought back to lab for metric measurements. For each seedling, shoot and root are separated by cutting the seedling 3 cm from the first branch of the root. The heights of the separated shoot of each plant are measured, followed by fresh shoot weight, and fresh root weight. The main root is vertically split into two halves and discoloration of xylem is scored as described above. To extract and count nematode eggs on root, roots are place in a container prefilled with 100 ml 10% sucrose and incubated on a shaker at room temperature overnight. The supernatant is then collected and nematode eggs are counted under a stereomicroscope.

Data are manually curated and entered into ARM database before being analyzed. The percentage of survival plants, fresh root weight, and nematode egg count are plotted as bar graph of mean±95% confidence interval from the mean using the ggplot2 package of R (R Core Team, 2016. R: A language and environment for statistical computing. R Foundation for Statistical Computing, Vienna, Austria. R-project.org/). Plant heights, fresh shoot weight, and disease scores are plotted as jittered dot of mean±nonparametric bootstrap (1000) of 95% confidence interval from the mean using the ggplot2 package of R.

Example 14: Assessment of Improved Biotic Stress Tolerance of Cotton in Field Conditions Field trials are conducted using chemically treated cotton seeds coated with fungal endophytes described herein and formulation control (no endophyte) and untreated controls (no endophyte and no formulation) as described in Example 3. Plots for in-field assessment harbor populations of root knot nematode (*Meloidogyne incognita*) and Reniform nematode (*Rotylenchulus reniformis*), respectively, at an approximately 1.0+E04 eggs per gram of fresh root weight. Opportunistically, these plots are infected with natural inoculum of *Fusarium virguliforme*, the causal agent of *Fusarium* SDS. Replicate plots, preferably at least 4 replicate plots, are planted per endophyte or control treatment in a randomized complete block design. Each plot consists of a 7.62 m (25 ft.) by 0.76 m (2.5 ft) row. The following early growth metrics are measured: percent emergence at 14 days post planting, standing count at 28 and 45 days post planting, plant vigor at 14, 28, and 45 days post planting, plant height at 45 days post planting, fresh shoot weight, fresh root weight, disease rating at a 0-3 scale (3 denotes strong disease symptoms) using the split-root scoring system at 45 days post planting, nematode count at 45 days post planting, and yield parameters.

At the end of the field trial employing endophyte treatment and control treatment plants, plants (preferably at least 4 plants) are randomly dug out from each row, kept in a plastic bag, and brought back to lab for metric measurements. For each seedling, shoot and root are separated by cutting the seedling 3 cm from the first branch of the root. The heights of the separated shoot of each plant are measured, followed by fresh shoot weight, and fresh root weight. The main root is vertically split into two halves and discoloration of xylem are scored as described above. To extract and count nematode eggs on root, roots are placed in a container prefilled with 100 ml 10% sucrose and incubated on a shaker at room temperature overnight. The supernatant is then collected and nematode eggs are counted under a stereomicroscope.

Data are manually curated and entered into ARM database before being analyzed. The percentage of survival plants, fresh root weight, and nematode egg count are plotted as bar graph of mean±95% confidence interval from the mean using the ggplot2 package of R (R Core Team, 2016. R: A language and environment for statistical computing. R Foundation for Statistical Computing, Vienna, Austria. R-project.org/). Plant heights, fresh shoot weight, and disease scores are plotted as jittered dot of mean±nonparametric bootstrap (1000) of 95% confidence interval from the mean using the ggplot2 package of R.

Example 15: Fungal Endophyte Seed Treatments Alter Traits in Cotton Cultivars in Field Trials A field trial is conducted using a randomized block design with replicate plots planted with seeds that are inoculated with one or more candidate endophytes (such as *Chaetomium globosum* e.g., TAM00554 (MIC-33414), *Epicoccum nigrum* e.g., TAM00194 (MIC-76091), *Cladosporium* sp. e.g., TAM00463 (MIC-91557)). One or more varieties of cotton seeds may be used to assess variety specific interactions with endophyte treatment and their affect on yield and insect resistance. The plants are grown under standard agricultural practices.

Yield from plots treated with the described microbial compositions is compared relative to the untreated control plots. *Thrips* damage assessment is scored on a scale, for example a scale from 0-5: 0=no damage, 1=noticeable feeding scars, but no stunting, 2=noticeable feeding and 25% stunting, 3=feeding with blackened leaf terminals and 50% stunting, 4=severe feeding and 75% stunting, and 5=severe feeding and 90% stunting. For fleahoppers, the number of insects per plant is quantified and reported as an average for each plot. Other mid-season plant traits may also be assessed in the field to determine the effect of the described fungal endophyte compositions.

Example 16: Modulation of Colonization Frequencies of Native Endophytes in Plants Grown from the Fungal Endophyte-Treated Seed To determine whether endophyte seed treatments could alter the microbiome of the plant grown from the seed, cotton seeds are inoculated with one or more candidate endophytes (such as *Chaetomium globosum* e.g., MIC-33414, *Epicoccum nigrum* e.g., MIC-76091, *Cladosporium* sp. e.g., MIC-91557). The plants may be grown under greenhouse or field conditions under standard agricultural practices. The microbial community of treated and untreated cotton plants may be analyzed by isolating fungi on PDA media from surface-sterilized above-ground stem/leaf tissue and separately from surface sterilized below-ground root tissue. The microbial community of treated and untreated cotton plants may be analyzed by isolating fungal or bacterial DNA from surface-sterilized above-ground stem/leaf tissue and separately from surface sterilized and sequencing the DNA of the community using techniques well known in the art including 16S or ITS community sequencing or metagenomic sequencing.

Example 17: Modulation of Phytohormone Levels in Plants Grown from the Fungal Endophyte-Treated Seed To determine whether fungal endophyte seed treatment affects phytohormone levels in plants grown from the seed, tissue is harvested from the root or leaf tissue of cotton plants inoculated with one or more candidate endophytes and untreated controls, under a variety of herbivory treatments. Phytohormone levels for abscisic acid (ABA), tuberonic acid (12-OH-JA, an oxidation product of JA-Ile) (TA), ascorbic acid (AA), 12-Oxophytodienoic acid (a JA precursor) (OPDA), JA isoleucine (JA-Ile), and salicylic acid (SA) are assessed by LC-MS in leaf and root tissues separately. All phytohormone level comparisons are made versus plants in the untreated control group.

The invention claimed is:

1. A synthetic composition, comprising:
   a) a fungal endophyte comprising at least one endophyte of the class Sordariomycetes; and
   b) at least one carrier selected from: alginic acid, carrageenan, dextrin, dextran. polyethylene glycol, polyvinyl pyrrolidone, methyl cellulose, polyvinyl alcohol, gelatin, a detergent, an insecticide, a fungicide, and combinations thereof,
   wherein the fungal endophyte is in contact with the carrier;
   wherein the fungal endophyte, when heterologously disposed to a cotton seed or cotton plant, is capable of improving resistance to pests selected from one or more of *Nezara viridula*, *Lygus Hesperus*, and root-knot nematode as compared to a reference cotton seed or cotton plant not further comprising the endophyte, and
   wherein the fungal endophyte is *Purpureocillium lavendulum* comprising the nucleic acid sequence of SEQ ID NO:94.

2. The synthetic composition according to claim 1, wherein the fungal endophyte comprises fungal spores.

3. The synthetic composition of claim 2, comprising about $10^2$, $10^3$, $10^4$, $10^5$, $10^6$, $10^7$, $10^8$, or $10^9$ colony forming units per gram or spores per gram.

4. The synthetic composition of claim 1, wherein the improved pest resistance is demonstrated by at least increased emergence, increased stand, increased survival, increased plant height, increased shoot biomass, increased root biomass, decreased disease score, increased leaf area, decreased pest abundance, decreased pest biomass, increased yield, improved vigor, or improved resistance to pathogenic bacteria, fungi or viruses.

5. The synthetic composition of claim 1, wherein the cotton seed comprising the fungal endophyte heterologously disposed on the cotton seed is grown into a fungal endophyte treated cotton plant.

6. The synthetic composition of claim 1, wherein the cotton plant comprises one or more cotton plant elements.

7. The synthetic composition of claim 6, wherein increased resistance to pests comprises one or more of:
   decreasing the amount of time the pest spends on the cotton plant or the cotton plant element;
   decreasing the number of times the pest approaches the cotton plant or cotton plant element;
   decreasing the number of pests that contact the cotton plant or cotton plant element; and
   increasing the amount of time before the pest approaches the cotton plant or cotton plant element,
compared to the reference cotton plant or a reference cotton plant element not further comprising the endophyte.

8. The synthetic composition of claim 6, wherein the cotton plant element comprises a reproductive cotton plant element comprising a boll or a square.

\* \* \* \* \*

UNITED STATES PATENT AND TRADEMARK OFFICE
CERTIFICATE OF CORRECTION

| | |
|---|---|
| PATENT NO. | : 11,807,586 B2 |
| APPLICATION NO. | : 15/853057 |
| DATED | : November 7, 2023 |
| INVENTOR(S) | : Gregory A. Sword |

Page 1 of 1

It is certified that error appears in the above-identified patent and that said Letters Patent is hereby corrected as shown below:

In the Claims

In Column 139, Claim 1, Line 62, delete "dextran." and insert -- dextran, --, therefor.

Signed and Sealed this
Sixteenth Day of July, 2024

Katherine Kelly Vidal
Director of the United States Patent and Trademark Office

SEQUENCE LISTING

<160> NUMBER OF SEQ ID NOS: 115

<210> SEQ ID NO 1
<211> LENGTH: 22
<212> TYPE: DNA

```
<213> ORGANISM: Artificial Sequence
<220> FEATURE:
<223> OTHER INFORMATION: primer - ITS_1

<400> SEQUENCE: 1
cttggtcatt tagaggaagt aa                                              22

<210> SEQ ID NO 2
<211> LENGTH: 20
<212> TYPE: DNA
<213> ORGANISM: Artificial Sequence
<220> FEATURE:
<223> OTHER INFORMATION: primer - ITS_2

<400> SEQUENCE: 2
gctgcgttct tcatcgatgc                                                 20

<210> SEQ ID NO 3
<211> LENGTH: 20
<212> TYPE: DNA
<213> ORGANISM: Artificial Sequence
<220> FEATURE:
<223> OTHER INFORMATION: primer - ITS_3

<400> SEQUENCE: 3
gcatcgatga agaacgcagc                                                 20

<210> SEQ ID NO 4
<211> LENGTH: 17
<212> TYPE: DNA
<213> ORGANISM: Artificial Sequence
<220> FEATURE:
<223> OTHER INFORMATION: primer - LR5

<400> SEQUENCE: 4
tcctgaggga aacttcg                                                    17

<210> SEQ ID NO 5
<211> LENGTH: 20
<212> TYPE: DNA
<213> ORGANISM: Artificial Sequence
<220> FEATURE:
<223> OTHER INFORMATION: primer - amplicon F

<400> SEQUENCE: 5
ggtgaatcgc acatgctaga                                                 20

<210> SEQ ID NO 6
<211> LENGTH: 20
<212> TYPE: DNA
<213> ORGANISM: Artificial Sequence
<220> FEATURE:
<223> OTHER INFORMATION: primer - amplicon R

<400> SEQUENCE: 6
cgaccagaca gagcgtatga                                                 20

<210> SEQ ID NO 7
<211> LENGTH: 23
<212> TYPE: DNA
<213> ORGANISM: Artificial Sequence
<220> FEATURE:
<223> OTHER INFORMATION: primer - bRPB2-7.1R

<400> SEQUENCE: 7
cccatrgcyt gyttmcccat dgc                                             23
```

<210> SEQ ID NO 8
<211> LENGTH: 20
<212> TYPE: DNA
<213> ORGANISM: Artificial Sequence
<220> FEATURE:
<223> OTHER INFORMATION: primer - fRPB2-7R

<400> SEQUENCE: 8
cccatwgcyt gcttmcccat                                                    20

<210> SEQ ID NO 9
<211> LENGTH: 20
<212> TYPE: DNA
<213> ORGANISM: Artificial Sequence
<220> FEATURE:
<223> OTHER INFORMATION: primer - fRPB2-5F

<400> SEQUENCE: 9
gaygaymgwg atcayttygg                                                    20

<210> SEQ ID NO 10
<211> LENGTH: 17
<212> TYPE: DNA
<213> ORGANISM: Artificial Sequence
<220> FEATURE:
<223> OTHER INFORMATION: primer - PGK_533-F

<400> SEQUENCE: 10
gtygayttca aygtycc                                                       17

<210> SEQ ID NO 11
<211> LENGTH: 20
<212> TYPE: DNA
<213> ORGANISM: Artificial Sequence
<220> FEATURE:
<223> OTHER INFORMATION: primer - PGK_533-R

<400> SEQUENCE: 11
acaccdggdg grccgttcca                                                    20

<210> SEQ ID NO 12
<211> LENGTH: 21
<212> TYPE: DNA
<213> ORGANISM: Artificial Sequence
<220> FEATURE:
<223> OTHER INFORMATION: primer - 60S-506F

<400> SEQUENCE: 12
cttvavytgg aacttgatgg t                                                  21

<210> SEQ ID NO 13
<211> LENGTH: 19
<212> TYPE: DNA
<213> ORGANISM: Artificial Sequence
<220> FEATURE:
<223> OTHER INFORMATION: primer - 60S-908R
<220> FEATURE:
<221> NAME/KEY: misc_feature
<222> LOCATION: (17)..(17)
<223> OTHER INFORMATION: n is a, c, g, or t

<400> SEQUENCE: 13
ghgacaagcg tttctcngg                                                     19

<210> SEQ ID NO 14

```
<211> LENGTH: 23
<212> TYPE: DNA
<213> ORGANISM: Artificial Sequence
<220> FEATURE:
<223> OTHER INFORMATION: primer - Btub2Fd

<400> SEQUENCE: 14
gtbcacctyc araccggyca rtg                                              23

<210> SEQ ID NO 15
<211> LENGTH: 26
<212> TYPE: DNA
<213> ORGANISM: Artificial Sequence
<220> FEATURE:
<223> OTHER INFORMATION: primer - Btub4Rd

<400> SEQUENCE: 15
ccrgaytgrc craaracraa gttgtc                                           26

<210> SEQ ID NO 16
<211> LENGTH: 19
<212> TYPE: DNA
<213> ORGANISM: Artificial Sequence
<220> FEATURE:
<223> OTHER INFORMATION: primer - ACT512f

<400> SEQUENCE: 16
atgtgcaagg ccggtttcg                                                   19

<210> SEQ ID NO 17
<211> LENGTH: 20
<212> TYPE: DNA
<213> ORGANISM: Unknown
<220> FEATURE:
<223> OTHER INFORMATION: primer - ACT783r

<400> SEQUENCE: 17
tacgagtcct tctggcccat                                                  20

<210> SEQ ID NO 18
<211> LENGTH: 17
<212> TYPE: DNA
<213> ORGANISM: Artificial Sequence
<220> FEATURE:
<223> OTHER INFORMATION: primer - LR0R

<400> SEQUENCE: 18
acccgctgaa cttaagc                                                     17

<210> SEQ ID NO 19
<211> LENGTH: 20
<212> TYPE: DNA
<213> ORGANISM: Artificial Sequence
<220> FEATURE:
<223> OTHER INFORMATION: primer - SSU_NS4

<400> SEQUENCE: 19
cttccgtcaa ttcctttaag                                                  20

<210> SEQ ID NO 20
<211> LENGTH: 19
<212> TYPE: DNA
<213> ORGANISM: Artificial Sequence
<220> FEATURE:
<223> OTHER INFORMATION: primer - SSU_NS1

<400> SEQUENCE: 20
```

```
gtagtcatat gcttgtctc                                                  19

<210> SEQ ID NO 21
<211> LENGTH: 21
<212> TYPE: DNA
<213> ORGANISM: Artificial Sequence
<220> FEATURE:
<223> OTHER INFORMATION: primer - SSU_SR1R

<400> SEQUENCE: 21
tacctggttg atcctgccag t                                               21

<210> SEQ ID NO 22
<211> LENGTH: 20
<212> TYPE: DNA
<213> ORGANISM: Artificial Sequence
<220> FEATURE:
<223> OTHER INFORMATION: primer - amplicon F

<400> SEQUENCE: 22
ctcctcctcc tcctcctgat                                                 20

<210> SEQ ID NO 23
<211> LENGTH: 20
<212> TYPE: DNA
<213> ORGANISM: Artificial Sequence
<220> FEATURE:
<223> OTHER INFORMATION: primer - amplicon R

<400> SEQUENCE: 23
tcacagagct acgcgacttg                                                 20

<210> SEQ ID NO 24
<211> LENGTH: 20
<212> TYPE: DNA
<213> ORGANISM: Artificial Sequence
<220> FEATURE:
<223> OTHER INFORMATION: primer - RPB1-Af

<400> SEQUENCE: 24
gartgyccdg gdcayttygg                                                 20

<210> SEQ ID NO 25
<211> LENGTH: 23
<212> TYPE: DNA
<213> ORGANISM: Artificial Sequence
<220> FEATURE:
<223> OTHER INFORMATION: primer - RPB1-Cr
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 25
ccngcdatnt crttrtccat rta                                             23

<210> SEQ ID NO 26
<211> LENGTH: 1415
<212> TYPE: DNA
<213> ORGANISM: Cladosporium cladosporioides

<400> SEQUENCE: 26
```

```
tcttggtcat ttagaggaag taaaagtcgt aacaaggtct ccgtaggtga acctgcggag        60
ggatcattac aagtgacccc ggtctaacca ccgggatgtt cataacccctt tgttgtccga      120 ctctgttgcc tccggggcga ccctgccttc gggcggggc tccgggtgga cacttcaaac       180
tcttgcgtaa ctttgcagtc tgagtaaact taattaataa attaaaactt ttaacaacgg      240
atctcttggt tctggcatcg atgaagaacg cagcgaaatg cgataagtaa tgtgaattgc      300
agaattcagt gaatcatcga atctttgaac gcacattgcg cccctggta ttccggggg        360 catgcctgtt cgagcgtcat ttcaccactc aagcctcgct tggtattggg catcgcggtc     420
cgccgcgtgc ctcaaatcga ccggctgggt cttctgtccc taagcgttg tggaaactat      480 tcgctaaagg gtgttcggga ggctacgccg taaaacaacc ccatttctaa ggttgacctc     540
ggatcaggta gggataccccg ctgaacttaa gcatatcaat aagcggagga aaagaaacca    600
acagggattg ctctagtaac ggcgagtgaa gcagcaatag ctcaaatttg aaatctggcg    660
tcttcgacgt ccgagttgta atttgtagag gatgcttctg agtaaccacc gacctaagtt    720
ccttggaaca ggacgtcata gagggtgaga atcccgtatg cggtcggaaa ggtgctctat    780
acgtagctcc ttcgacgagt cgagttgttt gggaatgcag ctctaaatgg gaggtaaatt    840
tcttctaaag ctaaatattg gccagagacc gatagcgcac aagtagagtg atcgaaagat    900
gaaaagcact ttggaaagag agttaaaaag cacgtgaaat tgttaaaagg gaagggattg    960
caaccagact tgctcgcggt gttccgccgg tcttctgacc ggtctactcg ccgcgttgca   1020
ggccagcatc gtctggtgcc gctggataag acttgaggaa tgtagctcct tcgggagtgt   1080
tatagcctct tgtgatgcag cgagcgccgg gcgaggtccg cgcttcggct aggatgctgg   1140
cgtaatggtc gtaatccgcc cgtcttgaaa cacggaccaa ggagtctaac atctatgcga   1200
gtgttcgggt gtcaaacccc tacgcgtaat gaaagtgaac ggaggtgaga accgcaaggt   1260
gcatcatcga ccgatcctga tgtcttcgga tggatttgag taagagcata gctgttggga   1320
cccgaaagat ggtgaactat gcctgaatag ggtgaagcca gaggaaactc tggcggaggc   1380
tcgcagcggt tccgacgtgc aaatcgatcg tcaaa                              1415
```

<210> SEQ ID NO 27
<211> LENGTH: 493
<212> TYPE: DNA
<213> ORGANISM: Cladosporium cladosporioides

<400> SEQUENCE: 27

```
gtctacccccc gggatgttca taacccttttg ttgtccgact ctgttgcctc cggggcgacc       60
ctgccttcgg gcgggggctc cgggtggaca cttcaaactc ttgcgtaact ttgcagtctg      120
agtaaacttg attaataaat taaaactttt aacaacggat ctcttggttc tggcatcgat      180
gaagaacgca gcgaaatgcg ataagtaatg tgaattgcag aattcagtga atcatcgaat     240
ctttgaacgc acattgcgcc cctggtatt ccggggggca tgcctgttcg agcgtcattt       300
caccactcaa gcctcgcttg gtattgggca acgcggtccg ccgcgtgcct caaatcgacc    360
ggctgggtct tctgtcccct aagcgttgtg gaaactattc gctaagggt gctcgggagg      420 ctacgccgta aaacaaaccc atttctaagg ttgacctcgg atcaggtagg gatacccgct    480
gaacttaagc ata                                                       493
```

<210> SEQ ID NO 28
<211> LENGTH: 484
<212> TYPE: DNA
<213> ORGANISM: Cladosporium cladosporioides

<400> SEQUENCE: 28

```
ccgggatgtt cataacccct tgttgtccga ctctgttgcc tccggggcga ccctgccttc    60
gggcggggc tccgggtgga cacttcaaac tcttgcgtaa ctttgcagtc tgagtaaact   120
taattaataa attaaaactt ttaacaacgg atctcttggt tctggcatcg atgaagaacg   180
cagcgaaatg cgataagtaa tgtgaattgc agaattcagt gaatcatcga atctttgaac   240
gcacattgcg cccctggta ttccggggg catgcctgtt cgagcgtcat ttccactc      300
aagcctcgct tggtattggg caacgcggtc cgccgcgtgc ctcaaatcga ccggctgggt   360
cttctgtccc ctaagcgttg tggaaactat tcgctaaagg gtgttcggga ggctacgccg   420
taaaacaacc ccatttctaa ggttgacctc ggatcaggta gggatacccg ctgaacttaa   480
gcat                                                                484
```

<210> SEQ ID NO 29
<211> LENGTH: 494
<212> TYPE: DNA
<213> ORGANISM: Unknown
<220> FEATURE:
<223> OTHER INFORMATION: Kingdom: Fungi, Phylum: Ascomycota, Class:
      Dothideomycetes, Order: Capnodiales, Family: Cladosporiaceae,
      Genus: Cladosporium

<400> SEQUENCE: 29

```
cggtctacca ccgggatgtt cataacccct tgttgtccga ctctgttgcc tccggggcga    60
ccctgccttc gggcggggc tccgggtgga cacttcaaac tcttgcgtaa ctttgcagtc   120
tgagtaaact taattaataa attaaaactt ttaacaacgg atctcttggt tctggcatcg   180
atgaagaacg cagcgaaatg cgataagtaa tgtgaattgc agaattcagt gaatcatcga   240
atctttgaac gcacattgcg cccctggta ttccggggg catgcctgtt cgagcgtcat    300
ttccactc aagcctcgct tggtattggg caacgcggtc cgccgcgtgc ctcaaatcga     360
ccggctgggt cttctgtccc ctaagcgttg tggaaactat tcgctaaagg gtgttcggga   420
ggctacgccg taaaacaacc ccatttctaa ggttgacctc ggatcaggta gggatacccg   480
ctgaacttaa gcat                                                     494
```

<210> SEQ ID NO 30
<211> LENGTH: 163
<212> TYPE: DNA
<213> ORGANISM: Cladosporium cladosporioides

<400> SEQUENCE: 30

```
taacccttg ttgtccgact ctgttgcctc cggggcgacc ctgccttcgg gcggggctc     60
cgggtggaca cttcaaactc ttgcgtaact ttgcagtctg agtaaattta attaataat   120
taaaactttt aacaacggat ctcttggttc tggcatcgat gaa                    163
```

<210> SEQ ID NO 31
<211> LENGTH: 484
<212> TYPE: DNA
<213> ORGANISM: Cladosporium gossypiicola

<400> SEQUENCE: 31

```
ccgggatgtt cataacccct tgttgtccga ctctgttgcc tccggggcga ccctgccttc    60
gggcggggc tccgggtgga cacttcaaac tcttgcgtaa ctttgcagtc tgagtaaact   120
taattaataa attaaaactt ttaacaacgg atctcttggt tctggcatcg atgaagaacg   180
```

```
cagcgaaatg cgataagtaa tgtgaattgc agaattcagt gaatcatcga atctttgaac    240
gcacattgcg ccccctggta ttccgggggg catgcctgtt cgagcgtcat ttcaccactc    300
aagcctcgct tggtattggg catcgcggtc cgccgcgtgc ctcaaatcga ccggctgggt    360
cttctgtccc ctaagcgttg tggaaactat tcgctaaagg gtgttcggga ggctacgccg    420
taaaacaacc ccatttctaa ggttgacctc ggatcaggta gggatacccg ctgaacttaa    480
gcat                                                                 484

<210> SEQ ID NO 32
<211> LENGTH: 486
<212> TYPE: DNA
<213> ORGANISM: Cladosporium herbarum

<400> SEQUENCE: 32
ccgggatgtt cataacccct tgttgtccga ctctgttgcc tccggggcga ccctgccttc    60
gggcgggggc tccgggtgga cacttcaaac tcttgcgtaa cttttgcagtc tgagtaaact    120 taattaataa attaaaactt ttaacaacgg atctcttggt tctggcatcg atgaagaacg    180
cagcgaaatg cgataagtaa tgtgaattgc agaattcagt gaatcatcga atctttgaac    240
gcacattgcg ccccctggta ttccgggggg catgcctgtt cgagcgtcat ttcaccactc    300
aagcctcgct tggtattggg caacgcggtc cgccgcgtgc ctcaaatcga ccggctgggt    360
cttctgtccc ctaagcgttg tggaaactat tcgctaaagg gtgctcggga ggctacgccg    420
taaaacaaac ccatttctaa ggttgacctc ggatcaggta gggatacccg ctgaacttaa    480
gcatat                                                               486

<210> SEQ ID NO 33
<211> LENGTH: 485
<212> TYPE: DNA
<213> ORGANISM: Cladosporium herbarum

<400> SEQUENCE: 33
ccgggatgtt cataacccct tgttgtccga ctctgttgcc tccggggcga ccctgccttc    60
gggcgggggc tccgggtgga cacttcaaac tcttgcgtaa ctttgcagtc tgagtaaatt    120
taattaataa attaaaactt ttaacaacgg atctcttggt tctggcatcg atgaagaacg    180
cagcgaaatg cgataagtaa tgtgaattgc agaattcagt gaatcatcga atctttgaac    240
gcacattgcg ccccctggta ttccgggggg catgcctgtt cgagcgtcat ttcaccactc    300
aagcctcgct tggtattggg caacgcggtc cgccgcgtgc ctcaaatcga ccggctgggt    360
cttctgtccc ctaagcgttg tggaaactat tcgctaaagg gtgctcggga ggctacgccg    420
taaaacaaac ccatttctaa ggttgacctc ggatcaggta gggatacccg ctgaacttaa    480
gcata                                                                485

<210> SEQ ID NO 34
<211> LENGTH: 1445
<212> TYPE: DNA
<213> ORGANISM: Cladosporium oxysporum

<400> SEQUENCE: 34
tccgtaggtg aacctgcgga gggatcatta caagtgaccc cggtctaacc accgggatgt    60
tcataaccct tgttgtccg actctgttgc ctcggggcg accctgcctt cgggcggggg    120
ctccgggtgg acacttcaaa ctcttgcgta actttgcagt ctgagtaaac ttaattaata    180
aattaaaact tttaacaacg gatctcttgg ttctggcatc gatgaagaac gcagcgaaat    240
```

```
gcgataagta atgtgaattg cagaattcag tgaatcatcg aatctttgaa cgcacattgc    300 gcccctggt attccggggg gcatgcctgt tcgagcgtca tttcaccact caagcctcgc    360
ttggtattgg gcaacgcggt ccgccgcgtg cctcaaatcg accggctggg tcttctgtcc    420
cctaagcgtt gtgaaacta ttcgctaaag ggtgctcggg aggctacgcc gtaaaacaaa    480
cccatttcta aggttgacct cggatcaggt agggatacccc gctgaactta agcatatcaa    540
taagcggagg aaaagaaacc aacagggatt gctctagtaa cggcgagtga agcagcaata    600
gctcaaattt gaaatctggc gtcttcgacg tccgagttgt aatttgtaga ggatgcttct    660
gagtaaccac cgacctaagt tccttggaac aggacgtcat agagggtgag aatcccgtat    720
gcggtcggaa aggtgctcta tacgtagctc cttcgacgag tcgagttgtt tgggaatgca    780
gctctaaatg ggaggtaaat ttcttctaaa gctaaatatt ggccagagac cgatagcgca    840
caagtagagt gatcgaaaga tgaaaagcac tttggaaaga gagttaaaaa gcacgtgaaa    900
ttgttaaaag ggaagggatt gcaaccgacc ttgctcgcgg tgttccgccg gtcttctgac    960
cggtctactc gccgcgttgc aggccagcat cgtctggtgc cgctggataa gacttgagga   1020
atgtagctcc ctcgggagtg ttatagcctc ttgtgatgca gcgagcgccg ggcgaggtcc   1080
gcgcttcggc taggatgctg gcgtaatggt cgtaatccgc ccgtcttgaa acacggacca   1140
aggagtctaa catctatgcg agtgttcggg tgtcaaaccc ctacgcgtaa tgaaagtgaa   1200
cggaggtgag aaccgcaagg tgcatcatcg accgatcctg atgtcttcgg atggatttga   1260
gtaagagcat agctgttggg acccgaaaga tggtgaacta tgcctgaata gggtgaagcc   1320
agaggaaact ctggtggagg ctcgcagcgg ttctgacgtg caaatcgatc gtcaaatttg   1380
ggtatagggg cgaaagacta atcgaaccat ctagtagctg gttcctgccg aagtttccct   1440
cagga                                                              1445

<210> SEQ ID NO 35
<211> LENGTH: 496
<212> TYPE: DNA
<213> ORGANISM: Unknown
<220> FEATURE:
<223> OTHER INFORMATION: Kingdom: Fungi, Phylum: Ascomycota, Class:
      Dothideomycetes, Order: Capnodiales, Family: Cladosporiaceae,
      Genus: Cladosporium

<400> SEQUENCE: 35
gtctaccacc gggatgttca taacccttttg ttgtccgact ctgttgcctc cggggcgacc     60
ctgccttcgg gcggggggctc cgggtggaca cttcaaactc ttgcgtaact ttgcagtctg    120
agtaaactta attaataaat taaaactttt aacaacggat ctcttggttc tggcatcgat    180
gaagaacgca gcgaaatgcg ataagtaatg tgaattgcag aattcagtga atcatcgaat    240
ctttgaacgc acattgcgcc cctggtatt ccgggggggca tgcctgttcg agcgtcattt    300
caccactcaa gcctcgcttg gtattgggca tcgcggtccg ccgcgtgcct caaatcgacc    360
ggctgggtct tctgtcccct aagcgttgtg gaaactattc gctaagggt gttcgggagg    420 ctacgccgta aaacaacccc atttctaagg ttgacctcgg atcaggtagg gataccccgct   480 gaacttaagc atatca                                                   496

<210> SEQ ID NO 36
<211> LENGTH: 492
<212> TYPE: DNA
<213> ORGANISM: Unknown
<220> FEATURE:
```

<223> OTHER INFORMATION: Kingdom: Fungi, Phylum: Ascomycota, Class:
Dothideomycetes, Order: Capnodiales, Family: Cladosporiaceae,
Genus: Cladosporium

<400> SEQUENCE: 36

| gtctaccacc gggatgttca taacccttg ttgtccgact ctgttgcctc cggggcgacc | 60 |
|---|---|
| ctgccttcgg gcgggggctc cgggtggaca cttcaaactc ttgcgtaact ttgcagtctg | 120 |
| agtaaactta attaataaat taaaactttt aacaacggat ctcttggttc tggcatcgat | 180 |
| gaagaacgca gcgaaatgcg ataagtaatg tgaattgcag aattcagtga atcatcgaat | 240 |
| ctttgaacgc acattgcgcc cctggtatt ccgggggca tgcctgttcg agcgtcattt | 300 |
| caccactcaa gcctcgcttg gtattgggca tcgcggtccg ccgcgtgcct caaatcgacc | 360 |
| ggctgggtct tctgtcccct aagcgttgtg gaaactattc gctaaagggt gttcgggagg | 420 |
| ctacgccgta aaacaacccc atttctaagg ttgacctcgg atcaggtagg gatacccgct | 480 |
| gaacttaagc at | 492 |

<210> SEQ ID NO 37
<211> LENGTH: 163
<212> TYPE: DNA
<213> ORGANISM: Unknown
<220> FEATURE:
<223> OTHER INFORMATION: Kingdom: Fungi, Phylum: Ascomycota, Class:
Dothideomycetes, Order: Capnodiales, Family: Cladosporiaceae,
Genus: Cladosporium

<400> SEQUENCE: 37

| gccttgctga attattcacc cttgtctttt gcgtacttct tgtttccttg gtgggttcgc | 60 |
|---|---|
| ccaccactag gacaaacata aaccttttgt aattgcaatc agcgtcagta acaaattaat | 120 |
| aattacaact ttcaacaacg gatctcttgg ttctggcatc gat | 163 |

<210> SEQ ID NO 38
<211> LENGTH: 496
<212> TYPE: DNA
<213> ORGANISM: Unknown
<220> FEATURE:
<223> OTHER INFORMATION: Kingdom: Fungi, Phylum: Ascomycota, Class:
Dothideomycetes, Order: Capnodiales, Family: Cladosporiaceae,
Genus: Cladosporium

<400> SEQUENCE: 38

| ggtctaccac cgggatgttc ataacccttt gttgtccgac tctgttgcct ccggggcgac | 60 |
|---|---|
| cctgccttcg ggcgggggct ccgggtggac acttcaaact cttgcgtaac tttgcagtct | 120 |
| gagtaaactt aattaataaa ttaaaacttt taacaacgga tctcttggtt ctggcatcga | 180 |
| tgaagaacgc agcgaaatgc gataagtaat gtgaattgca gaattcagtg aatcatcgaa | 240 |
| tctttgaacg cacattgcgc ccctggtatt ccgggggc atgcctgttc gagcgtcatt | 300 |
| tcaccactca gcctcgctt ggtattgggc aacgcggtcc gccgcgtgcc tcaaatcgac | 360 |
| cggctgggtc ttctgtcccc taagcgttgt ggaaactatt cgctaaaggg tgctcggag | 420 |
| gctacgccgt aaaacaaacc catttctaag gttgacctcg gatcaggtag ggatacccgc | 480 |
| tgaacttaag catatc | 496 |

<210> SEQ ID NO 39
<211> LENGTH: 490
<212> TYPE: DNA
<213> ORGANISM: Unknown
<220> FEATURE:
<223> OTHER INFORMATION: Kingdom: Fungi, Phylum: Ascomycota, Class:

Dothideomycetes, Order: Capnodiales, Family: Cladosporiaceae, Genus: Cladosporium

<400> SEQUENCE: 39

```
gtctaccacc gggatgttca taacccttg ttgtccgact ctgttgcctc cggggcgacc      60
ctgccttcgg gcggggcctc cgggtggaca cttcaaactc ttgcgtaact ttgcagtctg    120
agtaaacttg attaataaat taaaactttt aacaacggat ctcttggttc tggcatcgat    180
gaagaacgca gcgaaatgcg ataagtaatg tgaattgcag aattcagtga atcatcgaat    240
ctttgaacgc acattgcgcc cctggtatt ccggggggca tgcctgttcg agcgtcattt     300
caccactcaa gcctcgcttg gtattgggca acgcggtccg ccgcgtgcct caaatcgacc    360
ggctgggtct tctgtcccct aagcgttgtg gaaactattc gctaaagggt gctcgggagg    420
ctacgccgta aaacaaaccc atttctaagg ttgacctcgg atcaggtagg gatacccgct    480
gaacttaagc                                                          490
```

<210> SEQ ID NO 40
<211> LENGTH: 476
<212> TYPE: DNA
<213> ORGANISM: Sphaerulina pseudovirgaureae

<400> SEQUENCE: 40

```
ggctcgacct ccaaccctt gtgaacacaa cttgttgctt cggggcgac cctgccgttt       60
cgacggcgag cgcccccgga ggccttcaaa cactgcatct ttgcgtcgga gtttaagtaa    120
attaaacaaa actttcaaca acggatctct tggttctggc atcgatgaag aacgcagcga    180
aatgcgataa gtaatgtgaa ttgcagaatt cagtgaatca tcgaatcttt gaacgcacat    240
tgcgcccctt ggtattccga ggggcatgcc tgttcgagcg tcatttcacc actcaagcct    300
cgcttggtat tgggcgccgc ggtgttccgc gcgcctcaaa gtctccggct gagctgtccg    360
tctctaagcg ttgtgatttc attaatcgct tcggagcgcg ggcggtcgcg gccgttaaat    420
cttttcacaag gttgacctcg gatcaggtag ggatacccgc tgaacttaag catatc      476
```

<210> SEQ ID NO 41
<211> LENGTH: 1446
<212> TYPE: DNA
<213> ORGANISM: Epicoccum nigrum

<400> SEQUENCE: 41

```
tcttggtcat ttagaggaag taaaagtcgt aacaaggttt ccgtaggtga acctgcggaa     60
ggatcattac ctagagtttg tggacttcgg tctgctacct cttacccatg tcttttgagt    120
accttcgttt cctcggcggg tccgcccgcc ggttggacaa cattcaaacc ctttgcagtt    180
gcaatcagcg tctgaaaaaa cttaatagtt acaactttca acaacggatc tcttggttct    240
ggcatcgatg aagaacgcag cgaaatgcga taagtagtgt gaattgcaga attcagtgaa    300
tcatcgaatc tttgaacgca cattgcgccc ttggtattcc atggggcat gcctgttcga    360
gcgtcatttg taccttcaag ctctgcttgg tgttgggtgt tttgtctcgc ctccgcgcgc    420
agactcgcct taaacaatt ggcagccggc gtattgattt cggagcgcag tacatctcgc     480
gctttgcact cataacgacg acgtccaaaa gtacattttt acactcttga cctcggatca    540
ggtagggata cccgctgaac ttaagcatat caataagcgg aggaaaagaa accaacaggg    600
attgccctag taacgcgag tgaagcggca acagctcaaa tttgaaatct ggcgtctttg     660
gcgtccgagt tgtaatttgc agagggcgct ttggcattgg cagcggtcca agttccttgg    720
```

```
aacaggacgt cacagagggt gagaatcccg tacgtggtcg ctagccttta ccgtgtaaag    780
ccccttcgac gagtcgagtt gtttgggaat gcagctctaa atgggaggta aatttcttct    840
aaagctaaat actggccaga gaccgatagc gcacaagtag agtgatcgaa agatgaaaag    900
cactttggaa agagagttaa aaagcacgtg aaattgttga aagggaagcg cttgcagcca    960
gacttgcctg tagttgctca tccgggtttc tacccggtgc actcttctac gggcaggcca   1020
gcatcagttt gggcggttgg ataaaggtct ctgtcatgta cctcccttcg gggagatctt   1080 atagggaga cgacatgcaa ccagcctgga ctgaggtccg cgcatctgct aggatgctgg    1140
cgtaatggct gtaagcggcc cgtcttgaaa cacggaccaa ggagtctaac atctatgcga   1200
gtgtttgggt gtcaagcccg agcgcgtaat gaaagtgaac ggaggtggga acctttcggg   1260
gtgcaccatc gaccgatcct gatgtcttcg gatggatttg agtaagagca tagctgttgg   1320
gacccgaaag atggtgaact atgcttgaat agggtgaagc cagaggaaac tctggtggag   1380
gctcgcagcg gttctgacgt gcaaatcgat cgtcaaattt gggcataggg gcgaaagact   1440
aatcga                                                              1446
```

<210> SEQ ID NO 42
<211> LENGTH: 1188
<212> TYPE: DNA
<213> ORGANISM: Epicoccum nigrum

<400> SEQUENCE: 42

```
gacgatcgtg accacttcgg taagaagcgt ctcgatcttg ctgggccgct gatcgcgaac     60
ttattccgca tcctcttttt gaagttgacc aaggacgttt acaagtacct ccagaagtgc    120
gtcgagacca attccgactt caacgtccag atggctgtta gagctagtgt cattactaat    180
ggtctgaaat attcgctcgc cacgggaaac tggggtgatc agaagaaggc tgcctcagcg    240
aaagctggcg tctcccaggt cttgaaccgt tatacgtacg catctacgtt gtcgcatttg    300
cgacgaacaa acactccggt cggccgtgac ggcaagcttg caaagccccg tcagttgcac    360
aacagtcact ggggtcttgt atgccccgcc gagacacctg aaggacaggc ttgtggtctt    420
gtcaagaact tgtcgctgat gtgctacgtc agtgttggta gcgatgccgg gcccatatcc    480
gagttcatga agcagcgaaa catgcaggtc cttgaagaat atgatcaagc ccaaaatccc    540
gatgccacca aggtcttcgt caacggtgta tgggtcggtg ttcactccaa cgcgcagcag    600
ctcgtctcca cagtacagga gcttcgccgc aatggaaccc tatcctacga gatgagtctg    660
attcgagaca tccgtgaccg agagttcaaa atctttacag atgctggacg tgttatgagg    720
cctcttttcg tagtggagaa cgacgtgcgc aagccgaata ggaatcacct cgtctacaac    780
caagaacact acaacaaact agcccaagag caaatggcaa tgactcaggc aggcgtcggc    840
gaggaagaga agcagcctta tggttggaag ggcctgatcc aagatggtat catcgaatac    900
cttgacgctg aagaggagga cggccatg attgtcatgt cgcccgaaga tcttggcgag    960
tggcgtgata tgaaaatggg catcccacaa gatgctcgca acccacaagg caaagaccgt   1020
cttgcacgta tcaagcctaa gccagatcct cgcatttatg cctacacgca ttgcgagatc   1080
caccctgcta tgattctcgg tatctgtgcc agtatcattc ttttccggga ccacaaccag   1140
tcgcctcgta acacatacca gtctgctatg ggtaagcaag ccatgggt               1188
```

<210> SEQ ID NO 43
<211> LENGTH: 383
<212> TYPE: DNA
<213> ORGANISM: Epicoccum nigrum

<400> SEQUENCE: 43

```
gttcacctcc agaccggtca gtgcgtaagt acaccacttg catgttctct catggacggc        60
agctcacaag ggacagggta accaaatcgg tgctgccttc tggcagacca tctccggcga       120
gcatggcctc gacggctccg gtgtctacaa cggcacctcg gacctccagc tcgagcgcat       180
gaacgtctac ttcaacgagg tactagaaac gacacgcttt cctgagacgg actgcgagtg       240
ctgacctccc gcaggcctct ggcaacaagt tcgttcccg tgccgtcctc gtcgacttgg        300
agcccggtac aatggacgct gtccgcgctg ccccttcgg ccagctcttc cgtcccgata        360
acttcgtctt cggccagtct ggt                                              383
```

<210> SEQ ID NO 44
<211> LENGTH: 400
<212> TYPE: DNA
<213> ORGANISM: Epicoccum nigrum

<400> SEQUENCE: 44

```
gtgacaagcg tttctctgga actgtcaagc tccccaccgt tccccgtccc cgtaagttgc        60
acgcgcccaa ggattgcagt ggcaagagct gacagttttg caggcatggc catctgcgtt       120
ctcggtgacc agcacgatat cgatcgtgcc aagcaccacg gtgttgatgc catgtccact       180
gaggacttga agaagctcaa caagaacaag aagctcatca agaagctcgc acgcaagtac       240
gatgctttca tggcttccga cgccctgatc aagcagatcc ccgtctctt gggtcccggt        300 ctgtccaagg ctggaaagtt ccccactccc gtctctcacg ctgaggacct cgccaacaag       360
atgaccgatg tcaagtccac catcaagttc cagctgaaga                             400
```

<210> SEQ ID NO 45
<211> LENGTH: 272
<212> TYPE: DNA
<213> ORGANISM: Epicoccum nigrum

<400> SEQUENCE: 45

```
tacgagtcct tctgtcccat accgatcatg atactgcgtc acggttagct cgggggcag         60 gagctgccaa ggagagcgtc atacccatgg tgacggggac gaccgacaat ggaggctgca       120
ggctgttagg acatgctcgc gaaggtggcc tggcgacagg gcgggcgcaa tgcatggctg       180
cttatgctcc cgctgctgcc aggtggcggg ttggggactt acggaagact gctcggggcg       240
catcatcacc ggcgaaaccg gccttgcaca ta                                    272
```

<210> SEQ ID NO 46
<211> LENGTH: 1447
<212> TYPE: DNA
<213> ORGANISM: Epicoccum nigrum

<400> SEQUENCE: 46

```
tccgtaggtg aacctgcgga aggatcatta cctagagttt gtggacttcg gtctgctacc        60
tcttacccat gtcttttgag taccttcgtt tcctcggcgg gtccgcccgc cggttggaca       120
acattcaaac cctttgcagt tgcaatcagc gtctgaaaaa acttaatagt tacaactttc       180
aacaacggat ctcttggttc tggcatcgat gaagaacgca gcgaaatgcg ataagtagtg       240
tgaattgcag aattcagtga atcatcgaat ctttgaacgc acattgcgcc ccttggtatt       300
ccatggggca tgcctgttcg agcgtcattt gtaccttcaa gctctgcttg gtgttgggtg       360
ttttgtctcg cctccgcgcg cagactcgcc ttaaaacaat tggcagccgg cgtattgatt       420
```

```
tcggagcgca gtacatctcg cgctttgcac tcataacgac gacgtccaaa agtacatttt    480
tacactcttg acctcggatc aggtagggat acccgctgaa cttaagcata tcaataagcg    540
gaggaaaaga aaccaacagg gattgcccta gtaacggcga gtgaagcggc aacagctcaa    600
atttgaaatc tggcgtcttt ggcgtccgag ttgtaatttg cagagggcgc tttggcattg    660
gcagcggtcc aagttccttg aacaggacg tcacagaggg tgagaatccc gtacgtggtc    720
gctagccttt accgtgtaaa gcccttcga cgagtcgagt tgtttgggaa tgcagctcta    780
aatgggaggt aaatttcttc taaagctaaa tactggccag agaccgatag cgcacaagta    840
gagtgatcga agatgaaaa gcactttgga aagagagtta aaaagcacgt gaaattgttg    900
aaagggaagc gcttgcagcc agacttgcct gtagttgctc atccgggttt ctacccggtg    960
cactcttcta cgggcaggcc agcatcagtt tgggcggttg gataaaggtc tctgtcatgt   1020
acctcccttc ggggagatct tatagggag acgacatgca accagcctgg actgaggtcc   1080
gcgcatctgc taggatgctg gcgtaatggc tgtaagcggc ccgtcttgaa acacggacca   1140
aggagtctaa catctatgcg agtgtttggg tgtcaagccc gagcgcgtaa tgaaagtgaa   1200
cggaggtggg aaccttttcg ggtgcaccat cgaccgatcc tgatgtcttc ggatggattt   1260
gagtaagagc atagctgttg ggacccgaaa gatggtgaac tatgcttgaa tagggtgaag   1320
ccagaggaaa ctctggtgga ggctcgcagc ggttctgacg tgcaaatcga tcgtcaaatt   1380
tgggcatagg ggcgaaagac taatcgaact atctagtagc tggttcctgc cgaagtttcc   1440
ctcagga                                                             1447
```

<210> SEQ ID NO 47
<211> LENGTH: 1439
<212> TYPE: DNA
<213> ORGANISM: Epicoccum nigrum

<400> SEQUENCE: 47

```
tcttggtcat ttagaggaag taaaagtcgt aacaaggttt ccgtaggtga acctgcggaa     60
ggatcattac ctagagtttg tggacttcgg tctgctacct cttacccatg tcttttgagt    120
accttcgttt cctcggcggg tccgcccgcc ggttggacaa cattcaaacc ctttgcagtt    180
gcaatcagcg tctgaaaaaa cttaatagtt acaactttca acaacggatc tcttggttct    240
ggcatcgatg aagaacgcag cgaaatgcga taagtagtgt gaattgcaga attcagtgaa    300
tcatcgaatc tttgaacgca cattgcgccc cttggtattc catgggcat gcctgttcga    360 gcgtcatttg taccttcaag ctctgcttgg tgttgggtgt tttgtctcgc ctccgcgcgc    420
agactcgcct taaaacaatt ggcagccggc gtattgattt cggagcgcag tacatctcgc    480
gctttgcact cataacgacg acgtccaaaa gtacattttt acactcttga cctcggatca    540
ggtagggata cccgctgaac ttaagcatat caataagcgg aggaaaagaa accaacaggg    600
attgccctag taacggcgag tgaagcggca acagctcaaa tttgaaatct ggcgtctttg    660
gcgtccgagt tgtaatttgc agagggcgct ttggcattgg cagcggtcca agttccttgg    720
aacaggacgt cacagagggt gagaatcccg tacgtggtcg ctagccttta ccgtgtaaag    780
ccccttcgac gagtcgagtt gtttgggaat gcagctctaa atgggaggta aatttcttct    840
aaagctaaat actggccaga gaccgatagc gcacaagtag agtgatcgaa agatgaaaag    900
cactttggaa agagagttaa aaagcacgtg aaattgttga aagggaagcg cttgcagcca    960
gacttgcctg tagttgctca tccgggtttc tacccggtgc actcttctac gggcaggcca   1020
gcatcagttt gggcggttgg ataaaggtct ctgtcatgta cctcccttcg gggagatctt   1080
```

```
ataggggaga cgacatgcaa ccagcctgga ctgaggtccg cgcatctgct aggatgctgg    1140
cgtaatggct gtaagcggcc cgtcttgaaa cacggaccaa ggagtctaac atctatgcga    1200
gtgtttgggt gtcaagcccg agcgcgtaat gaaagtgaac ggaggtggga acctttcggg    1260
gtgcaccatc gaccgatcct gatgtcttcg gatggatttg agtaagagca tagctgttgg    1320
gacccgaaag atggtgaact atgcttgaat agggtgaagc cagaggaaac tctggtggag    1380
gctcgcagcg gttctgacgt gcaaatcgat cgtcaaattt gggcataggg gcgaaagac     1439

<210> SEQ ID NO 48
<211> LENGTH: 383
<212> TYPE: DNA
<213> ORGANISM: Epicoccum nigrum

<400> SEQUENCE: 48
ccagactggc cgaagacgaa gttatcggga cggaagagct ggccgaaggg gccggcgcgg      60
acagcgtcca ttgtaccggg ctccaagtcg acgaggacgg cacggggaac gaacttgttg     120
ccagaggcct gcgggaggtc agcactcgca gtccgtctca ggaaagcgtg tcgtttctag     180
tacctcgttg aagtagacgt tcatgcgctc gagctggagg tccgaggtgc cgttgtagac     240
accggagccg tcgaggccat gctcgccgga gatggtctgc cagaaggcag caccgatttg     300
gttaccctgt cccttgtgag ctgccgtcca tgagagaaca tgcaagtggt gtacttacgc     360
actgaccggt ctggaggtga acc                                            383

<210> SEQ ID NO 49
<211> LENGTH: 608
<212> TYPE: DNA
<213> ORGANISM: Epicoccum nigrum
<220> FEATURE:
<221> NAME/KEY: misc_feature
<222> LOCATION: (113)..(126)
<223> OTHER INFORMATION: n is a, c, g, or t

<400> SEQUENCE: 49
ctcctcctcc tcctcctgat cgaactcgcc ccccaccaac tccaccagcc cacccagccg      60
cccaaaaacc tccccatccc cgctagccgc ccccatggcc cggacaagca gcnnnnnnnn     120
nnnnnngtcc gggatggcct taggttcgct ctcgagctgc tccagccgcg acaggacatg     180
cagcagctcc ctgcgcagcg agtccggcgc cggcatgcgg ccccgcagcg gctggtcggc     240
gatgtatgtc ttgagcggga gcgcggcgcg caggatgagg tagggcgccg ctgcctgggc     300
gagtttgatg tgcgagtgcg agggcgaggg cgaggtactg gcggggcgtg cggccacgag     360
ggcgaagagg gaggccgtgc aggtgtagct catctttgtg cgcaaggtgg cggggaggac     420
ggccgtctgg ccggtgcgga cggagaggag gttggcgagg ggcgaggtgg tgatgggagg     480
gagttctcct tgtacgggag tgtggatgag ggaggtggtg aagaggttgc gggcgtatgt     540
cctgcggagg gtgtcgggga gggaggggga gtttagaggg ccgctgatca agtcgcgtag     600
ctctgtga                                                             608

<210> SEQ ID NO 50
<211> LENGTH: 485
<212> TYPE: DNA
<213> ORGANISM: Epicoccum nigrum

<400> SEQUENCE: 50
gacttcggtc tgctacctct tacccatgtc ttttgagtac cttcgtttcc tcggcgggtc      60
```

```
cgcccgccgg ttggacaaca ttcaaaccct tgcagttgc aatcagcgtc tgaaaaaact      120
taatagttac aactttcaac aacggatctc ttggttctgg catcgatgaa gaacgcagcg      180
aaatgcgata agtagtgtga attgcagaat tcagtgaatc atcgaatctt tgaacgcaca      240
ttgcgcccct tggtattcca tggggcatgc ctgttcgagc gtcatttgta ccttcaagct      300
ctgcttggtg ttgggtgttt tgtctcgcct ccgcgcgcag actcgcctta aaacaattgg      360
cagccggcgt attgatttcg gagcgcagta catctcgcgc tttgcactca taacgacgac      420
gtccaaaagt acatttttac actcttgacc tcggatcagg tagggatacc cgctgaactt      480
aagca                                                                  485

<210> SEQ ID NO 51
<211> LENGTH: 487
<212> TYPE: DNA
<213> ORGANISM: Epicoccum nigrum

<400> SEQUENCE: 51
ggacttcggt ctgctaccct ttacccatgt cttttgagta ccttcgtttc ctcggcgggt      60
ccgcccgccg gttggacaac attcaaaccc tttgcagttg caatcagcgt ctgaaaaaac      120
ttaatagtta caactttcaa caacggatct cttggttctg gcatcgatga agaacgcagc      180
gaaatgcgat aagtagtgtg aattgcagaa ttcagtgaat catcgaatct ttgaacgcac      240
attgcgcccc ttggtattcc atggggcatg cctgttcgag cgtcatttgt accttcaagc      300
tctgcttggt gttgggtgtt ttgtctcgcc tccgcgcgca gactcgcctt aaaacaattg      360
gcagccggcg tattgatttc ggagcgcagt acatctcgcg ctttgcactc ataacgacga      420
cgtccaaaag tacatttta cactcttgac ctcggatcag gtagggatac cgctgaact       480 taagcat                                                                487

<210> SEQ ID NO 52
<211> LENGTH: 490
<212> TYPE: DNA
<213> ORGANISM: Epicoccum nigrum

<400> SEQUENCE: 52
ggacttcggt ctgctaccct ttacccatgt cttttgagta ccttcgtttc ctcggcgggt      60
ccgcccgccg gttggacaac attcaaaccc tttgcagttg caatcagcgt ctgaaaaaac      120
ttaatagtta caactttcaa caacggatct cttggttctg gcatcgatga agaacgcagc      180
gaaatgcgat aagtagtgtg aattgcagaa ttcagtgaat catcgaatct ttgaacgcac      240
attgcgcccc ttggtattcc atggggcatg cctgttcgag cgtcatttgt accttcaagc      300
tctgcttggt gttgggtgtt ttgtctcgcc tccgcgcgca gactcgcctt aaaacaattg      360
gcagccggcg tattgatttc ggagcgcagt acatctcgcg ctttgcactc ataacgacga      420
cgtccaaaag tacatttta cactcttgac ctcggatcag gtagggatac cgctgaact       480 taagcatatc                                                             490

<210> SEQ ID NO 53
<211> LENGTH: 1182
<212> TYPE: DNA
<213> ORGANISM: Epicoccum nigrum

<400> SEQUENCE: 53
cccatggctt gcttacccat agcagactgg tatgtgttac gaggcgactg gttgtgatcc      60
gggaaaggaa tgatactggc acagataccg agaatcatag cagggtggat ctcgcaatgc      120
```

```
gtgtaggcat aaatgcgagg atccggctta ggcttgatac gcgcgagacg gtctttgccc      180
tgtggattgc gagcatcttg tgggataccc attttcatgt cacgccactc gccaagatct      240
tcgggcgaca tgacaatcat ggcagtctcc tcctcttccg cgtccaggta ttcaataaca      300
ccatcttgaa tgaggccctt ccaaccataa ggttctggca tcccctcttc ctcgctgaag      360
cctgcatcct gctcttgatt gagctggttg cagtggtctc ggttgtagac gaggtggttc      420
ctgttaggtt tgcgcacgtc gttctccact acgaagagag gcctcataac acgtccagca      480
tctgtgaaga ttttgaactc tcggtcacgg atgtctcgaa tcagactcat ctcgtaagag      540
agggttccat tacggcgaag ctcctgcact gtagagacga gctgctgtgc gttggagtgc      600
acaccgaccc atacaccgtt aacgaagacc ttggtggctt cggggttttg agcttgatca      660
tattcttcaa ggagcagcat gttccgctga cccatgaaat cggatatagg tccggcatcg      720
ctaccgacac tgacgtagca catcagggac aagttcttga caagaccaca ggcctgccct      780
tcaggtgtct cggcggggca cacaagaccc aatgactgt tgtgtaactg acggggcttt      840
gcgagcttgc cgtcacggcc gaccggggtg tttgttcgtc gcaaatgcga caatgtggat      900
gcgtatgtgt aacggttcaa gacctgtgag acaccagctt tcgccgaagc agccttcttc      960
tgatcacccc agtttcccgt ggcgagcgaa tatttcaaac cattagtaat gacactagct     1020
cggacggcca tctgcacgtt gaagtcggaa ttggtctcga cgcacttctg gaggtacttg     1080
taaacgtcct tggttaactt caggaagaga acgcgaaaca agttcgcaat cagcggccca     1140
gcgagatcga gacgcttctt accaaagtgg tcacgatcgt cc                        1182
```

<210> SEQ ID NO 54
<211> LENGTH: 1008
<212> TYPE: DNA
<213> ORGANISM: Epicoccum nigrum

<400> SEQUENCE: 54

```
gtcgacttca acgtccctct cgacgcagac aagaacatca ccaaccccca gcgcatcgtc       60
ggtgctctcc ccacaatcaa gtatgccgtc gagaacggag ctaaggccgt catccttatg      120
tcccacctcg gccgcccgga tggcaagccg aacccgaagt acagtctcaa gccggttgtt      180
tccgagcttg agaagcttct cggcaagagc gtgactttca cagatgactg cgtcggcaag      240
caggtcgagg agaccgtcaa caatgccaag gacggacagg tcatccttct tgagaacctc      300
cgcttccacg ctgaggagga gggcagctac aaggacgagg agggcaagaa gcagaaggtc      360
gacaaggcca aggttgagga gttccgcaag ggactgactg ctcttggtga tgtttacatc      420
agtgagtacg gccgtctgag gtcgcagttc ctgactaata tatccgcaga cgatgctttc      480
ggcacagctc accgtgctca cagctccatg gtcggcgttg acttgcccca gaaggcttcc      540
ggtttcctcg taaagaagga gctcgagtac tttgctaagg cgctcgagga gcccaagagg      600
cccttcctcg ccatcctcgg tggcgccaag gtctccgata agatccagct catcgacaac      660
ctgctcggca aggtcgacag cttgattatc tgtggcggta tgtcattcac attcaagaag      720
accctcgagg gcgtcagcat cggtgactct ctgttcgacg aggctggcag caagactgtc      780
aaggaccttg ttgagaaggc taagaaaaac aacgtcaaga ttgtcctgcc tgttgactac      840
atcaccgccg acaagttcga caaggacgcc aagacagggt acgctgagga caaggacggt      900
attccagatg gctggatggg tcttgactgc ggcaagaagt cgatcgagct ttacaaggag      960
gccatcggcg aggctcagac catcctgtgg aacggtcccg ctggtgtc                 1008
```

<210> SEQ ID NO 55
<211> LENGTH: 1182
<212> TYPE: DNA
<213> ORGANISM: Epicoccum nigrum

<400> SEQUENCE: 55

| | | | | | | |
|---|---|---|---|---|---|---|
| cccatggctt | gcttacccat | agcagactgg | tatgtgttac | gaggcgactg | gttgtgatcc | 60 |
| gggaaaggaa | tgatactggc | acagataccg | agaatcatag | cagggtggat | ctcgcaatgc | 120 |
| gtgtaggcat | aaatgcgagg | atccggctta | ggcttgatac | gcgcgagacg | tctttgccc | 180 |
| tgtggattgc | gagcatcttg | tgggataccc | attttcatgt | cacgccactc | gccaagatct | 240 |
| tcggcgaca | tgacaatcat | ggcagtctcc | tcctcttccg | cgtccaggta | ttcaataaca | 300 |
| ccatcttgaa | tgaggccctt | ccaaccataa | ggttctggca | tcccctcttc | ctcgctgaag | 360 |
| cctgcatcct | gctcttgatt | gagctggttg | cagtggtctc | ggttgtagac | gaggtggttc | 420 |
| ctgttaggtt | tgcgcacgtc | gttctccact | acgaagagag | gcctcataac | acgtccagca | 480 |
| tctgtgaaga | ttttgaactc | tcggtcacgg | atgtctcgaa | tcagactcat | ctcgtaagag | 540 |
| agggttccat | tacggcgaag | ctcctgcact | gtagagacga | gctgctgtgc | gttggagtgc | 600 |
| acaccgaccc | atacaccgtt | aacgaagacc | ttggtggctt | cggggttttg | agcttgatca | 660 |
| tattcttcaa | ggagcagcat | gttccgctga | cccatgaaat | cggatatagg | tccggcatcg | 720 |
| ctaccgacac | tgacgtagca | catcaggac | aagttcttga | caagaccaca | ggcctgccct | 780 |
| tcaggtgtct | cggcggggca | cacaagaccc | caatgactgt | tgtgtaactg | acggggcttt | 840 |
| gcgagcttgc | cgtcacggcc | gaccggggtg | tttgttcgtc | gcaaatgcga | caatgtggat | 900 |
| gcgtatgtgt | aacggttcaa | gacctgtgag | acaccagctt | tcgccgaagc | agccttcttc | 960 |
| tgatcacccc | agtttcccgt | ggcgagcgaa | tatttcaaac | cattagtaat | gacactagct | 1020 |
| cggacggcca | tctgcacgtt | gaagtcggaa | ttggtctcga | cgcacttctg | gaggtacttg | 1080 |
| taaacgtcct | tggttaactt | caggaagaga | acgcgaaaca | agttcgcaat | cagcggccca | 1140 |
| gcgagatcga | gacgcttctt | accaaagtgg | tcacgatcgt | cc | | 1182 |

<210> SEQ ID NO 56
<211> LENGTH: 400
<212> TYPE: DNA
<213> ORGANISM: Epicoccum nigrum

<400> SEQUENCE: 56

| | | | | | | |
|---|---|---|---|---|---|---|
| cttcagctgg | aacttgatgg | tggacttgac | gtcggtcatc | ttgttggcga | ggtcctcagc | 60 |
| gtgagagacg | ggagtgggga | actttccagc | cttggacaga | ccaggaccca | agagacgggg | 120 |
| gatctgcttg | atcagggcgt | cggaagccat | gaaagcatcg | tacttgcgtg | caagcttctt | 180 |
| gatcagcttc | ttgttcttgt | tgagcttctt | caagtcctca | gtggacatgg | catcaacacc | 240 |
| gtggtgcttg | gcacgatcga | tatcgtgctg | gtcaccgaga | acgcagatgg | ccatgcctgc | 300 |
| acaactgtca | gctcttgcta | ctgcaatcct | tgggcgcgcg | caacgtacga | ggacgggga | 360 |
| cggtggggag | cttgacggtt | ccagagaaac | gcttgtcacg | | | 400 |

<210> SEQ ID NO 57
<211> LENGTH: 489
<212> TYPE: DNA
<213> ORGANISM: Epicoccum nigrum

<400> SEQUENCE: 57

| | | | | | | |
|---|---|---|---|---|---|---|
| ggtgaatcgc | acatgctaga | tttccacatt | ctgaagaata | tcccagccaa | cgttattttg | 60 |

```
agcgaagact tccttctggg agacgagacc aacgctttcg cagactacgc gtgctacatg    120
cacgatgagg aggaggacga cgacgatgct agttgcttca tgattgacat cgactattcg    180
tacggcaatc cggccgtcga cacccgagag tatcgggaca accttgagac cgtgcgctac    240
ggagaggaag aggactggat cgacagtcta tctggcgacg aaaagagagg tgcccaagca    300
gctgtgcaac taagacgcgc gcagtgggat ccaacacaac ccatgactgg cgcgaacgcc    360
atgaacgtgg ttcctccgca gttccggcag gcaagtagtc atccgaagac tgtgcgcaag    420
cgtttgaagt tcgactgtg acgagaaaa aagactgtct agtgcagtct catacgctct    480
gtctggtcg                                                            489

<210> SEQ ID NO 58
<211> LENGTH: 490
<212> TYPE: DNA
<213> ORGANISM: Epicoccum nigrum

<400> SEQUENCE: 58
gtagacttcg gtctgctacc tcttacccat gtcttttgag taccttcgtt tcctcggcgg    60
gtccgcccgc cgattggaca acattcaaac cctttgcagt tgcaatcagc gtctgaaaaa    120
acataatagt tacaactttc aacaacggat ctcttggttc tggcatcgat gaagaacgca    180
gcgaaatgcg ataagtagtg tgaattgcag aattcagtga atcatcgaat ctttgaacgc    240
acattgcgcc ccttggtatt ccatggggca tgcctgttcg agcgtcattt gtaccttcaa    300
gctctgcttg gtgttgggtg tttgtctcgc ctctgcgtgt agactcgcct taaaacaatt    360
ggcagccggc gtattgattt cggagcgcag tacatctcgc gctttgcact cataacgacg    420
acgtccaaaa gtacattttt acactcttga cctcggatca ggtagggata cccgctgaac    480
ttaagcatat                                                           490

<210> SEQ ID NO 59
<211> LENGTH: 485
<212> TYPE: DNA
<213> ORGANISM: Epicoccum nigrum

<400> SEQUENCE: 59
agacttcggt ctgctacctc ttacccatgt cttttgagta ccttcgtttc ctcggcgggt    60
ccgcccgccg attggacaac attcaaaccc tttgcagttg caatcagcgt ctgaaaaaac    120
ataatagtta caactttcaa caacggatct cttggttctg gcatcgatga agaacgcagc    180
gaaatgcgat aagtagtgtg aattgcagaa ttcagtgaat catcgaatct ttgaacgcac    240
attgcgcccc ttggtattcc atggggcatg cctgttcgag cgtcatttgt accttcaagc    300
tctgcttggt gttgggtgtt tgtctcgcct ctgcgtgtag actcgcctta aacaattgg    360 cagccggcgt attgatttcg agcgcagta catctcgcgc tttgcactca taacgacgac    420
gtccaaaagt acattttta cactcttgacc tcggatcagg tagggatacc cgctgaactt    480
aagca                                                                485

<210> SEQ ID NO 60
<211> LENGTH: 489
<212> TYPE: DNA
<213> ORGANISM: Epicoccum nigrum

<400> SEQUENCE: 60
gtggacttcg gtctgctacc tcttacccat gtcttttgag taccttcgtt tcctcggcgg    60
```

```
gtccgcccgc cggttggaca acattcaaac cctttgcagt tgcaatcagc gtctgaaaaa    120
acttaatagt tacaactttc aacaacggat ctcttggttc tggcatcgat gaagaacgca    180
gcgaaatgcg ataagtagtg tgaattgcag aattcagtga atcatcgaat ctttgaacgc    240
acattgcgcc ccttggtatt ccatggggca tgcctgttcg agcgtcattt gtaccttcaa    300
gctctgcttg gtgttgggtg ttttgtctcg cctccgcgcg cagactcgcc ttaaaacaat    360
tggcagccgg cgtattgatt tcggagcgca gtacatctcg cgctttgcac tcataacgac    420
gacgtccaaa agtacatttt tacactcttg acctcggatc aggtagggat acccgctgaa    480
cttaagcat                                                            489
```

<210> SEQ ID NO 61
<211> LENGTH: 484
<212> TYPE: DNA
<213> ORGANISM: Unknown
<220> FEATURE:
<223> OTHER INFORMATION: Kingdom: Fungi, Phylum: Ascomycota, Class:
      Dothideomycetes, Order: Pleosporales, Family: Didymellaceae

<400> SEQUENCE: 61

```
cttcggtctg ctacctctta cccatgtctt ttgagtacct tcgtttcctc ggcgggtccg     60
cccgccgatt ggacaacatt caaacccttt gcagttgcaa tcagcgtctg aaaaaacata    120
atagttacaa ctttcaacaa cggatctctt ggttctggca tcgatgaaga acgcagcgaa    180
atgcgataag tagtgtgaat tgcagaattc agtgaatcat cgaatctttg aacgcacatt    240 gcgcccttg gtattccatg gggcatgcct gttcgagcgt catttgtacc ttcaagctct    300
gcttggtgtt gggtgtttgt ctcgcctctg cgtgtagact cgccttaaaa caattggcag    360
ccggcgtatt gatttcggag cgcagtacat ctcgcgcttt gcactcataa cgacgacgtc    420
caaaagtaca ttttacact cttgacctcg gatcaggtag ggatacccgc tgaacttaag    480
cata                                                                 484
```

<210> SEQ ID NO 62
<211> LENGTH: 533
<212> TYPE: DNA
<213> ORGANISM: Unknown
<220> FEATURE:
<223> OTHER INFORMATION: Kingdom: Fungi, Phylum: Ascomycota, Class:
      Dothideomycetes, Order: Pleosporales, Family: Massarinaceae,
      Genus: Stagonospora

<400> SEQUENCE: 62

```
agctactggc atggggactg ttagtctgca tggtatcact accgatgagc agcaggtccc     60
ctgtctatac ccttgttttt tgcgtaccta ttgtttcctc ggcgggcttg ctcgccggct    120
ggacaaaatc tataaccttt ttttaatctt caatcagcgt ctgaaattat acataataat    180
tacaactttc aacaacggat ctcttggttc tggcatcgat gaagaacgca gcgaaatgcg    240
ataagtagtg tgaattgcag aattcagtga atcatcgaat ctttgaacgc acattgcgcc    300
ccttggtatt ccatggggca tgcctgttcg agcgtcattt gtaccctcaa gctttgcttg    360
gtgttgggcg tcttgtcttt tatcagactc gccttaaagt aattggcagc cagtgttttt    420
ggtagtaagc gcagcacaat ttgcgtcttg gtccctaaac agtggcatcc acaaagcctc    480
tttctcactt ttgacctcgg atcaggtagg gatacccgct gaacttaagc ata           533
```

<210> SEQ ID NO 63
<211> LENGTH: 508
<212> TYPE: DNA

<213> ORGANISM: Alternaria eichhorniae

<400> SEQUENCE: 63
gggctggacc tctcggggtt acagccttgc tgaattattc acccttgtct tttgcgtact 60
tcttgtttcc ttggtgggtt cgcccaccac taggacaaac ataaaccttt tgtaattgca 120
atcagcgtca gtaacaaatt aataattaca actttcaaca acggatctct tggttctggc 180
atcgatgaag aacgcagcga aatgcgataa gtagtgtgaa ttgcagaatt cagtgaatca 240
tcgaatcttt gaacgcacat tgcgcccttt ggtattccaa agggcatgcc tgttcgagcg 300
tcatttgtac cctcaagctt tgcttggtgt tgggcgtctt gtctctagct ttgctggaga 360
ctcgccttaa agtaattggc agccggccta ctggtttcgg agcgcagcac aagtcgcact 420
ctctatcagc aaaggtctag catccattaa gccttttttt caacttttga cctcggatca 480
ggtagggata cccgctgaac ttaagcat 508

<210> SEQ ID NO 64
<211> LENGTH: 513
<212> TYPE: DNA
<213> ORGANISM: Alternaria eichhorniae

<400> SEQUENCE: 64
gcgggctgga cctctcgggg ttacagcctt gctgaattat tcacccttgt cttttgcgta 60
cttcttgttt ccttggtggg ttcgcccacc actaggacaa acataaacct tttgtaattg 120
caatcagcgt cagtaacaaa ttaataatta caactttcaa caacggatct cttggttctg 180
gcatcgatga agaacgcagc gaaatgcgat aagtagtgtg aattgcagaa ttcagtgaat 240
catcgaatct ttgaacgcac attgcgccct ttggtattcc aaagggcatg cctgttcgag 300
cgtcatttgt accctcaagc tttgcttggt gttgggcgtc ttgtctctag ctttgctgga 360
gactcgcctt aaagtaattg gcagccggcc tactggtttc ggagcgcagc acaagtcgca 420
ctctctatca gcaaaggtct agcatccatt aagccttttt ttcaactttt gacctcggat 480
caggtaggga tacccgctga acttaagcat atc 513

<210> SEQ ID NO 65
<211> LENGTH: 509
<212> TYPE: DNA
<213> ORGANISM: Alternaria eichhorniae

<400> SEQUENCE: 65
gggctggacc tctcggggtt acagccttgc tgaattattc acccttgtct tttgcgtact 60
tcttgtttcc ttggtgggtt cgcccaccac taggacaaac ataaaccttt tgtaattgca 120
atcagcgtca gtaacaaatt aataattaca actttcaaca acggatctct tggttctggc 180
atcgatgaag aacgcagcga aatgcgataa gtagtgtgaa ttgcagaatt cagtgaatca 240
tcgaatcttt gaacgcacat tgcgcccttt ggtattccaa agggcatgcc tgttcgagcg 300
tcatttgtac cctcaagctt tgcttggtgt tgggcgtctt gtctctagct ttgctggaga 360
ctcgccttaa agtaattggc agccggccta ctggtttcgg agcgcagcac aagtcgcact 420
ctctatcagc aaaggtctag catccattaa gccttttttt tcaacttttg acctcggatc 480
aggtagggat acccgctgaa cttaagcat 509

<210> SEQ ID NO 66
<211> LENGTH: 497
<212> TYPE: DNA
<213> ORGANISM: Alternaria eichhorniae

<400> SEQUENCE: 66

```
ctcggggtta cagccttgct gaattattca cccttgtctt ttgcgtactt cttgtttcct      60
tggtgggttc gcccaccact aggacaaaca taaaccttttt gtaattgcaa tcagcgtcag    120
taacaaatta ataattacaa ctttcaacaa cggatctctt ggttctggca tcgatgaaga    180
acgcagcgaa atgcgataag tagtgtgaat tgcagaattc agtgaatcat cgaatctttg    240
aacgcacatt gcgcccttttg gtattccaaa gggcatgcct gttcgagcgt catttgtacc    300
ctcaagcttt gcttggtgtt gggcgtcttg tctctagctt tgctggagac tcgccttaaa    360
gtaattggca gccggcctac tggtttcgga gcgcagcaca agtcgcactc tctatcagca    420
aaggtctagc atccattaag ccttttttc aactttgac ctcggatcag gtagggatac      480
ccgctgaact taagcat                                                   497
```

<210> SEQ ID NO 67
<211> LENGTH: 508
<212> TYPE: DNA
<213> ORGANISM: Alternaria planifunda

<400> SEQUENCE: 67

```
cgggctggca tccttcgggg ttacagcctt gctgaattat tcacccgtgt cttttgcgta     60
cttcttgttt ccttggtggg ttcgcccacc ataggacaaa ccataaacct tttgtaattg    120
caatcagcgt cagtaaaaaa attaataatt acaacttta caacggatc tcttggttct      180
ggcatcgatg aagaacgcag cgaaatgcga taagtagtgt gaattgcaga attcagtgaa    240
tcatcgaatc tttgaacgca cattgcgccc tttggtattc caagggcat gcctgttcga    300
gcgtcatttg taccctcaag ctttgcttgg tgttgggcgt cttgtctcca gttcgctgga    360
gactcgcctt aaagtaattg gcagccggcc tactggtttc ggagcgcagc acaagtcgcg    420
ctctcttcca gccaaggtca gcatccacaa agcctttttt caactttga cctcggatca    480
ggtagggata cccgctgaac ttaagcat                                       508
```

<210> SEQ ID NO 68
<211> LENGTH: 507
<212> TYPE: DNA
<213> ORGANISM: Bipolaris spicifera

<400> SEQUENCE: 68

```
gccgttcgcg gctggactat ttattaccct tgtcttttgc gcacttgttg tttcctgggc     60
gggttcgctc gccaccagga ccacaatata aaccttttt atgcagttgc aatcagcgtc    120
agtataacaa atgtaaatca tttacaactt tcaacacgg atctcttggt tctggcatcg    180
atgaagaacg cagcgaaatg cgatacgtag tgtgaattgc agaattcagt gaatcatcga    240
atctttgaac gcacattgcg ccctttggta ttccaaggg catgcctgtt cgagcgtcat    300
ttgtaccctc aagctttgct tggtgttggg cgttttttgtc tttggcccgc aaagactcg    360
ccttaaaatg attggcagcc ggcctactgg tttcgcagcg cagcacattt tgcgcttgc    420
aatcagcaaa agaggacggc aatccatcaa gactccttct cacgtttgac ctcggatcag    480
gtagggatac ccgctgaact taagcat                                        507
```

<210> SEQ ID NO 69
<211> LENGTH: 498
<212> TYPE: DNA
<213> ORGANISM: Bipolaris spicifera

```
<400> SEQUENCE: 69
ttcgcggctg gactatttat taccttgtc ttttgcgcac ttgttgtttc ctgggcgggt      60
tcgctcgcca ccaggaccac aatataaacc tttttatgc agttgcaatc agcgtcagta    120
taacaaatgt aaatcattta caactttcaa caacggatct cttggttctg catcgatga    180 agaacgcagc gaaatgcgat acgtagtgtg aattgcagaa ttcagtgaat catcgaatct    240
ttgaacgcac attgcgccct tggtattcc aaagggcatg cctgttcgag cgtcatttgt    300
accctcaagc tttgcttggt gttgggcgtt tttgtctttg gcccgccaaa gactcgcctt    360
aaaatgattg gcagccggcc tactggtttc gcagcgcagc acattttttgc gcttgcaatc    420 agcaaaagag gacggcaatc catcaagact ccttctcacg tttgacctcg gatcaggtag    480
ggatacccgc tgaactta                                                 498

<210> SEQ ID NO 70
<211> LENGTH: 511
<212> TYPE: DNA
<213> ORGANISM: Stemphylium herbarum

<400> SEQUENCE: 70
ggacctcacc tcggtgaggg ctccagcttg tctgaattat tcacccatgt cttttgcgca     60
cttcttgttt cctgggcggg ttcgcccgcc accaggacca aaccataaac cttttgtaa   120 ttgcaatcag cgtcagtaaa caatgtaatt attacaactt tcaacaacgg atctcttggt    180
tctggcatcg atgaagaacg cagcgaaatg cgatacgtag tgtgaattgc agaattcagt    240
gaatcatcga atctttgaac gcacattgcg ccctttggta ttccaaaggg catgcctgtt    300
cgagcgtcat ttgtaccctc aagctttgct tggtgttggg cgtctttgtc tctcacgaga    360
ctcgccttaa aatgattggc agccgaccta ctggtttcgg agcgcagcac aattcttgca    420
ctttgaatca gccttggttg agcatccatc aagaccacat tttttcaac ttttgacctc    480 ggatcaggta gggatacccg ctgaacttaa g                                  511

<210> SEQ ID NO 71
<211> LENGTH: 513
<212> TYPE: DNA
<213> ORGANISM: Stemphylium herbarum

<400> SEQUENCE: 71
ggacctcact tcggtgcggg ctccagcttg tctgaattat tcacccatgt cttttgcgca     60
cttcttgttt cctgggcggg ttcgcccgcc accaggacca aaccataaac cttttgtaa   120 ttgcaatcag cgtcagtaaa caatgtaatt attacaactt tcaacaacgg atctcttggt    180
tctggcatcg atgaagaacg cagcgaaatg cgatacgtag tgtgaattgc agaattcagt    240
gaatcatcga atctttgaac gcacattgcg ccctttggta ttccaaaggg catgcctgtt    300
cgagcgtcat ttgtaccctc aagctttgct tggtgttggg cgtcttttgt ctctcacgag    360
actcgcctta aaatgattgg cagccgacct actggtttcg gagcgcagca caattcttgc    420
actttgaatc agccttggtt gagcatccat caagaccaca tttttttaact tttgacctcg    480 gatcaggtag ggatacccgc tgaacttaag cat                                513

<210> SEQ ID NO 72
<211> LENGTH: 509
<212> TYPE: DNA
<213> ORGANISM: Unknown
<220> FEATURE:
<223> OTHER INFORMATION: Kingdom: Fungi, Phylum: Ascomycota, Class:
```

Dothideomycetes, Order: Pleosporales, Family: Pleosporaceae

<400> SEQUENCE: 72

```
cgatggggca gcccctcttt tggggttgcc ccctctggcg ccatattcac ccatgtcttt      60
ttgcgtacta cttgtttcct tggcgggttc gcccgccatt tggacctttta ctcaacccttt   120
ttttttttgt gcaattgcca tcagcgtcag caaaacaatg taatcaattt acaactttca    180
acaacggatc tcttggttct ggcatcgatg aagaacgcag cgaaatgcga taagtagtgt   240
gaattgcaaa attcagtgaa tcatcgaatc tttgaacgca cattgcgccc tttggtattc   300
caaagggcat gcctgttcga gcgtcatttg taccctcaag cttttgcttgg tgttgggcgt  360
ttcttgtcct gggccttgca gcccgggact cgccttaaaa tcattggcag ccggcctact   420
ggtttcggag cgcagcacat tttttgcgct cttgtccagc catggtcgtg catccaaaag   480
gtactttttt ttttttcacgt ttgacctcg                                      509
```

<210> SEQ ID NO 73
<211> LENGTH: 472
<212> TYPE: DNA
<213> ORGANISM: Preussia africana

<400> SEQUENCE: 73

```
tcgagataga acccttgcct ttttgagtac cttttcgttt cctcggcagg ctcgcctgcc      60
aatggggacc ccaacaaaca ctttgcagta cctgtaaaca gtctgaacaa acttttaaaa    120
attaaaactt tcaacaacgg atctcttggt tctggcatcg atgaagaacg cagcgaaatg    180
cgataagtag tgtgaattgc agaattcagt gaatcatcga atctttgaac gcacattgcg    240
cccttttggta ttccttaggg catgcctgtt cgagcgtcat tgaaaccttc aagctcagct    300
tggtgttggg tgactgtccg cttgcggact cgcctcaaaa tgattggcgg ccggtacttt    360
tggcttcgag cgcagcagaa acgcgaactc gaggcctgtg tgctggctcc cagaagctat    420
cttcacaatt ttgacctcgg atcaggtagg gatacccgct gaacttaagc at             472
```

<210> SEQ ID NO 74
<211> LENGTH: 1496
<212> TYPE: DNA
<213> ORGANISM: Curvularia protuberata

<400> SEQUENCE: 74

```
tcttggtcat ttagaggaag taaaagtcgt aacaaggtct ccgtaggtga acctgcggag      60
ggatcattac acaataacat atgaaggctg tacgccgctg cgcccccggg ccagttggct    120
gaggctggat tatttattac ccttgtcttt tgcgcacttg ttgtttcctg ggcgggttcg    180
cccgcctcca ggaccacacc ataaaccttt tttatgcagt tgcaatcagc gtcagtacaa    240
caaatgtaaa tcatttacaa ctttcaacaa cggatctctt ggttctggca tcgatgaaga   300
acgcagcgaa atgcgatacg tagtgtgaat tgcagaattc agtgaatcat cgaatctttg   360
aacgcacatt gcgcccttttg gtattccaaa gggcatgcct gttcgagcgt catttgtacc   420
ctcaagcttt gcttggtgtt gggcgttttt gtctttggtt tgccaaagac tcgccttaaa    480
acgattggca gccggcctcc tggttacgca gcgcagcaca ttttttgcgct tgcaatcagc   540
aagagggcgg cactccatca agactccttc tcacgtttga cctcggatca ggtagggata   600
cccgctgaac ttaagcatat caataagcgg aggaaaagaa accaacaggg attgccctag   660
taacggcgag tgaagcggca acagctcaaa tttgaaatct ggctctttta gggtccgagt   720
tgtaatttgc agagggcgct ttggctttgg cagcggtcca agttccttgg aacaggacgt   780
```

```
cacagagggt gagaatcccg tacgtggtcg ctagctattg ccgtgtaaag ccccttcgac    840
gagtcgagtt gtttgggaat gcagctctaa atgggaggta aatttcttct aaagctaaat    900
attggccaga gaccgatagc gcacaagtag agtgatcgaa agatgaaaag cactttggaa    960
agagagtcaa acagcacgtg aaattgttga aagggaagcg cttgcagcca gacttgcttg   1020
cagttgctca tccgggcttt tgcccggtgc actcttctgt aggcaggcca gcatcagttt   1080
gggcggtggg ataaaggtct ctgacacgtt ccttccttcg ggttggccat ataggggaga   1140
cgtcatacca ccagcctgga ctgaggtccg cgcatctgct aggatgctgg cgtaatggct   1200
gtaagcggcc cgtcttgaaa cacggaccaa ggagtctaac atctatgcga gtgtttgggt   1260
gtcaagcccg agcgcgtaat gaaagtgaac ggaggtggga acccgcaagg gcgcaccatc   1320
gaccgatcct gaagtttacg gaaggatttg agtaagagca tggctgttgg gacccgaaag   1380
atggtgaact atgcttgaat agggtgaagc cagaggaaac tctggtggag gctcgcagcg   1440
gttctgacgt gcaaatcgat cgtcaaattt gggcataggg gcgaaagact aatcga       1496
```

<210> SEQ ID NO 75
<211> LENGTH: 1010
<212> TYPE: DNA
<213> ORGANISM: Curvularia protuberata

<400> SEQUENCE: 75

```
acaccggcag ggccgttcca gaggatggtc tgcgcctcat cgatggcctc cttgtaaagc     60
ttgatcgact tctctccaca gtcgagaccc atccagccat ctgggatacc atccttgtcc    120
tcggcataac cgacgttggc gtccttgtcg aacttgtcgg cggtgatgta gtcaacaggc    180
agcacaatct tgacattgtt cttcttcgcc ttctccacga ggtccttgac ggtcttgcta    240
ccagcctcat cgaacaagct ttcaccaatc ttgacgccct cgagagtctt cttgaaggtg    300
aaggacatgc ctccgcaaat gatcaggctg ttgaccttgc caagcaggtt gtcgatcaat    360
tgaatcttgt cagagacctt ggcaccacca aggatggcga ggaaaggtcg cttggggttc    420
tcaagcgctt gtgcaaagta atcaagctcc ttcttgacaa ggaagccaga ggccttttgt    480
gggaggtcga caccgaccat ggagctgtgc gcgcggtgag cagtaccaaa agcgtcgtct    540
gtaaaccgtc agcctcgtgc tttcgcccat gaattcatag ttacttacta atgtagacgt    600
cgcccagagc agtcagtccc ttcctaaact catcgacctt gctcttgtcg accttctgct    660
tcttgcccgc atcatccttg tagctaccct cctcctcagc gtggaagcgc aggttctcga    720
ggaggatgac ctgaccaccg ctagcgttgt tgacggtatc ctctaccgac ttgccgacgc    780
agtcgtcggt gaaggtaacg ctcttgccga ggagcttctc gagttcggga acaaccggct    840
tgaggctgta cttcgcattg ggcttaccgt ctggccggcc aaggtgggac atgagaatga    900
cggccttggc gccattgtcg acggcgtact tgattgtggg aagtgcgcca acaatgcgct    960
ggttgttggt gatcttcttg tcggcgtcga gagggacgtt gaagtcgacc              1010
```

<210> SEQ ID NO 76
<211> LENGTH: 1497
<212> TYPE: DNA
<213> ORGANISM: Curvularia protuberata

<400> SEQUENCE: 76

```
tccgtaggtg aacctgcgga gggatcatta cacaataaca tatgaaggct gtacgccgct     60
gcgcccccgg gccagttggc tgaggctgga ttatttatta cccttgtctt ttgcgcactt    120
```

```
gttgtttcct gggcgggttc gcccgcctcc aggaccacac cataaacctt ttttatgcag    180
ttgcaatcag cgtcagtaca acaaatgtaa atcatttaca actttcaaca acggatctct    240
tggttctggc atcgatgaag aacgcagcga aatgcgatac gtagtgtgaa ttgcagaatt    300
cagtgaatca tcgaatcttt gaacgcacat tgcgcccttt ggtattccaa agggcatgcc    360
tgttcgagcg tcatttgtac cctcaagctt tgcttggtgt tgggcgtttt tgtctttggt    420
ttgccaaaga ctcgccttaa aacgattggc agccggcctc ctggttacgc agcgcagcac    480 attttttgcgc ttgcaatcag caagagggcg gcactccatc aagactcctt ctcacgtttg    540
acctcggatc aggtagggat acccgctgaa cttaagcata tcaataagcg gaggaaaaga    600
aaccaacagg gattgcccta gtaacggcga gtgaagcggc aacagctcaa atttgaaatc    660
tggctctttt agggtccgag ttgtaatttg cagagggcgc tttggctttg gcagcggtcc    720
aagttccttg gaacaggacg tcacagaggg tgagaatccc gtacgtggtc gctagctatt    780
gccgtgtaaa gccccttcga cgagtcgagt tgtttgggaa tgcagctcta aatgggaggt    840
aaatttcttc taaagctaaa tattggccag agaccgatag cgcacaagta gagtgatcga    900
aagatgaaaa gcactttgga aagagagtca aacagcacgt gaaattgttg aaagggaagc    960
gcttgcagcc agacttgctt gcagttgctc atccgggctt tgcccggtg cactcttctg    1020 taggcaggcc agcatcagtt tgggcggtgg gataaaggtc tctgacacgt tccttccttc    1080
gggttggcca tataggggag acgtcatacc accagcctgg actgaggtcc gcgcatctgc    1140
taggatgctg gcgtaatggc tgtaagcggc ccgtcttgaa acacggacca aggagtctaa    1200
catctatgcg agtgtttggg tgtcaagccc gagcgcgtaa tgaaagtgaa cggaggtggg    1260
aacccgcaag ggcgcaccat cgaccgatcc tgaagtttac ggaaggattt gagtaagagc    1320
atggctgttg ggacccgaaa gatggtgaac tatgcttgaa tagggtgaag ccagaggaaa    1380
ctctggtgga ggctcgcagc ggttctgacg tgcaaatcga tcgtcaaatt tgggcatagg    1440
ggcgaaagac taatcgaact atctagtagc tggttcctgc cgaagtttcc ctcagga      1497
```

<210> SEQ ID NO 77
<211> LENGTH: 1472
<212> TYPE: DNA
<213> ORGANISM: Curvularia spicifera

<400> SEQUENCE: 77

```
tccgtaggtg aacctgcgga gggatcatta cacaataaaa tacgaaggcc gttcgcggct    60
ggactattta ttaccccttgt cttttgcgca cttgttgttt cctgggcggg ttcgctcgcc    120
accaggacca caatataaac cttttttatg cagttgcaat cagcgtcagt ataacaaatg    180
taaatcattt acaactttca acaacggatc tcttggttct ggcatcgatg aagaacgcag    240
cgaaatgcga tacgtagtgt gaattgcaga attcagtgaa tcatcgaatc tttgaacgca    300
cattgcgccc tttggtattc caagggcat gcctgttcga gcgtcatttg taccctcaag    360 cttttgcttgg tgttgggcgt tttgtctttt ggcccgccaa agactcgcct taaaatgatt    420
ggcagccggc ctactggttt cgcagcgcag cacattttttg cgcttgcaat cagcaaagga    480
ggacggcaat ccatcaagac tccttctcac gtttgacctc ggatcaggta gggatacccg    540
ctgaacttaa gcatatcaat aagcggagga aaagaaacca caggggattg ccctagtaac    600
ggcgagtgaa gcggcaacag ctcaaatttg aaatctggct cttcagagt ccgagttgta    660 atttgcagag ggcgctttgg cttttggcagc ggtccaagtt ccttggaaca ggacgtcaca    720
gagggtgaga atcccgtacg tggtcgctag ctattgccgt gtaaagcccc ttcgacgagt    780
```

| | |
|---|---|
| cgagttgttt gggaatgcag ctctaaatgg gaggtaaatt tcttctaaag ctaaatattg | 840 |
| gccagagacc gatagcgcac aagtagagtg atcgaaagat gaaaagcact ttggaaagag | 900 |
| agtcaaacag cacgtgaaat tgttgaaagg gaagcgcttg cagccagact tgcttgcagt | 960 |
| tgctcatccg ggcttttgcc cggtgcactc ttctgcaggc aggccagcat cagtttgggc | 1020 |
| ggtgggataa aggtctctgt cacgtacctt ccttcgggtt ggccttatag gggagacgcc | 1080 |
| ataccaccag cctggactga ggtccgcgca tctgctagga tgctggcgta atggctgtaa | 1140 |
| gcggcccgtc ttgaaacacg gaccaaggag tctaacatct atgcgagtgt ttgggtgtca | 1200 |
| agcccgagcg cgtaatgaaa gtgaacgag gtgggaaccc gcaagggtgc accatcgacc | 1260 |
| gatcctgaag tttacggaag gatttgagta agagcatggc tgttgggacc cgaaagatgg | 1320 |
| tgaactatgc ttgaataggg tgaagccaga ggaaactctg gtggaggctc gcagcggttc | 1380 |
| tgacgtgcaa atcgatcgtc aaatttgggc ataggggcga agactaatc gaactatcta | 1440 |
| gtagctggtt cctgccgaag tttccctcag ga | 1472 |

<210> SEQ ID NO 78
<211> LENGTH: 1428
<212> TYPE: DNA
<213> ORGANISM: Curvularia spicifera

<400> SEQUENCE: 78

| | |
|---|---|
| aggtgaacct gcggagggat cattacacaa taaaatacga aggccgttcg cggctggact | 60 |
| atttattacc cttgtctttt gcgcacttgt tgtttcctgg gcgggttcgc tcgccaccag | 120 |
| gaccacaata taaacctttt ttatgcagtt gcaatcagcg tcagtataac aaatgtaaat | 180 |
| catttacaac tttcaacaac ggatctcttg gttctggcat cgatgaagaa cgcagcgaaa | 240 |
| tgcgatacgt agtgtgaatt gcagaattca gtgaatcatc gaatctttga acgcacattg | 300 |
| cgccctttgg tattccaaag ggcatgcctg ttcgagcgtc atttgtaccc tcaagctttg | 360 |
| cttggtgttg ggcgtttttg tctttggccc gccaaagact cgcctaaaa tgattggcag | 420 |
| ccggcctact ggtttcgcag cgcagcacat ttttgcgctt gcaatcagca aaagaggacg | 480 |
| gcaatccatc aagactcctt ctcacgtttg acctcggatc aggtagggat acccgctgaa | 540 |
| cttaagcata tcaataagcg gaggaaaaga accaacagg gattgcccta gtaacggcga | 600 |
| gtgaagcggc aacagctcaa atttgaaatc tggctctttc agagtccgag ttgtaatttg | 660 |
| cagagggcgc tttggctttg gcagcggtcc aagttccttg gaacaggacg tcacagaggg | 720 |
| tgagaatccc gtacgtggtc gctagctatt gccgtgtaaa gccccttcga cgagtcgagt | 780 |
| tgtttgggaa tgcagctcta aatgggaggt aaatttcttc taaagctaaa tattggccag | 840 |
| agaccgatag cgcacaagta gagtgatcga agatgaaaa gcactttgga aagagagtca | 900 |
| aacagcacgt gaaattgttg aaagggaagc gcttgcagcc agacttgctt gcagttgctc | 960 |
| atccgggctt tgcccggtg cactcttctg caggcaggcc agcatcagtt tgggcggtgg | 1020 |
| gataaaggtc tctgtcacgt accttccttc gggttggcct tataggggag acgccatacc | 1080 |
| accagcctgg actgaggtcc gcgcatctgc taggatgctg gcgtaatggc tgtaagcggc | 1140 |
| ccgtcttgaa acacggacca aggagtctaa catctatgcg agtgtttggg tgtcaagccc | 1200 |
| gagcgcgtaa tgaaagtgaa cggaggtggg aacccgcaag ggtgcaccat cgaccgatcc | 1260 |
| tgaagtttac ggaaggattt gagtaagagc atggctgttg gacccgaaa gatggtgaac | 1320 |
| tatgcttgaa tagggtgaag ccagaggaaa ctctggtgga ggctcgcagc ggttctgacg | 1380 | tgcaaatcga tcgtcaaatt tgggcatagg ggcgaaagac taatcgaa                1428

<210> SEQ ID NO 79
<211> LENGTH: 1197
<212> TYPE: DNA
<213> ORGANISM: Curvularia spicifera

<400> SEQUENCE: 79
cccatagctt gcttacccat agcagattgg tatgtgttac ggggcgactg gttgtgatct    60
gggaagggaa tgatactggc gcaaataccc aagatcatag ctgggtgaat ctcacaatgg   120
gtgtaggcgt ggatgcgagg atccggtagt ggcttgagac ggcggagtcg atccttgcct   180
tcagtagatc gctcagctgc aggcaagccc atcttcattt ctcgccattc ttccaagtcc   240
tcgggagaga atgttatcat tgcagtttct tcttcctcgg catcgaggta ttcaacgaca   300
ccgtcttgaa tgagacctct ccagccgtat gtagcctgct cgacttcctc ttgactccag   360
ccttgtcttg tactggtctc ttgctgttca gccttgagct tgttgctgat ttccttggta   420
aagatgaggt ggttccggtt tggctttcga atatcgtttt ctacaacgaa caaaggcctc   480
atgacacgac ccgcatctgt gaatatcttg aactctctgt cgcgaatatc acgaatcaaa   540
ctcatctcgt aagacagagt accattgcgc gaagctcct gcacgactgt gacaagctgc    600
tgagcatttg aatgaacacc aacccagaca ccgttaacga agaccttggt cgcatccggg   660
ttctggttct ggtcgtactc ctcgagaagt tgcatgttac gttgtgtcat gaagtcgata   720
atgggcgatg catcgctacc aacactgaca taacacataa gagacaagtt cttgaccaga   780
ccgcaagcct gtccttcggg cgtctcagca gggcagacaa gaccccaatg agagttgtga   840
agctgtcgcg gctttgccaa cttaccatca cgtccaacgg gggtgttcgt tcgacgcaga   900
tgggatagtg tggaggcata ggtgtatcgg ttcaacacct gcgaaacacc agccttggca   960
gatgcagcct tcttctgatc accccaattg cctgtagcca gagagtactt caggccgttt  1020
gtgatgatgc tggctttcac agccatttga acattgaagt cttggttgtt ttccacgcac  1080
cgctggaggt acttgtagac atccttggtg agcttcagga acaagattcg gaacaagttg  1140
gcaatcagag gtccagccag atctagtcgc ttctttccaa agtgatcacg atcgtcc     1197

<210> SEQ ID NO 80
<211> LENGTH: 387
<212> TYPE: DNA
<213> ORGANISM: Curvularia spicifera

<400> SEQUENCE: 80
gttcacctcc agaccggtca atgcgtaagt ctcgcgccgc ctgaaaacac cacgggaacg    60
actgctaaca gccgctacag ggtaaccaaa ttggtgccgc cttctggcag accatttccg   120
gcgagcatgg cctcgacggc tctggtgtct acaacggcac ctctgacctt cagctcgagc   180
gcatgaacgt ctacttcaac gaagtacgtc cctcggtgaa gctccaacag acaaaagacc   240
aatactgatg tgcagcaggc ttccaacaac aagttcgtgc cccgtgccgt cctcgtcgat   300
ctcgagcctg gtactatgga cgctgtccgc gctggtccct ttggtcagct cttccgcccc   360
gacaacttcg tcttcggcca gtcgggt                                       387

<210> SEQ ID NO 81
<211> LENGTH: 590
<212> TYPE: DNA
<213> ORGANISM: Curvularia spicifera

<400> SEQUENCE: 81

```
ctaccgcaag agcaactgtg caagtccagc ttcagtccct ttcgatcccc ctcgcccagg      60
aagagattca cccacgagcg caaccagtcc gaggcggtcc agcgtccacg tcctatgagc     120
gtttgcagca actcgccagc agttcagcac accaaaagag cctccatcta cgtctccgac     180
gcttccatca tcctagcgca acgctcaccc atggcttctc cggtttcccc accagactcc     240
atgtcctccc ccatccatga atcgtctgat gccgtcgacc actatgctat cctggagatc     300 accccctagag caactaccga tgaggtcaag gctgcctacc gccgactacg ggtcgtctac     360
ttctcaagtg acgcgaagaa gtaccgagca ctgcaggcgg ccttcgacgt cttgatggac     420
ccgcaatccc gcgaagctta cgacgcaacc tatcaaccaa ctgccgcagc accagtatcg     480
ctcgctagca ttggtgagat cctggactcg gggaagctat ggcgacagga cagcgcccac     540
ggagacgacc cagtaatccc agaagaggaa gaggaggagg aggaggaagt                590
```

<210> SEQ ID NO 82
<211> LENGTH: 491
<212> TYPE: DNA
<213> ORGANISM: Unknown
<220> FEATURE:
<223> OTHER INFORMATION: Kingdom: Fungi, Phylum: Ascomycota, Class:
      Eurotiomycetes, Order: Eurotiales, Family: Aspergillaceae, Genus:
      Penicillium

<400> SEQUENCE: 82

```
cggggcccaa cctcccaccc gtgttgcccg aacctatgtt gcctcggcgg gccccgcgcc      60
cgccgacggc cccctgaac gctgtctgaa gttgcagtct gagacctata acgaaattag      120
ttaaaacttt caacaacgga tctcttggtt ccggcatcga tgaagaacgc agcgaaatgc     180
gataactaat gtgaattgca gaattcagtg aatcatcgag tctttgaacg cacattgcgc     240
cctctggtat tccggagggc atgcctgtcc gagcgtcatt gctgccctca gcccggcttt    300
gtgtgttggg cccgtcccc ccgccgggg ggacgggccc gaaaggcagc ggcggcaccg     360
cgtccggtcc tcgagcgtat ggggcttcgt cacccgctct agtaggcccg gccggcgcca    420
gccgaccccc aacctttaat tatctcaggt tgacctcgga tcaggtaggg atacccgctg    480
aacttaagca t                                                         491
```

<210> SEQ ID NO 83
<211> LENGTH: 167
<212> TYPE: DNA
<213> ORGANISM: Phomopsis liquidambari

<400> SEQUENCE: 83

```
tataccttac tgttgcctcg gcgcatgctg gccccctcgg ggtcccctgg agacagggag      60
caggcacgcc ggcggccaag ttaactcttg tttttacact gaaactctga gaaaaaaaca     120
caaatgaatc aaaactttca acaacggatc tcttggttct ggcatcg                  167
```

<210> SEQ ID NO 84
<211> LENGTH: 482
<212> TYPE: DNA
<213> ORGANISM: Gibellulopsis nigrescens

<400> SEQUENCE: 84

```
acctgttgct tcggcggcgc gcctctcggg gcgtgcccgc cggcattatc agaatctctg      60
ttcgaacccg acgatacttc tgagtgttct aagcgaactg ttaaaacttt caacaacgga     120
tctcttggct ccagcatcga tgaagaacgc agcgaaacgc gatatgtaat gtgaattgca    180
```

```
gaattcagtg aatcatcgaa tctttgaacg cacatggcgc cttccagtat cctgggaggc    240
atgcctgtcc gagcgtcgtt tcaaccctcg agccccgtg gccggcgtt ggggaccgct    300 ccaggcagtc cccgaaaacc agtggcggac ccgacgggcc cttcctttgc gtagtaacat    360
ctgcctcgca tcgggagccc ccgggctatc cggcctctaa accccctca gcccgctcc    420 ggcggcacca aggttgacct cggatcaggt aggaataccc gctgaactta agcatatcaa    480
ta                                                                   482
```

```
<210> SEQ ID NO 85
<211> LENGTH: 507
<212> TYPE: DNA
<213> ORGANISM: Gibellulopsis nigrescens

<400> SEQUENCE: 85
cctttgtgac cttcataccct gttgcttcgg cggcgcgcct ctcggggcgt gcccgccggc    60
attatcagaa tctctgttcg aacccgacga tacttctgag tgttctaagc gaactgttaa   120
aactttcaac aacggatctc ttggctccag catcgatgaa gaacgcagcg aaacgcgata   180
tgtaatgtga attgcagaat tcagtgaatc atcgaatctt tgaacgcaca tggcgccttc   240
cagtatcctg ggaggcatgc ctgtccgagc gtcgtttcaa ccctcgagcc ccgtggccc    300 ggcgttgggg acctgcccag gcagtccccg aaaaccagtg gcggaccga cgggcccttc   360 cttttgcgtag taacatctgc ctcgcatcgg agccccgg gctatccggc tctaaaccc   420 ccctcaagcc cgctccggcg caccaaggt tgacctcgga tcaggtagga tacccgctg   480 aacttaagca tatcaataag cggagga                                       507
```

```
<210> SEQ ID NO 86
<211> LENGTH: 511
<212> TYPE: DNA
<213> ORGANISM: Gibellulopsis nigrescens

<400> SEQUENCE: 86
taccctttgt gaccttcata cctgttgctt cggcggcgcg cctctcgggg cgtgcccgcc    60
ggcattatca gaatctctgt tcgaacccga cgatacttct gagtgttcta agcgaactgt   120
taaaactttc aacaacggat ctcttggctc cagcatcgat gaagaacgca gcgaaacgcg   180
atatgtaatg tgaattgcag aattcagtga atcatcgaat cttttgaacgc acatggcgcc   240 ttccagtatc tggggaggca tgcctgtccg agcgtcgttt caaccctcga gccccgtgg    300 cccggcgttg gggacctgcc caggcagtcc ccgaaaacca gtggcggacc cgacgggccc   360
ttcctttgcg tagtaacatc tgcctcgcat cgggagcccc cgggctatcc ggcctctaaa   420 ccccctcaa gcccgctccg gcggcaccaa ggttgacctc ggatcaggta ggaatacccg   480
ctgaacttaa gcatatcaat aagcggagga a                                  511
```

```
<210> SEQ ID NO 87
<211> LENGTH: 1458
<212> TYPE: DNA
<213> ORGANISM: Acremonium alternatum

<400> SEQUENCE: 87
tcttggtcat ttagaggaag taaaagtcgt aacaaggtct ccgttggtga accagcggag    60
ggatcattac cgagtgtaaa aactcccaaa ccattgtgaa cttaccactg ttgcttcggc   120
ggcctcgccc cggcgcgtt cgcgcggccc ggacccaggc gtccgccgga ggctccaaac   180
tcttgtcttt tagtgtattt ctgagtggca taagcaaata aatcaaaact ttcagcaacg   240
```

```
gatctcttgg ttctggcatc gatgaagaac gcagcaaaat gcgataagta atgtgaattg    300
cagaattcag tgaatcatcg aatctttgaa cgcacattgc gcccgccagt attctggcgg    360
gcatgcctgt ctgagcgtca tttcaaccct caggacccgt tcgcgggacc tggcgttggg    420
gatcagcctg cccctggcgg cggctggccc tgaaatccag tggcggttcc ctcgcgaact    480
cctccgtgca gtaattaaac ctctcgcggc aggatagcgg ttgaaccacg ccgttaaacc    540
ccccacttct caaggttgac ctcagatcag gtaggaatac ccgctgaact taagcatatc    600
aataagcgga ggaaaagaaa ccaacaggga ttgccctagt aacggcgagt gaagcggcaa    660
cagctcaaat ttgaaatctg gcctcacggt ccgaattgta atttgtagag gatgtttctg    720
gcgacgtgtc ttccgagttc cctggaacgg gacgccatag agggtgagag ccccgtccgg    780
tcgtacacct agcctctgtg aaactccttc gacgagtcga gtagtttggg aatgctgctc    840
taaatgggag gtatacgtct tctaaagcta ataccggcc agagaccgat agcgcacaag    900
tagagtgatc gaaagatgaa aagcactttg aaaagagggt taaatagtac gtgaaattgc    960
tgaaagggaa gcgcttatga ccagacttgg gctcggtgaa tcatccggcg ttctcgccgg   1020
tgcactttgc cgtcccaggc cagcatcagt tcgcgccggg ggataaaggt ttcgggaatg   1080
tagctccttc gggagtgtta tagcccgttg cgtaataccc tggcgtggac tgaggtccgc   1140
gctctgcaag gatgctggcg taatggtcat cagtgacccg tcttgaaaca cggaccaagg   1200
agtcgtcttc gtatgcgagt gttcgggtgt caaaccccta cgcgtaatga aagtgaacgt   1260
aggagagagc ttcggcgcat ctccgaccga tcctgatgtt ctcggatgga tttgagtaag   1320
agcatacggg gccggacccg aaagaaggtg aactatgcct gtatagggtg aagccagagg   1380
aaactctggt ggaggctcgc agcggttctg acgtgcaaat cgatcgtcaa atatgggcat   1440
gggggcgaaa gactaatc                                                1458

<210> SEQ ID NO 88
<211> LENGTH: 290
<212> TYPE: DNA
<213> ORGANISM: Acremonium alternatum

<400> SEQUENCE: 88
atgtgcaagg ccggtttcgc cggtgacgat gctccccgag ctgttttccg taagtcaacc     60
ccactttcgc ttcccaagct cctaatcgcc cacacctggc gatatgggct ttgggggcct    120
gtaagcagcc gacacaagac taacgcgatg cgccagcttc cattgtcggt cgcccccgtc    180
accatgggta agtacgcgcg caaatgacac ctgtcagccc cctcgacgag cggcacaggc    240
tctgaccatt cgatagtatc atgattggta tgggacagaa ggactcgtac                290

<210> SEQ ID NO 89
<211> LENGTH: 380
<212> TYPE: DNA
<213> ORGANISM: Acremonium alternatum

<400> SEQUENCE: 89
ccggactggc cgaagacgaa gttgtcggga cggaagagct gaccgaaagg accggcgcgg     60
acggcatcca tggtaccggg ctcgagatcg acgaggacag cgcgaggaac gtacttgttg    120
ccagaggcct acagagggtc agcttggcca cagactgcgg gatactccaa attgctcacc    180
tcgttgaagt agacgctcat gcgctcgagc tggagtcag aggtgccgtt gtagacaccg    240
ttgctgtcga ggccatgctc gccagagatg gtctgccaga aggcagcacc aatctggtta    300
```

```
cctgctcgg aggttagaca tggtaggcga tatcacatat ggcggaagta cttacgcact      360
gaccggtctg gaggtgaacc                                                 380
```

<210> SEQ ID NO 90
<211> LENGTH: 1231
<212> TYPE: DNA
<213> ORGANISM: Acremonium alternatum

<400> SEQUENCE: 90

```
gatgatcgtg atcacttcgg gaaaaagcgc cttgacctgg ctgggcccct cttagctaaa       60
ttgttccgca acattattcg caggatcaac aacgagctgt cgacctacct caggcgatgt      120
gtcgagggcg gcaggaactt caacctcgct gtcggcatca agcctggcac actgtcgaac      180
gggttgaagt actctttggc aacaggcaac tggggagacc aaaagaaggc aatgagctcg      240
gttgctggag tgtcccaggt tctcaaccgc tacacatttg cgtcaacctt gtctcatttg      300
aggcgcacca acaccccat  tggccgtgat ggaaagctgg cgaagcctcg gcagctacac      360
aacacgcatt gggtcttgt  gtgtcccgcc gagacccccg agggtcaggc ttgtggtttg      420
gtgaagaacc tgtcactgat gtgtcacgtt ccgttggca  cacctagcga acctctctac      480
ggatacttca tcaaccgtgg catggaagtg ctcgaagagt acgagcccca gcggttcccc      540
aacgccacca aggtgttcat caacggtgcc tgggtcggtg tgcacacaag cccgaaagat      600
ctcgtggata gcatcatgca tctgcggcgc tatggtgacc tgaaccatga agcttccgtc      660
atccgcgaca ttcgggatcg agagttcagg gtcgtcacgg atgctggtcg tgttatgcgc      720
ccagtattca ccgtgcagca agaagacaag ctagacgggc cgagaaggg  ctcgttgtgc      780 atgaccaagg agcatcttgc cggttttggat gactggcatc tggtcaacga ggagagggaa     840
gagatggcca cgggctggga gtacctcgtg aagagtgggt gtattgagta cttggacgcc      900
gaagaagaag agacggcaat gatttgcatg acaccagaag acttggagtc ttaccgcaag      960
gagaagtacc tcgatcagaa accccaggag cacaacgtgg aagccgagcc caacaagcga     1020
ctcaagacga agaccaaccc gacgacacac atgtacaccc actgcgagat tcatcccagt     1080
atgatcctcg gtatctgcgc cagcatcatc cccttcccgg atcataacca ggcatgtctc     1140
tacgccacca gacctcgaga ttacttacta atattgcatc tagtcgcccc gtaatactta     1200
ccaatctgcc atgggcaagc aggccatggg c                                    1231
```

<210> SEQ ID NO 91
<211> LENGTH: 790
<212> TYPE: DNA
<213> ORGANISM: Acremonium alternatum

<400> SEQUENCE: 91

```
gaatgccccg gtcatttttgg tcacatcgag ctggcaaagc ccgtttacca ccccggcttc      60
atcaagaaag tcaagaagat tttggagatt gtctgccaca actgcagcaa ggtcttggcc     120
gatgaagttg gtctcacctg atccatgtct tgttccttag atgctaacat ggacctctca     180
gagcgacccc gagtttgtca ctgcgatccg tacgcgcgac ccgaaagtcc gcttccagcg     240
agtctgggct gtgtgcaaga agaagcggaa gtgtgagaac gaggatcgcc aagacaagaa     300
ggaagaggag ttcgcgcccg gcatgaagcc gcagacgcac aaccacggcg gctgtggaaa     360
cgagatgccc gcggttcgtc aagctggttt gcgtctcaac gcgcagttcg agatcaagga     420
agagggcgga gctaagcgca aggatactca agttatcctg cccgaccaag ctcacacaat     480
cctgcggcgg atatcggaac aggacctccg acacatgggc ctcaactcag agtatgcccg     540
```

```
cccagagtgg atggttctta ccgtccttcc ggtcccccg cctcccgttc gtccaagtat      600
ttccatggac ggcactggca cgggaatgcg aacgaggat gatttgactt acaagcttgg     660
tgatatcatc cgagccaacg gaaacgtcaa gcaggctatc cgcgaaggct cgccggccca     720
cattgctcgc gatttcgaag agctgctcca gtaccatgta gccacctaca tggataatga     780
tattgctgga                                                            790
```

```
<210> SEQ ID NO 92
<211> LENGTH: 593
<212> TYPE: DNA
<213> ORGANISM: Acremonium alternatum

<400> SEQUENCE: 92
gtcctcgcct aatcaggagt cactagacga catacccgag gacgacatga tgggcgacct      60
tgcgcttggc ctttcgagca gcttcaagca acacgccctc cggaactcaa agggcaagac     120
cttctgggat accttctccg agacgagcag tgtcgcagga ccgagaacca cgccacctcc     180
gccgggagtg atggctcgac gtccatcgtc cggcaggagt gaggatgtga ccatggattc     240
gccgctccag caaagcagca tgccttggct acaaacacgg cacctttccg actcccagcg     300
ctcggactcg gcacctgcgg ccaaggagaa ggactccccg gcccagccac ccaccgctgc     360
agagataacg cgccgaatca acaacaaacg ccgccgtgac gatgacttcg acccggtgag     420
cttcaaacgc cgcgcagtga gtcccgggct cagcgtccac aactcgccgc tcccgcagag     480
cccaatgcag cagagcggtg cgccatgggg ttccaggccg ggaagcaatg ggggcgacaa     540
ggcgggaagc agtgcaccta gcgaatctgg tggtagcacg tcagggaata gga            593
```

```
<210> SEQ ID NO 93
<211> LENGTH: 497
<212> TYPE: DNA
<213> ORGANISM: Unknown
<220> FEATURE:
<223> OTHER INFORMATION: Kingdom: Fungi, Phylum: Ascomycota, Class:
      Sordariomycetes, Order: Hypocreales, Family: Nectriaceae, Genus:
      Fusarium

<400> SEQUENCE: 93
cccctgtgac ataccaattg ttgcctcggc ggatcagccc gctcccggta aaacgggacg      60
gcccgccaga ggaccctaa actctgtttc tatatgtaac ttctgagtaa aaccataaat     120
aaatcaaaac tttcaacaac ggatctcttg gttctggcat cgatgaagaa cgcagcaaaa     180
tgcgataagt aatgtgaatt gcagaattca gtgaatcatc gaatctttga acgcacattg     240
cgcccgccag tattctggcg ggcatgcctg ttcgagcgtc atttcaaccc tcaagccccc     300
gggtttggtg ttggggatcg gcgagcctca cggcaagccg gccccgaaat acagtggcgg     360
tctcgctgca gcttccattg cgtagtagta aaaccctcgc aactggtacg cggcgcggcc     420
aagccgttaa accccaact tctgaatgtt gacctcggat caggtaggaa tacccgctga     480
acttaagcat atcaata                                                    497
```

```
<210> SEQ ID NO 94
<211> LENGTH: 552
<212> TYPE: DNA
<213> ORGANISM: Purpureocillium lavendulum

<400> SEQUENCE: 94
ctcccaaccc actgtgacct tacctcagtt gcctcggcgg gaacgccccg gccgccggcc      60
```

| | |
|---|---:|
| cccgcgccgg cgccggaccc aggcgcccgc cgcagggacc ccaaactctc ttgcattacg | 120 |
| cccagcgggc ggaatttctt ctctgagttg cacaagcaaa aacaaatgaa tcaaaacttt | 180 |
| caacaacgga tctcttggtt ctggcatcga tgaagaacgc agcgaaatgc gataagtaat | 240 |
| gtgaattgca gaattcagtg aatcatcgaa tctttgaacg cacattgcgc ccgccagcat | 300 |
| tctggcgggc atgcctgttc gagcgtcatt tcaaccctcg agccccccg ggggcctcgg | 360 |
| tgttggggga cggcacacca gccgcccccg aaatgcagtg cgaccccgc cgcagcctcc | 420 |
| cctgcgtagt agcacacacc tcgcaccgga gcgcggaggc ggtcacgccg taaaacgccc | 480 |
| aactttctta gagttgacct cggatcaggt aggaataccc gctgaactta agcatatcaa | 540 |
| taagcggagg aa | 552 |

<210> SEQ ID NO 95
<211> LENGTH: 491
<212> TYPE: DNA
<213> ORGANISM: Phialemonium inflatum

<400> SEQUENCE: 95

| | |
|---|---:|
| acatacccgt accgttgcct cggcgggcgg ccccagggcg gggccgcagc ctccccagcg | 60 |
| gaggcgcccg ccgcaggtcg caaaactata actatattta gtggcatctc tgagtaactt | 120 |
| ccaaacaatc aaaactttca caacggatc tcttggttct ggcatcgatg aagaacgcag | 180 |
| cgaaatgcga taagtaatgt gaattgcaga attcagtgaa tcatcgaatc tttgaacgca | 240 |
| cattgcgccc gccagcattc tggcgggcat gcctgtccga gcgtcatttc aaccctcaag | 300 |
| ccctgcttgg tgttggggca ctacgcgcga gcgtaggccc tcaaaatcag tggcggaccc | 360 |
| gctggaggtc cggcgtagt aacacatctc gcccgaggtc cccagcgtgc cctgccgtt | 420 |
| aaaccccccaa atttacagaa ggttgacctc ggatcaggta ggaatacccg ctgaacttaa | 480 |
| gcatatcaat a | 491 |

<210> SEQ ID NO 96
<211> LENGTH: 519
<212> TYPE: DNA
<213> ORGANISM: Chaetomium coarctatum

<400> SEQUENCE: 96

| | |
|---|---:|
| ttgtgacgtt acctaaaccg ttgcttcggc gggcggcccc ggggtttacc ccccgggcgc | 60 |
| ccctgggccc caccgcgggc gccgccgga ggtcaccaaa ctcttgataa tttatggcct | 120 |
| ctctgagtct tctgtactga ataagtcaaa actttcaaca acggatctct tggttctggc | 180 |
| atcgatgaag aacgcagcga atgcgataa gtaatgtgaa ttgcagaatt cagtgaatca | 240 |
| tcgaatcttt gaacgcacat tgcgcccgcc agtattctgg cgggcatgcc tgttcgagcg | 300 |
| tcatttcaac catcaagccc cgggcttgtg ttggggacct gcggctgccg caggccctga | 360 |
| aaagcagtgg cgggctcgct gtcacaccga gcgtagtagc atatatctcg ctctgggcgt | 420 |
| gctgcgggtt ccggccgtta aaccaccttt taacccaagg ttgacctcgg atcaggtagg | 480 |
| aagacccgct gaacttaagc atatcaataa gcggaggaa | 519 |

<210> SEQ ID NO 97
<211> LENGTH: 527
<212> TYPE: DNA
<213> ORGANISM: Chaetomium globosum

<400> SEQUENCE: 97

| | |
|---|---:|
| aaactcccta aaccattgtg aacgttacct ataccgttgc ttcggcgggc ggccccgggg | 60 |

```
tttaccccc gggcgccct gggcccacc gcgggcgcc gccggaggtc accaaactct    120
tgataattta tggcctctct gagtcttctg tactgaataa gtcaaaactt tcaacaacgg    180
atctcttggt tctggcatcg atgaagaacg cagcgaaatg cgataagtaa tgtgaattgc    240
agaattcagt gaatcatcga atctttgaac gcacattgcg cccgccagca ttctggcggg    300
catgcctgtt cgagcgtcat ttcaaccatc aagcccccgg gcttgtgttg gggacctgcg    360
gctgccgcag gccctgaaaa gcagtggcgg gctcgctgtc gcaccgagcg tagtagcata    420
catctcgctc tggtcgcgcc gcgggttccg gccgttaaac cacctttta cccaaggttg    480 acctcggatc aggtaggaag acccgctgaa cttaagcata tcaataa    527
```

<210> SEQ ID NO 98
<211> LENGTH: 1453
<212> TYPE: DNA
<213> ORGANISM: Chaetomium globosum

<400> SEQUENCE: 98

```
tcttggtcat ttagaggaag taaaagtcgt aacaaggtct ccgttggtga accagcggag    60
ggatcattac agagttgcaa aactccctaa accattgtga acgttaccta taccgttgct    120
tcggcgggcg ccccgggggt ttaccccccg gcgcccctg gccccaccg cgggcgcccg    180 ccggaggtca ccaaactctt gataatttat ggcctctctg agtcttctgt actgaataag    240
tcaaaacttt caacaacgga tctcttggtt ctggcatcga tgaagaacgc agcgaaatgc    300
gataagtaat gtgaattgca gaattcagtg aatcatcgaa tctttgaacg cacattgcgc    360
ccgccagcat tctggcgggc atgcctgttc gagcgtcatt tcaaccatca gcccccggg    420 cttgtgttgg ggacctgcgg ctgccgcagg ccctgaaaag cagtggcggg ctcgctgtcg    480
caccgagcgt agtagcatac atctcgctct ggtcgcgccg cgggttccgg ccgttaaacc    540 acctttaac ccaaggttga cctcggatca ggtaggaaga cccgctgaac ttaagcatat    600
caataagcgg aggaaaagaa accaacaggg attgccctag taacggcgag tgaagcggca    660
acagctcaaa tttgaaatct ggcttcggcc cgagttgtaa tttgcagagg aagctttagg    720
cgcggcacct tctgagtccc ctggaacggg gcgccataga gggtgagagc cccgtatagt    780
tggatgccta gctgtgtaa agctccttcg acgagtcgag tagtttggga atgctgctca    840
aaatgggagg taaatttctt ctaaagctaa ataccggcca gagaccgata gcgcacaagt    900
agagtgatcg aaagatgaaa agcactttga aaagagggtt aaatagcacg tgaaattgtt    960
gaaagggaag cgcttgtgac cagacttgcg ccgggcggat catccggtgt tctcaccggt    1020
gcactccgcc cggctcaggc cagcatcggt tctcgcgggg ggataaaggt cctgggaacg    1080
tagctcctcc gggagtgtta tagcccgggg cgtaatgccc tcgcggggac cgaggttcgc    1140
gcatctgcaa ggatgctggc gtaatggtca tcagcgaccc gtcttgaaac acggaccaag    1200
gagtcaaggt tttgcgcgag tgtttgggtg taaaacccgc acgcgtaatg aaagtgaacg    1260
taggtgagag cttcggcgca tcatcgaccg atcctgatgt tttcggatgg atttgagtag    1320
gagcgttaag ccttggaccc gaaagatggt gaactatgct tggatagggt gaagccagag    1380
gaaactctgg tggaggctcg cagcggttct gacgtgcaaa tcgatcgtca aatctgagca    1440
tgggggcgaa aga    1453
```

<210> SEQ ID NO 99
<211> LENGTH: 266
<212> TYPE: DNA

<213> ORGANISM: Chaetomium globosum

<400> SEQUENCE: 99

| | | | | | |
|---|---|---|---|---|---|
| atgtgcaagg | ccggtttcgc | cggtgatgat | gcaccccgcg | ctgttttccg | taagtctccc | 60 |
| agccccggcc | ccggcccggt | cggcgataag | ccgagctccg | gacgctcgtt | ggcacaaaca | 120 |
| gacaagctaa | cagcgccgtt | tagcgtcgat | tgtcggtcgt | ccccgtcacc | atgggtaggc | 180 |
| tttcagttcc | ggtatctctg | cgatatgggg | tcgctggcta | acgcgccgct | agtattatga | 240 |
| tcggtatggg | gcagaaggac | tcgtac | | | 266 |

<210> SEQ ID NO 100
<211> LENGTH: 923
<212> TYPE: DNA
<213> ORGANISM: Chaetomium globosum

<400> SEQUENCE: 100

| | | | | | |
|---|---|---|---|---|---|
| tcctgaggga | aacttcggcg | gtaaccagct | actagatggt | tcgattagtc | tttcgccccc | 60 |
| atgctcagat | ttgacgatcg | atttgcacgt | cagaaccgct | gcgagcctcc | accagagttt | 120 |
| cctctggctt | caccctatcc | aagcatagtt | caccatcttt | cgggtccaag | gcttaacgct | 180 |
| cctactcaaa | tccatccgaa | aacatcagga | tcggtcgatg | atgcgccgaa | gctctcacct | 240 |
| acgttcactt | tcattacgcg | tgcgggtttt | acacccaaac | actcgcgcaa | aaccttgact | 300 |
| ccttggtccg | tgtttcaaga | cgggtcgctg | atgaccatta | cgccagcatc | cttgcagatg | 360 |
| cgcgaacctc | ggtccccgcg | agggcattac | gccccgggct | ataacactcc | cggaggagct | 420 |
| acgttcccag | gacctttatc | ccccgcgag | aaccgatgct | ggcctgagcc | gggcggagtg | 480 |
| caccggtgag | aacaccggat | gatccgcccg | gcgcaagtct | ggtcacaagc | gcttcccttt | 540 |
| caacaatttc | acgtgctatt | taaccctctt | ttcaaagtgc | ttttcatctt | tcgatcactc | 600 |
| tacttgtgcg | ctatcggtct | ctggccggta | tttagcttta | gaagaaattt | acctcccatt | 660 |
| ttgagcagca | ttcccaaact | actcgactcg | tcgaaggagc | tttacacagg | ctaggcatcc | 720 |
| aactatacgg | ggctctcacc | ctctatggcg | ccccgttcca | ggggactcag | aaggtgccgc | 780 |
| gcctaaagct | tcctctgcaa | attacaactc | gggccgaagc | cagatttcaa | atttgagctg | 840 |
| ttgccgcttc | actcgccgtt | actagggcaa | tccctgttgg | tttctttcc | tccgcttatt | 900 |
| gatatgctta | agttcagcgg | gtc | | | 923 |

<210> SEQ ID NO 101
<211> LENGTH: 797
<212> TYPE: DNA
<213> ORGANISM: Chaetomium globosum

<400> SEQUENCE: 101

| | | | | | |
|---|---|---|---|---|---|
| gagtgtccag | gtcactttgg | ccacattgag | ctatccagac | ccgttttcca | ccccgggttc | 60 |
| atcaggcgtg | tcaaaaagtt | gctcgagatg | gtctgccaca | actgcagcaa | ggtgttggct | 120 |
| gatcgtgtta | gtgcaccttg | cctgaccgag | tgatgatttg | ttttggcatg | ctaactcttc | 180 |
| accaggagga | cgagcaatat | gctgctgcca | tgcggattcg | ggaccccaaa | gtacgcttca | 240 |
| agcgagtttg | ggatatttgc | aagagtaaga | agcgctgcga | aaacgaagtg | cgcaagggga | 300 |
| aagatggcga | gttcaaaccc | gacagcgaaa | accaagccgc | agagggtggc | catggaggat | 360 |
| gtggcaacac | gcagccagtc | attgccagc | aggctctcac | cctgtgggc | agcgtcgaga | 420 |
| ccaaggacga | ggatggtgtg | aagaccaagg | agaagaaggt | catcacccca | gaaatggccc | 480 |
| tgaacatctt | ccgtcgcatg | tcggacgacg | agatgattga | cattggccctc | aatatttccc | 540 |

```
aagctcgtcc ggaatggatg atcatcacgg ttcttcctgt cccgcctcct ccggtgcgcc      600
ccagtatttc catggacgga actggaacag gcttgcggaa tgaggacgat ctgacgtata      660
aactcggcga tatcatccgc gccaatggca acgtccgcca ggctattgcc gagggctctc      720
ctcagcatat catcaccgac tttgagaacc tactccagta ccacgtcgct acgtacatgg      780
ataatgacat cgccggt                                                    797
```

<210> SEQ ID NO 102
<211> LENGTH: 1132
<212> TYPE: DNA
<213> ORGANISM: Chaetomium globosum

<400> SEQUENCE: 102

```
cttccgtcaa tttctttaag tttcagcctt gcgaccatac tcccccagga gcccaaacat       60
tttgatttat cgtaaggtgc cgaacgggtc aaaaaataac gccgtccgat ccctaatcgg      120
catagtttag gttaagacta cgacggtatc tgatcgtatt cgatcccta actttcgttc      180 ctgattaatg aaaacatcct tggcaaatgc tttcgcagta gttagtcttc aataaatcca      240
agaatttcac ctctgacaat tgaatactga tgccccgac tgtccctatt aatcattacg      300
gcggtcctag aaaccaacaa aatagaacca cacgtcctat tctattattc catgctaatg      360
tattcgagca taggccttct ttaagcgatc taatttgttc agagtaaaag tcctggttcc      420
ccggcacacc cagtgaaggg catgcggttc tccagaagga aagacccagc cgagccagtg      480
cacgcggtga ggcggaccgg ccggctaggc ccaaggttca actacgagct ttttaacctc      540
aacaacttta atatacgcta ttggagctgg aattaccgcg gctgctggca ccagacttgc      600
cctccaattg ttcctcgtta agggatttaa attgtactca ttccaattac aagacccgaa      660
agagccctgt atcagtattt attgtcacta cctccccgtg tcgggattgg gtaatttgcg      720
cgcctgctgc cttcctttgg atgtagtagc cgtttctcag gctccttctc cggggtcgag      780 ccctaacct ccgttacccg ttgtcaccac ggctggccaa gacccagccg tcgaaagttg      840 ataggggcaga aatttgaatg aaccatcgcc ggcgcaaggc cgtgcgattc gagaagttat      900
tatgaatcac cagagagccc cgaagggcat tggttttaa tctaataaat acatcccttc      960
cgaagtcggg attttttagca tgtattagct ctagaattac cacggttatc catgtagtaa     1020
ggtactatca aataaacgat aactgattta atgagccatt cgcagtttcg cggtataatt     1080
gcttatactt agacatgcat ggcttaatct ttgagacaag catatgacta ct             1132
```

<210> SEQ ID NO 103
<211> LENGTH: 925
<212> TYPE: DNA
<213> ORGANISM: Chaetomium globosum

<400> SEQUENCE: 103

```
cttccgtcaa tttctttaag tttcagcctt gcgaccatac tcccccagga gcccaaacat       60
tttgatttat cgtaaggtgc cgaacgggtc aaaaaataac gccgtccgat ccctaatcgg      120
catagtttag gttaagacta cgacggtatc tgatcgtatt cgatcccta actttcgttc      180 ctgattaatg aaaacatcct tggcaaatgc tttcgcagta gttagtcttc aataaatcca      240
agaatttcac ctctgacaat tgaatactga tgccccgac tgtccctatt aatcattacg      300
gcggtcctag aaaccaacaa aatagaacca cacgtcctat tctattattc catgctaatg      360
tattcgagca taggccttct ttaagcgatc taatttgttc agagtaaaag tcctggttcc      420
```

```
ccggcacacc cagtgaaggg catgcggttc tccagaagga aagacccagc cgagccagtg    480
cacgcggtga ggcggaccgg ccggctaggc ccaaggttca actacgagct ttttaacctc    540
aacaacttta atatacgcta ttggagctgg aattaccgcg gctgctggca ccagacttgc    600
cctccaattg ttcctcgtta agggatttaa attgtactca ttccaattac aagacccgaa    660
agagccctgt atcagtattt attgtcacta cctccccgtg tcgggattgg gtaatttgcg    720
cgcctgctgc cttcctttgg atgtagtagc cgtttctcag gctccttctc cggggtcgag    780 ccctaacccct ccgttacccg ttgtcaccac ggctggccaa gacccagccg tcgaaagttg    840 ataggggcaga aatttgaatg aaccatcgcc ggcgcaaggc cgtgcgattc gagaagttat    900
tatgaatcac cagagagccc cgaag                                         925

<210> SEQ ID NO 104
<211> LENGTH: 518
<212> TYPE: DNA
<213> ORGANISM: Chaetomium globosum

<400> SEQUENCE: 104
gttcacctcc agaccggcca gtgcgtaagt tggaccgaat cgaacattac gaccgaccgg     60
ccgcgcagga taactgacat ggagctctct agggtaacca aatcggtgcc gctttctggt    120
acgtccaagc aaagcaaaca ctcttggctg atgacaatcg agactgactt cttttcaggc    180
agaccatctc tggcgagcac ggcctcgaca gcaatggcgt gtatgtgggc atgacagttc    240
ccaaccgata aatccccgct caccgcttcg ataggtacaa cggcacctcc gagctccagc    300
tcgagcgtat gaacgtgtac ttcaacgagg tcagtcgggt caaataattt tacacgaccg    360
agtgatggcg tgctcatagt attatacagg cttccggcaa caagtatgtt cctcgcgctg    420
tcctcgtcga cttggagccc ggcaccatgg atgccgtccg tgccggcccc ttcggccagc    480
tcttccgccc ggacaacttc gtcttcggcc agtcgggt                            518

<210> SEQ ID NO 105
<211> LENGTH: 568
<212> TYPE: DNA
<213> ORGANISM: Chaetomium globosum

<400> SEQUENCE: 105
gaggaggagg aggagaggtt ggagagggag gcgttgcgtg ccgaggcgct ttgtgaggtc     60
aggcgggtta tggcgctgct ggaggatacg ctgcttgcgg acgggcggga gtgggttttg    120
ggcggtggtg gtggcggtga tggtggtggc agtgagggtg cgagaaaagg ccgacgttg    180 gcggatatcg aggccgtgtg ggtgcttcac tggatgattg gcattcctgg tgcgctgttc    240
aacgccgggt atgtgagcgc cgagcggttt ccgcgggtgt atgcgtgggt ggcgcggttt    300
caggcggcgg ttggggcggc gaaggccggg gtggtggtga agggcatgag cggggaggag    360
gcggcggtag tgttgaaggg gcagagagaa ggggtaggat atttttgagaa ggaggggagag    420 gtggacgccg cggacccgat cgtcaaggtg tacggattgg agaaagggag cagggtcgag    480
gtgtggccga cggactccgg ggctgggcat cgggatcagg gctgcctggt gagcctcgac    540
gccgaggaaa tagtctggga gacggacg                                      568

<210> SEQ ID NO 106
<211> LENGTH: 520
<212> TYPE: DNA
<213> ORGANISM: Chaetomium globosum

<400> SEQUENCE: 106
```

```
ttgtgacgtt acctataccg ttgcttcggc gggcggcccc ggggtttacc ccccgggcgc    60
ccctgggccc caccgcgggc gcccgccgga ggtcaccaaa ctcttgataa tttatggcct   120
ctctgagtct tctgtactga ataagtcaaa actttcaaca acggatctct tggttctggc   180
atcgatgaag aacgcagcga aatgcgataa gtaatgtgaa ttgcagaatt cagtgaatca   240
tcgaatcttt gaacgcacat tgcgcccgcc agcattctgg cgggcatgcc tgttcgagcg   300
tcatttcaac catcaagccc ccgggcttgt gttgggacc  tgcggctgcc gcaggccctg   360
aaaagcagtg gcgggctcgc tgtcgcaccg agcgtagtag catacatctc gctctggtcg   420
cgccgcgggt tccggccgtt aaaccacctt ttaacccaag gttgacctcg gatcaggtag   480
gaagacccgc tgaacttaag catatcaata agcggaggaa                         520
```

<210> SEQ ID NO 107
<211> LENGTH: 523
<212> TYPE: DNA
<213> ORGANISM: Chaetomium globosum

<400> SEQUENCE: 107

```
cattgtgaac gttacctata ccgttgcttc ggcgggcggc cccggggttt acccccgggg    60 cgccctggg  ccccaccgcg gcgcccgcc  ggaggtcacc aaactcttga taatttatgg   120
cctctctgag tcttctgtac tgaataagtc aaaactttca acaacggatc tcttggttct   180
ggcatcgatg aagaacgcag cgaaatgcga taagtaatgt gaattgcaga attcagtgaa   240
tcatcgaatc tttgaacgca cattgcgccc gccagcattc tggcgggcat gcctgttcga   300
gcgtcatttc aaccatcaag cccccgggct tgtgttgggg acctgcggct gccgcaggcc   360
ctgaaaagca gtggcgggct cgctgtcgca ccgagcgtag tagcatacat ctcgctctgg   420
tcgcgccgcg gggttccggcc gttaaaccac cttttaaccc aaggttgacc tcggatcagg   480
taggaagacc cgctgaactt aagcatatca ataagcggag gaa                      523
```

<210> SEQ ID NO 108
<211> LENGTH: 518
<212> TYPE: DNA
<213> ORGANISM: Chaetomium piluliferum

<400> SEQUENCE: 108

```
cattgtgacg ttaccttcaa accgttgctt cggcgggcgg cccgggtccg cccggtgccc    60
cctggccccc tagcggggcg cccgccggag gaaaacccaa ctcttgatta ttatggcctc   120
tctgagtctt ctgtactgaa taagtcaaaa ctttcaacaa cggatctctt ggttctggca   180
tcgatgaaga acgcagcgaa atgcgataag taatgtgaat tgcagaattc agtgaatcat   240
cgaatctttg aacgcacatt gcgcccgcca gtattctggc gggcatgcct gttcgagcgt   300
catttcaacc atcaagcccc aggcttgtgt tggggacctg cggctgccgc aggccctgaa   360
aaccagtggc gggctcgctg tcacaccggg cgtagtagat tttatctcgc tctgggcgtg   420
ctgcgggttc cggccgttaa aaaacccttt taacccaagg ttgacctcgg atcaggtagg   480
aatacccgct gaacttaagc atatcaataa gcggagga                           518
```

<210> SEQ ID NO 109
<211> LENGTH: 558
<212> TYPE: DNA
<213> ORGANISM: Unknown
<220> FEATURE:
<223> OTHER INFORMATION: Kingdom: Fungi, Phylum: Ascomycota, Class:
      Sordariomycetes, Order: Sordariales, Family: Chaetomiaceae, Genus:

Chaetomium

<400> SEQUENCE: 109

```
tcgttggtga ccagcggagg gatcattaca gagttgcaaa actccctaaa ccattgtgaa      60
cgttacctaa accgttgctt cggcgggcgg ccccggggtt tacccccggg gcgcccctgg     120
gccccaccgc gggcgcccgc cggaggtcac caaactcttg ataatttatg gcctctctga     180
gtcttctgta ctgaataagt caaaactttc aacaacggat ctcttggttc tggcatcgat     240
gaagaacgca gcgaaatgcg ataagtaatg tgaattgcag aattcagtga atcatcgaat     300
ctttgaacgc acattgcgcc cgccagtatt ctggcgggca tgcctgttcg agcgtcattt     360
caaccatcaa gccccgggct tgtgttgggg acctgcggct gccgcaggcc ctgaaaagca     420
gtggcgggct cgctgtcaca ccgagcgtag tagcatatat ctcgctctgg gcgtgctgcg     480
ggttccggcc gttaaaccac cttttaaccc aaggttgacc tcggatcagg taggaagacc     540
cgctgaactt aagcatat                                                    558
```

<210> SEQ ID NO 110
<211> LENGTH: 507
<212> TYPE: DNA
<213> ORGANISM: Unknown
<220> FEATURE:
<223> OTHER INFORMATION: Kingdom: Fungi

<400> SEQUENCE: 110

```
ctttgtgacc ttcatacctg ttgcttcggc ggcgcgcctc tcgggcgtg cccgccggca       60
ttatcagaat ctctgttcga acccgacgat acttctgagt gttctaagcg aactgttaaa     120
actttcaaca acggatctct tggctccagc atcgatgaag aacgcagcga aacgcgatat     180
gtaatgtgaa ttgcagaatt cagtgaatca tcgaatcttt gaacgcacat ggcgccttcc     240
agtatcctgg gaggcatgcc tgtccgagcg tcgtttcaac cctcgagccc cgtggcccg      300
gcgttgggga cctgcccagg cagtcccga aaaccagtgg cggacccgac gggcccttcc      360
tttgcgtagt aacatctgcc tcgcatcggg agccccggg ctatccggcc tctaaaccc       420
cctcaagccc gctccggcgg caccaaggtt gacctcggat caggtaggaa tacccgctga     480
acttaagcat atcaataagc ggaggaa                                          507
```

<210> SEQ ID NO 111
<211> LENGTH: 475
<212> TYPE: DNA
<213> ORGANISM: Unknown
<220> FEATURE:
<223> OTHER INFORMATION: Kingdom: Fungi, Phylum: Basidiomycota, Class:
      Tremellomycetes, Order: Tremellales, Family: Incertae sedis,
      Genus: Cryptococcus

<400> SEQUENCE: 111

```
gcctttaccg gctggtaggg tttggacggt ctctttaggg agccggccta atctcacaca      60
ccgtgaactg tggcttcggc catttacaca aactgttagt aatgaatgtc atatcataac     120
aaacataaaa cttttaacaa cggatctctt ggctctcgca tcgatgaaga acgcagcgaa     180
ttgcgataag taatgtgaat tgcagaattc agtgaatcat cgaatctttg aacgcacctt     240
gcgcccttg gtattccgaa gggcatgcct gtttgagtgt catgaaacct caccccattt      300
aggttttgc ctgagtggtc ggtggattgg gtgttgccga tatactggct cgcctgaaaa     360
gcataagcgc cttggatgta atacgtttca tccttctggg tggctgataa ccccacatat    420
ctcatgatct ggcctcaaat caggtagggc tacccgctga acttaagcat atcaa          475
```

<210> SEQ ID NO 112
<211> LENGTH: 499
<212> TYPE: DNA
<213> ORGANISM: Unknown
<220> FEATURE:
<223> OTHER INFORMATION: Kingdom: Fungi, Phylum: Basidiomycota, Class:
      Tremellomycetes, Order: Tremellales, Family: Incertae sedis,
      Genus: Cryptococcus
<220> FEATURE:
<221> NAME/KEY: misc_feature
<222> LOCATION: (90)..(90)
<223> OTHER INFORMATION: n is a, c, g, or t

<400> SEQUENCE: 112

```
ccctttgtga ccttcatacc tgttgcttcg gcggcgcgcc tctcgggcg tgcccgccgg      60 cattatcaga atctctgttc gaacccgacn atacttctga gtgttctaag cgaactgtta    120
aaactttcaa caacggatct cttggctcca gcatcgatga agaacgcagc gaaacgcgat    180
atgtaatgtg aattgcagaa ttcagtgaat catcgaatct ttgaacgcac atggcgcctt    240
ccagtatcct gggaggcatg cctgtccgag cgtcgtttca accctcgagc ccccgtggcc    300
cggcgttggg gacctgccca ggcagtcccc gaaaaccagt ggcggacccg acgggccctt    360
cctttgcgta gtaacatctg cctcgcatcg ggagccccg ggctatccgg cctctaaacc    420
cccctcaagc ccgctccggc ggcaccaagg ttgacctcgg atcaggtagg aatacccgct    480
gaacttaagc atatcaata                                                 499
```

<210> SEQ ID NO 113
<211> LENGTH: 169
<212> TYPE: DNA
<213> ORGANISM: Unknown
<220> FEATURE:
<223> OTHER INFORMATION: Kingdom: Fungi

<400> SEQUENCE: 113

```
taaccctttg ttgtccgact ctgttgcctc cggggcgacc ctgccttcgg gcggggctc      60 cgggtggaca cttcaaactc ttgcgtaact ttgcagtctg agtaaactta attaataaat    120
taaaactttt aacaacggat ctcttggttc tggcatcgat gaagaacgc                169
```

<210> SEQ ID NO 114
<211> LENGTH: 1443
<212> TYPE: DNA
<213> ORGANISM: Unknown
<220> FEATURE:
<223> OTHER INFORMATION: Kingdom: Fungi, Phylum: Ascomycota, Class:
      Dothideomycetes, Order: Capnodiales, Family: Cladosporiaceae,
      Genus: Cladosporium

<400> SEQUENCE: 114

```
tcttggtcat ttagaggaag taaaagtcgt aacaaggtct ccgtaggtga acctgcggag      60
ggatcattac aagtgacccc ggtctaacca ccgggatgtt cataacccctt tgttgtccga    120 ctctgttgcc tccggggcga ccctgccttc gggcggggc tccggtgga cacttcaaac    180 tcttgcgtaa ctttgcagtc tgagtaaact taattaataa attaaaactt ttaacaacgg    240
atctcttggt tctggcatcg atgaagaacg cagcgaaatg cgataagtaa tgtgaattgc    300
agaattcagt gaatcatcga atctttgaac gcacattgcg ccccctggta ttccgggggg    360
catgcctgtt cgagcgtcat ttcaccactc aagcctcgct tggtattggg catcgcggtc    420
cgccgcgtgc ctcaaatcga ccggctgggt cttctgtccc ctaagcgttg tggaaactat    480
```

```
tcgctaaagg gtgttcggga ggctacgccg taaaacaacc ccatttctaa ggttgacctc      540
ggatcaggta gggatacccg ctgaacttaa gcatatcaat aagcggagga aaagaaacca      600
acagggattg ctctagtaac ggcgagtgaa gcagcaatag ctcaaatttg aaatctggcg      660
tcttcgacgt ccgagttgta atttgtagag gatgcttctg agtaaccacc gacctaagtt      720
ccttggaaca ggacgtcata gagggtgaga atcccgtatg cggtcggaaa ggtgctctat      780
acgtagctcc ttcgacgagt cgagttgttt gggaatgcag ctctaaatgg gaggtaaatt      840
tcttctaaag ctaaatattg gccagagacc gatagcgcac aagtagagtg atcgaaagat      900
gaaaagcact ttggaaagag agttaaaaag cacgtgaaat tgttaaaagg gaagggattg      960
caaccagact tgctcgcggt gttccgccgg tcttctgacc ggtctactcg ccgcgttgca     1020
ggccagcatc gtctggtgcc gctggataag acttgaggaa tgtagctcct tcggagtgt      1080 tatagcctct tgtgatgcag cgagcgccgg gcgaggtccg cgcttcggct aggatgctgg     1140
cgtaatggtc gtaatccgcc cgtcttgaaa cacggaccaa ggagtctaac atctatgcga     1200
gtgttcgggt gtcaaacccc tacgcgtaat gaaagtgaac ggaggtgaga accgcaaggt     1260
gcatcatcga ccgatcctga tgtcttcgga tggatttgag taagagcata gctgttggga     1320
cccgaaagat ggtgaactat gcctgaatag ggtgaagcca gaggaaactc tggtggaggc     1380
tcgcagcggt tctgacgtgc aaatcgatcg tcaaatttgg gtataggggc gaaagactaa     1440
tcg                                                                    1443

<210> SEQ ID NO 115
<211> LENGTH: 489
<212> TYPE: DNA
<213> ORGANISM: Unknown
<220> FEATURE:
<223> OTHER INFORMATION: Kingdom: Fungi, Phylum: Ascomycota, Class:
      Dothideomycetes, Order: Capnodiales, Family: Cladosporiaceae,
      Genus: Cladosporium

<400> SEQUENCE: 115
ccgggatgtt cataacccctt tgttgtccga ctctgttgcc tccggggcga ccctgccttc       60 gggcggggc tccgggtgga cacttcaaac tcttgcgtaa ctttgcagtc tgagtaaact      120
taattaataa attaaaactt ttaacaacgg atctcttggt tctggcatcg atgaagaacg      180
cagcgaaatg cgataagtaa tgtgaattgc agaattcagt gaatcatcga atctttgaac      240
gcacattgcg cccctggta ttccggggg catgcctgtt cgagcgtcat ttcaccactc      300
aagcctcgct tggtattggg caacgcggtc cgccgcgtgc ctcaaatcga ccggctgggt      360
cttctgtccc ctaagcgttg tggaaactat tcgctaaagg gtgttcggga ggctacgccg      420
taaaacaacc ccatttctaa ggttgacctc ggatcaggta gggatacccg ctgaacttaa      480
gcatatcaa                                                              489
```